US012129465B2

(12) United States Patent
Ellis et al.

(10) Patent No.: US 12,129,465 B2
(45) Date of Patent: Oct. 29, 2024

(54) STABLE CORONAVIRUS PROTEINS AND VACCINE COMPOSITIONS THEREOF

(71) Applicants: UNIVERSITY OF WASHINGTON, Seattle, WA (US); FRED HUTCHINSON CANCER RESEARCH CENTER, Seattle, WA (US)

(72) Inventors: Daniel Ellis, Seattle, WA (US); Neil King, Seattle, WA (US); Jesse Bloom, Seattle, WA (US); Tyler Starr, Seattle, WA (US); Allison Greaney, Seattle, WA (US)

(73) Assignees: UNIVERSITY OF WASHINGTON, Seattle, WA (US); FRED HUTCHINSON RESEARCH CENTER, Seattle, WA (US)

( * ) Notice: Subject to any disclaimer, the term of this patent is extended or adjusted under 35 U.S.C. 154(b) by 103 days.

(21) Appl. No.: 17/563,271

(22) Filed: Dec. 28, 2021

(65) Prior Publication Data
US 2022/0325279 A1    Oct. 13, 2022

Related U.S. Application Data

(60) Provisional application No. 63/210,654, filed on Jun. 15, 2021, provisional application No. 63/188,651, filed on May 14, 2021, provisional application No. 63/132,863, filed on Dec. 31, 2020.

(51) Int. Cl.
*C07K 14/165* (2006.01)
*A61K 39/215* (2006.01)
*C12N 15/11* (2006.01)
*C12N 15/64* (2006.01)
*C12Q 1/6811* (2018.01)

(52) U.S. Cl.
CPC ............ *C12N 15/11* (2013.01); *A61K 39/215* (2013.01); *C07K 14/165* (2013.01); *C12N 15/64* (2013.01); *C12Q 1/6811* (2013.01)

(58) Field of Classification Search
CPC .................... C12N 15/11; C12N 15/64; C12N 2770/20034; C12N 2770/20022; C12Q 1/6811; A61K 2039/55555; A61K 2039/55566; A61K 39/12; A61P 31/14; C07K 14/005
See application file for complete search history.

(56) References Cited

PUBLICATIONS

Li et al., 2020, Cell, 182: 1284-1294 (Year: 2020).*
Singh et al., 2017, Curr Prot Peptide Sci, 18:1-11 (Year: 2017).*
Zhang et al., 2018, Stucture, 26: 1474-1485 (Year: 2018).*
Frokjaer et al., 2005, Nat Rev Drug Discovery, 4: 298-306 (Year: 2005).*
Skwarczynski et al, 2016, Chem Sci, 7: 842-854 (Year: 2016).*
Ulmer et al., 2006, Nat Biotechnol, 24(11): 1377-1383 (Year: 2006).*
Pedelacq et al., 2006, Nat Biotechnol, 24(11): 79-88 (Year: 2006).*
GenBank Accession MN908947, Severe acute respiratory syndrome coronavirus 2 isolate Wuhan-Hu-1, complete genome, 2020, p. 1-10 (Year: 2020).*
Cohen et al. (2021). Mosaic nanoparticles elicit cross-reactive immune responses to zoonotic coronaviruses in mice. Science 317(6530), 735-741.
Cohen et al. (2022). Mosaic RBD nanoparticles protect against challenge by diverse sarbecoviruses in animal models. Science 377(6606), eabq0839.
Dickey et al. (2023). Design of a stabilized RBD enables potently neutralizing SARS-CoV-2 single-component nanoparticle vaccines. Cell Rep. 42(3), 112266.
He et al. (2021). Single-component, self-assembling, protein nanoparticles presenting the receptor binding domain and stabilized spike as SARS-CoV-2 vaccine candidates. Sci. Adv. 7(12), eabf1591.
Ellis et al. (2021). Stabilization of the SARS-CoV-2 spike receptor-binding domain using deep mutational scanning and structure-based design. Front. Immunol. 12, 710263.
Joyce et al. (2021). SARS-CoV-2 ferritin nanoparticle vaccines elicit broad SARS coronavirus immunogenicity. bioRxiv 2021.05.09.443331.
Joyce et al. (2021). SARS-CoV-2 ferritin nanoparticle vaccines elicit broad SARS coronavirus immunogenicity. Cell Rep. 37(12), 110143.
Leonard et al. (2021). Stabilization of the SARS-CoV-2 Receptor Binding Domain by Protein Core Redesign and Deep Mutational Scanning. bioRxiv 2021.11.22.469552.
Leonard et al. (2022). Stabilization of the SARS-CoV-2 receptor binding domain by protein core redesign and deep mutational scanning. Protein Eng. Des. Sel. 35, gzac002.
Rahikainen et al. (2021). Overcoming Symmetry Mismatch in Vaccine Nanoassembly through Spontaneous Amidation. Angew. Chem. Int. Ed. Engl. 60(1), 321-330.
Starr et al. (2020). Deep mutational scanning of SARS-CoV-2 receptor binding domain reveals constraints on folding and ACE2 binding. bioRxiv 2020.06.17.157982.
Starr et al. (2020). Deep Mutational Scanning of SARS-CoV-2 Receptor Binding Domain Reveals Constraints on Folding and ACE2 Binding. Cell 182(5), 1295-1310.

(Continued)

*Primary Examiner* — David Steadman
*Assistant Examiner* — Joseph Spangler
(74) *Attorney, Agent, or Firm* — MCDONNELL BOEHNEN HULBERT & BERGHOFF LLP

(57) ABSTRACT

Provided herein are compositions and methods comprising mutated coronavirus "S" spike proteins or receptor binding domains thereof that have an increased expression level, yield and stability compared to its corresponding native or wild-type coronavirus spike protein under the same expression, culture or storage conditions. These mutated spike proteins can be used for generating a protein-based vaccine against one or more coronaviruses.

31 Claims, 49 Drawing Sheets

Specification includes a Sequence Listing.

(56) References Cited

PUBLICATIONS

Walls et al. (2020). Elicitation of Potent Neutralizing Antibody Responses by Designed Protein Nanoparticle Vaccines for SARS-CoV-2. Cell 183(5), 1367-1382.

Zhang et al. (2021). Mechanism of a COVID-19 nanoparticle vaccine candidate that elicits a broadly neutralizing antibody response to SARS-CoV-2 variants. Sci. Adv. 7(43), eabj3107.

Icosavax Launches COVID-19 Vaccine Program with Preclinical Data and $16.5 Million in New Funding, Oct. 30, 2020. Press release. <https://ir.icosavax.com/news-releases/news-release-details/icosavax-launches-covid-19-vaccine-program-preclinical-data-and>.

Icosavax Initiates Phase 1/2 Trial of COVID-19 VLP Vaccine Candidate, Jun. 8, 2021. Press release. <https://ir.icosavax.com/news-releases/news-release-details/icosavax-initiates-phase-12-trial-covid-19-vlp-vaccine-candidate>.

Icosavax Announces Topline Interim Phase 1/2 Results for IVX-411 Against SARS-CoV-2, Mar. 25, 2022. Press release. <https://ir.icosavax.com/news-releases/news-release-details/icosavax-announces-topline-interim-phase-12-results-ivx-411>.

Icosavax Announces Results from IVX-411 Drug Product Investigation and Outlines Additional Corporate Milestones, Jul. 28, 2022. Press release. <https://ir.icosavax.com/news-releases/news-release-details/icosavax-announces-results-ivx-411-drug-product-investigation>.

* cited by examiner

Rpk1: Y365W
Rpk2: F338L + Y365W
Rpk3: Y365W + L513M
Rpk4: F392W
Rpk5: Y365W + F392W
Rpk6: F338M + A363L + Y365F + F377V
Rpk7: Y365F + F392W
Rpk8: Y365F + V395I
Rpk9: Y365F + F392W + V395I

Rpk10: Y365W + L513I + F515L
Rpk11: F338L + A363L + Y365M
Rpk12: I358F + Y365W
Rpk13: F338L + I358F + Y365W
Rpk14: I358F + Y365W + L513M
Rpk15: I358F + Y365F + V395I
Rpk16: I358F + Y365W + F392W
Rpk17: I358F + Y365F + F392W + V395I

FIG. 1B

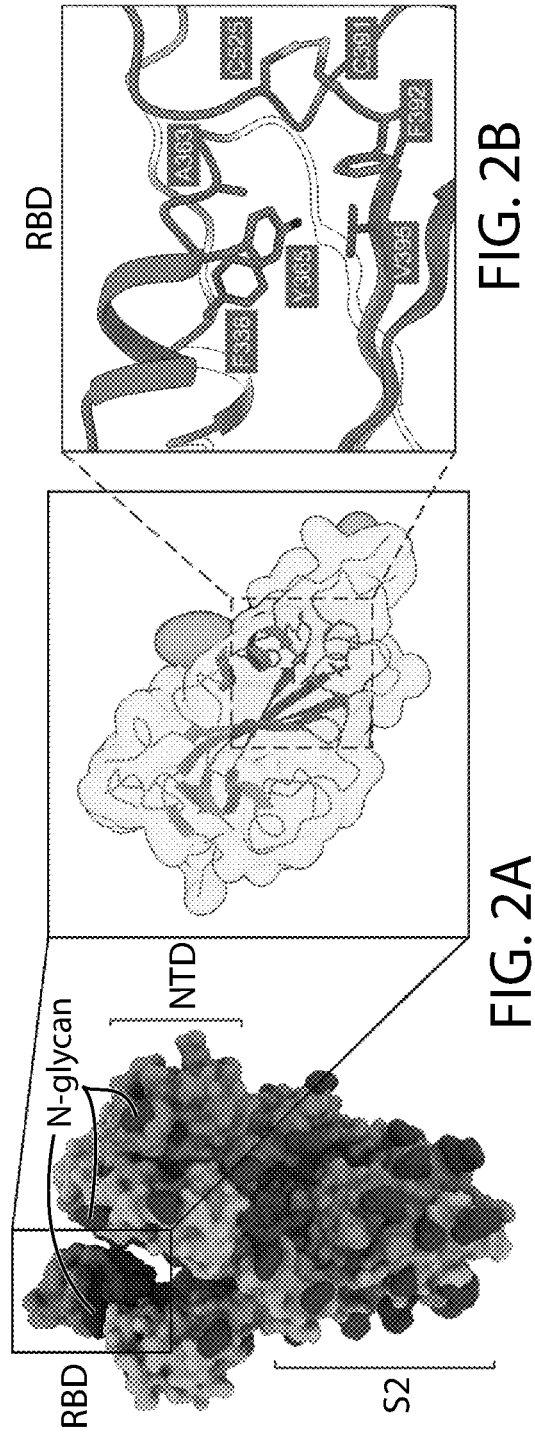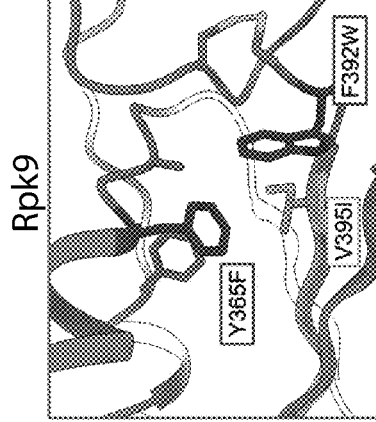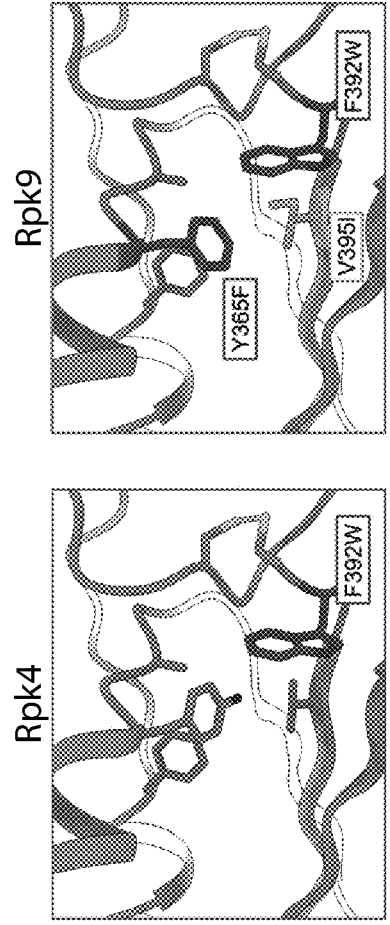
FIG. 2A
FIG. 2B
FIG. 2C

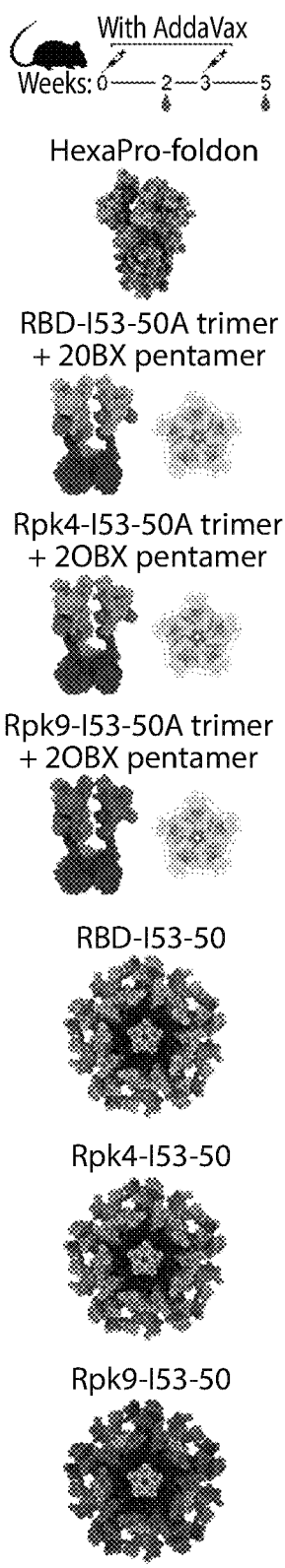
FIG. 6A
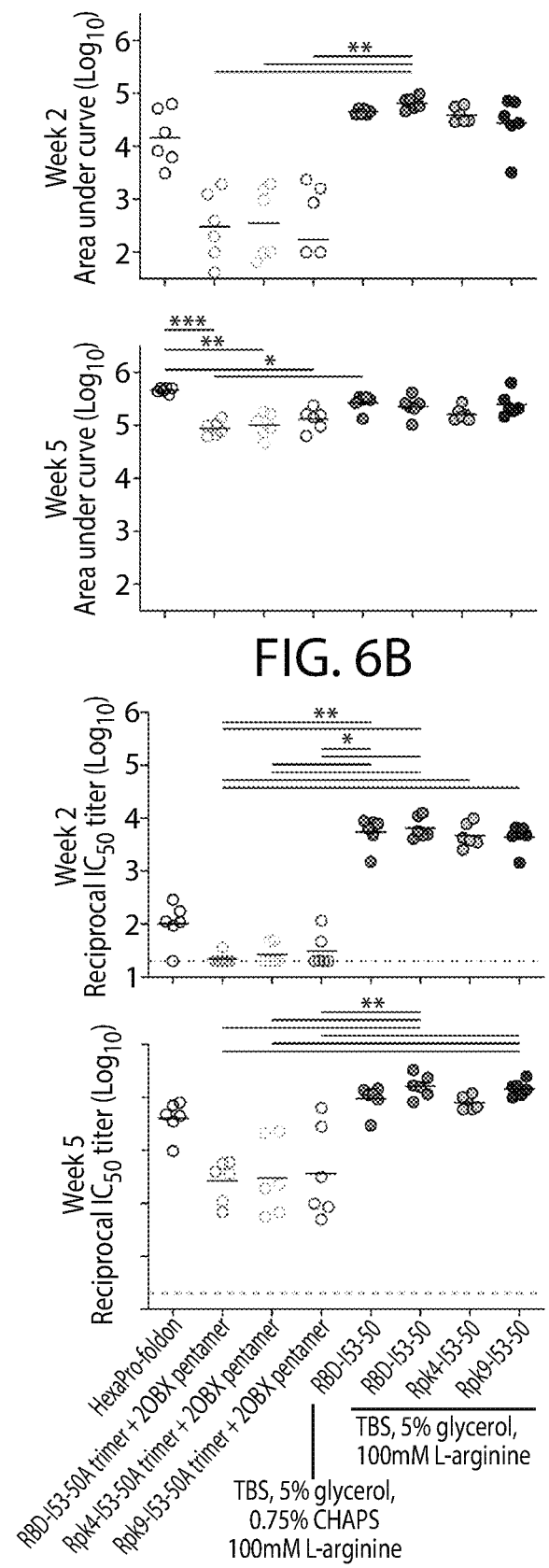
FIG. 6B
FIG. 6C

SEQUENCE LISTING

```
<160> NUMBER OF SEQ ID NOS: 61

<210> SEQ ID NO 1
<211> LENGTH: 1016
<212> TYPE: PRT
<213> ORGANISM: Severe acute respiratory syndrome coronavirus 2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560
```

-continued

Pro Phe Gln Gln Phe Gly Arg Asp Ile Ala Asp Thr Thr Asp Ala Val
            565                 570                 575
Arg Asp Pro Gln Thr Leu Glu Ile Leu Asp Ile Thr Pro Cys Ser Phe
        580                 585                 590
Gly Gly Val Ser Val Ile Thr Pro Gly Thr Asn Thr Ser Asn Gln Val
    595                 600                 605
Ala Val Leu Tyr Gln Asp Val Asn Cys Thr Glu Val Pro Val Ala Ile
610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
        660                 665                 670
Ser Tyr Gln Thr Gln Thr Asn Ser Pro Arg Arg Ala Arg Ser Val Ala
    675                 680                 685
Ser Gln Ser Ile Ile Ala Tyr Thr Met Ser Leu Gly Ala Glu Asn Ser
690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
        740                 745                 750
Leu Leu Gln Tyr Gly Ser Phe Cys Thr Gln Leu Asn Arg Ala Leu Thr
    755                 760                 765
Gly Ile Ala Val Glu Gln Asp Lys Asn Thr Gln Glu Val Phe Ala Gln
770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
        820                 825                 830
Phe Ile Lys Gln Tyr Gly Asp Cys Leu Gly Asp Ile Ala Ala Arg Asp
    835                 840                 845
Leu Ile Cys Ala Gln Lys Phe Asn Gly Leu Thr Val Leu Pro Pro Leu
850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
            885                 890                 895
Pro Phe Ala Met Gln Met Ala Tyr Arg Phe Asn Gly Ile Gly Val Thr
        900                 905                 910
Gln Asn Val Leu Tyr Glu Asn Gln Lys Leu Ile Ala Asn Gln Phe Asn
    915                 920                 925
Ser Ala Ile Gly Lys Ile Gln Asp Ser Leu Ser Ser Thr Ala Ser Ala
930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
            965                 970                 975
Leu Asn Asp Ile Leu Ser Arg Leu Asp Lys Val Glu Ala Glu Val Gln

```
                980             985             990
Ile Asp Arg Leu Ile Thr Gly Arg  Leu Gln Ser Leu Gln  Thr Tyr Val
            995                 1000                1005

Thr Gln  Gln Leu Ile Arg Ala  Ala
    1010                 1015

<210> SEQ ID NO 2
<211> LENGTH: 202
<212> TYPE: PRT
<213> ORGANISM: Severe acute respiratory syndrome coronavirus 2

<400> SEQUENCE: 2

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys
        195                 200

<210> SEQ ID NO 3
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
```

```
            65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205

<210> SEQ ID NO 4
<211> LENGTH: 21
<212> TYPE: PRT
<213> ORGANISM: Severe acute respiratory syndrome coronavirus 2

<400> SEQUENCE: 4

Arg Lys Arg Ile Ser Asn Cys Val Ala Asp Tyr Ser Val Leu Tyr Asn
1               5                   10                  15

Ser Ala Ser Phe Ser
            20

<210> SEQ ID NO 5
<211> LENGTH: 19
<212> TYPE: PRT
<213> ORGANISM: Severe acute respiratory syndrome coronavirus 2

<400> SEQUENCE: 5

Phe Lys Cys Tyr Gly Val Ser Pro Thr Lys Leu Asn Asp Leu Cys Phe
1               5                   10                  15

Thr Asn Val

<210> SEQ ID NO 6
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Phe Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Trp Thr Asn Ile Tyr Ala Asp Ser Phe Val Ile Arg Gly Asp Glu Val
65                  70                  75                  80
```

```
Arg Gln Ile Ala Pro Gly Gln Thr Gly Lys Ile Ala Asp Tyr Asn Tyr
                85                  90                  95
Lys Leu Pro Asp Asp Phe Thr Gly Cys Val Ile Ala Trp Asn Ser Asn
            100                 105                 110
Asn Leu Asp Ser Lys Val Gly Gly Asn Tyr Asn Tyr Leu Tyr Arg Leu
        115                 120                 125
Phe Arg Lys Ser Asn Leu Lys Pro Phe Glu Arg Asp Ile Ser Thr Glu
    130                 135                 140
Ile Tyr Gln Ala Gly Ser Thr Pro Cys Asn Gly Val Glu Gly Phe Asn
145                 150                 155                 160
Cys Tyr Phe Pro Leu Gln Ser Tyr Gly Phe Gln Pro Thr Tyr Gly Val
                165                 170                 175
Gly Tyr Gln Pro Tyr Arg Val Val Val Leu Ser Phe Glu Leu Leu His
            180                 185                 190
Ala Pro Ala Thr Val Cys Gly Pro Lys Lys Ser Thr Gly Gly Ser Gly
        195                 200                 205
Gly Ser Gly Ser Gly Gly Ser Gly Gly Ser Gly Ser Glu Lys Ala Ala
    210                 215                 220
Lys Ala Glu Glu Ala Ala Arg Lys Met Glu Glu Leu Phe Lys Lys His
225                 230                 235                 240
Lys Ile Val Ala Val Leu Arg Ala Asn Ser Val Glu Glu Ala Ile Glu
                245                 250                 255
Lys Ala Val Ala Val Phe Ala Gly Gly Val His Leu Ile Glu Ile Thr
            260                 265                 270
Phe Thr Val Pro Asp Ala Asp Thr Val Ile Lys Ala Leu Ser Val Leu
    275                 280                 285
Lys Glu Lys Gly Ala Ile Ile Gly Ala Gly Thr Val Thr Ser Val Glu
290                 295                 300
Gln Ala Arg Lys Ala Val Glu Ser Gly Ala Glu Phe Ile Val Ser Pro
305                 310                 315                 320
His Leu Asp Glu Glu Ile Ser Gln Phe Ala Lys Glu Lys Gly Val Phe
                325                 330                 335
Tyr Met Pro Gly Val Met Thr Pro Thr Glu Leu Val Lys Ala Met Lys
            340                 345                 350
Leu Gly His Thr Ile Leu Lys Leu Phe Pro Gly Glu Val Val Gly Pro
        355                 360                 365
Gln Phe Val Lys Ala Met Lys Gly Pro Phe Pro Asn Val Lys Phe Val
    370                 375                 380
Pro Thr Gly Gly Val Asn Leu Asp Asn Val Ala Glu Trp Phe Lys Ala
385                 390                 395                 400
Gly Val Leu Ala Val Gly Val Gly Ser Ala Leu Val Lys Gly Thr Pro
                405                 410                 415
Asp Glu Val Arg Glu Lys Ala Lys Ala Phe Val Glu Lys Ile Arg Gly
            420                 425                 430
Ala Thr Glu
        435

<210> SEQ ID NO 7
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Phe Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Trp Thr Asn Ile Tyr Ala Asp Ser Phe Val Ile Arg Gly Asp Glu Val
65              70                  75                  80

Arg Gln Ile Ala Pro Gly Gln Thr Gly Asn Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
        115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Lys Gly Phe Asn
145                 150                 155                 160

Cys Tyr Phe Pro Leu Gln Ser Tyr Gly Phe Gln Pro Thr Tyr Gly Val
            165                 170                 175

Gly Tyr Gln Pro Tyr Arg Val Val Leu Ser Phe Glu Leu Leu His
        180                 185                 190

Ala Pro Ala Thr Val Cys Gly Pro Lys Lys Ser Thr Gly Gly Ser Gly
            195                 200                 205

Gly Ser Gly Ser Gly Gly Ser Gly Gly Ser Gly Ser Glu Lys Ala Ala
        210                 215                 220

Lys Ala Glu Glu Ala Ala Arg Lys Met Glu Glu Leu Phe Lys Lys His
225                 230                 235                 240

Lys Ile Val Ala Val Leu Arg Ala Asn Ser Val Glu Glu Ala Ile Glu
            245                 250                 255

Lys Ala Val Ala Val Phe Ala Gly Gly Val His Leu Ile Glu Ile Thr
            260                 265                 270

Phe Thr Val Pro Asp Ala Asp Thr Val Ile Lys Ala Leu Ser Val Leu
    275                 280                 285

Lys Glu Lys Gly Ala Ile Ile Gly Ala Gly Thr Val Thr Ser Val Glu
    290                 295                 300

Gln Ala Arg Lys Ala Val Glu Ser Gly Ala Glu Phe Ile Val Ser Pro
305                 310                 315                 320

His Leu Asp Glu Glu Ile Ser Gln Phe Ala Lys Glu Lys Gly Val Phe
            325                 330                 335

Tyr Met Pro Gly Val Met Thr Pro Thr Glu Leu Val Lys Ala Met Lys
            340                 345                 350

Leu Gly His Thr Ile Leu Lys Leu Phe Pro Gly Glu Val Val Gly Pro
            355                 360                 365

Gln Phe Val Lys Ala Met Lys Gly Pro Phe Pro Asn Val Lys Phe Val
    370                 375                 380

Pro Thr Gly Gly Val Asn Leu Asp Asn Val Ala Glu Trp Phe Lys Ala
385                 390                 395                 400

Gly Val Leu Ala Val Gly Val Gly Ser Ala Leu Val Lys Gly Thr Pro
            405                 410                 415
```

```
Asp Glu Val Arg Glu Lys Ala Lys Ala Phe Val Glu Lys Ile Arg Gly
            420                 425                 430
Ala Thr Glu
        435

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Lys Ala Ala Lys Ala Glu Glu Ala Ala Arg Lys
1               5                   10

<210> SEQ ID NO 9
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Glu Leu Phe Lys Lys His Lys Ile Val Ala Val Leu Arg Ala Asn
1               5                   10                  15

Ser Val Glu Glu Ala Ile Glu Lys Ala Val Ala Val Phe Ala Gly Gly
            20                  25                  30

Val His Leu Ile Glu Ile Thr Phe Thr Val Pro Asp Ala Asp Thr Val
        35                  40                  45

Ile Lys Ala Leu Ser Val Leu Lys Glu Lys Gly Ala Ile Ile Gly Ala
    50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Glu Ile Ser Gln Phe
                85                  90                  95

Cys Lys Glu Lys Gly Val Phe Tyr Met Pro Gly Val Met Thr Pro Thr
            100                 105                 110

Glu Leu Val Lys Ala Met Lys Leu Gly His Thr Ile Leu Lys Leu Phe
        115                 120                 125

Pro Gly Glu Val Val Gly Pro Gln Phe Val Lys Ala Met Lys Gly Pro
    130                 135                 140

Phe Pro Asn Val Lys Phe Val Pro Thr Gly Gly Val Asn Leu Asp Asn
145                 150                 155                 160

Val Cys Glu Trp Phe Lys Ala Gly Val Leu Ala Val Gly Val Gly Ser
                165                 170                 175

Ala Leu Val Lys Gly Thr Pro Asp Glu Val Arg Glu Lys Ala Lys Ala
            180                 185                 190

Phe Val Glu Lys Ile Arg Gly Cys Thr Glu
        195                 200

<210> SEQ ID NO 10
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 10

Glu Glu Leu Phe Lys Lys His Lys Ile Val Ala Val Leu Arg Ala Asn
1               5                   10                  15

Ser Val Glu Glu Ala Ile Glu Lys Ala Val Ala Val Phe Ala Gly Gly
            20                  25                  30

Val His Leu Ile Glu Ile Thr Phe Thr Val Pro Asp Ala Asp Thr Val
                35                  40                  45

Ile Lys Ala Leu Ser Val Leu Lys Glu Lys Gly Ala Ile Ile Gly Ala
    50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Ile Ser Gln Phe
                85                  90                  95

Cys Lys Glu Lys Gly Val Phe Tyr Met Pro Gly Val Met Thr Pro Thr
                100                 105                 110

Glu Leu Val Lys Ala Met Lys Leu Gly His Asp Ile Leu Lys Leu Phe
            115                 120                 125

Pro Gly Glu Val Val Gly Pro Gln Phe Val Lys Ala Met Lys Gly Pro
    130                 135                 140

Phe Pro Asn Val Lys Phe Val Pro Thr Gly Gly Val Asn Leu Asp Asn
145                 150                 155                 160

Val Cys Glu Trp Phe Lys Ala Gly Val Leu Ala Val Gly Val Gly Asp
                165                 170                 175

Ala Leu Val Lys Gly Asp Pro Asp Glu Val Arg Glu Lys Ala Lys Lys
            180                 185                 190

Phe Val Glu Lys Ile Arg Gly Cys Thr Glu
            195                 200

<210> SEQ ID NO 11
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Glu Leu Phe Lys Lys His Lys Ile Val Ala Val Leu Arg Ala Asn
1               5                   10                  15

Ser Val Glu Glu Ala Ile Glu Lys Ala Val Ala Val Phe Ala Gly Gly
            20                  25                  30

Val His Leu Ile Glu Ile Thr Phe Thr Val Pro Asp Ala Asp Thr Val
                35                  40                  45

Ile Lys Ala Leu Ser Val Leu Lys Glu Lys Gly Ala Ile Ile Gly Ala
    50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Ile Ser Gln Phe
                85                  90                  95

Cys Lys Glu Lys Gly Val Phe Tyr Met Pro Gly Val Met Thr Pro Thr
                100                 105                 110

Glu Leu Val Lys Ala Met Lys Leu Gly His Asp Ile Leu Lys Leu Phe
            115                 120                 125

Pro Gly Glu Val Val Gly Pro Glu Phe Val Glu Ala Met Lys Gly Pro
    130                 135                 140
```

```
Phe Pro Asn Val Lys Phe Val Pro Thr Gly Gly Val Asp Leu Asp Asp
145                 150                 155                 160

Val Cys Glu Trp Phe Asp Ala Gly Val Leu Ala Val Gly Val Gly Asp
                165                 170                 175

Ala Leu Val Glu Gly Asp Pro Asp Glu Val Arg Glu Asp Ala Lys Glu
            180                 185                 190

Phe Val Glu Glu Ile Arg Gly Cys Thr Glu
            195                 200
```

<210> SEQ ID NO 12
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Glu Glu Leu Phe Lys Lys His Lys Ile Val Ala Val Leu Arg Ala Asn
1               5                   10                  15

Ser Val Glu Glu Ala Ile Glu Lys Ala Val Ala Val Phe Ala Gly Gly
            20                  25                  30

Val His Leu Ile Glu Ile Thr Phe Thr Val Pro Asp Ala Asp Thr Val
        35                  40                  45

Ile Lys Ala Leu Ser Val Leu Lys Glu Lys Gly Ala Ile Ile Gly Ala
50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Glu Ile Ser Gln Phe
                85                  90                  95

Cys Lys Glu Lys Gly Val Phe Tyr Met Pro Gly Val Met Thr Pro Thr
            100                 105                 110

Glu Leu Val Lys Ala Met Lys Leu Gly His Asp Ile Leu Lys Leu Phe
        115                 120                 125

Pro Gly Glu Val Val Gly Pro Gln Phe Val Lys Ala Met Lys Gly Pro
130                 135                 140

Phe Pro Asn Val Lys Phe Val Pro Thr Gly Gly Val Asn Leu Asp Asn
145                 150                 155                 160

Val Cys Lys Trp Phe Lys Ala Gly Val Leu Ala Val Gly Val Gly Lys
                165                 170                 175

Ala Leu Val Lys Gly Lys Pro Asp Glu Val Arg Glu Lys Ala Lys Lys
            180                 185                 190

Phe Val Lys Lys Ile Arg Gly Cys Thr Glu
            195                 200
```

<210> SEQ ID NO 13
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (123)..(123)
<223> OTHER INFORMATION: T or D
<220> FEATURE:
<221> NAME/KEY: MOD_RES
<222> LOCATION: (136)..(136)
<223> OTHER INFORMATION: Q or E
<220> FEATURE:

```
<221> NAME/KEY: MOD_RES
<222> LOCATION: (139)..(139)
<223> OTHER INFORMATION: K or E
<220> FEATURE:
<221> NAME/KEY: MOD_RES
<222> LOCATION: (157)..(157)
<223> OTHER INFORMATION: N or D
<220> FEATURE:
<221> NAME/KEY: MOD_RES
<222> LOCATION: (160)..(160)
<223> OTHER INFORMATION: N or D
<220> FEATURE:
<221> NAME/KEY: MOD_RES
<222> LOCATION: (163)..(163)
<223> OTHER INFORMATION: E or K
<220> FEATURE:
<221> NAME/KEY: MOD_RES
<222> LOCATION: (166)..(166)
<223> OTHER INFORMATION: K or D
<220> FEATURE:
<221> NAME/KEY: MOD_RES
<222> LOCATION: (176)..(176)
<223> OTHER INFORMATION: S, K, or D
<220> FEATURE:
<221> NAME/KEY: MOD_RES
<222> LOCATION: (180)..(180)
<223> OTHER INFORMATION: K or E
<220> FEATURE:
<221> NAME/KEY: MOD_RES
<222> LOCATION: (182)..(182)
<223> OTHER INFORMATION: T, D, or K
<220> FEATURE:
<221> NAME/KEY: MOD_RES
<222> LOCATION: (189)..(189)
<223> OTHER INFORMATION: K or D
<220> FEATURE:
<221> NAME/KEY: MOD_RES
<222> LOCATION: (192)..(192)
<223> OTHER INFORMATION: A, E, or K
<220> FEATURE:
<221> NAME/KEY: MOD_RES
<222> LOCATION: (195)..(195)
<223> OTHER INFORMATION: E or K
<220> FEATURE:
<221> NAME/KEY: MOD_RES
<222> LOCATION: (196)..(196)
<223> OTHER INFORMATION: K or E

<400> SEQUENCE: 13

Glu Glu Leu Phe Lys Lys His Lys Ile Val Ala Val Leu Arg Ala Asn
1               5                   10                  15

Ser Val Glu Glu Ala Ile Glu Lys Ala Val Ala Val Phe Ala Gly Gly
            20                  25                  30

Val His Leu Ile Glu Ile Thr Phe Thr Val Pro Asp Ala Asp Thr Val
        35                  40                  45

Ile Lys Ala Leu Ser Val Leu Lys Glu Lys Gly Ala Ile Ile Gly Ala
    50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Glu Ile Ser Gln Phe
                85                  90                  95

Cys Lys Glu Lys Gly Val Phe Tyr Met Pro Gly Val Met Thr Pro Thr
            100                 105                 110

Glu Leu Val Lys Ala Met Lys Leu Gly His Xaa Ile Leu Lys Leu Phe
        115                 120                 125

Pro Gly Glu Val Val Gly Pro Xaa Phe Val Xaa Ala Met Lys Gly Pro
    130                 135                 140

Phe Pro Asn Val Lys Phe Val Pro Thr Gly Gly Val Xaa Leu Asp Xaa
145                 150                 155                 160
```

```
Val Cys Xaa Trp Phe Xaa Ala Gly Val Leu Ala Val Gly Val Gly Xaa
                165             170                 175

Ala Leu Val Xaa Gly Xaa Pro Asp Glu Val Arg Glu Xaa Ala Lys Xaa
            180             185                 190

Phe Val Xaa Xaa Ile Arg Gly Cys Thr Glu
        195             200
```

<210> SEQ ID NO 14
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asn Gln His Ser His Lys Asp Tyr Glu Thr Val Arg Ile Ala Val Val
1               5                   10                  15

Arg Ala Arg Trp His Ala Glu Ile Val Asp Ala Cys Val Ser Ala Phe
            20                  25                  30

Glu Ala Ala Met Ala Asp Ile Gly Gly Asp Arg Phe Ala Val Asp Val
        35                  40                  45

Phe Asp Val Pro Gly Ala Tyr Glu Ile Pro Leu His Ala Arg Thr Leu
    50                  55                  60

Ala Glu Thr Gly Arg Tyr Gly Ala Val Leu Gly Thr Ala Phe Val Val
65                  70                  75                  80

Asn Gly Gly Ile Tyr Arg His Glu Phe Val Ala Ser Ala Val Ile Asp
                85                  90                  95

Gly Met Met Asn Val Gln Leu Ser Thr Gly Val Pro Val Leu Ser Ala
            100                 105                 110

Val Leu Thr Pro His Arg Tyr Arg Asp Ser Asp Ala His Thr Leu Leu
        115                 120                 125

Phe Leu Ala Leu Phe Ala Val Lys Gly Met Glu Ala Ala Arg Ala Cys
    130                 135                 140

Val Glu Ile Leu Ala Ala Arg Glu Lys Ile Ala Ala
145                 150                 155
```

<210> SEQ ID NO 15
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asn Gln His Ser His Lys Asp His Glu Thr Val Arg Ile Ala Val Val
1               5                   10                  15

Arg Ala Arg Trp His Ala Glu Ile Val Asp Ala Cys Val Ser Ala Phe
            20                  25                  30

Glu Ala Ala Met Arg Asp Ile Gly Gly Asp Arg Phe Ala Val Asp Val
        35                  40                  45

Phe Asp Val Pro Gly Ala Tyr Glu Ile Pro Leu His Ala Arg Thr Leu
    50                  55                  60

Ala Glu Thr Gly Arg Tyr Gly Ala Val Leu Gly Thr Ala Phe Val Val
65                  70                  75                  80

Asn Gly Gly Ile Tyr Arg His Glu Phe Val Ala Ser Ala Val Ile Asp
                85                  90                  95
```

Gly Met Met Asn Val Gln Leu Asp Thr Gly Val Pro Val Leu Ser Ala
                100                 105                 110

Val Leu Thr Pro His Arg Tyr Arg Asp Ser Asp Ala His Thr Leu Leu
            115                 120                 125

Phe Leu Ala Leu Phe Ala Val Lys Gly Met Glu Ala Ala Arg Ala Cys
        130                 135                 140

Val Glu Ile Leu Ala Ala Arg Glu Lys Ile Ala Ala
145                 150                 155

<210> SEQ ID NO 16
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Gln His Ser His Lys Asp His Glu Thr Val Arg Ile Ala Val Val
1               5                   10                  15

Arg Ala Arg Trp His Ala Glu Ile Val Asp Ala Cys Val Ser Ala Phe
            20                  25                  30

Glu Ala Ala Met Arg Asp Ile Gly Gly Asp Arg Phe Ala Val Asp Val
        35                  40                  45

Phe Asp Val Pro Gly Ala Tyr Glu Ile Pro Leu His Ala Arg Thr Leu
    50                  55                  60

Ala Glu Thr Gly Arg Tyr Gly Ala Val Leu Gly Thr Ala Phe Val Val
65                  70                  75                  80

Asp Gly Gly Ile Tyr Asp His Glu Phe Val Ala Ser Ala Val Ile Asp
                85                  90                  95

Gly Met Met Asn Val Gln Leu Asp Thr Gly Val Pro Val Leu Ser Ala
                100                 105                 110

Val Leu Thr Pro His Glu Tyr Glu Asp Ser Asp Ala Asp Thr Leu Leu
            115                 120                 125

Phe Leu Ala Leu Phe Ala Val Lys Gly Met Glu Ala Ala Arg Ala Cys
        130                 135                 140

Val Glu Ile Leu Ala Ala Arg Glu Lys Ile Ala Ala
145                 150                 155

<210> SEQ ID NO 17
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Gln His Ser His Lys Asp His Glu Thr Val Arg Ile Ala Val Val
1               5                   10                  15

Arg Ala Arg Trp His Ala Glu Ile Val Asp Ala Cys Val Ser Ala Phe
            20                  25                  30

Glu Ala Ala Met Arg Asp Ile Gly Gly Asp Arg Phe Ala Val Asp Val
        35                  40                  45

Phe Asp Val Pro Gly Ala Tyr Glu Ile Pro Leu His Ala Arg Thr Leu
    50                  55                  60

Ala Glu Thr Gly Arg Tyr Gly Ala Val Leu Gly Thr Ala Phe Val Val
65                  70                  75                  80

```
Asn Gly Gly Ile Tyr Arg His Glu Phe Val Ala Ser Ala Val Ile Asn
                85                  90                  95

Gly Met Met Asn Val Gln Leu Asn Thr Gly Val Pro Val Leu Ser Ala
            100                 105                 110

Val Leu Thr Pro His Asn Tyr Asp Lys Ser Lys Ala His Thr Leu Leu
        115                 120                 125

Phe Leu Ala Leu Phe Ala Val Lys Gly Met Glu Ala Ala Arg Ala Cys
    130                 135                 140

Val Glu Ile Leu Ala Ala Arg Glu Lys Ile Ala Ala
145                 150                 155

<210> SEQ ID NO 18
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Y or H
<220> FEATURE:
<221> NAME/KEY: MOD_RES
<222> LOCATION: (37)..(37)
<223> OTHER INFORMATION: A or R
<220> FEATURE:
<221> NAME/KEY: MOD_RES
<222> LOCATION: (81)..(81)
<223> OTHER INFORMATION: N or D
<220> FEATURE:
<221> NAME/KEY: MOD_RES
<222> LOCATION: (86)..(86)
<223> OTHER INFORMATION: R or D
<220> FEATURE:
<221> NAME/KEY: MOD_RES
<222> LOCATION: (96)..(96)
<223> OTHER INFORMATION: D or N
<220> FEATURE:
<221> NAME/KEY: MOD_RES
<222> LOCATION: (104)..(104)
<223> OTHER INFORMATION: S, D, or N
<220> FEATURE:
<221> NAME/KEY: MOD_RES
<222> LOCATION: (118)..(118)
<223> OTHER INFORMATION: R, E, or N
<220> FEATURE:
<221> NAME/KEY: MOD_RES
<222> LOCATION: (120)..(120)
<223> OTHER INFORMATION: R, D, or E
<220> FEATURE:
<221> NAME/KEY: MOD_RES
<222> LOCATION: (121)..(121)
<223> OTHER INFORMATION: D or K
<220> FEATURE:
<221> NAME/KEY: MOD_RES
<222> LOCATION: (123)..(123)
<223> OTHER INFORMATION: D or K
<220> FEATURE:
<221> NAME/KEY: MOD_RES
<222> LOCATION: (125)..(125)
<223> OTHER INFORMATION: H or D

<400> SEQUENCE: 18

Asn Gln His Ser His Lys Asp Xaa Glu Thr Val Arg Ile Ala Val Val
1               5                   10                  15

Arg Ala Arg Trp His Ala Glu Ile Val Asp Ala Cys Val Ser Ala Phe
            20                  25                  30

Glu Ala Ala Met Xaa Asp Ile Gly Gly Asp Arg Phe Ala Val Asp Val
        35                  40                  45
```

```
Phe Asp Val Pro Gly Ala Tyr Glu Ile Pro Leu His Ala Arg Thr Leu
    50                  55                  60

Ala Glu Thr Gly Arg Tyr Gly Ala Val Leu Gly Thr Ala Phe Val Val
65                  70                  75                  80

Xaa Gly Gly Ile Tyr Xaa His Glu Phe Val Ala Ser Ala Val Ile Xaa
                85                  90                  95

Gly Met Met Asn Val Gln Leu Xaa Thr Gly Val Pro Val Leu Ser Ala
            100                 105                 110

Val Leu Thr Pro His Xaa Tyr Xaa Xaa Ser Xaa Ala Xaa Thr Leu Leu
        115                 120                 125

Phe Leu Ala Leu Phe Ala Val Lys Gly Met Glu Ala Ala Arg Ala Cys
    130                 135                 140

Val Glu Ile Leu Ala Ala Arg Glu Lys Ile Ala Ala
145                 150                 155

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Glu Ala Glu Leu Ala Tyr Leu Leu Gly Leu Ala Tyr Lys Leu
1               5                   10                  15

Gly Glu Tyr Arg Ile Ala Ile Arg Ala Tyr Arg Ile Ala Leu Lys Arg
                20                  25                  30

Asp Pro Asn Asn Ala Glu Ala Trp Tyr Asn Leu Gly Asn Ala Tyr Tyr
            35                  40                  45

Lys Gln Gly Arg Tyr Arg Glu Ala Ile Glu Tyr Tyr Gln Lys Ala Leu
    50                  55                  60

Glu Leu Asp Pro Asn Asn Ala Glu Ala Trp Tyr Asn Leu Gly Asn Ala
65                  70                  75                  80

Tyr Tyr Glu Arg Gly Glu Tyr Glu Glu Ala Ile Glu Tyr Tyr Arg Lys
                85                  90                  95

Ala Leu Arg Leu Asp Pro Asn Asn Ala Asp Ala Met Gln Asn Leu Leu
            100                 105                 110

Asn Ala Lys Met Arg Glu Glu
        115

<210> SEQ ID NO 20
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Lys Tyr Asp Gly Ser Lys Leu Arg Ile Gly Ile Leu His Ala Arg Trp
1               5                   10                  15

Asn Ala Glu Ile Ile Leu Ala Leu Val Leu Gly Ala Leu Lys Arg Leu
                20                  25                  30

Gln Glu Phe Gly Val Lys Arg Glu Asn Ile Ile Ile Glu Thr Val Pro
            35                  40                  45

Gly Ser Phe Glu Leu Pro Tyr Gly Ser Lys Leu Phe Val Glu Lys Gln
    50                  55                  60
```

```
Lys Arg Leu Gly Lys Pro Leu Asp Ala Ile Ile Pro Ile Gly Val Leu
 65                  70                  75                  80

Ile Lys Gly Ser Thr Met His Phe Glu Tyr Ile Cys Asp Ser Thr Thr
                 85                  90                  95

His Gln Leu Met Lys Leu Asn Phe Glu Leu Gly Ile Pro Val Ile Phe
            100                 105                 110

Gly Val Leu Thr Cys Leu Thr Asp Glu Gln Ala Glu Ala Arg Ala Gly
        115                 120                 125

Leu Ile Glu Gly Lys Met His Asn His Gly Glu Asp Trp Gly Ala Ala
    130                 135                 140

Ala Val Glu Met Ala Thr Lys Phe Asn
145                 150

<210> SEQ ID NO 21
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ile Leu Pro Ser Pro Gly Met Pro Ala Leu Leu Ser Leu Val
 1               5                  10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Ile Ser
        50                  55                  60

Asn Cys Val Ala Asp Tyr Ser Val Leu Tyr Asn Ser Ala Ser Phe Ser
 65                  70                  75                  80

Thr Phe Lys Cys Tyr Gly Val Ser Pro Thr Lys Leu Asn Asp Leu Cys
                 85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Ser Glu Lys Ala Ala
                245                 250                 255

Lys Ala Glu Glu Ala Ala Arg Lys Met Glu Glu Leu Phe Lys Lys His
```

```
                    260                 265                 270
Lys Ile Val Ala Val Leu Arg Ala Asn Ser Val Glu Glu Ala Ile Glu
            275                 280                 285

Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
    370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
        435                 440                 445

Asp Glu Val Arg Glu Lys Ala Lys Ala Phe Val Glu Lys Ile Arg Gly
    450                 455                 460

Ala Thr Glu Gly Gly Ser His His His His His His
465                 470                 475

<210> SEQ ID NO 22
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
    50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140
```

```
Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
            165                 170                 175

Ile Tyr Gln Ala Gly Ser Thr Pro Cys Asn Gly Val Glu Gly Phe Asn
        180                 185                 190

Cys Tyr Phe Pro Leu Gln Ser Tyr Gly Phe Gln Pro Thr Asn Gly Val
    195                 200                 205

Gly Tyr Gln Pro Tyr Arg Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
            275                 280                 285

Lys Ala Val Ala Val Phe Ala Gly Gly Val His Leu Ile Glu Ile Thr
            290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
            355                 360                 365

Tyr Met Pro Gly Val Met Thr Pro Thr Glu Leu Val Lys Ala Met Lys
            370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
            435                 440                 445

Asp Glu Val Arg Glu Lys Ala Lys Ala Phe Val Glu Lys Ile Arg Gly
450                 455                 460

Ala Thr Glu Gly Gly Ser His His His His His His
465                 470                 475

<210> SEQ ID NO 23
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30
```

-continued

```
Arg Phe Pro Asn Ile Thr Asn Leu Cys Pro Leu Gly Glu Val Phe Asn
         35                  40                  45

Ala Thr Arg Phe Ala Ser Val Tyr Ala Trp Asn Arg Lys Arg Ile Ser
 50                  55                  60

Asn Cys Val Ala Asp Trp Ser Val Leu Tyr Asn Ser Ala Ser Phe Ser
 65                  70                  75                  80

Thr Phe Lys Cys Tyr Gly Val Ser Pro Thr Lys Leu Asn Asp Leu Cys
                 85                  90                  95

Phe Thr Asn Val Tyr Ala Asp Ser Phe Val Ile Arg Gly Asp Glu Val
             100                 105                 110

Arg Gln Ile Ala Pro Gly Gln Thr Gly Lys Ile Ala Asp Tyr Asn Tyr
         115                 120                 125

Lys Leu Pro Asp Asp Phe Thr Gly Cys Val Ile Ala Trp Asn Ser Asn
 130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                 165                 170                 175

Ile Tyr Gln Ala Gly Ser Thr Pro Cys Asn Gly Val Glu Gly Phe Asn
             180                 185                 190

Cys Tyr Phe Pro Leu Gln Ser Tyr Gly Phe Gln Pro Thr Asn Gly Val
         195                 200                 205

Gly Tyr Gln Pro Tyr Arg Val Val Leu Ser Phe Glu Leu Leu His
 210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                 245                 250                 255

Lys Ala Glu Glu Ala Ala Arg Lys Met Glu Glu Leu Phe Lys Lys His
             260                 265                 270

Lys Ile Val Ala Val Leu Arg Ala Asn Ser Val Glu Glu Ala Ile Glu
         275                 280                 285

Lys Ala Val Ala Val Phe Ala Gly Gly Val His Leu Ile Glu Ile Thr
 290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                 325                 330                 335

Gln Ala Arg Lys Ala Val Glu Ser Gly Ala Glu Phe Ile Val Ser Pro
             340                 345                 350

His Leu Asp Glu Glu Ile Ser Gln Phe Ala Lys Glu Lys Gly Val Phe
         355                 360                 365

Tyr Met Pro Gly Val Met Thr Pro Thr Glu Leu Val Lys Ala Met Lys
 370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                 405                 410                 415

Pro Thr Gly Gly Val Asn Leu Asp Asn Val Ala Glu Trp Phe Lys Ala
             420                 425                 430

Gly Val Leu Ala Val Gly Val Gly Ser Ala Leu Val Lys Gly Thr Pro
         435                 440                 445
```

Asp Glu Val Arg Glu Lys Ala Lys Ala Phe Val Lys Ile Arg Gly
    450                 455                 460

Ala Thr Glu Gly Gly Ser His His His His His His His
465                 470                 475

<210> SEQ ID NO 24
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Ile Ser
        50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Met Ser Phe Glu Leu Leu His
210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Gly Val His Leu Ile Glu Ile Thr
290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

```
Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
            355                 360                 365

Tyr Met Pro Gly Val Met Thr Pro Thr Glu Leu Val Lys Ala Met Lys
370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
            405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
            435                 440                 445

Asp Glu Val Arg Glu Lys Ala Lys Ala Phe Val Glu Lys Ile Arg Gly
            450                 455                 460

Ala Thr Glu Gly Gly Ser His His His His His His
465                 470                 475

<210> SEQ ID NO 25
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Ile Ser
        50                  55                  60

Asn Cys Val Ala Asp Tyr Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Trp Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
```

```
            210                 215                 220
Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
                260                 265                 270

Lys Ile Val Ala Val Leu Arg Ala Asn Ser Val Glu Glu Ala Ile Glu
                275                 280                 285

Lys Ala Val Ala Val Phe Ala Gly Val His Leu Ile Glu Ile Thr
290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
                340                 345                 350

His Leu Asp Glu Glu Ile Ser Gln Phe Ala Lys Glu Lys Gly Val Phe
                355                 360                 365

Tyr Met Pro Gly Val Met Thr Pro Thr Glu Leu Val Lys Ala Met Lys
                370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
                435                 440                 445

Asp Glu Val Arg Glu Lys Ala Lys Ala Phe Val Glu Lys Ile Arg Gly
                450                 455                 460

Ala Thr Glu Gly Gly Ser His His His His His His His
465                 470                 475

<210> SEQ ID NO 26
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
                35                  40                  45

Ala Thr Arg Phe Ala Ser Val Tyr Ala Trp Asn Arg Lys Arg Ile Ser
                50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95
```

```
Trp Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
    370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
        435                 440                 445

Asp Glu Val Arg Glu Lys Ala Lys Ala Phe Val Glu Lys Ile Arg Gly
    450                 455                 460

Ala Thr Glu Gly Gly Ser His His His His His His
465                 470                 475

<210> SEQ ID NO 27
<211> LENGTH: 478
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 27

```
Met Gly Ile Leu Pro Ser Pro Gly Met Pro Ala Leu Leu Ser Leu Val
 1               5                  10                  15

Ser Leu Leu Ser Val Leu Leu Met Gly Cys Val Ala Glu Thr Gly Thr
             20                  25                  30

Arg Phe Pro Asn Ile Thr Asn Leu Cys Pro Met Gly Glu Val Phe Asn
         35                  40                  45

Ala Thr Arg Phe Ala Ser Val Tyr Ala Trp Asn Arg Lys Arg Ile Ser
     50                  55                  60

Asn Cys Val Leu Asp Phe Ser Val Leu Tyr Asn Ser Ala Ser Phe Ser
65                  70                  75                  80

Thr Val Lys Cys Tyr Gly Val Ser Pro Thr Lys Leu Asn Asp Leu Cys
                 85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
                260                 265                 270

Lys Ile Val Ala Val Leu Arg Ala Asn Ser Val Glu Glu Ala Ile Glu
            275                 280                 285

Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
    370                 375                 380

Leu Gly His Thr Ile Leu Lys Leu Phe Pro Gly Glu Val Val Gly Pro
385                 390                 395                 400
```

```
Gln Phe Val Lys Ala Met Lys Gly Pro Phe Pro Asn Val Lys Phe Val
                405                 410                 415
Pro Thr Gly Gly Val Asn Leu Asp Asn Val Ala Glu Trp Phe Lys Ala
            420                 425                 430
Gly Val Leu Ala Val Gly Val Gly Ser Ala Leu Val Lys Gly Thr Pro
        435                 440                 445
Asp Glu Val Arg Glu Lys Ala Lys Ala Phe Val Glu Lys Ile Arg Gly
450                 455                 460
Ala Thr Glu Gly Gly Ser His His His His His His His
465                 470                 475

<210> SEQ ID NO 28
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Ile Leu Pro Ser Pro Gly Met Pro Ala Leu Leu Ser Leu Val
1               5                   10                  15
Ser Leu Leu Ser Val Leu Leu Met Gly Cys Val Ala Glu Thr Gly Thr
                20                  25                  30
Arg Phe Pro Asn Ile Thr Asn Leu Cys Pro Phe Gly Glu Val Phe Asn
            35                  40                  45
Ala Thr Arg Phe Ala Ser Val Tyr Ala Trp Asn Arg Lys Arg Ile Ser
        50                  55                  60
Asn Cys Val Ala Asp Phe Ser Val Leu Tyr Asn Ser Ala Ser Phe Ser
65                  70                  75                  80
Thr Phe Lys Cys Tyr Gly Val Ser Pro Thr Lys Leu Asn Asp Leu Cys
                85                  90                  95
Trp Thr Asn Val Tyr Ala Asp Ser Phe Val Ile Arg Gly Asp Glu Val
            100                 105                 110
Arg Gln Ile Ala Pro Gly Gln Thr Gly Lys Ile Ala Asp Tyr Asn Tyr
        115                 120                 125
Lys Leu Pro Asp Asp Phe Thr Gly Cys Val Ile Ala Trp Asn Ser Asn
130                 135                 140
Asn Leu Asp Ser Lys Val Gly Gly Asn Tyr Asn Tyr Leu Tyr Arg Leu
145                 150                 155                 160
Phe Arg Lys Ser Asn Leu Lys Pro Phe Glu Arg Asp Ile Ser Thr Glu
                165                 170                 175
Ile Tyr Gln Ala Gly Ser Thr Pro Cys Asn Gly Val Glu Gly Phe Asn
            180                 185                 190
Cys Tyr Phe Pro Leu Gln Ser Tyr Gly Phe Gln Pro Thr Asn Gly Val
        195                 200                 205
Gly Tyr Gln Pro Tyr Arg Val Val Val Leu Ser Phe Glu Leu Leu His
210                 215                 220
Ala Pro Ala Thr Val Cys Gly Pro Lys Lys Ser Thr Gly Gly Ser Gly
225                 230                 235                 240
Gly Ser Gly Ser Gly Gly Ser Gly Gly Ser Gly Ser Glu Lys Ala Ala
                245                 250                 255
Lys Ala Glu Glu Ala Ala Arg Lys Met Glu Glu Leu Phe Lys Lys His
            260                 265                 270
Lys Ile Val Ala Val Leu Arg Ala Asn Ser Val Glu Glu Ala Ile Glu
        275                 280                 285
```

```
Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
                340                 345                 350

His Leu Asp Glu Glu Ile Ser Gln Phe Ala Lys Glu Lys Gly Val Phe
            355                 360                 365

Tyr Met Pro Gly Val Met Thr Pro Thr Glu Leu Val Lys Ala Met Lys
370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
                435                 440                 445

Asp Glu Val Arg Glu Lys Ala Lys Ala Phe Val Glu Lys Ile Arg Gly
            450                 455                 460

Ala Thr Glu Gly Gly Ser His His His His His His
465                 470                 475

<210> SEQ ID NO 29
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Ile Ser
    50                  55                  60

Asn Cys Val Ala Asp Phe Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Ile Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
```

```
            165                 170                 175
Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
            195                 200                 205

Gly Tyr Gln Pro Tyr Arg Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
            275                 280                 285

Lys Ala Val Ala Val Phe Ala Gly Gly Val His Leu Ile Glu Ile Thr
            290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
            355                 360                 365

Tyr Met Pro Gly Val Met Thr Pro Thr Glu Leu Val Lys Ala Met Lys
            370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
            435                 440                 445

Asp Glu Val Arg Glu Lys Ala Lys Ala Phe Val Glu Lys Ile Arg Gly
450                 455                 460

Ala Thr Glu Gly Gly Ser His His His His His His
465                 470                 475

<210> SEQ ID NO 30
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
            35                  40                  45
```

-continued

```
Ala Thr Arg Phe Ala Ser Val Tyr Ala Trp Asn Arg Lys Arg Ile Ser
    50                  55                  60
Asn Cys Val Ala Asp Phe Ser Val Leu Tyr Asn Ser Ala Ser Phe Ser
65                  70                  75                  80
Thr Phe Lys Cys Tyr Gly Val Ser Pro Thr Lys Leu Asn Asp Leu Cys
                85                  90                  95
Trp Thr Asn Ile Tyr Ala Asp Ser Phe Val Ile Arg Gly Asp Glu Val
                100                 105                 110
Arg Gln Ile Ala Pro Gly Gln Thr Gly Lys Ile Ala Asp Tyr Asn Tyr
            115                 120                 125
Lys Leu Pro Asp Asp Phe Thr Gly Cys Val Ile Ala Trp Asn Ser Asn
130                 135                 140
Asn Leu Asp Ser Lys Val Gly Gly Asn Tyr Asn Tyr Leu Tyr Arg Leu
145                 150                 155                 160
Phe Arg Lys Ser Asn Leu Lys Pro Phe Glu Arg Asp Ile Ser Thr Glu
                165                 170                 175
Ile Tyr Gln Ala Gly Ser Thr Pro Cys Asn Gly Val Glu Gly Phe Asn
                180                 185                 190
Cys Tyr Phe Pro Leu Gln Ser Tyr Gly Phe Gln Pro Thr Asn Gly Val
            195                 200                 205
Gly Tyr Gln Pro Tyr Arg Val Val Leu Ser Phe Glu Leu Leu His
            210                 215                 220
Ala Pro Ala Thr Val Cys Gly Pro Lys Lys Ser Thr Gly Gly Ser Gly
225                 230                 235                 240
Gly Ser Gly Ser Gly Gly Ser Gly Gly Ser Glu Lys Ala Ala
                245                 250                 255
Lys Ala Glu Glu Ala Ala Arg Lys Met Glu Glu Leu Phe Lys Lys His
            260                 265                 270
Lys Ile Val Ala Val Leu Arg Ala Asn Ser Val Glu Glu Ala Ile Glu
        275                 280                 285
Lys Ala Val Ala Val Phe Ala Gly Gly Val His Leu Ile Glu Ile Thr
    290                 295                 300
Phe Thr Val Pro Asp Ala Asp Thr Val Ile Lys Ala Leu Ser Val Leu
305                 310                 315                 320
Lys Glu Lys Gly Ala Ile Ile Gly Ala Gly Thr Val Thr Ser Val Glu
                325                 330                 335
Gln Ala Arg Lys Ala Val Glu Ser Gly Ala Glu Phe Ile Val Ser Pro
            340                 345                 350
His Leu Asp Glu Glu Ile Ser Gln Phe Ala Lys Glu Lys Gly Val Phe
        355                 360                 365
Tyr Met Pro Gly Val Met Thr Pro Thr Glu Leu Val Lys Ala Met Lys
    370                 375                 380
Leu Gly His Thr Ile Leu Lys Leu Phe Pro Gly Glu Val Val Gly Pro
385                 390                 395                 400
Gln Phe Val Lys Ala Met Lys Gly Pro Phe Pro Asn Val Lys Phe Val
                405                 410                 415
Pro Thr Gly Gly Val Asn Leu Asp Asn Val Ala Glu Trp Phe Lys Ala
            420                 425                 430
Gly Val Leu Ala Val Gly Val Gly Ser Ala Leu Val Lys Gly Thr Pro
        435                 440                 445
Asp Glu Val Arg Glu Lys Ala Lys Ala Phe Val Glu Lys Ile Arg Gly
    450                 455                 460
Ala Thr Glu Gly Gly Ser His His His His His His His
```

<210> SEQ ID NO 31
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
    50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Ile Ser Leu Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Gly Val His Leu Ile Glu Ile Thr
    290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

```
His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
        435                 440                 445

Asp Glu Val Arg Glu Lys Ala Lys Ala Phe Val Glu Lys Ile Arg Gly
        450                 455                 460

Ala Thr Glu Gly Gly Ser His His His His His His
465                 470                 475
```

<210> SEQ ID NO 32
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Leu Gly Glu Val Phe Asn
        35                  40                  45

Ala Thr Arg Phe Ala Ser Val Tyr Ala Trp Asn Arg Lys Arg Ile Ser
    50                  55                  60

Asn Cys Val Leu Asp Met Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240
```

Gly Ser Gly Ser Gly Gly Ser Gly Gly Ser Gly Ser Glu Lys Ala Ala
                245                 250                 255

Lys Ala Glu Glu Ala Ala Arg Lys Met Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Val His Leu Ile Glu Ile Thr
    290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
    370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
            420                 425                 430

Gly Val Leu Ala Val Gly Val Gly Ser Ala Leu Val Lys Gly Thr Pro
        435                 440                 445

Asp Glu Val Arg Glu Lys Ala Lys Ala Phe Val Glu Lys Ile Arg Gly
    450                 455                 460

Ala Thr Glu Gly Gly Ser His His His His His His
465                 470                 475

<210> SEQ ID NO 33
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Phe Ser
    50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr

```
                 115                 120                 125
Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
                180                 185                 190

Cys Tyr Phe Pro Leu Gln Ser Tyr Gly Phe Gln Pro Thr Asn Gly Val
                195                 200                 205

Gly Tyr Gln Pro Tyr Arg Val Val Leu Ser Phe Glu Leu Leu His
        210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
                260                 265                 270

Lys Ile Val Ala Val Leu Arg Ala Asn Ser Val Glu Glu Ala Ile Glu
                275                 280                 285

Lys Ala Val Ala Val Phe Ala Gly Gly Val His Leu Ile Glu Ile Thr
290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
                340                 345                 350

His Leu Asp Glu Glu Ile Ser Gln Phe Ala Lys Glu Lys Gly Val Phe
                355                 360                 365

Tyr Met Pro Gly Val Met Thr Pro Thr Glu Leu Val Lys Ala Met Lys
370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
                435                 440                 445

Asp Glu Val Arg Glu Lys Ala Lys Ala Phe Val Glu Lys Ile Arg Gly
450                 455                 460

Ala Thr Glu Gly Gly Ser His His His His His His
465                 470                 475

<210> SEQ ID NO 34
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

-continued

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Leu Gly Glu Val Phe Asn
            35                  40                  45

Ala Thr Arg Phe Ala Ser Val Tyr Ala Trp Asn Arg Lys Arg Phe Ser
        50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
        370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
```

```
                420                 425                 430
Gly Val Leu Ala Val Gly Val Gly Ser Ala Leu Val Lys Gly Thr Pro
            435                 440                 445

Asp Glu Val Arg Glu Lys Ala Lys Ala Phe Val Glu Lys Ile Arg Gly
            450                 455                 460

Ala Thr Glu Gly Gly Ser His His His His His His
465                 470                 475
```

<210> SEQ ID NO 35
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Phe Ser
        50                  55                  60

Asn Cys Val Ala Asp Trp Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Met Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
            260                 265                 270

Lys Ile Val Ala Val Leu Arg Ala Asn Ser Val Glu Glu Ala Ile Glu
        275                 280                 285

Lys Ala Val Ala Val Phe Ala Gly Gly Val His Leu Ile Glu Ile Thr
    290                 295                 300
```

```
Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
            325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
            355                 360                 365

Tyr Met Pro Gly Val Met Thr Pro Thr Glu Leu Val Lys Ala Met Lys
    370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
            405                 410                 415

Pro Thr Gly Gly Val Asn Leu Asp Asn Val Ala Glu Trp Phe Lys Ala
            420                 425                 430

Gly Val Leu Ala Val Gly Val Ser Ala Leu Val Lys Gly Thr Pro
            435                 440                 445

Asp Glu Val Arg Glu Lys Ala Lys Ala Phe Val Glu Lys Ile Arg Gly
    450                 455                 460

Ala Thr Glu Gly Gly Ser His His His His His His
465                 470                 475

<210> SEQ ID NO 36
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
            35                  40                  45

Ala Thr Arg Phe Ala Ser Val Tyr Ala Trp Asn Arg Lys Arg Phe Ser
    50                  55                  60

Asn Cys Val Ala Asp Phe Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Ile Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190
```

```
Cys Tyr Phe Pro Leu Gln Ser Tyr Gly Phe Gln Pro Thr Asn Gly Val
        195                 200                 205

Gly Tyr Gln Pro Tyr Arg Val Val Leu Ser Phe Glu Leu Leu His
210                 215                 220

Ala Pro Ala Thr Val Cys Gly Pro Lys Ser Thr Gly Gly Ser Gly
225                 230                 235                 240

Gly Ser Gly Ser Gly Gly Ser Gly Gly Ser Gly Ser Glu Lys Ala Ala
                245                 250                 255

Lys Ala Glu Glu Ala Ala Arg Lys Met Glu Glu Leu Phe Lys Lys His
                260                 265                 270

Lys Ile Val Ala Val Leu Arg Ala Asn Ser Val Glu Glu Ala Ile Glu
                275                 280                 285

Lys Ala Val Ala Val Phe Ala Gly Gly Val His Leu Ile Glu Ile Thr
                290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
                340                 345                 350

His Leu Asp Glu Glu Ile Ser Gln Phe Ala Lys Glu Lys Gly Val Phe
                355                 360                 365

Tyr Met Pro Gly Val Met Thr Pro Thr Glu Leu Val Lys Ala Met Lys
                370                 375                 380

Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
                435                 440                 445

Asp Glu Val Arg Glu Lys Ala Lys Ala Phe Val Glu Lys Ile Arg Gly
                450                 455                 460

Ala Thr Glu Gly Gly Ser His His His His His His
465                 470                 475

<210> SEQ ID NO 37
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
                35                  40                  45

Ala Thr Arg Phe Ala Ser Val Tyr Ala Trp Asn Arg Lys Arg Phe Ser
                50                  55                  60

Asn Cys Val Ala Asp Trp Ser Val Leu Tyr Asn Ser Ala Ser Phe Ser
```

```
             65                  70                  75                  80
      Thr Phe Lys Cys Tyr Gly Val Ser Pro Thr Lys Leu Asn Asp Leu Cys
                          85                  90                  95

Trp Thr Asn Val Tyr Ala Asp Ser Phe Val Ile Arg Gly Asp Glu Val
                          100                 105                 110

Arg Gln Ile Ala Pro Gly Gln Thr Gly Lys Ile Ala Asp Tyr Asn Tyr
                          115                 120                 125

Lys Leu Pro Asp Asp Phe Thr Gly Cys Val Ile Ala Trp Asn Ser Asn
                  130                 135                 140

Asn Leu Asp Ser Lys Val Gly Gly Asn Tyr Asn Tyr Leu Tyr Arg Leu
      145                 150                 155                 160

Phe Arg Lys Ser Asn Leu Lys Pro Phe Glu Arg Asp Ile Ser Thr Glu
                          165                 170                 175

Ile Tyr Gln Ala Gly Ser Thr Pro Cys Asn Gly Val Glu Gly Phe Asn
                          180                 185                 190

Cys Tyr Phe Pro Leu Gln Ser Tyr Gly Phe Gln Pro Thr Asn Gly Val
                          195                 200                 205

Gly Tyr Gln Pro Tyr Arg Val Val Leu Ser Phe Glu Leu Leu His
                  210                 215                 220

Ala Pro Ala Thr Val Cys Gly Pro Lys Lys Ser Thr Gly Ser Gly
      225                 230                 235                 240

Gly Ser Gly Ser Gly Gly Ser Gly Gly Ser Gly Ser Glu Lys Ala Ala
                          245                 250                 255

Lys Ala Glu Glu Ala Ala Arg Lys Met Glu Glu Leu Phe Lys Lys His
                  260                 265                 270

Lys Ile Val Ala Val Leu Arg Ala Asn Ser Val Glu Glu Ala Ile Glu
                  275                 280                 285

Lys Ala Val Ala Val Phe Ala Gly Gly Val His Leu Ile Glu Ile Thr
                  290                 295                 300

Phe Thr Val Pro Asp Ala Asp Thr Val Ile Lys Ala Leu Ser Val Leu
      305                 310                 315                 320

Lys Glu Lys Gly Ala Ile Ile Gly Ala Gly Thr Val Thr Ser Val Glu
                          325                 330                 335

Gln Ala Arg Lys Ala Val Glu Ser Gly Ala Glu Phe Ile Val Ser Pro
                  340                 345                 350

His Leu Asp Glu Glu Ile Ser Gln Phe Ala Lys Glu Lys Gly Val Phe
                  355                 360                 365

Tyr Met Pro Gly Val Met Thr Pro Thr Glu Leu Val Lys Ala Met Lys
                  370                 375                 380

Leu Gly His Thr Ile Leu Lys Leu Phe Pro Gly Glu Val Val Gly Pro
      385                 390                 395                 400

Gln Phe Val Lys Ala Met Lys Gly Pro Phe Pro Asn Val Lys Phe Val
                          405                 410                 415

Pro Thr Gly Gly Val Asn Leu Asp Asn Val Ala Glu Trp Phe Lys Ala
                  420                 425                 430

Gly Val Leu Ala Val Gly Val Gly Ser Ala Leu Val Lys Gly Thr Pro
                  435                 440                 445

Asp Glu Val Arg Glu Lys Ala Lys Ala Phe Val Glu Lys Ile Arg Gly
                  450                 455                 460

Ala Thr Glu Gly Gly Ser His His His His His His
      465                 470                 475

<210> SEQ ID NO 38
```

```
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Phe Ser
    50                  55                  60

Asn Cys Val Ala Asp Phe Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Trp Thr Asn Ile Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Gly Ser Gly
225                 230                 235                 240

Gly Ser Gly Ser Gly Ser Gly Ser Gly Ser Glu Lys Ala Ala
                245                 250                 255

Lys Ala Glu Glu Ala Ala Arg Lys Met Glu Glu Leu Phe Lys Lys His
                260                 265                 270

Lys Ile Val Ala Val Leu Arg Ala Asn Ser Val Glu Glu Ala Ile Glu
            275                 280                 285

Lys Ala Val Ala Val Phe Ala Gly Gly Val His Leu Ile Glu Ile Thr
        290                 295                 300

Phe Thr Val Pro Asp Ala Asp Thr Val Ile Lys Ala Leu Ser Val Leu
305                 310                 315                 320

Lys Glu Lys Gly Ala Ile Ile Gly Ala Gly Thr Val Thr Ser Val Glu
                325                 330                 335

Gln Ala Arg Lys Ala Val Glu Ser Gly Ala Glu Phe Ile Val Ser Pro
            340                 345                 350

His Leu Asp Glu Glu Ile Ser Gln Phe Ala Lys Glu Lys Gly Val Phe
        355                 360                 365

Tyr Met Pro Gly Val Met Thr Pro Thr Glu Leu Val Lys Ala Met Lys
```

```
                    370                 375                 380
Leu Gly His Thr Ile Leu Lys Leu Phe Pro Gly Glu Val Val Gly Pro
385                 390                 395                 400

Gln Phe Val Lys Ala Met Lys Gly Pro Phe Pro Asn Val Lys Phe Val
                405                 410                 415

Pro Thr Gly Gly Val Asn Leu Asp Asn Val Ala Glu Trp Phe Lys Ala
                420                 425                 430

Gly Val Leu Ala Val Gly Val Gly Ser Ala Leu Val Lys Gly Thr Pro
                435                 440                 445

Asp Glu Val Arg Glu Lys Ala Lys Ala Phe Val Glu Lys Ile Arg Gly
                450                 455                 460

Ala Thr Glu Gly Gly Ser His His His His His His
465                 470                 475

<210> SEQ ID NO 39
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
                20                  25                  30

Arg Phe Pro Asn Ile Thr Asn Leu Cys Pro Phe Gly Glu Val Phe Asn
                35                  40                  45

Ala Thr Arg Phe Ala Ser Val Tyr Ala Trp Asn Arg Lys Arg Ile Ser
50                  55                  60

Asn Cys Val Ala Asp Tyr Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
                100                 105                 110

Arg Gln Ile Ala Pro Gly Gln Thr Gly Lys Ile Ala Asp Tyr Asn Tyr
                115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
                180                 185                 190

Cys Tyr Phe Pro Leu Gln Ser Tyr Gly Phe Gln Pro Thr Asn Gly Val
                195                 200                 205

Gly Tyr Gln Pro Tyr Arg Val Val Val Leu Ser Phe Glu Leu Leu His
                210                 215                 220

Ala Pro Ala Thr Val Cys Gly Pro Lys Lys Ser Thr Gly Leu Asn Asp
225                 230                 235                 240

Ile Phe Glu Ala Gln Lys Ile Glu Trp His Glu His His His His His
                245                 250                 255
```

His His His

<210> SEQ ID NO 40
<211> LENGTH: 259
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 40

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
    50                  55                  60

Asn Cys Val Ala Asp Tyr Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Trp Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Leu Asn Asp
225                 230                 235                 240

Ile Phe Glu Ala Gln Lys Ile Glu Trp His Glu His His His His His
                245                 250                 255

His His His

<210> SEQ ID NO 41
<211> LENGTH: 259
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 41

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Thr
            20                  25                  30

```
Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
 50                  55                  60

Asn Cys Val Ala Asp Phe Ser Val Leu Tyr Asn Ser Ala Ser Phe Ser
 65                  70                  75                  80

Thr Phe Lys Cys Tyr Gly Val Ser Pro Thr Lys Leu Asn Asp Leu Cys
                 85                  90                  95

Trp Thr Asn Ile Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Gly Leu Asn Asp
225                 230                 235                 240

Ile Phe Glu Ala Gln Lys Ile Glu Trp His Glu His His His His His
                245                 250                 255

His His His

<210> SEQ ID NO 42
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asn Gln His Ser His Lys Asp His Glu Thr Val Arg Ile Ala Val
 1               5                  10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125
```

```
Leu Phe Leu Ala Leu Phe Ala Val Lys Gly Met Glu Ala Ala Arg Ala
            130                 135                 140

Cys Val Glu Ile Leu Ala Ala Arg Glu Lys Ile Ala Ala Gly Ser Leu
145                 150                 155                 160

Glu His His His His His His
                165

<210> SEQ ID NO 43
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Ser Ala
            20                  25                  30

Phe Glu Ala Glu Met Ala Asp Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Asn Tyr His Asp Ser Ala Glu His His Arg
        115                 120                 125

Phe Phe Phe Glu His Phe Thr Val Lys Gly Lys Glu Ala Ala Arg Ala
    130                 135                 140

Cys Val Glu Ile Leu Ala Ala Arg Glu Lys Ile Ala Ala Gly Ser Leu
145                 150                 155                 160

Glu His His His His His His
                165

<210> SEQ ID NO 44
<211> LENGTH: 1288
<212> TYPE: PRT
<213> ORGANISM: Severe acute respiratory syndrome coronavirus 2

<400> SEQUENCE: 44

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

```
Lys Ser Asn Ile Ile Arg Gly Trp Ile Phe Gly Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Pro Ser Ala
```

```
                930             935             940
Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Pro Pro Glu Ala Glu Val Gln
            980             985             990

Ile Asp Arg Leu Ile Thr Gly Arg  Leu Gln Ser Leu Gln  Thr Tyr Val
            995            1000            1005

Thr Gln  Gln Leu Ile Arg Ala  Ala Glu Ile Arg Ala  Ser Ala Asn
    1010            1015            1020

Leu Ala  Ala Thr Lys Met Ser  Glu Cys Val Leu Gly  Gln Ser Lys
    1025            1030            1035

Arg Val  Asp Phe Cys Gly Lys  Gly Tyr His Leu Met  Ser Phe Pro
    1040            1045            1050

Gln Ser  Ala Pro His Gly Val  Val Phe Leu His Val  Thr Tyr Val
    1055            1060            1065

Pro Ala  Gln Glu Lys Asn Phe  Thr Thr Ala Pro Ala  Ile Cys His
    1070            1075            1080

Asp Gly  Lys Ala His Phe Pro  Arg Glu Gly Val Phe  Val Ser Asn
    1085            1090            1095

Gly Thr  His Trp Phe Val Thr  Gln Arg Asn Phe Tyr  Glu Pro Gln
    1100            1105            1110

Ile Ile  Thr Thr Asp Asn Thr  Phe Val Ser Gly Asn  Cys Asp Val
    1115            1120            1125

Val Ile  Gly Ile Val Asn Asn  Thr Val Tyr Asp Pro  Leu Gln Pro
    1130            1135            1140

Glu Leu  Asp Ser Phe Lys Glu  Leu Asp Lys Tyr Phe  Lys Asn
    1145            1150            1155

His Thr  Ser Pro Asp Val Asp  Leu Gly Asp Ile Ser  Gly Ile Asn
    1160            1165            1170

Ala Ser  Val Val Asn Ile Gln  Lys Glu Ile Asp Arg  Leu Asn Glu
    1175            1180            1185

Val Ala  Lys Asn Leu Asn Glu  Ser Leu Ile Asp Leu  Gln Glu Leu
    1190            1195            1200

Gly Lys  Tyr Glu Gln Gly Ser  Gly Tyr Ile Pro Glu  Ala Pro Arg
    1205            1210            1215

Asp Gly  Gln Ala Tyr Val Arg  Lys Asp Gly Glu Trp  Val Leu Leu
    1220            1225            1230

Ser Thr  Phe Leu Gly Arg Ser  Leu Glu Val Leu Phe  Gln Gly Pro
    1235            1240            1245

Gly His  His His His His  His His Ser Ala Trp  Ser His Pro
    1250            1255            1260

Gln Phe  Glu Lys Gly Gly Gly  Ser Gly Gly Gly  Ser Gly Gly
    1265            1270            1275

Ser Ala  Trp Ser His Pro  Gln Phe Glu Lys
    1280            1285

<210> SEQ ID NO 45
<211> LENGTH: 1262
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 45

```
Met Ala Arg Ala Trp Ile Phe Phe Leu Leu Cys Leu Ala Gly Arg Ala
1               5                   10                  15

Leu Ala Gln Cys Val Asn Leu Thr Thr Arg Thr Gln Leu Pro Pro Ala
            20                  25                  30

Tyr Thr Asn Ser Phe Thr Arg Gly Val Tyr Tyr Pro Asp Lys Val Phe
        35                  40                  45

Arg Ser Ser Val Leu His Ser Thr Gln Asp Leu Phe Leu Pro Phe Phe
    50                  55                  60

Ser Asn Val Thr Trp Phe His Ala Ile His Val Ser Gly Thr Asn Gly
65                  70                  75                  80

Thr Lys Arg Phe Asp Asn Pro Val Leu Pro Phe Asn Asp Gly Val Tyr
                85                  90                  95

Phe Ala Ser Thr Glu Lys Ser Asn Ile Ile Arg Gly Trp Ile Phe Gly
            100                 105                 110

Thr Thr Leu Asp Ser Lys Thr Gln Ser Leu Leu Ile Val Asn Asn Ala
        115                 120                 125

Thr Asn Val Val Ile Lys Val Cys Glu Phe Gln Phe Cys Asn Asp Pro
130                 135                 140

Phe Leu Gly Val Tyr Tyr His Lys Asn Asn Lys Ser Trp Met Glu Ser
145                 150                 155                 160

Glu Phe Arg Val Tyr Ser Ser Ala Asn Asn Cys Thr Phe Glu Tyr Val
                165                 170                 175

Ser Gln Pro Phe Leu Met Asp Leu Glu Gly Lys Gln Gly Asn Phe Lys
            180                 185                 190

Asn Leu Arg Glu Phe Val Phe Lys Asn Ile Asp Gly Tyr Phe Lys Ile
        195                 200                 205

Tyr Ser Lys His Thr Pro Ile Asn Leu Val Arg Asp Leu Pro Gln Gly
210                 215                 220

Phe Ser Ala Leu Glu Pro Leu Val Asp Leu Pro Ile Gly Ile Asn Ile
225                 230                 235                 240

Thr Arg Phe Gln Thr Leu Leu Ala Leu His Arg Ser Tyr Leu Thr Pro
                245                 250                 255

Gly Asp Ser Ser Ser Gly Trp Thr Ala Gly Ala Ala Ala Tyr Tyr Val
            260                 265                 270

Gly Tyr Leu Gln Pro Arg Thr Phe Leu Leu Lys Tyr Asn Glu Asn Gly
        275                 280                 285

Thr Ile Thr Asp Ala Val Asp Cys Ala Leu Asp Pro Leu Ser Glu Thr
290                 295                 300

Lys Cys Thr Leu Lys Ser Phe Thr Val Glu Lys Gly Ile Tyr Gln Thr
305                 310                 315                 320

Ser Asn Phe Arg Val Gln Pro Thr Glu Ser Ile Val Arg Phe Pro Asn
                325                 330                 335

Ile Thr Asn Leu Cys Pro Phe Gly Glu Val Phe Asn Ala Thr Arg Phe
            340                 345                 350

Ala Ser Val Tyr Ala Trp Asn Arg Lys Arg Ile Ser Asn Cys Val Ala
        355                 360                 365

Asp Tyr Ser Val Leu Tyr Asn Ser Ala Ser Phe Ser Thr Phe Lys Cys
    370                 375                 380

Tyr Gly Val Ser Pro Thr Lys Leu Asn Asp Leu Cys Phe Thr Asn Val
385                 390                 395                 400

Tyr Ala Asp Ser Phe Val Ile Arg Gly Asp Glu Val Arg Gln Ile Ala
```

```
                    405                 410                 415
Pro Gly Gln Thr Gly Lys Ile Ala Asp Tyr Asn Tyr Lys Leu Pro Asp
            420                 425                 430

Asp Phe Thr Gly Cys Val Ile Ala Trp Asn Ser Asn Asn Leu Asp Ser
            435                 440                 445

Lys Val Gly Gly Asn Tyr Asn Tyr Leu Tyr Arg Leu Phe Arg Lys Ser
            450                 455                 460

Asn Leu Lys Pro Phe Glu Arg Asp Ile Ser Thr Glu Ile Tyr Gln Ala
465                 470                 475                 480

Gly Ser Thr Pro Cys Asn Gly Val Glu Gly Phe Asn Cys Tyr Phe Pro
                    485                 490                 495

Leu Gln Ser Tyr Gly Phe Gln Pro Thr Asn Gly Val Gly Tyr Gln Pro
                    500                 505                 510

Tyr Arg Val Val Val Leu Ser Phe Glu Leu Leu His Ala Pro Ala Thr
            515                 520                 525

Val Cys Gly Pro Lys Lys Ser Thr Asn Leu Val Lys Asn Lys Cys Val
            530                 535                 540

Asn Phe Asn Phe Asn Gly Leu Thr Gly Thr Gly Val Leu Thr Glu Ser
545                 550                 555                 560

Asn Lys Lys Phe Leu Pro Phe Gln Gln Phe Gly Arg Asp Ile Ala Asp
                    565                 570                 575

Thr Thr Asp Ala Val Arg Asp Pro Gln Thr Leu Glu Ile Leu Asp Ile
            580                 585                 590

Thr Pro Cys Ser Phe Gly Gly Val Ser Val Ile Thr Pro Gly Thr Asn
            595                 600                 605

Thr Ser Asn Gln Val Ala Val Leu Tyr Gln Asp Val Asn Cys Thr Glu
610                 615                 620

Val Pro Val Ala Ile His Ala Asp Gln Leu Thr Pro Thr Trp Arg Val
625                 630                 635                 640

Tyr Ser Thr Gly Ser Asn Val Phe Gln Thr Arg Ala Gly Cys Leu Ile
                    645                 650                 655

Gly Ala Glu His Val Asn Asn Ser Tyr Glu Cys Asp Ile Pro Ile Gly
            660                 665                 670

Ala Gly Ile Cys Ala Ser Tyr Gln Thr Gln Thr Asn Ser Pro Gly Ser
            675                 680                 685

Ala Ser Ser Val Ala Ser Gln Ser Ile Ile Ala Tyr Thr Met Ser Leu
            690                 695                 700

Gly Ala Glu Asn Ser Val Ala Tyr Ser Asn Asn Ser Ile Ala Ile Pro
705                 710                 715                 720

Thr Asn Phe Thr Ile Ser Val Thr Thr Glu Ile Leu Pro Val Ser Met
                    725                 730                 735

Thr Lys Thr Ser Val Asp Cys Thr Met Tyr Ile Cys Gly Asp Ser Thr
            740                 745                 750

Glu Cys Ser Asn Leu Leu Leu Gln Tyr Gly Ser Phe Cys Thr Gln Leu
            755                 760                 765

Asn Arg Ala Leu Thr Gly Ile Ala Val Glu Gln Asp Lys Asn Thr Gln
770                 775                 780

Glu Val Phe Ala Gln Val Lys Gln Ile Tyr Lys Thr Pro Pro Ile Lys
785                 790                 795                 800

Asp Phe Gly Gly Phe Asn Phe Ser Gln Ile Leu Pro Asp Pro Ser Lys
                    805                 810                 815

Pro Ser Lys Arg Ser Pro Ile Glu Asp Leu Leu Phe Asn Lys Val Thr
            820                 825                 830
```

-continued

Leu Ala Asp Ala Gly Phe Ile Lys Gln Tyr Gly Asp Cys Leu Gly Asp
        835                 840                 845

Ile Ala Ala Arg Asp Leu Ile Cys Ala Gln Lys Phe Asn Gly Leu Thr
850                 855                 860

Val Leu Pro Pro Leu Leu Thr Asp Glu Met Ile Ala Gln Tyr Thr Ser
865                 870                 875                 880

Ala Leu Leu Ala Gly Thr Ile Thr Ser Gly Trp Thr Phe Gly Ala Gly
                885                 890                 895

Pro Ala Leu Gln Ile Pro Phe Pro Met Gln Met Ala Tyr Arg Phe Asn
        900                 905                 910

Gly Ile Gly Val Thr Gln Asn Val Leu Tyr Glu Asn Gln Lys Leu Ile
        915                 920                 925

Ala Asn Gln Phe Asn Ser Ala Ile Gly Lys Ile Gln Asp Ser Leu Ser
930                 935                 940

Ser Thr Pro Ser Ala Leu Gly Lys Leu Gln Asp Val Val Asn Gln Asn
945                 950                 955                 960

Ala Gln Ala Leu Asn Thr Leu Val Lys Gln Leu Ser Ser Asn Phe Gly
                965                 970                 975

Ala Ile Ser Ser Val Leu Asn Asp Ile Leu Ser Arg Leu Asp Pro Pro
                980                 985                 990

Glu Ala Glu Val Gln Ile Asp Arg Leu Ile Thr Gly Arg Leu Gln Ser
        995                 1000                1005

Leu Gln Thr Tyr Val Thr Gln Gln Leu Ile Arg Ala Ala Glu Ile
    1010                1015                1020

Arg Ala Ser Ala Asn Leu Ala Ala Thr Lys Met Ser Glu Cys Val
    1025                1030                1035

Leu Gly Gln Ser Lys Arg Val Asp Phe Cys Gly Lys Gly Tyr His
    1040                1045                1050

Leu Met Ser Phe Pro Gln Ser Ala Pro His Gly Val Val Phe Leu
    1055                1060                1065

His Val Thr Tyr Val Pro Ala Gln Glu Lys Asn Phe Thr Thr Ala
    1070                1075                1080

Pro Ala Ile Cys His Asp Gly Lys Ala His Phe Pro Arg Glu Gly
    1085                1090                1095

Val Phe Val Ser Asn Gly Thr His Trp Phe Val Thr Gln Arg Asn
    1100                1105                1110

Phe Tyr Glu Pro Gln Ile Ile Thr Thr Asp Asn Thr Phe Val Ser
    1115                1120                1125

Gly Asn Cys Asp Val Val Ile Gly Ile Val Asn Asn Thr Val Tyr
    1130                1135                1140

Asp Pro Leu Gln Pro Glu Leu Asp Ser Phe Lys Glu Glu Leu Asp
    1145                1150                1155

Lys Tyr Phe Lys Asn His Thr Ser Pro Asp Val Asp Leu Gly Asp
    1160                1165                1170

Ile Ser Gly Ile Asn Ala Ser Val Val Asn Ile Gln Lys Glu Ile
    1175                1180                1185

Asp Arg Leu Asn Glu Val Ala Lys Asn Leu Asn Glu Ser Leu Ile
    1190                1195                1200

Asp Leu Gln Glu Leu Gly Lys Tyr Glu Gln Gly Ser Gly Tyr Ile
    1205                1210                1215

Pro Glu Ala Pro Arg Asp Gly Gln Ala Tyr Val Arg Lys Asp Gly
    1220                1225                1230

-continued

```
Glu Trp Val Leu Leu Ser Thr Phe Leu Gly Arg Ser Leu Glu Val
    1235                1240                1245

Leu Phe Gln Gly Pro Gly His His His His His His His
    1250                1255                1260

<210> SEQ ID NO 46
<211> LENGTH: 1262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Ala Arg Ala Trp Ile Phe Phe Leu Leu Cys Leu Ala Gly Arg Ala
1               5                   10                  15

Leu Ala Gln Cys Val Asn Leu Thr Thr Arg Thr Gln Leu Pro Pro Ala
            20                  25                  30

Tyr Thr Asn Ser Phe Thr Arg Gly Val Tyr Tyr Pro Asp Lys Val Phe
        35                  40                  45

Arg Ser Ser Val Leu His Ser Thr Gln Asp Leu Phe Leu Pro Phe Phe
    50                  55                  60

Ser Asn Val Thr Trp Phe His Ala Ile His Val Ser Gly Thr Asn Gly
65                  70                  75                  80

Thr Lys Arg Phe Asp Asn Pro Val Leu Pro Phe Asn Asp Gly Val Tyr
                85                  90                  95

Phe Ala Ser Thr Glu Lys Ser Asn Ile Ile Arg Gly Trp Ile Phe Gly
            100                 105                 110

Thr Thr Leu Asp Ser Lys Thr Gln Ser Leu Leu Ile Val Asn Asn Ala
        115                 120                 125

Thr Asn Val Val Ile Lys Val Cys Glu Phe Gln Phe Cys Asn Asp Pro
    130                 135                 140

Phe Leu Gly Val Tyr Tyr His Lys Asn Asn Lys Ser Trp Met Glu Ser
145                 150                 155                 160

Glu Phe Arg Val Tyr Ser Ser Ala Asn Asn Cys Thr Phe Glu Tyr Val
                165                 170                 175

Ser Gln Pro Phe Leu Met Asp Leu Glu Gly Lys Gln Gly Asn Phe Lys
            180                 185                 190

Asn Leu Arg Glu Phe Val Phe Lys Asn Ile Asp Gly Tyr Phe Lys Ile
        195                 200                 205

Tyr Ser Lys His Thr Pro Ile Asn Leu Val Arg Asp Leu Pro Gln Gly
    210                 215                 220

Phe Ser Ala Leu Glu Pro Leu Val Asp Leu Pro Ile Gly Ile Asn Ile
225                 230                 235                 240

Thr Arg Phe Gln Thr Leu Leu Ala Leu His Arg Ser Tyr Leu Thr Pro
                245                 250                 255

Gly Asp Ser Ser Ser Gly Trp Thr Ala Gly Ala Ala Ala Tyr Tyr Val
            260                 265                 270

Gly Tyr Leu Gln Pro Arg Thr Phe Leu Leu Lys Tyr Asn Glu Asn Gly
        275                 280                 285

Thr Ile Thr Asp Ala Val Asp Cys Ala Leu Asp Pro Leu Ser Glu Thr
    290                 295                 300

Lys Cys Thr Leu Lys Ser Phe Thr Val Glu Lys Gly Ile Tyr Gln Thr
305                 310                 315                 320

Ser Asn Phe Arg Val Gln Pro Thr Glu Ser Ile Val Arg Phe Pro Asn
                325                 330                 335
```

```
Ile Thr Asn Leu Cys Pro Phe Gly Glu Val Phe Asn Ala Thr Arg Phe
        340                 345                 350

Ala Ser Val Tyr Ala Trp Asn Arg Lys Arg Ile Ser Asn Cys Val Ala
        355                 360                 365

Asp Phe Ser Val Leu Tyr Asn Ser Ala Ser Phe Ser Thr Phe Lys Cys
        370                 375                 380

Tyr Gly Val Ser Pro Thr Lys Leu Asn Asp Leu Cys Trp Thr Asn Ile
385                 390                 395                 400

Tyr Ala Asp Ser Phe Val Ile Arg Gly Asp Glu Val Arg Gln Ile Ala
                405                 410                 415

Pro Gly Gln Thr Gly Lys Ile Ala Asp Tyr Asn Tyr Lys Leu Pro Asp
        420                 425                 430

Asp Phe Thr Gly Cys Val Ile Ala Trp Asn Ser Asn Asn Leu Asp Ser
        435                 440                 445

Lys Val Gly Gly Asn Tyr Asn Tyr Leu Tyr Arg Leu Phe Arg Lys Ser
        450                 455                 460

Asn Leu Lys Pro Phe Glu Arg Asp Ile Ser Thr Glu Ile Tyr Gln Ala
465                 470                 475                 480

Gly Ser Thr Pro Cys Asn Gly Val Glu Gly Phe Asn Cys Tyr Phe Pro
                485                 490                 495

Leu Gln Ser Tyr Gly Phe Gln Pro Thr Asn Gly Val Gly Tyr Gln Pro
        500                 505                 510

Tyr Arg Val Val Val Leu Ser Phe Glu Leu Leu His Ala Pro Ala Thr
        515                 520                 525

Val Cys Gly Pro Lys Lys Ser Thr Asn Leu Val Lys Asn Lys Cys Val
        530                 535                 540

Asn Phe Asn Phe Asn Gly Leu Thr Gly Thr Gly Val Leu Thr Glu Ser
545                 550                 555                 560

Asn Lys Lys Phe Leu Pro Phe Gln Gln Phe Gly Arg Asp Ile Ala Asp
                565                 570                 575

Thr Thr Asp Ala Val Arg Asp Pro Gln Thr Leu Glu Ile Leu Asp Ile
        580                 585                 590

Thr Pro Cys Ser Phe Gly Gly Val Ser Val Ile Thr Pro Gly Thr Asn
        595                 600                 605

Thr Ser Asn Gln Val Ala Val Leu Tyr Gln Asp Val Asn Cys Thr Glu
        610                 615                 620

Val Pro Val Ala Ile His Ala Asp Gln Leu Thr Pro Thr Trp Arg Val
625                 630                 635                 640

Tyr Ser Thr Gly Ser Asn Val Phe Gln Thr Arg Ala Gly Cys Leu Ile
                645                 650                 655

Gly Ala Glu His Val Asn Asn Ser Tyr Glu Cys Asp Ile Pro Ile Gly
        660                 665                 670

Ala Gly Ile Cys Ala Ser Tyr Gln Thr Gln Thr Asn Ser Pro Gly Ser
        675                 680                 685

Ala Ser Ser Val Ala Ser Gln Ser Ile Ile Ala Tyr Thr Met Ser Leu
        690                 695                 700

Gly Ala Glu Asn Ser Val Ala Tyr Ser Asn Asn Ser Ile Ala Ile Pro
705                 710                 715                 720

Thr Asn Phe Thr Ile Ser Val Thr Thr Glu Ile Leu Pro Val Ser Met
                725                 730                 735

Thr Lys Thr Ser Val Asp Cys Thr Met Tyr Ile Cys Gly Asp Ser Thr
        740                 745                 750
```

```
Glu Cys Ser Asn Leu Leu Gln Tyr Gly Ser Phe Cys Thr Gln Leu
            755                 760                 765

Asn Arg Ala Leu Thr Gly Ile Ala Val Glu Gln Asp Lys Asn Thr Gln
    770                 775                 780

Glu Val Phe Ala Gln Val Lys Gln Ile Tyr Lys Thr Pro Pro Ile Lys
785                 790                 795                 800

Asp Phe Gly Gly Phe Asn Phe Ser Gln Ile Leu Pro Asp Pro Ser Lys
                805                 810                 815

Pro Ser Lys Arg Ser Pro Ile Glu Asp Leu Leu Phe Asn Lys Val Thr
            820                 825                 830

Leu Ala Asp Ala Gly Phe Ile Lys Gln Tyr Gly Asp Cys Leu Gly Asp
            835                 840                 845

Ile Ala Ala Arg Asp Leu Ile Cys Ala Gln Lys Phe Asn Gly Leu Thr
850                 855                 860

Val Leu Pro Pro Leu Leu Thr Asp Glu Met Ile Ala Gln Tyr Thr Ser
865                 870                 875                 880

Ala Leu Leu Ala Gly Thr Ile Thr Ser Gly Trp Thr Phe Gly Ala Gly
                885                 890                 895

Pro Ala Leu Gln Ile Pro Phe Pro Met Gln Met Ala Tyr Arg Phe Asn
            900                 905                 910

Gly Ile Gly Val Thr Gln Asn Val Leu Tyr Glu Asn Gln Lys Leu Ile
            915                 920                 925

Ala Asn Gln Phe Asn Ser Ala Ile Gly Lys Ile Gln Asp Ser Leu Ser
    930                 935                 940

Ser Thr Pro Ser Ala Leu Gly Lys Leu Gln Asp Val Val Asn Gln Asn
945                 950                 955                 960

Ala Gln Ala Leu Asn Thr Leu Val Lys Gln Leu Ser Ser Asn Phe Gly
                965                 970                 975

Ala Ile Ser Ser Val Leu Asn Asp Ile Leu Ser Arg Leu Asp Pro Pro
            980                 985                 990

Glu Ala Glu Val Gln Ile Asp Arg Leu Ile Thr Gly Arg Leu Gln Ser
            995                 1000                1005

Leu Gln Thr Tyr Val Thr Gln Leu Ile Arg Ala Ala Glu Ile
    1010                1015                1020

Arg Ala Ser Ala Asn Leu Ala Ala Thr Lys Met Ser Glu Cys Val
    1025                1030                1035

Leu Gly Gln Ser Lys Arg Val Asp Phe Cys Gly Lys Gly Tyr His
    1040                1045                1050

Leu Met Ser Phe Pro Gln Ser Ala Pro His Gly Val Val Phe Leu
    1055                1060                1065

His Val Thr Tyr Val Pro Ala Gln Glu Lys Asn Phe Thr Thr Ala
    1070                1075                1080

Pro Ala Ile Cys His Asp Gly Lys Ala His Phe Pro Arg Glu Gly
    1085                1090                1095

Val Phe Val Ser Asn Gly Thr His Trp Phe Val Thr Gln Arg Asn
    1100                1105                1110

Phe Tyr Glu Pro Gln Ile Ile Thr Thr Asp Asn Thr Phe Val Ser
    1115                1120                1125

Gly Asn Cys Asp Val Val Ile Gly Ile Val Asn Asn Thr Val Tyr
    1130                1135                1140

Asp Pro Leu Gln Pro Glu Leu Asp Ser Phe Lys Glu Glu Leu Asp
    1145                1150                1155

Lys Tyr Phe Lys Asn His Thr Ser Pro Asp Val Asp Leu Gly Asp
```

-continued

```
                1160                1165                1170

Ile Ser Gly Ile Asn Ala Ser Val Val Asn Ile Gln Lys Glu Ile
        1175                1180                1185

Asp Arg Leu Asn Glu Val Ala Lys Asn Leu Asn Glu Ser Leu Ile
    1190                1195                1200

Asp Leu Gln Glu Leu Gly Lys Tyr Glu Gln Gly Ser Gly Tyr Ile
    1205                1210                1215

Pro Glu Ala Pro Arg Asp Gly Gln Ala Tyr Val Arg Lys Asp Gly
    1220                1225                1230

Glu Trp Val Leu Leu Ser Thr Phe Leu Gly Arg Ser Leu Glu Val
    1235                1240                1245

Leu Phe Gln Gly Pro Gly His His His His His His
    1250                1255                1260

<210> SEQ ID NO 47
<211> LENGTH: 833
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Arg Ala Trp Ile Phe Phe Leu Leu Cys Leu Ala Gly Arg Ala
1               5                   10                  15

Leu Ala Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255
```

-continued

```
Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Pro Leu Val Pro Arg Gly Ser Gly Gly
    610                 615                 620

Gly Gly Asp Pro Glu Pro Lys Ser Cys Asp Lys Thr His Thr Cys Pro
625                 630                 635                 640

Pro Cys Pro Ala Pro Glu Leu Leu Gly Gly Pro Ser Val Phe Leu Phe
                645                 650                 655

Pro Pro Lys Pro Lys Asp Thr Leu Met Ile Ser Arg Thr Pro Glu Val
            660                 665                 670

Thr Cys Val Val Val Asp Val Ser His Glu Asp Pro Glu Val Lys Phe
```

```
                675                 680                 685
Asn Trp Tyr Val Asp Gly Val Glu Val His Asn Ala Lys Thr Lys Pro
    690                 695                 700
Arg Glu Glu Gln Tyr Asn Ser Thr Tyr Arg Val Val Ser Val Leu Thr
705                 710                 715                 720
Val Leu His Gln Asp Trp Leu Asn Gly Lys Glu Tyr Lys Cys Lys Val
                725                 730                 735
Ser Asn Lys Ala Leu Pro Ala Pro Ile Glu Lys Thr Ile Ser Lys Ala
            740                 745                 750
Lys Gly Gln Pro Arg Glu Pro Gln Val Tyr Thr Leu Pro Pro Ser Arg
        755                 760                 765
Asp Glu Leu Thr Lys Asn Gln Val Ser Leu Thr Cys Leu Val Lys Gly
    770                 775                 780
Phe Tyr Pro Ser Asp Ile Ala Val Glu Trp Glu Ser Asn Gly Gln Pro
785                 790                 795                 800
Glu Asn Asn Tyr Lys Thr Thr Pro Pro Val Leu Asp Ser Asp Gly Ser
                805                 810                 815
Phe Phe Leu Tyr Ser Lys Leu Thr Val Asp Lys Ser Arg Trp Gln Gln
            820                 825                 830
Gly

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Ile Leu Pro Ser Pro Gly Met Pro Ala Leu Leu Ser Leu Val
1               5                   10                  15
Ser Leu Leu Ser Val Leu Leu Met Gly Cys Val Ala Glu Thr Gly Thr
            20                  25                  30

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Ser His His His His His His His
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Lys Ala Ala Lys Ala Glu Glu Ala Ala Arg
1               5                   10

<210> SEQ ID NO 51
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Pro Pro Ile
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Pro Pro Phe
1

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 53

His His His His His His His His
1               5

<210> SEQ ID NO 54
<211> LENGTH: 1273
<212> TYPE: PRT
<213> ORGANISM: Severe acute respiratory syndrome coronavirus 2

<400> SEQUENCE: 54

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590
```

```
Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
```

```
                    1010                1015                1020

Leu Ala Ala Thr Lys Met Ser Glu Cys Val Leu Gly Gln Ser Lys
                1025                1030                1035

Arg Val Asp Phe Cys Gly Lys Gly Tyr His Leu Met Ser Phe Pro
                1040                1045                1050

Gln Ser Ala Pro His Gly Val Val Phe Leu His Val Thr Tyr Val
                1055                1060                1065

Pro Ala Gln Glu Lys Asn Phe Thr Thr Ala Pro Ala Ile Cys His
                1070                1075                1080

Asp Gly Lys Ala His Phe Pro Arg Glu Gly Val Phe Val Ser Asn
                1085                1090                1095

Gly Thr His Trp Phe Val Thr Gln Arg Asn Phe Tyr Glu Pro Gln
                1100                1105                1110

Ile Ile Thr Thr Asp Asn Thr Phe Val Ser Gly Asn Cys Asp Val
                1115                1120                1125

Val Ile Gly Ile Val Asn Asn Thr Val Tyr Asp Pro Leu Gln Pro
                1130                1135                1140

Glu Leu Asp Ser Phe Lys Glu Glu Leu Asp Lys Tyr Phe Lys Asn
                1145                1150                1155

His Thr Ser Pro Asp Val Asp Leu Gly Asp Ile Ser Gly Ile Asn
                1160                1165                1170

Ala Ser Val Val Asn Ile Gln Lys Glu Ile Asp Arg Leu Asn Glu
                1175                1180                1185

Val Ala Lys Asn Leu Asn Glu Ser Leu Ile Asp Leu Gln Glu Leu
                1190                1195                1200

Gly Lys Tyr Glu Gln Tyr Ile Lys Trp Pro Trp Tyr Ile Trp Leu
                1205                1210                1215

Gly Phe Ile Ala Gly Leu Ile Ala Ile Val Met Val Thr Ile Met
                1220                1225                1230

Leu Cys Cys Met Thr Ser Cys Cys Ser Cys Leu Lys Gly Cys Cys
                1235                1240                1245

Ser Cys Gly Ser Cys Cys Lys Phe Asp Glu Asp Asp Ser Glu Pro
                1250                1255                1260

Val Leu Lys Gly Val Lys Leu His Tyr Thr
                1265                1270

<210> SEQ ID NO 55
<211> LENGTH: 11
<212> TYPE: PRT
<213> ORGANISM: Severe acute respiratory syndrome coronavirus 2

<400> SEQUENCE: 55

Leu Cys Pro Phe Gly Glu Val Phe Asn Ala Thr
1               5                   10

<210> SEQ ID NO 56
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
```

```
                    20                  25                  30
Asn Cys Val Ala Asp Phe Ser Val Leu Tyr Asn Ser Ala Ser Phe Ser
                35                  40                  45
Thr Phe Lys Cys Tyr Gly Val Ser Pro Thr Lys Leu Asn Asp Leu Cys
            50                  55                  60
Trp Thr Asn Ile Tyr Ala Asp Ser Phe Val Ile Arg Gly Asp Glu Val
65                  70                  75                  80
Arg Gln Ile Ala Pro Gly Gln Thr Gly Lys Ile Ala Asp Tyr Asn Tyr
                85                  90                  95
Lys Leu Pro Asp Asp Phe Thr Gly Cys Val Ile Ala Trp Asn Ser Asn
            100                 105                 110
Asn Leu Asp Ser Lys Val Gly Gly Asn Tyr Asn Tyr Leu Tyr Arg Leu
            115                 120                 125
Phe Arg Lys Ser Asn Leu Lys Pro Phe Glu Arg Asp Ile Ser Thr Glu
        130                 135                 140
Ile Tyr Gln Ala Gly Ser Thr Pro Cys Asn Gly Val Glu Gly Phe Asn
145                 150                 155                 160
Cys Tyr Phe Pro Leu Gln Ser Tyr Gly Phe Gln Pro Thr Tyr Gly Val
                165                 170                 175
Gly Tyr Gln Pro Tyr Arg Val Val Val Leu Ser Phe Glu Leu Leu His
                180                 185                 190
Ala Pro Ala Thr Val Cys Gly Pro Lys Lys
            195                 200

<210> SEQ ID NO 57
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Arg Phe Pro Asn Ile Thr Asn Leu Cys Pro Phe Gly Glu Val Phe Asn
1               5                   10                  15
Ala Thr Arg Phe Ala Ser Val Tyr Ala Trp Asn Arg Lys Arg Ile Ser
                20                  25                  30
Asn Cys Val Ala Asp Phe Ser Val Leu Tyr Asn Ser Ala Ser Phe Ser
            35                  40                  45
Thr Phe Lys Cys Tyr Gly Val Ser Pro Thr Lys Leu Asn Asp Leu Cys
        50                  55                  60
Trp Thr Asn Ile Tyr Ala Asp Ser Phe Val Ile Arg Gly Asp Glu Val
65                  70                  75                  80
Arg Gln Ile Ala Pro Gly Gln Thr Gly Asn Ile Ala Asp Tyr Asn Tyr
                85                  90                  95
Lys Leu Pro Asp Asp Phe Thr Gly Cys Val Ile Ala Trp Asn Ser Asn
            100                 105                 110
Asn Leu Asp Ser Lys Val Gly Gly Asn Tyr Asn Tyr Leu Tyr Arg Leu
            115                 120                 125
Phe Arg Lys Ser Asn Leu Lys Pro Phe Glu Arg Asp Ile Ser Thr Glu
        130                 135                 140
Ile Tyr Gln Ala Gly Ser Thr Pro Cys Asn Gly Val Lys Gly Phe Asn
145                 150                 155                 160
Cys Tyr Phe Pro Leu Gln Ser Tyr Gly Phe Gln Pro Thr Tyr Gly Val
                165                 170                 175
```

```
Gly Tyr Gln Pro Tyr Arg Val Val Val Leu Ser Phe Glu Leu Leu His
            180                 185                 190

Ala Pro Ala Thr Val Cys Gly Pro Lys Lys
        195                 200

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Thr Asn Val Tyr Ala Asp Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Thr Asn Val Tyr Ala Asp Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Thr Asn Ile Tyr Ala Asp Ser
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 61

His His His His His His
1               5
```

STABLE CORONAVIRUS PROTEINS AND VACCINE COMPOSITIONS THEREOF

CROSS-REFERENCE TO RELATED APPLICATIONS

This application claims benefit under 35 U.S.C. § 119(e) to U.S. Provisional Application No. 63/132,863 filed Dec. 31, 2020, U.S. Provisional Application No. 63/188,651 filed May 14, 2021, and U.S. Provisional Application No. 63/210,654, filed Jun. 15, 2021, the contents of each of which are incorporated herein by reference in their entirety.

GOVERNMENT SUPPORT

This invention was made with government support under AI141707 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 23, 2021, is named 034186-098380WOPT_SL.txt and is 186,061 bytes in size.

FIELD OF THE INVENTION

The field of the invention relates to methods and compositions for improving stability of protein-based vaccines.

BACKGROUND

Coronaviruses maintain a prominent pandemic threat, with the 2019/2020 pandemic induced by the SARS-CoV-2 virus causing hundreds of thousands of deaths worldwide and a massive economic slowdown. It is likely that SARS-CoV-2 could maintain persistent epidemics even after the current pandemic is diminished. Effective vaccines against SARS-CoV-2 or other future emerging coronaviruses are therefore highly desirable.

SUMMARY

The compositions and methods described herein are based, in part, on the discovery of single or paired amino acid mutations in the SARS-CoV-2 S "spike" protein amino acid sequence that enhance both yield and stability of the expressed protein (under the same or similar culture conditions). This enhanced spike protein (also referred herein as a "spike protein-derived antigen") stability allows for the production of a vaccine having a longer shelf-life than vaccines based on the wild-type or native protein (under the same or similar storage conditions).

Accordingly, provided herein in one aspect is a non-naturally occurring polypeptide comprising a first coronavirus receptor binding domain (RBD) comprising at least 90% identity to residues 328-531 of SEQ ID NO:1, and further comprising at least two mutations relative to the RBD of SEQ ID NO: 1, wherein the at least two mutations are selected from the group consisting of: F338LY365W; Y365W/L513W; Y365W/F392W; F338M/A363L/Y365F/F377V; Y365F/F392W; Y365F/V395I; Y365F/F392W/V395I; Y365W/L513L/F515L; F338L/A363L/Y365M; F338L/I358F/Y365W; I358F/V365W/L513M; I358F/Y365W/F392W; F338M/I358F/A363L/Y365F/F377V; I358F/Y365F/F392W; I358F/Y365F/V395I; I358F/Y365F/F392W/V395I; I358F/V365W/L513I/F515L; and F338L/I358F/A363L/Y365M, or at corresponding residues of a second coronavirus receptor binding domain as determined by a sequence alignment of SEQ ID NO: 1 with the sequence of the second coronavirus receptor binding domain using Blast-p (Altschul, S. F., Gish, W., Miller, W., Myers, E. W. & Lipman, D. J. (1990) "Basic local alignment search tool." J. Mol. Biol. 215:403-410). In one embodiment, the Blast-p program used is the National Center for Biotechnology Information (NCBI) online alignment tool. Alternatively, the Blast-p program can be downloaded onto a device and used locally. One of skill in the art will readily understand the use of Blast-p alignment tools, however for the avoidance of doubt protocol 1 and protocol 2 are provided herewith for the online and downloaded alignment tools, respectively.

Protocol 1: For use with the BLASTp alignment online from the National Center for Biotechnology Information (NCBI) server.
1. Set up a BLAST alignment using the following settings:
   Use the option for "Align two or more sequences"
   Enter the reference strain sequence for the relevant SARS-CoV-2 protein (i.e., SEQ ID NO: 1) into the "Enter Query Sequence" section
   Enter any corresponding coronavirus spike protein sequence into the "Enter Subject Sequence" section
   Algorithm: blastp (protein-protein BLAST)
   Expect threshold: 0.1
   Word size: 6
   Max matches in a query range: 0
   Matrix: BLOSUM62
   Gap costs:
      Existence: 11
      Extension: 1
   Filter low complexity regions?: No
   Mask:
      For lookup table only?: No
      Lower case letters?: No
2. Run the analysis by clicking the "BLAST" button
3. Click on the "Alignments" tab to show the alignment between the two sequences.
4. For each sequence position of interest, identify the number according to the "Query" sequence. Then identify the corresponding residue position in the "Sbjct" sequence that has been aligned with the position of the "Query" sequence.

Protocol 2: For use with the protein BLASTp alignment tool downloaded onto a local computer or server.
1. Install BLAST for command line execution using the manufacturer's instructions or identify a computer or server that already has it installed.
2. Generate a file in FASTA format that contains the desired subtype-specific reference strain for the SARS-CoV-2 protein (i.e., SEQ ID NO: 1). In the command below, this file will be named "query.fasta".
3. Generate a second file in FASTA format that contains a corresponding protein sequence of a different coronavirus from the same subtype. In the command below, this file will be named "sbjet.fasta".
4. Execute the following command using a program such as Terminal, iTerm2, Windows Console, Linux console or other similar terminal emulators. This will generate results in a file named "results.txt".
   blastp-query query.fasta-subject sbjct.fasta-matrix BLOSUM62-evalue 0.1-word size 6-gapopen 11-gapextend 1-out results.txt 5. Open results.txt and view the section showing alignment of the two sequences. For each sequence position of interest, identify the number according to the "Query" sequence. Then identify the corresponding residue position in the "Sbjct" sequence that has been aligned with the position of the "Query" sequence.

It will be apparent to those of skill in the art that other protein alignment tools can also be used to identify sequence identity between a query sequence and a reference sequence (e.g., SEQ ID NO: 1). Given that the query sequence and the reference sequence share significant sequence identity, it is expected that other protein alignment tools will produce similar, if not identical results to Blast-p using the protocols described herein. The protocols described herein have been shown to be accurate and effective for this purpose and are provided herein to aid the skilled artisan in identifying amino acid residues to be mutated in the query sequence.

Another aspect provided herein comprises a non-naturally occurring polypeptide comprising: a first coronavirus receptor binding domain (RBD) comprising at least 90% identity to residues 328-531 of SEQ ID NO:1, and further comprising at least two mutations relative to the RBD of SEQ ID NO: 1, wherein the at least two mutations are selected from the group consisting of: F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338L/A363L/Y365M; F338L/I358F/Y365W; I358F/Y365W/L513M; I358F/Y365W/F392W; F338M/I358F/A363L/Y365F/F377V; I358F/Y365F/F392W; I358F/Y365F/V395I; I358F/Y365F/F392W/V395I; I358F/Y365W/L513I/F515L; and F338L/I358F/A363L/Y365M; or a second coronavirus RBD comprising at least two mutations corresponding to F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338L/A363L/Y365M; F338L/I358F/Y365W; I358F/Y365W/L513M; I358F/Y365W/F392W; F338M/I358F/A363L/Y365F/F377V; I358F/Y365F/F392W; I358F/Y365F/V395I; I358F/Y365F/F392W/V395I; I358F/Y365W/L513I/F515L; or F338L/I358F/A363L/Y365M of SEQ ID NO: 1, wherein corresponding sites are determined by a sequence alignment of SEQ ID NO: 1 with spike protein sequence of the second coronavirus receptor binding domain using Blast-p parameters of protocol 1 or protocol 2.

Another aspect provided herein comprises a non-naturally occurring polypeptide comprising: a first coronavirus receptor binding domain (RBD) comprising at least 90% identity to residues 328-531 of SEQ ID NO:1 or to corresponding residues of the receptor binding domain of a second coronavirus as determined by a sequence alignment of SEQ ID NO: 1 with the sequence of the second coronavirus receptor binding domain using Blast-p, and further comprising at least two mutations relative to the RBD of SEQ ID NO: 1 or the corresponding residues in the second coronavirus, wherein the at least two mutations enhance the stability of the polypeptide relative to the stability of a wild-type polypeptide lacking the at least two mutations. In certain embodiments, the stability of the non-naturally occurring coronavirus receptor binding domain polypeptide and the stability of its corresponding wild-type polypeptide are assessed under the same conditions.

In one embodiment of this aspect and all other aspects provided herein, the at least two mutations are at amino acids: 338 & 365; 365 & 513; 365 & 392; 338, 363, 365 & 377; 365 & 392; 365 & 395; 365, 392& 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; and/or 338, 358, 363, & 365 of SEQ ID NO: 1, or at corresponding residues of the second coronavirus receptor binding domain as determined by a sequence alignment of SEQ ID NO: 1 with the sequence of the second coronavirus receptor binding domain using Blast-p.

In another embodiment of this aspect and all other aspects provided herein, the at least two mutations are selected from the group consisting of: F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338L/A3631L/Y365M; F338L/I358F/Y365W; I358F/V365W/L513M; I358F/Y365W/F392W; F338M/I358F/A363L/Y365F/F377V; I358F/V365F/F392W; I358F/Y365F/V395I; I358F/Y365F/F392W/V395I; I358F/Y365W/L513I/F515L; and F338L/I358F/A363L/Y365M of SEQ ID NO: 1 or at corresponding residues of a second coronavirus as determined by a sequence alignment of SEQ ID NO: 1 with the sequence of the second coronavirus receptor binding domain using Blast-p.

In another embodiment of this aspect and all other aspects provided herein, the receptor binding domain polypeptide further comprises additional amino acid residues outside of the RBD of SEQ ID NO: 1. In another embodiment of this aspect and all other aspects provided herein, the receptor binding domain polypeptide as described herein is comprised by a coronavirus spike protein polypeptide. In another embodiment of this aspect and all other aspects provided herein, the receptor binding domain polypeptide or the coronavirus spike protein polypeptide can include, for example, a fusion polypeptide. The receptor binding domain polypeptide or the coronavirus spike protein polypeptide can also include, for example, a leader sequence, e.g., for secretion. In various embodiments, a leader sequence and/or an amino terminal methionine can be present or, alternatively, can be removed, e.g., by proteolytic cleavage.

In another embodiment of this aspect and all other aspects provided herein, the coronavirus receptor binding domain (RBD) comprises at least 95% identity to residues 328-531 of SEQ ID NO:1.

In another embodiment of this aspect and all other aspects provided herein, the at least two mutations at amino acids 338 & 365; 365 & 513; 365 & 392; 338, 363, 365 & 377; 365 & 392; 365 & 395; 365, 392 & 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; and/or 338, 358, 363, & 365 of SEQ ID NO: 1, or at corresponding residues of the second coronavirus receptor binding domain are the only mutations in the receptor binding domain relative to wild type.

In another embodiment of this aspect and all other aspects provided herein, the expression of the RBD polypeptide when expressed in a cell is increased as compared to expression of the wild-type RBD polypeptide lacking the at least two mutations (i.e., under the same or similar expression conditions or culture conditions).

In another embodiment of this aspect and all other aspects provided herein, the RBD polypeptide binds to a coronavirus antibody or binds a coronavirus cognate receptor.

In another embodiment of this aspect and all other aspects provided herein, the coronavirus antibody comprises a SARS-CoV-2 antibody.

In another embodiment of this aspect and all other aspects provided herein, the receptor for the coronavirus corresponding to the polypeptide comprises an angiotensin converting enzyme (ACE) receptor.

In another embodiment of this aspect and all other aspects provided herein, the ACE receptor is the ACE2 receptor.

In another embodiment of this aspect and all other aspects provided herein, the second coronavirus comprises a sequence of a coronavirus selected from: Severe acute respiratory syndrome associated coronavirus 2 (SARS-CoV-2), Severe acute respiratory syndrome associated coronavirus (SARS-CoV); Middle East respiratory syndrome (MERS); 229E; NL63; OC43; HKU1, or a naturally occurring variant thereof.

In another embodiment of this aspect and all other aspects provided herein, the receptor binding domain polypeptide comprises at least 90% sequence identity to SEQ ID NO: 1.

In another embodiment of this aspect and all other aspects provided herein, the RBD is fused to a second, heterologous polypeptide.

In another embodiment of this aspect and all other aspects provided herein, the RBD is fused to a nanoparticle, nanostructure or heterologous protein scaffold. In certain embodiments, the heterologous protein scaffold comprises the I53-50 trimeric "A" component of SEQ ID NO: 3. In other embodiments, the heterologous protein scaffold comprises a heterologous protein scaffold as described in Table 1 of U.S. Pat. No. 10,351,603, the contents of which are incorporated by reference in its entirety.

In another embodiment of this aspect and all other aspects provided herein, the polypeptide and/or the second polypeptide is an antigenic polypeptide.

Another aspect provided herein is a coronavirus spike protein comprising the polypeptide of claim 1.

Another aspect provided herein is a composition comprising the polypeptide as described herein and a pharmaceutically acceptable carrier. In one embodiment, the polypeptide is in an admixture with the pharmaceutically acceptable carrier. In one embodiment, the polypeptide and the pharmaceutically acceptable carrier are provided as a suspension.

In one embodiment of this aspect and all other aspects provided herein, the pharmaceutical composition further comprises an adjuvant.

In another embodiment of this aspect and all other aspects provided herein, the shelf-life of the composition is longer than a composition comprising a wild-type RBD polypeptide lacking the at least two mutations.

In another embodiment of this aspect and all other aspects provided herein, the composition is formulated as a vaccine.

Also provided herein, in another aspect, is a non-naturally occurring coronavirus spike protein subunit 1 polypeptide comprising at least two mutations, wherein the at least two mutations comprise at least one cavity-filling mutation and at least a second mutation.

In another embodiment of this aspect and all other aspects provided herein, the at least two mutations enhance the stability of the coronavirus polypeptide relative to the stability of a wild-type polypeptide lacking the at least one cavity-filling mutation and at least a second mutation.

In another embodiment of this aspect and all other aspects provided herein, the at least one cavity-filling mutation comprises mutation of a residue in a linoleic acid binding pocket of the coronavirus spike protein, subunit 1.

In another embodiment of this aspect and all other aspects provided herein, the at least one cavity-filling mutation comprises mutation of a residue within residues 328-531 of SEQ ID NO: 1 or at corresponding residues of a second coronavirus spike protein, subunit 1 as determined by a sequence alignment of SEQ ID NO: 1 with the sequence of the second coronavirus spike protein, subunit 1 using Blast-p (e.g., protocols 1 or 2 as described herein).

In another embodiment of this aspect and all other aspects provided herein, the at least one cavity-filling mutation comprises mutation of a residue of SEQ ID NO: 1 between residues 335-345; 355-375, or 378-395 or at corresponding residues of a second coronavirus spike protein, subunit 1 as determined by a sequence alignment of SEQ ID NO: 1 with the sequence of the second coronavirus spike protein, subunit 1 using Blast-p (e.g., protocols 1 or 2 as described herein).

In another embodiment of this aspect and all other aspects provided herein, the at least one cavity-filling mutation comprises mutation of a residue of SEQ ID NO: 1 at amino acid 336, 338, 341, 342, 358, 361, 363, 365, 368, 374, 377, 387, or 392 or of a corresponding residue of a second coronavirus spike protein, subunit 1 as determined by a sequence alignment of SEQ ID NO: 1 with the sequence of the second coronavirus using Blast-p (e.g., protocols 1 or 2 as described herein).

In another embodiment of this aspect and all other aspects provided herein, the at least one cavity-filling mutation and the at least one second mutation are at residues 338 & 365; 365 & 513; 365 & 392; 338, 363, 365 & 377; 365 & 392; 365 & 395; 365, 392 & 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; and/or 338, 358, 363, & 365 of SEQ ID NO: 1, or at corresponding residues of a second coronavirus spike protein, subunit 1 as determined by a sequence alignment of SEQ ID NO: 1 with the sequence of the second coronavirus spike protein, subunit 1 using Blast-p (e.g., protocols 1 or 2 as described herein).

In another embodiment of this aspect and all other aspects provided herein, the at least one cavity-filling mutation and the at least one second mutation are selected from the group consisting of: F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338I/A363L/Y365M; F338L/I358F/Y365W; I358F/Y365W/L513M; I358F/Y365W/F392W; F338M/I358F/A363L/Y365F/F377V; I358F/Y365F/F392W; I358F/Y365F/V395I; I358F/Y365F/F392W/V395I; I358F/Y365W/L513I/F515L; and F338L/I358F/A363L/Y365M of SEQ ID NO: 1, or from corresponding residues of a second coronavirus spike protein, subunit 1 as determined by a sequence alignment of SEQ ID NO: 1 with the sequence of the second coronavirus spike protein, subunit 1 using Blast-p (e.g., protocol 1 or 2 as described herein).

In another embodiment of this aspect and all other aspects provided herein, the coronavirus spike protein, subunit 1 polypeptide comprises at least 95% identity to residues 328-531 of SEQ ID NO: 1 or a receptor binding domain sequence of a second coronavirus spike protein, subunit 1 as determined by a sequence alignment of SEQ ID NO: 1 with the sequence of the second coronavirus spike protein, subunit 1 using Blast-p (e.g., protocol 1 or 2 as described herein).

In another embodiment of this aspect and all other aspects provided herein, the at least two mutations at amino acids 338 & 365; 365 & 513; 365 & 392; 338, 363, 365 & 377; 365 & 392; 365 & 395; 365, 392 & 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; and/or 338, 358, 363, & 365 of SEQ ID NO: 1, or at corresponding residues of the second coronavirus receptor binding domain are the only mutations in the spike protein, subunit 1 relative to SEQ ID NO: 1.

In another embodiment of this aspect and all other aspects provided herein, the coronavirus polypeptide comprises at least 95% identity to SEQ ID NO: 1 or to a wild-type spike protein, subunit 1 amino acid sequence of a second coronavirus.

In another embodiment of this aspect and all other aspects provided herein, the expression of the coronavirus polypeptide when expressed in a cell is increased as compared to expression of a wild-type polypeptide lacking the at least one cavity-filling mutation and at least one second mutation under the same expression conditions.

In another embodiment of this aspect and all other aspects provided herein, the coronavirus polypeptide binds to a coronavirus antibody or binds a cognate coronavirus receptor.

In another embodiment of this aspect and all other aspects provided herein, the coronavirus antibody comprises a SARS-CoV-2 antibody.

In another embodiment of this aspect and all other aspects provided herein, the cognate coronavirus receptor comprises an angiotensin converting enzyme (ACE) receptor.

In another embodiment of this aspect and all other aspects provided herein, the ACE receptor is the ACE2 receptor.

In another embodiment of this aspect and all other aspects provided herein, the coronavirus polypeptide is an engineered mutant polypeptide of a coronavirus selected from: Severe acute respiratory syndrome associated coronavirus 2 (SARS-CoV-2), Severe acute respiratory syndrome associated coronavirus (SARS-CoV); Middle East respiratory syndrome (MERS); 229E; NL63; OC43; or HKU1.

In another embodiment of this aspect and all other aspects provided herein, the coronavirus spike protein, subunit 1 polypeptide comprises at least 90% sequence identity to SEQ ID NO: 1.

In another embodiment of this aspect and all other aspects provided herein, the coronavirus polypeptide is fused to a second, heterologous polypeptide.

In another embodiment of this aspect and all other aspects provided herein, the coronavirus polypeptide is fused to a nanoparticle, nano-structure or protein scaffold. In certain embodiments, the heterologous protein scaffold comprises the I53-50 trimeric "A" component of SEQ ID NO: 3. In other embodiments, the heterologous protein scaffold comprises a heterologous protein scaffold as described in Table 1 of U.S. Pat. No. 10,351,603, the contents of which are incorporated by reference in its entirety.

In another embodiment of this aspect and all other aspects provided herein, the coronavirus polypeptide or the second, heterologous polypeptide is an antigenic polypeptide.

Also provided herein, in another aspect, is a composition comprising a coronavirus polypeptide as described herein and a pharmaceutically acceptable carrier (e.g., in an admixture or forming a suspension).

In one embodiment of this aspect and all other aspects provided herein, the composition comprising a coronavirus polypeptide and a pharmaceutically acceptable carrier further comprises an adjuvant.

In another embodiment of this aspect and all other aspects provided herein, the shelf-life of the composition is longer than a composition comprising a wild-type coronavirus polypeptide lacking the at least one cavity-filling mutation and at least second mutation when stored under the same or similar storage conditions.

In another embodiment of this aspect and all other aspects provided herein, the composition comprising a coronavirus polypeptide and a pharmaceutically acceptable carrier is formulated as a vaccine.

Another aspect provided herein relates to a cell expressing a receptor binding domain having at least two mutations as described herein, or a coronavirus polypeptide having at least two mutations as described herein.

Another aspect provided herein relates to a nucleic acid sequence encoding a receptor binding domain having at least two mutations as described herein, or a coronavirus polypeptide having at least two mutations as described herein.

Also provided herein, in another aspect, is a method of vaccinating a subject against a coronavirus, the method comprising administering a pharmaceutical or vaccine composition as described herein to a subject.

Another aspect provided herein relates to a method of making a vaccine, the method comprising combining a composition comprising a receptor binding domain having at least two mutations as described herein, or a coronavirus polypeptide having at least two mutations as described herein with an adjuvant and a pharmaceutically acceptable carrier.

Another aspect provided herein relates to a fusion polypeptide composition comprising a coronavirus receptor binding domain (RBD) comprising a mutation selected from the group consisting of I358F, Y365F, Y365W, V367F and F392W, relative to the coronavirus polypeptide of SEQ ID NO: 1, fused to a heterologous protein scaffold. In one embodiment, the heterologous protein scaffold comprises a polypeptide of SEQ ID NO: 3. In another embodiment, each cysteine in the polypeptide of SEQ ID NO: 3 is mutated to alanine.

In another embodiment, the heterologous protein scaffold comprises a heterologous protein scaffold as described in Table 1 of U.S. Pat. No. 10,351,603, the contents of which are incorporated by reference in their entirety.

In another embodiment, the fusion polypeptide composition further comprises a pharmaceutically acceptable carrier.

In another embodiment, the fusion polypeptide composition further comprises an adjuvant.

In another embodiment, provided herein is a vaccine composition comprising the fusion polypeptide composition.

In another embodiment, provided herein is a cell expressing the fusion polypeptide.

In another embodiment, provided herein is a composition comprising a nucleic acid encoding the fusion polypeptide.

In another embodiment, provided herein is a method of vaccinating a subject against a coronavirus, the method comprising administering a composition comprising a fusion polypeptide composition as described herein to the subject.

In another embodiment, provided herein is a method of making a vaccine, the method comprising combining a fusion polypeptide composition as described herein or a nucleic acid encoding such a fusion polypeptide composition with an adjuvant and a pharmaceutically acceptable carrier.

Another aspect provided herein relates to a polypeptide comprising a coronavirus receptor binding domain (RBD) comprising a mutation selected from the group consisting of I358F, Y365F, Y365W, V367F, F392W, G502D, N501F, N501T, Q498Y, F338L, F338M, A363L, Y365M, F377V, V395I, LS13I, LS13M, and F515L, relative to a coronavirus polypeptide of SEQ ID NO: 1.

In one embodiment of this aspect and all other aspects provided herein, the mutation is selected from the group consisting of I358F, Y365F, Y365W, V367F, and F392W.

In another embodiment of this aspect and all other aspects provided herein, the polypeptide comprises a second mutation selected from the group consisting of I358F, Y365F, Y365W, V367F, F392W, G502D, N501F, N501T, Q498Y, F338L, F338M, A363L, Y365M, F377V, V395I, L513I, L513M, and F515L.

In another embodiment of this aspect and all other aspects provided herein, the polypeptide comprises a third mutation selected from the group consisting of I358F, Y365F, Y365W, V367F, F392W, G502D, N501F, N501T, Q498Y, F338L, F338M, A363L, Y365M, F377V, V395I, L513I, LS13M, and F515L.

In another embodiment of this aspect and all other aspects provided herein, the polypeptide comprises the polypeptide sequence of SEQ ID NO: 56 or SEQ ID NO: 57.

In another embodiment of this aspect and all other aspects provided herein, the polypeptide comprises a heterologous protein scaffold.

In another embodiment of this aspect and all other aspects provided herein, the heterologous protein scaffold has at least 90%, at least 95%, or at least 98% identity to a polypeptide sequence of SEQ ID NO: 3.

In another embodiment of this aspect and all other aspects provided herein, the heterologous protein scaffold comprises a polypeptide of SEQ ID NO: 3.

In another embodiment of this aspect and all other aspects provided herein, the polypeptide comprises the polypeptide sequence of SEQ ID NO: 6 or SEQ ID NO: 7.

Another aspect provided herein relates to a polypeptide complex comprising or consisting of a first component consisting of the polypeptide of any one of claims and a second component that has at least 95%, at least 96%, at least 97%, at least 98%, at least 99%, or 100% identity to any one of SEQ ID NO: 13-18.

Also provided herein, in another aspect, is a vaccine composition comprising a composition or the polypeptide complex as described herein.

In one embodiment of this aspect and all other aspects provided herein, the composition further comprises a pharmaceutically acceptable carrier.

In another embodiment of this aspect and all other aspects provided herein, the vaccine composition further comprises an adjuvant.

Another aspect provided herein relates to a cell expressing a polypeptide as described herein.

Another aspect provided herein relates to a nucleic acid encoding a polypeptide as described herein.

Another aspect provided herein relates to a method of vaccinating a subject against a coronavirus, the method comprising administering a polypeptide, a protein complex, or a vaccine composition as described herein to the subject.

Another aspect provided herein relates to a method of making a vaccine, the method comprising combining a polypeptide as described herein with an adjuvant and a pharmaceutically acceptable carrier.

Another aspect provided herein relates to a method of making a vaccine, the method comprising combining a first component consisting of a polypeptide as described herein; a second component that has at least 95%, at least 96%, at least 97%, at least 98%, at least 99%, or 100% identity to any one of SEQ ID NO: 13-18; a pharmaceutically acceptable carrier; and optionally an adjuvant.

Accordingly, provided herein in one aspect is a non-naturally occurring polypeptide comprising a first coronavirus receptor binding domain (RBD) comprising at least 90% identity to residues 328-531 of SEQ ID NO:1, and further comprising at least one mutation relative to the RBD of SEQ ID NO: 1, wherein the at least one mutation is selected from the group consisting of: I358F, Y365F, Y365W, V367F, F392W, G502D, N501F, N501T, Q498Y, F338L, F338M, A363L, Y365M, F377V, V395I, L513I, L513M, and F515L, or at corresponding residues of a second coronavirus receptor binding domain as determined by a sequence alignment of SEQ ID NO: 1 with the sequence of the second coronavirus receptor binding domain using Blast-p (Altschul, S. F., Gish, W., Miller, W., Myers, E. W. & Lipman, D. J. (1990) "Basic local alignment search tool." J. Mol. Biol. 215:403-410). In one embodiment, the Blast-p program used is the National Center for Biotechnology Information (NCBI) online alignment tool. Alternatively, the Blast-p program can be downloaded onto a device and used locally.

In one embodiment of this aspect and all other aspects provided herein, the mutation is selected from the group consisting of I358F, Y365F, Y365W, V367F, and F392W.

In another embodiment of this aspect and all other aspects provided herein, the polypeptide comprises a second mutation selected from the group consisting of I358F, Y365F, Y365W, V367F, F392W, G502D, N501F, N501T, Q498Y, F338L, F338M, A363L, Y365M, F377V, V395I, L513I, L513M, and F515L.

In another embodiment of this aspect and all other aspects provided herein, the polypeptide comprises a third mutation selected from the group consisting of I358F, Y365F, Y365W, V367F, F392W, G502D, N501F, N501T, Q498Y, F338L, F338M, A363L, Y365M, F377V, V395I, L513I, L513M, and F515L.

Another aspect described herein relates to a polypeptide comprising a first coronavirus receptor binding domain (RBD) comprising at least 90% identity to residues 328-531 of SEQ ID NO:1, and further comprising at least two mutations relative to the RBD of SEQ ID NO: 1, wherein the at least two mutations are selected from the group consisting of:

F338L/Y365W;
Y365W/L513M;
Y365W/F392W;
F338M/A363L/Y365F/F377V;
Y365F/F392W;
Y365F/V395I;
Y365F/F392W/V395I;
Y365W/LS31/F515L;
F338L/A363L/Y365M;
F338L/I358F/Y365W;
I358F/Y365W/L513M;
I358F/Y365W/F392W;
F338M/I358F/A363L/Y365F/F377V;
I358F/Y365F/F392W;
I358F/Y365F/V395I;
I358F/Y365F/F392W/V395I;
I358F/Y365W/L513I/F515L; and
F338L/I358F/A363L/Y365M;
or, a second coronavirus RBD comprising at least two mutations corresponding to
F338L/Y365W;
Y365W/L513M;
Y365W/F392W;
F338M/A363L/Y365F/F377V;
Y365F/F392W;
Y365F/V395I;
Y365F/F392W/V395I;

Y365W/L513I/F515L;
F338L/A3631L/Y365M;
F338L/I358F/Y365W;
I358F/V365W/LS13M;
I358F/Y365W/F392W;
F338M/I358F/A363L/Y365F/F377V;
I358F/Y365F/F392W;
I358F/Y365F/V395I;
I358F/Y365F/F392W/V395I;
I358F/Y365W/L513I/F515L; and
F338L/I358F/A363L/Y365M of SEQ ID NO: 1, wherein corresponding sites are determined by a sequence alignment of SEQ ID NO: 1 with spike protein sequence of the second coronavirus receptor binding domain using Blast-p parameters of protocol 1 or protocol 2.

BRIEF DESCRIPTION OF THE FIGURES

The patent or application file contains no drawings executed in color.

FIGS. 1A-1B. Exemplary non-naturally occurring SARS-CoV-2 stabilized receptor binding domains having one or more mutations and show enhanced expression compared to the starting construct (i.e., native or wild-type SARS-CoV-2 spike protein). FIG. 1A Reducing and non-reducing SDS-PAGE analysis of supernatants used to express designed repacked RBD ("Rpk") variants genetically fused to the I53-50A trimeric nanoparticle component. The wildtype control contains no mutations to the RBD, and the negative control uses a plasmid that does not encode for any secreted protein. Migration of monomeric and oxidized dimeric species are marked. FIG. 1B List of mutations included in all constructs. Mutations listed in bold were validated alone in Starr et al. 2020.

FIGS. 2A-2C. Structural models showing the location of stabilizing mutations to the SARS-CoV-2 RBD. FIG. 2A Surface representation of the SARS-CoV-2 spike protein based on PDB-ID 6VYB (left) with the box highlighting the RBD, and a zoom-in of the RBD with a transparent surface representation, including a representation of N-glycans. FIG. 2B Zoom-in on the region of the SARS-CoV-2 receptor binding domain that contains most designed mutations. FIG. 2C Structural models of two representative designed sets of mutations, named Rpk4 and Rpk9, which stabilize the RBD.

FIG. 4A Size-exclusion chromatography (SEC) purification of wild-type and stabilized RBDs after expression from equal volumes of HEK293F cultures followed by IMAC purification and concentration. Monomeric RBDs (left) were purified using a Superdex 75 Increase 10/300 GL while fusions to the I53-50A trimer (right) were purified using a Superdex 200 Increase 10/300 GL. Cropped gels show equivalently diluted SEC load samples. FIG. 4B Thermal denaturation of wild-type and stabilized RBD monomers (left) and fusions to the I53-50A trimer (right), monitored by nanoDSF using intrinsic tryptophan fluorescence. Top panels show the barycentric mean (BCM) of each fluorescence emission spectrum as a function of temperature, while lower panels show smoothed first derivatives used to calculate melting temperatures.

FIG. 4C Hydrogen/deuterium-exchange mass spectrometry (HDX-MS) of wild-type and stabilized RBDs fused to I53-50A trimers. Structural model (top, from PDB 6W41) shows panoramic difference uptake results of both Rpk4-I53-50A and Rpk9-I53-50A trimers compared to wild-type RBD-I53-50A trimer, with shading determined based on decreased uptake level in mutant trimers measured at 1 min. The box highlights the peptide segment from residues 392-399, with exchange for this peptide shown at multiple timepoints: 3 sec, 15 sec, 1 min, 30 min, and 20 h (bottom). Each point is an average of two measurements. Standard deviations are shown unless smaller than the points plotted. FIG. 4C discloses SEQ ID NOs: 58-60, respectively, in order of appearance. FIG. 4D Fluorescence of SYPRO Orange when mixed with equal concentrations of wild-type and stabilized RBD monomers, with greater signal indicating greater levels of exposed hydrophobicity. FIG. 4E Binding kinetics of immobilized CV30 and CR3022 monoclonal antibodies to monomeric wild-type and stabilized RBDs as assessed by BLI. Experimental data from five concentrations of RBDs in two-fold dilution series (grey traces) were fitted (black lines) with binding equations describing a 1:1 interaction. Structural models (left) were generated by structural alignment of the SARS-CoV-2 bound to CV30 Fab (PDB 6XE1) and CR3022 Fab (PDB 6W41).

FIG. 5A Schematic of assembly of I53-50 nanoparticle immunogens displaying RBD antigens (designated by addition "-I53-50"). FIG. 5B Negative stain electron microscopy (nsEM) of wild-type RBD-I53-50, Rpk4-I53-50, and Rpk9-I53-50 (scale bar, 200 nm). FIG. 5C-5E show summarized quality control results for wild-type RBD-I53-50, Rpk4-I53-50, and Rpk9-I53-50 before and after a single freeze/thaw cycle in four different buffers. FIG. 5C The ratio of absorbance at 320 to 280 nm in UV-Vis spectra, an indicator of the presence of soluble aggregates. FIG. 5D Dynamic Light Scattering (DLS) measurements, which monitor both proper nanoparticle assembly and formation of aggregates. FIG. 5E Fractional reactivity of I53-50 nanoparticle immunogens against immobilized hACE2-Fc receptor (top) and CR3022 (bottom). The pre-freeze and post-freeze data were separately normalized to the respective CHAPS-containing samples for each nanoparticle.

FIGS. 6A-6C. Potent immunogenicity of the parental wild-type RBD-I53-50 nanoparticle immunogen is maintained with addition of Rpk mutations. FIG. 6A Female BALB/c mice (six per group) were immunized at weeks 0 and 3. Each group received equimolar amounts of RBD antigen adjuvanted with AddaVax, which in total antigen equates to 5 µg per dose for HexaPro-foldon and 0.88 µg per dose for all other immunogens. Serum collection was performed at weeks 2 and 5 weeks. The RBD-I53-50 immunogen was prepared in two different buffer conditions, with one group including CHAPS as an excipient. FIG. 6B Binding titers against HexaPro-foldon at weeks 2 and 5, as assessed by AUC from ELISA measurements of serial dilutions of serum. Each circle represents the AUC measurement from an individual mouse and horizontal lines show the geometric mean of each group. One mouse with a near-zero AUC at week 2 for group four was not plotted but still included in the geometric mean calculation. FIG. 6C Autologous (D614G) pseudovirus neutralization using a lentivirus backbone. Each circle represents the neutralizing antibody titer at 50% inhibition ($IC_{50}$) for an individual mouse and horizontal lines show the geometric mean of each group. Statistical analysis was performed using one-sided nonparametric Kruskal-Wallis test with Dunn's multiple comparisons. *, p<0.05; , p<0.01; , p<0.001.

FIG. 7A Summary of DLS measurements over four weeks. Hydrodynamic diameter remained consistent for all nanoparticles except wild-type RBD-I53-50 at 35-40° C., which showed signs of aggregation after 28 days of storage. FIG. 7B Binding against immobilized hACE2-Fc receptor (dashed lines) and CR3022 mAb (solid lines) by BLI, normalized to −80° C. sample for each time point. Antigenic integrity remained consistent for the stabilized nanoparticle immunogens, while the binding signal of wild-type RBD-I53-50 incubated at 35-40° C. decreased by 60% (hACE2-Fc) and 30% (CR3022). FIG. 7C Summary of SDS-PAGE and nsEM over four weeks. No degradation was observed by SDS-PAGE. Partial aggregation was only observed by nsEM on day 28 for the WT nanoparticle stored at 35-40° C. Electron micrographs for day 28 after storage at 35-40° C. are shown, with boxes indicating instances of aggregates (scale bar, 200 nm). All samples were formulated in TBS, 5% glycerol, 100 mM L-arginine.

FIG. 8A SEC purification of wild-type (HexaPro-foldon) and Rpk9 (Rpk9-HexaPro-foldon) prefusion-stabilized S ectodomains after expression from equal volumes of HEK293F cultures followed by IMAC purification and concentration. S ectodomains were purified using a Superose 6 Increase 10/300 GL. FIG. 8B Reducing and non-reducing SDS-PAGE of intermediates and final products during the purification of HexaPro-foldon and Rpk9-HexaPro-foldon. FIG. 8C Thermal denaturation of HexaPro-foldon and Rpk9-HexaPro-foldon, monitored by nanoDSF using intrinsic tryptophan fluorescence. The barycentric mean (BCM) of the fluorescence emission spectra is plotted as a function of temperature. FIG. 8D nsEM of HexaPro-foldon and Rpk9-HexaPro-foldon (scale bar, 100 nm).

DETAILED DESCRIPTION

Figure 1A:
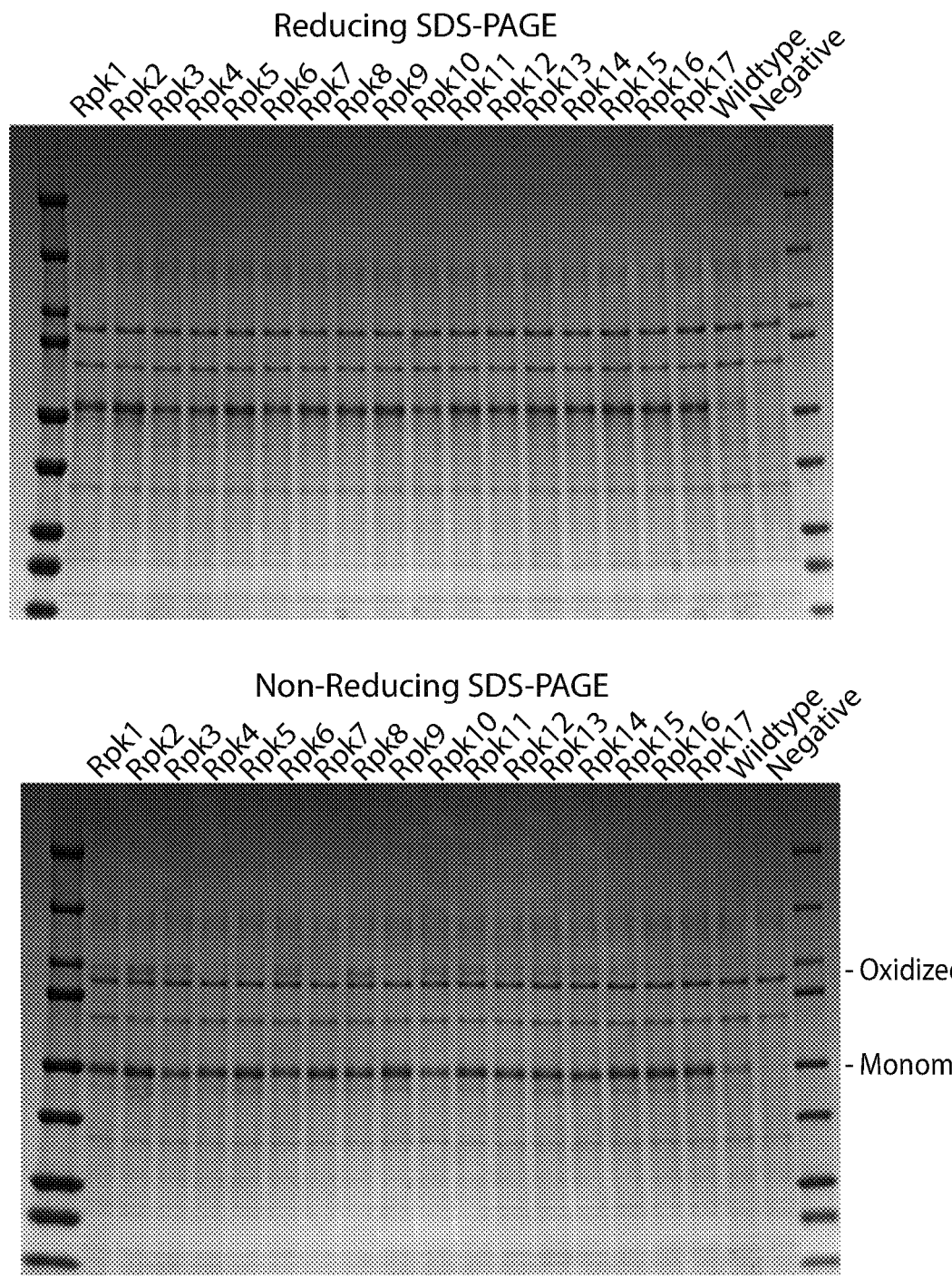
Figure 3:
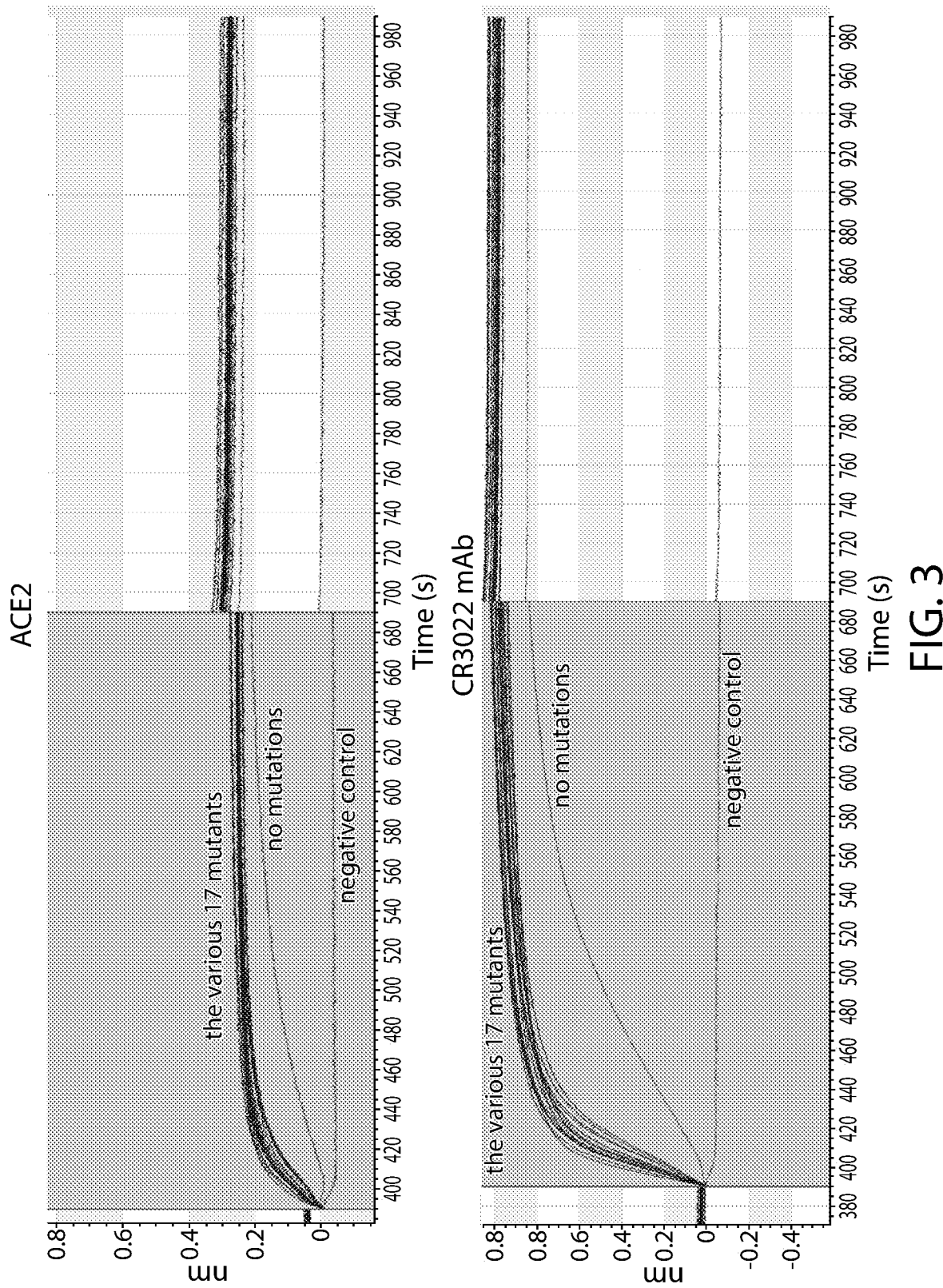
FIG. 3. Bio-layer interferometry (BLI) measuring binding of human ACE2 receptor and CR3022 antibody to supernatants used to express stabilized RBDs genetically fused to the I53-50A trimeric component. ACE2 and CR3022 were immobilized on sensors before exposing to supernatants. Data from (i) all designs, (ii) a construct containing a wildtype RBD, and (iii) negative control serum is shown in the graph. Each of the mutated SARS-CoV-2 spike proteins of FIG. 1 was determined to be antigenically intact when tested against both the SARS-CoV-2 cognate receptor, the angiotensin converting enzyme-2 (ACE2) receptor, and the CR3022 mAb that recognizes the SARS-CoV-2 spike protein. Measurements from supernatants also confirm that each of these mutants expressed at far higher levels than the starting construct.

Provided herein are compositions and methods comprising coronavirus "S" spike proteins with at least one, two or more amino acid mutations that increase their expression level, yield and/or stability compared to a native or wild-type coronavirus spike protein (e.g., SARS-CoV-2 S protein) under the same expression, culture or storage conditions. These mutated spike proteins can be used for generating a protein-based vaccine against SARS-CoV-2, a different coronavirus known to infect humans, or a pan-coronavirus vaccine that provides protection against multiple coronaviruses known to infect humans.

In one embodiment, the S protein comprises a single mutation that increases the expression level, yield and/or stability of a mutant coronavirus spike protein under certain expression, culture, or storage conditions compared to a native or wild-type coronavirus spike protein. In an alternative embodiment, the S protein comprises a plurality of mutations (e.g., 2, 3, 4, or 5).

Definitions

The terms "non-naturally occurring" or "mutant" as used herein refer to a coronavirus polypeptide (e.g., stabilized coronavirus S protein or RBD polypeptide) that comprises at least one or at least two amino acid residue mutations and that preferably comprise enhanced stability and/or expression compared to its corresponding native or wild-type coronavirus sequence. In some embodiments, the mutant polypeptides described herein are "substantially similar" to their native counterpart, for example, except for the at least two mutations. In some embodiments, the native counterpart can include a naturally occurring coronavirus variant.

For the avoidance of doubt, naturally occurring variants of a coronavirus sequence (e.g., SARS-Cov-2 variants: B.1.1.7; B.1.351; P.1; B.1.427; B.1.429; B.1.526; B.1.526.1; B.1.525; P.2; B.1.617; B.1.617.1; B.1.617.2; and B.1.617.3) are not considered "non-naturally occurring" or "mutant" coronavirus sequences, however such variants can be used as a reference coronavirus sequence as that term is used herein.

As used herein, the term "non-naturally occurring coronavirus spike protein subunit 1 polypeptide" refers to a polypeptide that comprises, at a minimum, the receptor binding domain sequence (residues 328-531 of SEQ ID NO:1), residues that permit the structural formation of a linoleic acid binding pocket, and at least one or at least two amino acid mutations. In one embodiment, one of the at least two mutations comprises a "cavity-filling mutation," as that term is used herein.

A molecule is said to be "substantially similar" to another molecule if both molecules have substantially similar structures (i.e., they are at least 90% similar in amino acid sequence as determined by Blast-p alignment set at default parameters) and are substantially similar in at least one relevant function (e.g., antigenic activity as determined by recognition of the polypeptide by an antibody that binds the native coronavirus counterpart). That is, a mutant polypeptide differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "mutant," when used with reference to a polypeptide, are variations in primary, secondary, or tertiary structure, as compared to a reference polypeptide (e.g., as compared to a wild-type coronavirus polypeptide). Mutants can also include insertions, deletions or substitutions of amino acids, including insertions and substitutions of amino acids and other molecules) that do not normally occur in the peptide sequence that is the basis of the variant, including but not limited to insertion of ornithine which does not normally occur in human proteins.

As used herein, the terms "corresponding to" or "corresponding wild-type coronavirus" refers to a wild-type coronavirus polypeptide sequence (or a naturally occurring variant thereof) from which the non-naturally occurring coronavirus polypeptide (e.g., spike polypeptide) or RBD polypeptide is produced. Typically, the wild-type coronavirus sequence (or its naturally occurring variant) is from the same strain as the non-naturally occurring coronavirus polypeptide. For example, a mutated SARS-CoV-2 polypeptide as described herein will correspond to a wild-type coronavirus polypeptide for a SARS-CoV-2 sequence or a naturally occurring variant thereof (e.g., South Africa variant, Brazilian variant, Los Angeles variant etc).

As used herein, the term "naturally occurring variant" refers to a coronavirus sequence that spontaneously arises in a population of susceptible individuals.

As used herein, the term "increased stability" or "enhanced stability" refers to a mutated coronavirus protein sequence that degrades at a slower rate in a cell, solution or formulation than the corresponding native or wild-type coronavirus protein sequence (or naturally occurring variant thereof) under the same conditions and thus persists for at least 12 h longer than the corresponding native or wild-type coronavirus protein sequence (or naturally occurring variant thereof), for example, as assessed using a thermal melt assay as described in the working Examples herein. In certain examples, the mutated coronavirus protein sequence persists in a cell, solution or formulation for at least 24 h, 36 h, 48 h, 72 h, 7 days, 8 days, 9 days, 10 days, 2 weeks, one month, 2 months, 3 months, 4 months, 5 months, 6 months, 9 months, one year, two years or more compared to the persistence of the corresponding native or wild-type coronavirus protein sequence. In some embodiments, higher expression levels can also be indicative of, or a result of, enhanced stability of a polypeptide.

As used herein, the term "increased yield" or "enhanced yield" refers to an increase of at least 10% in the amount of mutated coronavirus protein recovered from a cell system in which the protein is produced compared to the amount of native or wild-type protein (or a naturally occurring variant thereof) recovered from the same cell system under the same growth and isolation conditions. In certain embodiments, "enhanced yield" refers to an increase of at least 20%, at least 30%, at least 50%, at least 75%, at least 90%, at least 1-fold, at least 2-fold, at least 5-fold, at least 10-fold, at least 100-fold or more mutated coronavirus protein recovered from a cell system in which the protein is produced compared to the amount of native or wild-type protein recovered from the same cell system under the same growth conditions.

As used herein, the term "cavity filling mutation" refers to the substitution of an amino acid residue in a wild-type coronavirus spike protein by an amino acid that is expected to "fill" an internal cavity of the mature coronavirus spike protein. For example, the substituted amino acid is of an appropriate size or charge that it protrudes into the cavity and sterically reduces the cavity size and/or impairs a cognate ligand from binding within the cavity or pocket.

As used herein, the term "adjuvant" refers to a protein or chemical that, when administered with a vaccine antigen, enhances the immune response to the vaccine antigen. An adjuvant is distinguished from an antigenic moiety or carrier protein in that the adjuvant is not chemically coupled to the immunogen or the antigen. Adjuvants are well known in the art and include, for example, mineral oil emulsions such as Freund's complete or Freund's incomplete adjuvant (Freund, Adv. Tuberc. Res. 7:130 (1956); Calbiochem, San Diego Calif.), aluminum salts, especially aluminum hydroxide or ALHYDROGEL™ (approved for use in humans by the U.S. Food and Drug Administration), muramyl dipeptide (MDP) and its analogs such as [Thr1]-MDP (Byers and Allison, Vaccine 5:223 (1987)), monophosphoryl lipid A (Johnson et al., Rev. Infect. Dis. 9:S512 (1987)), and the like.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

Coronaviruses

Coronaviruses are a family of hundreds of viruses that can cause fever, respiratory problems, and sometimes gastrointestinal symptoms. SARS-CoV-2, the virus that causes Coronavirus Disease 2019 (COVID-19) is one of seven members of this family known to infect humans, and the third in the past three decades to jump from animals to humans. Other coronaviruses known to infect humans include alphacoronaviruses 229E and NL63, and betacoronaviruses OC43, HKU1, SARS-CoV (the coronavirus that causes severe acute respiratory syndrome, or SARS), and MERS-CoV (the coronavirus that causes Middle East Respiratory Syndrome, or MERS).

Although the methods and compositions described herein are discussed in the context of coronaviruses that infect humans, the methods and compositions described herein can also be used for generating stable coronavirus proteins from viruses that infect other mammals, including pets or livestock (e.g., swine, cattle, dogs, etc). Such viruses include, but are not limited to, porcine transmissible gastroenteritis virus, porcine respiratory coronavirus, porcine epidemic diarrhea virus (PEDV), porcine hemagglutinating encephalomyelitis virus, porcine deltacoronavirus (PDCoV), bovine coronavirus (BCV), feline coronavirus (FCoV), canine coronavirus (CCoV), avian infectious bronchitis virus (IBV), and turkey coronavirus (TCV). In addition, the coronaviruses described herein include those that are currently known and those that are later discovered. Specifically contemplated herein are coronaviruses that are the cause of an ongoing or future epidemic or pandemic.

As used herein, the term "coronavirus" refers to an enveloped virus with a positive-sense single-stranded RNA genome and a helical symmetry. The genomic size of coronaviruses ranges from approximately 27 to 32 kilobases, which is the longest size for any known RNA virus. Large Spike (S) glycoproteins protrude from the virus particle giving coronaviruses a distinctive corona-like appearance when visualized by electron microscopy. Coronaviruses infect a wide variety of species, including canine, feline, porcine, murine, bovine, avian and human (Holmes, et al., 1996. Coronaviridae: the viruses and their replication, p. 1075-1094. In D. M. K. a. P. M. H. B. N. Fields (ed.), Fields Virology. Lippincott-Raven, Philadelphia, Pa.). However, the natural host range of each coronavirus strain is narrow, typically consisting of a single species.

Coronaviruses typically bind to target cells through Spike-receptor interactions and enter cells by receptor mediated endocytosis or fusion with the plasma membrane (Holmes, et al., 1996, supra). The Spike-receptor interaction is a strong determinant of species specificity as demonstrated for both group 1 and group 2 coronaviruses. The genome of SARS-CoV contains a single stranded (+)-sense RNA. Complete and partial genome sequences of several SARS coronavirus isolates have been reported, including SARS coronavirus Urbani (GenBank accession #AY278741), SARS coronavirus Tor2 (GenBank accession #AY274119), SARS coronavirus CUHK-W1 (GenBank accession #AY278554), SARS-CoV Shanghai LY (GenBank accession #H012999; GenBank accession #AY322205; GenBank accession #AY322206), SARS-CoV Shanghai QXC (GenBank accession #AH013000; GenBank accession #AY322208; GenBank accession #AY322197; GenBank accession #AY322199), and SARS-CoV ZJ-HZ01 (GenBank accession #AY322206), gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2|SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118.1|SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1 SARS coronavirus Sin2679, gi|30468045|gb|AY283797.1| SARS coronavirus Sin2748, gi|31982987|gb|AY286320.2| SARS coronavirus isolate ZJ-HZ01, gi|30275666|gb|AY278488.2| SARS coronavirus BJ01.

The S (spike) protein may form non-covalently linked homotrimers (oligomers), which may mediate receptor binding and virus infectivity. Homotrimers of S proteins are likely necessary for presenting the correct native conformation of receptor binding domains and for eliciting a neutralizing antibody response. In addition, intracellular processing of S protein is associated with significant post-translation oligosaccharide modification. The post-translation oligosaccharide modification (glycosylation) expected by N-glycan motif analysis indicates that the S protein has as many as 23 sites for such modification. In addition, C-terminal cysteine residues may also participate in protein folding and preserving the native (functional) S protein conformation. The S protein of some coronaviruses {e.g., some strains of group II and III viruses) can be proteolytically processed near the center of the S protein by a trypsin-like protease in the Golgi apparatus or by extracellularly localized enzymes into to a linked polypeptide, containing an N-terminal SI and a C-terminal S2 polypeptide. Some members of the type II group of coronaviruses and group I viruses may not be so processed.

Diagnosis: A subject, e.g., a human, is diagnosed as having a coronavirus infection based on diagnostic test results. A subject can be suspected of having a coronavirus infection (e.g., COVID-19, SARS, MERS etc.) based on one or more presenting symptoms such as, fever, chills, cough, shortness of breath/difficulty breathing, fatigue, muscle/body aches, headache, new loss of taste or smell, sore throat, congestion or runny nose, nausea, vomiting, or diarrhea. However, certain subjects may present with an asymptomatic infection (e.g., SARS-CoV-2 infection) and are thus suspected of having a coronavirus infection when they have been in contact with a subject having a coronavirus infection. In both scenarios, an active coronavirus infection can be confirmed using a method known in the art that detects one or more of viral antigens and viral nucleic acid in a sample taken from a subject. Examples include using a reverse-transcriptase polymerase chain reaction (RT-PCR) diagnostic assay from a nasopharyngeal swab or sputum to detect viral RNA. Other nucleic acid amplification methods, e.g., any of a number of isothermal amplification methods, can also be used, and have sensitivity close to, if not equal to RT-PCR. Isothermal amplification methods have the advantage of not requiring a thermal cycler to generate an amplified product, and can more rapidly provide results in a highly sensitive manner. In another embodiment, an active coronavirus infection can be determined by detecting one or more coronavirus polypeptides (such as an antigen) in a biological sample obtained from the subject. Lateral flow assays for viral antigens can provide qualitative, and sometimes quantitative diagnostic results. Viral polypeptides can also be detected by other methods known in the art, such as Western blot.

Assessing the presence of a coronavirus antibody can be used to determine if a subject has been exposed to a coronavirus in the past or alternatively as a means to monitor the effectiveness of a vaccine (i.e., ability of a mutated spike protein to raise an immune response). Methods for assessing the presence of a coronavirus antibody are known in the art and are not discussed in detail herein.

Alternatively, the presence or production of coronavirus virions can be determined directly or indirectly by using, for example, electron microscopy.

Protein Sequence: The amino acid sequence of the native or wild-type SARS-CoV-2 S protein, subunit 1 is:

(SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAA.

Throughout the specification, SEQ ID NO: 1 is used as a 'base' or 'reference' sequence to which other coronavirus amino acid sequences can be aligned using an alignment program known in the art (e.g., Blast-p). An alignment of a different (or second) coronavirus sequence's spike protein sequence with the SARS-CoV-2 spike protein sequence of SEQ ID NO: 1 can be used to determine the corresponding site in the different (or second) coronavirus at which to introduce a given amino acid mutation or mutations to achieve stabilization as described herein. In one embodiment, the different coronavirus sequence is aligned against SEQ ID NO: 1 using Blast-p (Altschul, S. F., Gish, W., Miller, W., Myers, E. W. & Lipman, D. J. (1990) "Basic local alignment search tool." J. Mol. Biol. 215:403-410). In one embodiment, the Blast-p program used is the National Center for Biotechnology Information (NCBI) online alignment tool. Alternatively, the Blast-p program can be downloaded onto a device and used locally. One of skill in the art will readily understand the use of Blast-p alignment tools, however for the avoidance of doubt protocol 1 and protocol 2 are provided herewith for the online and downloaded alignment tools, respectively.

Protocol 1: For use with the BLASTp alignment online from the National Center for Biotechnology Information (NCBI) server.

1. Set up a BLAST alignment using the following settings:
   Use the option for "Align two or more sequences"
   Enter the reference strain sequence for the relevant SARS-CoV-2 protein (i.e., SEQ ID NO: 1) into the "Enter Query Sequence" section
   Enter any corresponding coronavirus spike protein sequence into the "Enter Subject Sequence" section
   Algorithm: blastp (protein-protein BLAST)
   Expect threshold: 0.1
   Word size: 6
   Max matches in a query range: 0
   Matrix: BLOSUM62
   Gap costs:
      Existence: 11
      Extension: 1
   Filter low complexity regions?: No
   Mask:
      For lookup table only?: No
      Lower case letters?: No
2. Run the analysis by clicking the "BLAST" button
3. Click on the "Alignments" tab to show the alignment between the two sequences.
4. For each sequence position of interest, identify the number according to the "Query" sequence. Then identify the corresponding residue position in the "Sbjct" sequence that has been aligned with the position of the "Query" sequence.

Protocol 2: For use with the protein BLASTp alignment tool downloaded onto a local computer or server.
1. Install BLAST for command line execution using the manufacturer's instructions or identify a computer or server that already has it installed.
2. Generate a file in FASTA format that contains the desired subtype-specific reference strain for the SARS-CoV-2 protein (i.e., SEQ ID NO: 1). In the command below, this file will be named "query.fasta".
3. Generate a second file in FASTA format that contains a corresponding protein sequence of a different coronavirus from the same subtype. In the command below, this file will be named "sbjct.fasta".
4. Execute the following command using a program such as Terminal, iTerm2, Windows Console, Linux console or other similar terminal emulators. This will generate results in a file named "results.txt".
   blastp-query query.fasta-subject sbjct.fasta-matrix BLOSUM62-evalue 0.1-word size 6-gapopen 11-gapextend 1-out results.txt
5. Open results.txt and view the section showing alignment of the two sequences. For each sequence position of interest, identify the number according to the "Query" sequence. Then identify the corresponding residue position in the "Sbjct" sequence that has been aligned with the position of the "Query" sequence.

It will be apparent to those of skill in the art that other protein alignment tools (e.g., Clustalw or Clustal-omega) can also be used to identify sequence identity between a query sequence and a reference sequence (e.g., SEQ ID NO: 1). Given that the query sequence and the reference sequence share significant sequence identity, it is expected that other protein alignment tools will produce similar, if not identical results to Blast-p using the protocols described herein. The protocols described herein have been shown to be accurate and effective for this purpose and are provided herein to aid the skilled artisan in identifying amino acid residues to be mutated in the query sequence.

Receptor Binding Domain (RBD) Polypeptides

A virus-surface "spike" protein mediates the entry of coronavirus into host cells. The spike proteins of SARS-CoV and SARS-CoV-2 each contain a receptor binding domain that specifically recognizes angiotensin converting enzyme-2 (ACE2) as its receptor. Given the importance of this domain in viral uptake and function, the receptor binding domain is relatively well conserved among the coronaviruses that are known to infect humans. The sequence of the receptor binding domain for the spike protein of SARS-CoV-2 is:

(SEQ ID NO: 2)
RFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPD

DFTGCVIAWNSNNLDSKVGGNYNYLYRLFRKSNLKPFERDISTEIYQAGS

TPCNGVEGFNCYFPLQSYGFQPTNGVGYQPYRVVVLSFELLHAPATVCGP

KK.

Throughout the specification, SEQ ID NO: 2 is used as a 'base' or 'reference' receptor binding domain sequence to which other coronavirus RBD sequences can be aligned using an alignment program known in the art (e.g., Blast-p, ClustalW etc.). An alignment of at least a second coronavirus RBD sequence with SEQ ID NO: 2 can be used to determine the corresponding site in the second coronavirus RBD sequence for a given amino acid mutation in SARS-CoV-2. In such embodiments, Blast-p can be used to align the coronavirus RBD query sequence with SEQ ID NO: 2 using protocol 1 or protocol 2 as described herein. The receptor binding domain polypeptides comprise at least two mutations within SEQ ID NO: 2 (or equivalent for a different coronavirus). In some embodiments, the receptor binding domain polypeptides can comprise an additional mutation. This additional mutation can also be in the RBD region or can occur outside of the RBD region. Typically, the at least one, two or more amino acid mutations do not include those mutations that are found in naturally occurring variants of a given coronavirus sequence. For example, L452R and E484K, which are present in naturally occurring variants of SARS-CoV-2 are not counted as the at least one, two or more amino acid mutations as described herein.

In some embodiments, the receptor binding domain polypeptides described herein are used in the generation of a protein vaccine against one or more coronaviruses. As will be appreciated by those of skill in the art and particularly when used in the setting of a vaccine, the mutated coronavirus protein need not necessarily retain receptor binding properties to its cognate receptor; thus the at least one amino acid mutation or at least two amino acid mutations do not need to be designed to retain the function of the RBD. Given that maintenance of coronavirus protein functions is not necessary, coronavirus proteins having at least 90% identity to SEQ ID NO: 1 or SEQ ID NO: 2 are specifically contemplated herein (e.g., at least 95%, at least 99% identity to SEQ ID NO: 1 or 2) provided that they retain the ability to act as a coronavirus antigen (i.e., stimulate the production of coronavirus-binding antibodies in a subject or bind a coronavirus antibody directed against the corresponding wild-type coronavirus). That is, the receptor binding domain polypeptides described herein are "immunogenic," i.e., immunization of a subject with a receptor binding domain polypeptide (optionally bound to an appropriate support (such as a protein, a lipid or a polypeptide)), induces an immune response (of the B cell type and/or of the T cell type), directed against the RBD polypeptide.

The term "epitope" refers to an antigenic determinant in a molecule such as an antigen, i.e., to a part in or fragment of the molecule that is recognized by the immune system, for example, that is recognized by a T cell or B cell, in particular when presented in the context of MHC molecules. An epitope of a protein antigen can comprise a continuous or discontinuous portion of said protein and can be between 5 and 100, between 5 and 50, between 8 and 30, between 10 and 25 amino acids in length, for example, the epitope may be preferably 9, 10, 11, 12, 13, 14, 15, 16, 17, 18, 19, 20, 21, 22, 23, 24, or 25 amino acids in length.

The ability of a protein to raise an immune response can be attributed, in part, to its secondary structure and the conformation in which the protein is folded. In some embodiments, a certain conformation is preferred for generating an antigenic response and/or for augmenting stability of the protein. The secondary structure of SARS-CoV-2 bound to the ACE2 receptor is described in Shang et al. "Structural Basis of Receptor Recognition by SARS-CoV-2" Nature 581:221-224 (2020), the contents of which are incorporated herein by reference in their entirety. With knowledge of the crystal structure of SARS-CoV-2, one of skill in the art can use educated reasoning or computational software to determine whether a given receptor binding domain polypeptide is likely to comprise a shape or secondary structure that would induce an immune response in a subject.

In certain embodiments, at least two amino acids are mutated in a coronavirus receptor binding domain, which enhance the yield of the protein in a cell system and/or enhance the stability of the coronavirus protein in a cell, solution, or formulation as compared to its corresponding wild-type protein. In other embodiments, at least one amino acid is mutated in a coronavirus receptor binding domain, which enhances the yield of the protein in a cell system and/or enhances the stability of the coronavirus protein in a cell, solution, or formulation as compared to its corresponding wild-type protein.

In some embodiments, the at least two mutations comprise at least two mutations are introduced within the RBD region of the spike protein (SEQ ID NO: 2 or residues 328-531 of SEQ ID NO: 1). In some embodiments, the at least one amino acid mutation is introduced within the RBD region of the spike protein.

In certain embodiments, the at least two mutations are at amino acids residues: 338 & 365; 365 & 513; 365 & 392; 338, 363, 365 & 377; 365 & 392; 365 & 395; 365, 392 & 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; or 338, 358, 363, & 365 of SEQ ID NO: 1, or at corresponding residues of a second coronavirus receptor binding domain as determined by a sequence alignment of SEQ ID NO: 1 with the sequence of the second coronavirus receptor binding domain using Blast-p.

In certain embodiments, the at least one amino acid mutation is at amino acid residue: 338, 358, 363, 365, 367, 377, 392, 395; 498, 501, 502, 513, or 515. In other embodiments, the at least one amino acid mutation is: I358F, Y365F, Y365W, V367F, F392W, G502D, N501F, N501T, Q498Y, F338L, F338M, A363L, Y365M, F377V, V395I, L513I, LS13M, or F515L.

In certain embodiments, the at least two mutations are selected from the group consisting of: F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338L/A363L/Y365M; F338L/I358F/Y365W; I358F/Y365W/L513M; I358F/Y365W/F392W; F338M/I358F/A363L/Y365F/F377V; I358F/Y365F/F392W; I358F/Y365F/V395I; I358F/Y365F/F392W/V395I; I358F/Y365W/L513I/F515L; and F338L/I358F/A363L/Y365M of SEQ ID NO: 1 or at corresponding residues of a second coronavirus as determined by a sequence alignment of SEQ ID NO: 1 with the sequence of the second coronavirus receptor binding domain using Blast-p.

In one embodiment, the receptor binding domain polypeptide comprises a fusion protein.

Linoleic Acid Binding Pocket

The SARS-CoV-2 "S" (spike) protein has been shown to comprise a "pocket" or "cavity" that has recently been determined to be a linoleic acid binding pocket (Toelzer et al. *Science* "Free fatty acid binding pocket in the locked structure of SARS-CoV-2 spike protein" (2020)). The residues in the linoleic acid binding pocket are conserved in all 7 coronaviruses that infect humans (Toelzer, supra) indicating that this cavity is functionally conserved. Toelzer et al. also indicate that binding of linoleic acid to SARS-CoV-2 S protein stabilizes the closed conformation of the S protein. It is contemplated herein that mutations within the linoleic acid binding pocket or sub-domains of the linoleic acid binding pocket can be used to mimic the effects of linoleic acid and/or to stabilize the closed conformation of the S protein. In some embodiments, an amino acid mutation in this region is a 'cavity-filling' mutation.

In one embodiment, the "cavity-filling mutation," as that term is used herein, fills a site within the linoleic acid binding pocket (e.g., sterically protrudes into the cavity). The cavities in a native coronavirus spike protein can be identified by methods known in the art, such as by visual inspection of a crystal structure representation of the spike protein of, e.g., SARS-CoV-2 (see e.g., Shang et al. "*Structural Basis of Receptor Recognition by SARS-CoV-2*" Nature 581:221-224 (2020)), or by using computational protein design software (such as BioLuminate™ (BioLuminate, Schrodinger LLC, New York), Discovery Studio™ (Discovery Studio Modeling Environment, Accelrys, San Diego), MOE™ (Molecular Operating Environment, Chemical Computing Group Inc., Montreal), and Rosetta™ (Rosetta, University of Washington, Seattle), among others). Such models permit one of skill in the art to design cavity-filling mutations that are expected to augment the stability of a given coronavirus spike protein.

The amino acids to be replaced for cavity-filling mutations can include small aliphatic (e.g. Gly, Ala, and Val) or small polar amino acids (e.g. Ser and Thr), which are replaced by similar amino acids that are sterically larger and able to "fill" the cavity (e.g., large aliphatic amino acids (Ile, Leu and Met) or large aromatic amino acids (His, Phe, Tyr and Trp)). In other embodiments, a charged amino acid can replace or be replaced by a non-charged amino acid, thereby altering the secondary structure of the protein and the cavity. Such residues for replacement can also include amino acids that are buried in a given protein conformation, but exposed to solvent in a second conformation.

In certain embodiments, at least one of the at least two mutations in the SARS-CoV-2 spike protein is at a residue involved in the linoleic binding pocket. In some embodiments, it is preferred that the mutations "fill" the linoleic acid binding pocket (e.g., using a larger amino acid with similar charge or hydrophobicity). Such mutations can stabilize a particular conformation of the protein and/or decrease the rate of degradation of the protein compared to the corresponding wild-type coronavirus. For ease of reference, the residues involved in linoleic acid binding are separated herein into three sub-domains. These sub-domains are based simply on the close proximity of several residues involved in linoleic acid binding.

| Linoleic Acid Binding Pocket Sub-domain Residues (numbering based on SEQ ID NO: 1) | SARS-CoV-2 sequence (bolded residues are involved in linoleic acid binding) | SEQ ID NO: |
|---|---|---|
| 335-345 | LCPFGEVFNAT | 55 |
| 355-375 | RKRISNCVADYSVLYNSASFS | 4 |
| 377-395 | FKCYGVSPTKLNDLCFTNV | 5 |

Non-naturally occurring coronavirus spike protein subunit 1 polypeptides can comprise at least one cavity filling mutation or mutation in a residue in the linoleic acid binding pocket and at least one additional mutation that together enhance the stability and/or yield of the polypeptides as those terms are used herein.

In some embodiments, the cavity-filling mutation comprises mutation of a residue of SEQ ID NO: 1 at amino acid 336, 338, 341, 342, 358, 361, 363, 365, 368, 374, 377, 387, or 392 or of a corresponding residue of a second coronavirus spike protein, subunit 1 as determined by a sequence alignment of SEQ ID NO: 1 (or a naturally occurring variant thereof) with the sequence of the second coronavirus (or a naturally occurring variant thereof) using Blast-p. In other embodiments, the cavity-filling mutation and the at least one second mutation are at residues 338 & 365; 365 & 513; 365 & 392; 338, 363, 365 & 377; 365 & 392; 365 & 395; 365, 392 & 395; 365, 513, & 515; 338, 363, & 365; 338, 358 & 365; 358, 365, & 513; 358, 365 & 392; 338, 358, 363, 365 & 377; 358, 365, & 392; 358, 365 & 395; 358, 365, 392, & 395; 358, 365, 513 & 515; and/or 338, 358, 363, & 365 of SEQ ID NO: 1, or at corresponding residues of a second coronavirus spike protein, subunit 1 as determined by a sequence alignment of SEQ ID NO: 1 with the sequence of the second coronavirus spike protein, subunit 1 using Blast-p (e.g., protocol 1 or 2 as described herein).

In some embodiments, the cavity-filling mutation and the at least one second mutation are selected from the group consisting of: F338L/Y365W; Y365W/L513M; Y365W/F392W; F338M/A363L/Y365F/F377V; Y365F/F392W; Y365F/V395I; Y365F/F392W/V395I; Y365W/L513I/F515L; F338L/A363L/Y365M; F338L/I358F/Y365W; I358F/Y365W/L513M; I358F/Y365W/F392W; F338M/I358F/A363L/Y365F/F377V; I358F/Y365F/F392W; I358F/Y365F/V395I; I358F/Y365F/F392W/V395I; I358F/Y365W/L513I/F515L; and F338L/I358F/A363L/Y365M of SEQ ID NO: 1, or from corresponding residues of a second coronavirus spike protein, subunit 1 as determined by a sequence alignment of SEQ ID NO: 1 with the sequence of the second coronavirus spike protein, subunit 1 using Blast-p (e.g., protocol 1 or 2 as described herein).

Coronavirus spike proteins having a cavity-filling mutation as described herein and further having at least 90% identity to SEQ ID NO: 1 or SEQ ID NO: 2 are specifically contemplated herein (e.g., at least 95%, at least 99% identity to SEQ ID NO: 1 or 2) provided that they retain the ability to act as an antigen for the coronavirus (i.e., stimulate the production of coronavirus antibodies in a subject). That is, the non-naturally-occurring coronavirus spike protein polypeptides described herein are "immunogenic," i.e., immunization of a subject with the polypeptide (optionally bound to an appropriate support (such as a protein, a lipid or a polypeptide)), induces an immune response (of the B cell type and/or of the T cell type) directed against the polypeptide.

The RBD polypeptides or spike polypeptides as described herein may have one of more amino acid substitutions from known variants of the coronavirus. For example and without limitation, the polypeptides may comprise 1, 2, 3, 4, 5, 6, 7, or all 8 positions relative to SEQ ID NO: 1 selected from the group consisting of L18F, T20N, P26S, deletion of residues 69-70, D80A, D138Y, R190S, D215G, K417N, K417T, G446S, L452R, Y453F, T478I, E484K, S494P, N501Y, A570D, D614G, H655Y, P681H, A701V, and T716L. The polypeptides may comprise one of the following naturally occurring mutations or combinations of mutations:

N501Y, optionally further including 1, 2, 3, 4, or 5 of deletion of one or both of residues 69-70, A570D, D614G, P681H, and/or T716L (UK variant);

K417N/E484K/N501Y, optionally further including 1, 2, 3, 4, or 5 of L18F, D80A, D215G, D614G, and/or A701V (South African variant);

K417N or T/E484K/N501Y, optionally further including 1, 2, 3, 4, or 5 of L18F, T20N, P26S, D138Y, R190S, D614G, and/or H655Y (Brazil variant); or L452R (Los Angeles variant).

In some embodiments, the polypeptides as disclosed herein comprise the polypeptide sequence of SEQ ID NO: 56 or SEQ ID NO: 57.

```
                                        (SEQ ID NO: 56)
RFPNITNLCPFGEVFNATRFASVYAWNRKRISNCVADFSVLYNSASFSTF

KCYGVSPTKLNDLCWTNIYADSFVIRGDEVRQIAPGQTGKIADYNYKLPD

DFTGCVIAWNSNNLDSKVGGNYNYLYRLFRKSNLKPFERDISTEIYQAGS

TPCNGVEGFNCYFPLQSYGFQPTYGVGYQPYRVVVLSFELLHAPATVCGP

KK
                                        (SEQ ID NO: 57)
RFPNITNLCPFGEVFNATRFASVYAWNRKRISNCVADFSVLYNSASFSTF

KCYGVSPTKLNDLCWTNIYADSFVIRGDEVRQIAPGQTGNIADYNYKLPD

DFTGCVIAWNSNNLDSKVGGNYNYLYRLFRKSNLKPFERDISTEIYQAGS

TPCNGVKGFNCYFPLQSYGFQPTYGVGYQPYRVVVLSFELLHAPATVCGP

KK
```

Amino Acid Mutations/Substitutions

Provided herein are mutated coronavirus S proteins or receptor binding domains thereof having at least two amino acid mutations or substitutions that confer enhanced stability of the mutated protein as compared to its corresponding native or wild-type coronavirus S protein. Exemplified in this specification are mutated SARS-CoV-2 S proteins or receptor binding domains thereof, however the methods and compositions described herein can be applied to any coronavirus S protein, including both coronaviruses that infect humans and those that infect other mammals (i.e., bats, bovines, porcines etc. . . . ). One of skill in the art can readily identify corresponding residues to those outlined in the specification for SARS-CoV-2 by aligning the amino acid sequence for another coronavirus with that of SARS-CoV-2 (i.e., SEQ ID NO: 1 or 2).

Alignment can provide guidance regarding residues likely to be necessary for function, whether the function is direct contact of a given residue or residues with receptor, or, for example, residues involved in maintaining a conformation that permits other residues to make such contact; non-limiting examples of the latter include those residues likely to line the linoleic acid binding pocket or aid in maintaining a given conformation of the spike protein. Where, for example, an alignment shows two identical or similar amino acids at corresponding positions, it is more likely that that site is important functionally (i.e., linoleic acid binding or receptor binding). The variant amino acid sequence can be at least 90%, at least 95%, at least 96%, at least 97%, at least 98%, at least 99%, or more, identical to a native or reference sequence, e.g., SEQ ID NO: 1. The degree of homology (percent identity) between a native and a mutant sequence can be determined, for example, by comparing the two sequences using computer programs commonly employed for this purpose and freely available on the world wide web. The variant amino acid or DNA sequence can be at least 90% s, at least 91%, at least 92%, at least 93%, at least 94%, at least 95%, at least 96%, at least 97%, at least 98%, at least 99%, or more, similar to the sequence from which it is derived (referred to herein as an "original," "native," or "wild-type" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the B world wide web at, with default parameters set or using protocol 1 or protocol 2 as described herein.

When a cavity-filling mutation is desired, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn), preferably where a smaller residue is substituted by a larger one that sterically "fills" the cavity or is altered in charge to induce changes in the cavity size and/or structure. Other such substitutions, e.g., substitutions of entire regions having similar hydrophobicity characteristics, are well known and can conserve function. Polypeptides comprising desired amino acid substitutions can be tested in any one of the assays described herein to confirm that (i) a desired conformation is maintained such that the antigenic activity of a native or reference polypeptide is substantially retained, or (ii) the stability of the protein is enhanced.

In some embodiments, the amino acid substitutions can comprise a conservative amino acid substitution. The terminology "conservative amino acid substitution" is well known in the art, and relates to substitution of a particular amino acid by one having a similar characteristic (e.g., similar charge or hydrophobicity). Conservative mutations as described herein can include substitution of amino acid residues with e.g., similar charge or hydrophobicity but differing in size or bulkiness (e.g., to provide a cavity-filling function). A list of exemplary conservative amino acid substitutions is given in the table below.

TABLE 2

CONSERVATIVE AMINO ACID SUBSTITUTIONS

| For Amino Acid | Code | Replace With |
| --- | --- | --- |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Alternatively, a non-conservative amino acid substitution may be preferred, for example, when eradication of a flexible portion of the native coronavirus S protein secondary structure is desired, for example, by adding a cysteine residue (or vice versa). "Non-conservative substitution" refers to the substitution of an amino acid in one class with an amino acid from another class; for example, substitution of an Ala with Asp, Asn, Glu, or Gln. Additional non-limiting examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

As will be appreciated by those of skill in the art, a mutant coronavirus polypeptide (e.g., a RBD polypeptide or a stabilized coronavirus S polypeptide) as described herein can have a mixture of conservative and non-conservative amino acid substitutions in any desired configuration. The polypeptides described herein can be tested for antigenic activity, receptor binding domain activity or conformation using methods known in the art or described in the Examples.

Cysteine residues can be important for protein secondary structure or conformation. Mutations of cysteine residues are contemplated herein provided that the secondary structure of the mutated protein is functional and/or antigenic as determined, for example, by assessing binding to its cognate receptor (e.g., ACE2 receptor), assessing secondary structure using crystallography or EM, or confirming binding to an antibody against the native or wild-type protein. Cysteine residues not involved in maintaining the proper conformation of the polypeptide also can be substituted, for example, with serine to improve the oxidative stability of the molecule and prevent aberrant crosslinking. Conversely, cysteine bond(s) can be added to the polypeptide to improve its stability or facilitate oligomerization.

In some embodiments, a stabilized coronavirus S protein or RBD polypeptide, as described herein, can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, the stabilized coronavirus S protein or RBD polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. a mutant coronavirus polypeptide, can be modified, e.g. by addition of a moiety to one or more of the amino acids that together comprise the peptide. Non-limiting examples of modifications and/or moieties include PEGylation; glycosylation; HESylation; ELPylation; lipidation; acetylation; amidation; end-capping modifications; cyano groups; phosphorylation; albumin conjugation, and cyclization. Modifications or moieties that improve solubilization in a given solution (i.e., aqueous) solution are specifically contemplated herein.

Alterations of the original amino acid sequence can be accomplished by any of a number of techniques known to one of skill in the art. Mutations can be introduced at the nucleic acid level, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

The mutated spike proteins or RBC polypeptides described herein can be synthesized using well known methods including recombinant methods and chemical synthesis. Recombinant methods of producing a polypeptide through the introduction of a vector including nucleic acid encoding the polypeptide into a suitable host cell are well known in the art, e.g., as described in Sambrook et al., Molecular Cloning: A Laboratory Manual, 2d Ed, Vols 1 to 8, Cold Spring Harbor, NY (1989); M. W. Pennington and B. M. Dunn, Methods in Molecular Biology: Peptide Synthesis Protocols, Vol 35, Humana Press, Totawa, NJ (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, NY (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, NC (2000); N. L. Benoiton, Chemistry of Peptide Synthesis, CRC Press, Boca Raton, FL (2005); J. Jones, Amino Acid and Peptide Synthesis, 2nd Ed, Oxford University Press, Cary, NC (2002); and P. Lloyd-Williams, F. Albericio, and E. Giralt, Chemical Approaches to the synthesis of peptides and proteins, CRC Press, Boca Raton, FL (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

Production and Purification of RBD Polypeptides or Mutated Coronavirus S Proteins A RBD polypeptide or mutated coronavirus S protein, as those terms are used herein, can be produced chemically by e.g., solution or solid-phase peptide synthesis, or semi-synthesis in solution beginning with protein fragments coupled through conventional solution methods, as described by Dugas et al (1981). However, it is generally preferred to synthesize the polypeptides described herein using recombinant methods.

Systems for cloning and expressing polypeptides useful with the methods and compositions described herein include various microorganisms and cells that are well known in recombinant technology and thus are not described in detail herein. These include, for example, various strains of *E. coli, Bacillus, Streptomyces*, and *Saccharomyces*, as well as mammalian, yeast and insect cells. A polypeptide as described herein can be produced as a peptide or fusion protein, if so desired. Suitable vectors for producing peptides and polypeptides are known and available from private and public laboratories and depositories and from commercial vendors. Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus expression vectors, such as vaccinia or swinepox. Suitable non-pathogenic viral expression vectors that can be engineered to carry the synthetic gene into the cells of the host include poxvirus expression vectors, such as vaccinia, adenovirus, retroviruses and the like. A number of such non-pathogenic viral expression vectors are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques.

In some embodiments, it can be desirable to isolate and/or purify a synthesized mutant polypeptide, as described herein. Protein purification techniques are well known to those of skill in the art and as such are not described in detail herein. These techniques can involve, at one level, the homogenization and crude fractionation of the cells, tissue or organ to polypeptide and non-polypeptide fractions. The mutant coronavirus spike protein or receptor binding domain polypeptide can be further purified using chromatographic and electrophoretic techniques to achieve partial or complete purification (or purification to homogeneity). Analytical methods particularly suited to the preparation of a pure peptide or polypeptide are ion-exchange chromatography, gel exclusion chromatography, polyacrylamide gel electrophoresis, affinity chromatography, immunoaffinity chromatography and isoelectric focusing. A particularly efficient method of purifying peptides/polypeptides is fast performance liquid chromatography (FPLC) or even high performance liquid chromatography (HPLC).

A "purified polypeptide" is intended to refer to a composition, isolatable from other components, wherein the mutant coronavirus S polypeptide or receptor binding domain thereof is purified to any degree relative to the organism producing recombinant protein or in its naturally-obtainable state. An isolated or purified polypeptide, therefore, also refers to a/polypeptide free from the environment in which it may naturally occur. In one embodiment, "purified" will refer to a polypeptide composition that has been subjected to fractionation to remove various other components, and which composition substantially retains the ability to bind to a coronavirus antibody that binds the native or wild-type coronavirus S protein. Where the term "substantially purified" is used, this designation will refer to a composition in which the coronavirus polypeptide forms the major component of the composition, such as constituting about 50%, about 60%, about 70%, about 80%, about 90%, about 95%, or more of the proteins in the composition.

There is no general requirement that the polypeptides described herein be provided in the most purified state. Indeed, it is contemplated that less purified products will have utility in certain embodiments. Partial purification can be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Various methods for quantifying the degree of purification of a given polypeptide are known to those of skill in the art and include, for example, determining the specific activity of an active fraction, or assessing the amount of polypeptides within a fraction by SDS/PAGE analysis.

Coronavirus Fusion Proteins and Scaffolds

In some embodiments, the receptor binding domain polypeptides or the mutated coronavirus S proteins described herein comprise a fusion protein. In some embodiments, the RBD polypeptides or mutated coronavirus S proteins described herein are fused to a scaffold, a nanoparticle, a heterologous protein scaffold, or a polymer. In certain embodiments, the heterologous protein scaffold comprises the I53-50 trimeric "A" component of SEQ ID NO: 3. In other embodiments, the heterologous protein scaffold comprises a heterologous protein scaffold as described in Table 1 of U.S. Pat. No. 10,351,603, the contents of which are incorporated by reference in its entirety.

In some embodiments, the mutant coronavirus polypeptides described herein are provided as a fusion protein. Such fusion proteins can comprise, for example, an antigenic moiety to enhance the resulting immune response. Such antigenic moieties can include a foreign molecule such as a carrier protein that is foreign to the individual to be vaccinated using the fusion proteins described herein. Foreign proteins that activate the immune response and can be conjugated to a fusion protein as described herein include proteins or other molecules with molecular weights of at least about 20,000 Daltons, preferably at least about 40,000 Daltons and more preferably at least about 60,000 Daltons. Carrier proteins useful in this context include, for example, GST, hemocyanins such as from the keyhole limpet, serum albumin or cationized serum albumin, thyroglobulin, ovalbumin, various toxoid proteins such a tetanus toxoid or diphtheria toxoid, immunoglobulins, heat shock proteins, and the like.

Methods to chemically couple one protein (e.g., a RBD polypeptide or mutated coronavirus S protein) to another protein (e.g., carrier or antigenic moiety) are well known in the art and include, for example, conjugation by a water soluble carbodiimide such as 1-ethyl-3-(3dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate and, conjugation with glutaraldehyde Protein-Based Virus-Like Particles The disclosure further provides protein-based Virus-Like Particles (VLPs). The pbVLP may comprise a receptor binding domain polypeptide or mutated coronavirus S proteins described, comprising a fusion protein, wherein the fusion protein comprises a multimerization domain, such as a "first component" as described herein.

The VLPs for use with the methods and compositions described herein can comprise multimeric protein assemblies adapted for display of the ectodomain of the RBD or an ectodomain of the coronavirus spike protein, or an antigenic fragment thereof. The VLPs for use with the methods and compositions described herein can comprise at least a first plurality of polypeptides. The first plurality of polypeptides (also referred to a "first component") can be derived from a naturally-occurring protein sequence by substitution of at least one amino acid residue or by additional at the N- or C-terminus of one or more residues. In some cases, the first component comprises a protein sequence determined by computational methods. This first component can form the entire core of the VLP; or the core of the VLP can comprise one or more additional polypeptides (also referred to a "second component" or third, fourth, fifth component and so on), such that the VLP comprises two, three, four, five, six, seven, or more pluralities of polypeptides. In some cases, the first plurality will form trimers related by 3-fold rotational symmetry and the second plurality will form pentamers related by 5-fold rotational symmetry. In such cases, the VLP forms an "icosahedral particle" having 153 symmetry. Together these one or more pluralities of polypeptides can be arranged such that the members of each plurality of polypeptides are related to one another by symmetry operators. A general computational method for designing self-assembling protein materials, involving symmetrical docking of protein building blocks in a target symmetric architecture, is disclosed in U.S. Patent Pub. No. US 2015/0356240 A1, the contents of which are incorporated herein by reference in its entirety.

The "core" of the VLP is used herein to describe the central portion of the VLP that links together the several copies of the RBD or coronavirus S protein ectodomain, or antigenic fragments thereof, displayed by the VLP. In an embodiment, the first component comprises a first polypeptide comprising an RBD, a linker, and a first polypeptide comprising a multimerization domain.

Non-limiting embodiments are shown in FIG. 6A, which depicts an RBD genetically fused to a component of the VLP, which optionally is expressed recombinantly in a host cell (e.g., 293F cells); along with a pentameric protein assembly, which is optionally expressed recombinantly in the same or a different host cell (e.g., E. coli cells), these two pluralities of polypeptides self-assembling into a VLP displaying 20 antigen trimers around an icosahedral core.

In some cases, the VLP is adapted to display the RBD or spike protein from two or more diverse strains of coronavirus. In non-limiting examples, the same VLP displays mixed populations of protein antigens or mixed heterotrimers of protein antigens from different strains of coronavirus.

The VLPs for use with the methods and compositions described herein display antigenic proteins in various ways including as gene fusion or by other means disclosed herein. As used herein, "linked to" or "attached to" denotes any means known in the art for causing two polypeptides to associate. The association can be direct or indirect, reversible or irreversible, weak or strong, covalent or non-covalent, and selective or nonselective.

In some embodiments, attachment is achieved by genetic engineering to create an N- or C-terminus fusion of an antigen to one of the pluralities of polypeptides composing the VLP. Thus, the VLP can consist of, or consist essentially of, one, two, three, four, five, six, seven, eight, nine, or ten pluralities of polypeptides displaying one, two, three, four, five, six, seven, eight, nine, or ten pluralities of antigens, where at least one of the pluralities of antigens is genetically fused to at least one of the plurality of polypeptides. In some cases, the VLP consists essentially of one plurality of polypeptides capable of self-assembly and comprising the plurality of antigenic proteins genetically fused thereto. In some cases, the VLP consists essentially of a first plurality of polypeptides comprising a plurality of antigens; and a second plurality of polypeptides capable of co-assembling into a two-component VLP, one plurality of polypeptides linking the antigenic protein to the VLP and the other plurality of polypeptides promoting self-assembly of the VLP.

In some embodiments, attachment is achieved by post-translational covalent attachment between one or more pluralities of polypeptides and one or more pluralities of antigenic protein. In some cases, chemical cross-linking is used to non-specifically attach the antigen to a VLP polypeptide. In some cases, chemical cross-linking is used to specifically attach the antigenic protein to a VLP polypeptide (e.g. to the first polypeptide or the second polypeptide). Various specific and non-specific cross-linking chemistries are known in the art, such as Click chemistry and other methods. In general, any cross-linking chemistry used to link two proteins can be adapted for use with the presently disclosed VLPs. In particular, chemistries used in creation of immunoconjugates or antibody drug conjugates may be used. In some cases, an VLP is created using a cleavable or non-cleavable linker. Processes and methods for conjugation of antigens to carriers are provided by, e.g., U.S. Patent Pub. No. US 2008/0145373 A1, the contents of which are incorporated herein by reference in its entirety.

The components of the VLP of the present disclosure can have any of various amino acids sequences. U.S. Patent Pub No. US 2015/0356240 A1 (the contents of which are incorporated herein by reference in their entirety) describes various methods for designing protein assemblies. As described in US Patent Pub No. US 2016/0122392 A1 and in International Patent Pub. No. WO 2014/124301 A1, the polypeptides were designed for their ability to self-assemble in pairs to form VLPs, such as icosahedral particles. The design involved design of suitable interface residues for each member of the polypeptide pair that can be assembled to form the VLP. The VLPs so formed include symmetrically repeated, non-natural, non-covalent polypeptide-polypeptide interfaces that orient a first assembly and a second assembly into a VLP, such as one with an icosahedral symmetry.

In some embodiments, the RBD or coronavirus S protein ectodomain, or antigenic fragments thereof, are expressed as a fusion protein with the first multimerization domain. In some embodiments, the first multimerization domain and RBD or coronavirus S protein ectodomain are joined by a linker sequence. In some embodiments, the linker sequence comprises a foldon, wherein the foldon sequence is EKAAKAEEAARK (SEQ ID NO: 8).

Non-limiting examples of designed protein complexes useful in protein-based VLPs of the present disclosure include those disclosed in U.S. Pat. No. 9,630,994; Int'l Pat. Pub No. WO2018187325A1; U.S. Pat. Pub. No. 2018/0137234 A1; U.S. Pat. Pub. No. 2019/0155988 A2, each of which is incorporated by reference herein in its entirety. Illustrative sequences are provided in Table 3.

Table 3

TABLE 3

| Name | Component Multimer | Amino Acid Sequence | Identified interface residues |
|---|---|---|---|
| I53-50A SEQ ID NO: 9 | trimer | EELFKKHKIVAVLRANSVE EAIEKAVAVFAGGVHLIEI TFTVPDADTVIKALSVLKE KGAIIGAGTVTSVEQCRKA VESGAEFIVSPHLDEEISQ FCKEKGVFYMPGVMTPTEL | I53-50A: 25, 29, 33, 54, |

TABLE 3-continued

| Name | Component Multimer | Amino Acid Sequence | Identified interface residues |
|---|---|---|---|
| | | VKAMKLGHTILKLFPGEVV GPQFVKMKGPFPNVKFVP TGGVNLDNVCEWFKAGVLA VGVGSALVKGTPDEVREKA KAFVEKIRGCTE | 57 |
| I53-50A.1 SEQ ID NO: 10 | trimer | EELFKKHKIVAVLRANSVE EAIEKAVAVFAGGVHLIEI TFTVPDADTVIKALSVLKE KGAIIGAGTVTSVEQCRKA VESGAEFIVSPHLDEEISQ FCKEKGVFYMPGVMTPTEL VKAMKLGHDILKLFPGEVV GPQFVKMKGPFPNVKFVP TGGVNLDNVCEWFKAGVLA VGVGDALVKGDPDEVREKA KKFVEKIRGCTE | I53-50A: 25, 29, 33, 54, 57 |
| I53-50A.1NegT2 SEQ ID NO: 11 | trimer | EELFKKHKIVAVLRANSVE EAIEKAVAVFAGGVHLIEI TFTVPDADTVIKALSVLKE KGAIIGAGTVTSVEQCRKA VESGAEFIVSPHLDEEISQ FCKEKGVFYMPGVMTPTEL VKAMKLGHDILKLFPGEVV GPEFVEAMKGPFPNVKFVP TGGVDLDDVCEWFDAGVLA VGVGDALVEGDPDEVREDA KEFVEEIRGCTE | I53-50A: 25, 29, 33, 54, 57 |
| I53-50A.1PosT1 SEQ ID NO: 12 | trimer | EELFKKHKIVAVLRANSVE EAIEKAVAVFAGGVHLIEI TFTVPDADTVIKALSVLKE KGAIIGAGTVTSVEQCRKA VESGAEFIVSPHLDEEISQ FCKEKGVFYMPGVMTPTEL VKAMKLGHDILKLFPGEVV GPQFVKMKGPFPNVKFVP TGGVNLDNVCKWFKAGVLA VGVGKALVKGKPDEVREKA KKFVKKIRGCTE | I53-50A: 25, 29, 33, 54, 57 |
| I53-50A genus SEQ ID NO: 13 | trimer | EELFKKHKIVAVLRANSVE EAIEKAVAVFAGGVHLIEI TFTVPDADTVIKALSVLKE KGAIIGAGTVTSVEQCRKA VESGAEFIVSPHLDEEISQ FCKEKGVFYMPGVMTPTEL VKAMKLGH(T/D)ILKLFP GEVVGP(Q/E)FV(K/E)A MKGPFPNVKFVPTGGV(N/ D)LD(N/D)VC(E/K)WF (K/D)AGVLAVGVG(S/K/ D)ALV(K/E)G(T/D/K)P DEVRE(K/D)AK(A/E/K) FV(E/K)(K/E)IRGCTE | |
| I53-50B SEQ ID NO: 14 | pentamer | NQHSHKDYETVRIAVVRAR WHAEIVDACVSAFEAAMAD IGGDRFAVDVFDVPGAYEI PLHARTLAETGRYGAVLGT AFVVNGGIYRHEEVASAVI DGMMNVQLSTGVPVLSAVL TPHRYRDSDAHTLLFLALF AVKGMEAARACVEILAARE KIAA | I53-50B: 24, 28, 36, 124, 125, 127, 128, 129, 131, 132, 133, 135, 139 |
| I53-50B.1 SEQ ID NO: 15 | pentamer | NQHSHKDHETVRIAVVRAR WHAEIVDACVSAFEAAMRD IGGDRFAVDVFDVPGAYEI PLHARTLAETGRYGAVLGT AFVVNGGIYRHEEVASAVI DGMMNVQLDTGVPVLSAVL TPHRYRDSDAHTLLFLALF AVKGMEAARACVEILAARE KIAA | I53-50B: 24, 28, 36, 124, 125, 127, 128, 129, 131, 132, 133, 135, 139 |
| I53-50B.1NegT2 SEQ ID NO: 16 | pentamer | NQHSHKDHETVRIAVVRAR WHAEIVDACVSAFEAAMRD IGGDRFAVDVFDVPGAYEI PLHARTLAETGRYGAVLGT AFVVDGGIYDHEFVASAVI DGMMNVQLDTGVPVLSAVL TPHEYEDSDADTLLFLALF AVKGMEAARACVEILAARE KIAA | I53-50B: 24, 28, 36, 124, 125, 127, 128, 129, 131, 132, 133, 135, 139 |
| I53-50B.4PosT1 I53-50B.4PT1 SEQ ID NO: 17 | trimer | NQHSHKDHETVRIAVVRAR WHAEIVDACVSAFEAAMRD IGGDRFAVDVFDVPGAYEI PLHARTLAETGRYGAVLGT AFVVNGGIYRHEEVASAVI NGMMNVQLNTGVPVLSAVL TPHNYDKSKAHTLLFLALF AVKGMEAARACVEILAARE KIAA | I53-50B: 24, 28, 36, 124, 125, 127, 128, 129, 131, 132, 133, 135, 139 |
| I53-50B genus SEQ ID NO: 18 | pentamer | NQHSHKD(Y/H)ETVRIAV VRARWHAEIVDACVSAFEA AM(A/R)DIGGDRFAVDVF DVPGAYEIPLHARTLAETG RYGAVLGTAFVV(N/D)GG IY(R/D)HEFVASAVI(D/ N)GMMNVQL(S/D/N)TGV PVLSAVLTPH(R/E/N)Y (R/D/E)(D/K)S(D/K) A(H/D)TLLFLALFAVKGM EAARACVEILAAREKIAA | |
| I53_dn5A SEQ ID NO: 20 | | KYDGSKLRIGILHARWNAE IILALVLGALKRLQEFGVK RENIIIETVPGSFELPYGS KLFVEKQKRLGKPLDAIIP IGVLIKGSTMHFEYICDST THQLMKLNFELGIPVIEGV LTCLTDEQAEARAGLIEGK MHNHGEDWGAAAVEMATKF N | |
| I53_dn5B SEQ ID NO: 19 | | EEAELAYLLGELAYKLGEY RIAIRAYRIALKRDPNNAE AWYNLGNAYYKQGRYREAI EYYQKALELDPNNAEAWYN LGNAYYERGEYEEAIEYYR KALRLDPNNADAMQNLLNA KMREE | |

In some embodiments, the VLP comprises a fusion protein that has at least 95%, at least 96%, at least 97%, at least 98%, at least 991%, or 100% identity to any one of SEQ ID NOs: 9-13 and comprises an RBD or coronavirus spike protein as disclosed herein; and a second component that has at least 95%, at least 96%, at least 97%, at least 98%, at least 99%, or 100% identity to any one of SEQ ID NOs: 13-18.

In some embodiments, the VLP comprises a fusion protein that has at least 95%, at least 96%, at least 97%, at least 98%, at least 99%, or 100% identity to SEQ ID NO: 19 and comprises an RBD or coronavirus spike protein as disclosed herein; and a second component that has at least 95%, at least 96%, at least 97%, at least 98%, at least 99%, or 100% identity to SEQ ID NO: 20.

In some embodiments, the polypeptides as disclosed herein comprise the polypeptide sequence of SEQ ID NO: 6 or SEQ ID NO: 7.

```
                                                  (SEQ ID NO: 6)
RFPNITNLCPFGEVFNATRFASVYAWNRKRISNCVADFSVLYNSASFSTF

KCYGVSPTKLNDLCWTNIYADSFVIRGDEVRQIAPGQTGKIADYNYKLPD

DFTGCVIAWNSNNLDSKVGGNYNYLYRLFRKSNLKPFERDISTEIYQAGS

TPCNGVEGFNCYFPLQSYGFQPTYGVGYQPYRVVVLSFELLHAPATVCGP

KKSTGGSGGSGSGGSGGSGSEKAAKAEEAARKMEELFKKHKIVAVLRANS

VEEATEKAVAVFAGGVHLIEITFTVPDADTVIKALSVLKEKGAIIGAGTV

TSVEQARKAVESGAEFIVSPHLDEEISQFAKEKGVFYMPGVMTPTELVKA

MKLGHTILKLFPGEVVGPQFVKAMKGPFPNVKFVPTGGVNLDNVAEWFKA

GVLAVGVGSALVKGTPDEVREKAKAFVEKIRGATE (SEQ ID NO: 7)
RFPNITNLCPFGEVFNATRFASVYAWNRKRISNCVADFSVLYNSASFSTF

KCYGVSPTKLNDLCWTNIYADSFVIRGDEVRQIAPGQTGNIADYNYKLPD

DFTGCVIAWNSNNLDSKVGGNYNYLYRLFRKSNLKPFERDISTEIYQAGS

TPCNGVKGFNCYFPLQSYGFQPTYGVGYQPYRVVVLSFELLHAPATVCGP

KKSTGGSGGSGSGGSGGSGSEKAAKAEEAARKMEELFKKHKIVAVLRANS

VEEATEKAVAVFAGGVHLIEITFTVPDADTVIKALSVLKEKGAIIGAGTV

TSVEQARKAVESGAEFIVSPHLDEEISQFAKEKGVFYMPGVMTPTELVKA

MKLGHTILKLFPGEVVGPQFVKAMKGPFPNVKFVPTGGVNLDNVAEWFKA

GVLAVGVGSALVKGTPDEVREKAKAFVEKIRGATE
```

Protein Stability

Most biological products are prone to degradation such as thermal, photochemical, or oxidative degradation. Because biological products such as vaccines and insulin need to be distributed worldwide, and because ambient temperatures in different regions vary greatly, vaccines with an enhanced shelf-life (or stabilized proteins therein) are preferred over proteins/compositions that rapidly degrade. Increased intracellular stability can also provide greater yields of recombinant proteins. The mutated coronavirus spike proteins or receptor binding domains thereof as described herein have increased stability as compared to their wild-type counterparts. The stability of these proteins can be determined using one or more assays known in the art or using the methods described in the working Examples. Exemplary protein stability assays include, but are not limited to, differential scanning calorimetry, pulse-chase method, bleach chase method, cyclohexamide-chase method, circular dichroism spectroscopy, and fluorescence-based activity assays.

The stability of a given composition, also referred to herein as "shelf-life" of the composition when applied to an isolated preparation or a vaccine preparation, depends on the conditions in which the composition is stored as well as the formulation of the composition (e.g., addition of chemical components) or the physical state in which the composition is provided (e.g., lyophilized, dried, frozen, etc).

The term "lyophilization," or "lyophilized" as used herein, refers to a dehydration process, commonly referred to as "freeze drying" used to preserve a composition as described herein or make the composition more convenient for storage and transport. Freeze-drying works by freezing the composition and then reducing the surrounding pressure to allow the frozen water in the composition to sublimate directly from the solid phase to the gas phase. In some embodiments, lyophilization can be used to preserve vaccine compositions as described herein, thereby allowing the vaccine compositions to be portable and to be stored at room temperature without the need of refrigeration.

In addition to the increased stability of the antigen provided by the mutations described herein, the addition of anti-oxidants or other agents that aim to increase shelf-life of vaccine compositions are also contemplated herein. In some embodiments, the compositions described herein are contemplated to be stored at room temperature and avoid the need for refrigeration.

Regardless of the method of storage, the mutated coronavirus spike proteins or RBDs thereof will have both an increase in the protein stability and composition shelf-life over the protein stability and composition shelf-life for the corresponding wild-type coronavirus spike protein or RBD thereof.

Formulations comprising the mutated coronavirus proteins or peptides described herein are stable in that their characteristics change little over a given period of time at a defined temperature. In general, formulations as described herein are stable for at least about a month. In some embodiments, the formulations are stable for at least about 6 weeks, at least about 2 months, at least about 4 months, at least about 6 months, at least about 8 months, at least about 10 months, at least about 12 months (1 year), at least about 14 months, at least about 16 months, at least about 18 months (1.5 years), at least about 20 months, at least about 22 months, at least about 24 months (2 years), at least about 26 months, at least about 28 months, at least about 30 months, at least about 32 months, at least about 34 months, at least about 36 months (3 years), at least about 38 months, at least about 40 months, at least about 42 months, at least about 44 months, at least about 46 months or at least about 48 months (4 years).

The temperatures over which a formulation is stable are generally below about 30° C. In some embodiments, the formulation's stability is in reference to a temperature below about 25° C., about 20° C., about 15° C., about 10° C., about 8° C., about 5° C., about 4° C., or about 2° C. Thus, in some embodiments, the temperature is in the range of about 25° C. to about 2° C., about 20° C. to about 2° C., about 15° C. to about 2° C., about 10° C. to about 2° C., about 8° C. to about 2° C., or about 5° C. to about 2° C. In other embodiments, the temperature is in the range of about 25° C. to about 5° C., about 20° C. to about 5° C., about 15° C. to about 5° C., about 10° C. to about 5° C., or about 8° C. to about 5° C. In still other embodiments, the temperature is in the range of about 25° C. to about 8° C., about 20° C. to about 8° C., about 15° C. to about 8° C., or about 10° C. to about 8° C.

In yet other embodiments, the temperature is in the range of about 25° C. to about 10° C., about 20° C. to about 10° C., about 15° C. to about 10° C., about 25° C. to about 15° C., about 20° C. to about 15° C., or about 25° C. to about 20° C. In some embodiments, the composition can be stored at 4° C. or −20° C. for longer term storage.

Vaccine Compositions

The RBD polypeptides, mutated coronavirus S proteins or fusion proteins comprising the same as described herein can be used in the production of a vaccine formulation. Such vaccine formulations can provide protection against each of the seven coronaviruses known to infect humans individually, or can provide protection against at least 2, at least 3, at least 4, at least 5, or at least 6 of the seven coronaviruses known to infect humans. In one embodiment, a vaccine formulation as described herein can provide protection against all 7 of the coronaviruses known to infect humans. It is also specifically contemplated herein that the vaccine formulations described herein can provide protection against coronaviruses that are expected to move from an animal species (e.g., bats) to humans in the future. In other embodiments, the vaccine formulations described herein can provide protection of an animal against one or more coronaviruses to which they are susceptible. RNA and/or DNA vaccine formulations encoding the mutated spike protein polypeptides described herein are also specifically contemplated herein.

In some embodiments, the immunity generated against the coronavirus antigens described herein is long lasting (e.g., at least 2 years, at least 5 years, at least 10 years, at least 20 years, at least 30 years, at least 40 years, or even for the entire lifespan of the subject). Alternatively, in some embodiments, it is contemplated herein that the vaccine formulations as described herein are administered on an annual basis, tailored to prevalent or predicted prevalent strains of the target virus, analogous to immunization with the influenza vaccine, and can provide protection for at least 3 months from the last administration, at least 6 months, at least 8 months, at least one year, at least 1.5 years, or at least two years.

One of skill in the art will recognize that 100% efficacy of a coronavirus vaccine formulation is not required in order to impart community-based immunity or herd immunity to the one or more coronaviruses. Thus, in some embodiments, the vaccine formulations described herein are at least 40% effective in a population of vaccinated individuals, e.g., at least 50%, at least 60%, at least 70%, at least 80%, at least 90%, at least 95%, at least 99% effective in a population of vaccinated individuals.

In some embodiments, in an effort to reduce community transmission and to prevent/control coronavirus infection and spread, the vaccines described herein can be administered as a universal vaccination to healthy children and individuals. Children can play an important role in the transmission of coronavirus within schools, families and communities, particularly because they tend to have milder symptoms and are not necessarily diagnosed as having a coronavirus infection. Studies with influenza vaccines have shown that vaccination of approximately 80% of schoolchildren in a community has decreased respiratory illnesses in adults and excess deaths in the elderly (Reichert et al., 2001). This concept is known as community immunity or "herd immunity" and is thought to play an important part of protecting the community against disease. Because vaccinated people have antibodies that neutralize a particular virus, they are much less likely to transmit the virus to other people. This concept can be applied to coronavirus infections as well. Thus, even people who have not been vaccinated (and those whose vaccinations have become weakened or whose vaccines are not fully effective) often can be shielded by the herd immunity because vaccinated people around them are not getting sick or transmitting the virus. Herd immunity is more effective as the percentage of people vaccinated increases. It is thought that approximately 60% (but preferably closer to 90-95%) of the people in the community must be protected by a vaccine to achieve herd immunity. People who are not immunized increase the chance that they and others will get the disease.

Thus, provided herein in another aspect is a method of inducing a substantially protective immunity to coronavirus infection to a population or a community in order to reduce the incidence of coronavirus infections among immunocompromised individuals or non-vaccinated individuals by administering the vaccine formulations described herein to a population in a community. In one embodiment, most school-aged children are immunized against a coronavirus infection by administering a vaccine as described herein (e.g., at least 50%, at least 60%, at least 70%, at least 80%, at least 90%, at least 95% or more of school-aged children are immunized). In another embodiment, most healthy individuals in a community (e.g., at least 50%, at least 60%, at least 70%, at least 80%, at least 90%, at least 95% or more) are immunized against a given coronavirus or group of coronaviruses by administering a vaccine as described herein. In another embodiment, the vaccines described herein can be used as part of a "dynamic vaccination" strategy. Dynamic vaccination is the steady production of a low-efficacy vaccine that is related to an emerging or existing pandemic strain, but due to an antigenic drift may not provide complete protection in a mammal (see Germann et al., 2006). Because of the uncertainty about the future identity of a pandemic strain, it is almost impossible to stockpile a well matched pandemic strain. However, vaccination with a poorly matched but potentially efficacious vaccine may slow the spread of the pandemic virus and/or reduce the severity of symptoms of a pandemic strain of coronavirus. In one embodiment, a vaccine as described herein is directed against one or more strains of SARS-CoV-2 that are responsible for the 2019/2020 COVID-19 pandemic.

The vaccine formulations described herein can prevent at least one of the symptoms associated with the coronavirus infection or can completely prevent presentation of any symptom. Common symptoms of a coronavirus infection include, but are not limited to, fever, chills, cough, shortness of breath/difficulty breathing, fatigue, muscle/body aches, headache, new loss of taste or smell, sore throat, congestion or runny nose, nausea, vomiting, or diarrhea. A reduction in a symptom may be determined subjectively or objectively, e.g., self-assessment by a subject, by a clinician's assessment or by conducting an appropriate assay or measurement (e.g. body temperature, degree of pneumonia infection, lung scarring etc.), including, e.g., a quality of life assessment, a slowed progression of a coronavirus infection or additional symptoms, a reduced severity of coronavirus-associated disease symptoms or a suitable assays (e.g. antibody titer and/or T-cell activation assay).

Preferably, the vaccine formulations described herein will reduce transmission of active coronavirus from a vaccinated individual to others within a community of individuals or between two different individuals by at least 40%, at least 50%, at least 60%, at least 70%, at least 80%, at least 90%, at least 95%, at least 99% or even 100% (i.e., no detectable transmission among a vaccinated individual and two or more individuals).

In some embodiments, the vaccine formulations described herein comprise one or more adjuvants. Non-limiting examples of adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one aspect, an adjuvant effect is achieved by use of an agent, such as alum, used in about 0.05 to about 0.1% solution in phosphate buffered saline. Alternatively, vaccines as described herein can be made as an admixture with synthetic polymers of sugars (Carbopol®) used as an about 0.25% solution. Some adjuvants, for example, certain organic molecules obtained from bacteria, act on the host rather than on the antigen. An example is muramyl dipeptide (N-acetylmuramyl-L-alanyl-D-isoglutamine (MDP)), a bacterial peptidoglycan. In other embodiments, hemocyanins and hemoerythrins may also be used with the vaccine formulations as described herein. Hemocyanin from keyhole limpet (KLH) can be used in certain embodiments, although other molluscan and arthropod hemocyanins and hemoerythrins may be used in alternative embodiments.

Various polysaccharide adjuvants can also be used. For example, the effect of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin. In another embodiment, one can use a lipophilic disaccharide-tripeptide derivative of muramyl dipeptide, which is described for use in artificial liposomes formed from phosphatidyl choline and phosphatidyl glycerol.

Amphipathic and surface active agents, e.g., saponin and derivatives such as QS21 (Cambridge Biotech), form yet another group of adjuvants for use in vaccine formulations as described herein. Nonionic block copolymer surfactants (Rabinovich et al., 1994) can also be used. Oligonucleotide adjuvants (Yamamoto et al., 1988), Quil A and lentinen are other adjuvants that can be used in certain embodiments.

In addition, refined detoxified endotoxins can be used to produce an adjuvant response in vertebrates, either alone or in a multi-adjuvant formulation. For example, a combination of detoxified endotoxins with trehalose dimycolate or a combination of detoxified endotoxins with trehalose dimycolate and endotoxic glycolipids are contemplated herein. Alternatively, a combination of detoxified endotoxins with cell wall skeleton (CWS) or CWS and trehalose dimycolate or combinations of just CWS and trehalose dimycolate, without detoxified endotoxins are also contemplated.

Those of skill in the art will know the different kinds of adjuvants that can be conjugated to or admixed with vaccines as described herein, and these include alkyl lysophospholipids (ALP); BCG; and biotin (including biotinylated derivatives) among others. Certain adjuvants particularly contemplated for use are the teichoic acids from Gram negative bacterial cells. These include the lipoteichoic acids (LTA), ribitol teichoic acids (RTA) and glycerol teichoic acid (GTA). Active forms of their synthetic counterparts can also be used.

Various adjuvants, even those that are not commonly used in humans, are envisioned for use in vaccines for other vertebrates.

Vaccine formulations can comprise a coronavirus polypeptide as described herein or a fusion protein thereof that is microencapsulated or macroencapsulated, using methods well known in the art (e.g., liposomes (see, for example, Garcon and Six, J. Immunol. 146:3697 (1991)), into, for example, the inner capsid protein of bovine rotavirus (Redmond et al., Mol. Immunol. 28:269 (1991)) into immune stimulating molecules (ISCOMS) composed of saponins such as Quil A (Morein et al., Nature 308:457 (1984)); Morein et al., in Immunological Adjuvants and Vaccines (G. Gregoriadis al. eds.) pp. 153-162, Plenum Press, NY (1987)) or into controlled-release biodegradable microspheres composed, for example, of lactide-glycolide copolymers (O'Hagan et al., Immunology 73:239 (1991); O'Hagan et al., Vaccine 11:149 (1993)).

The stabilized coronavirus polypeptides described herein or fusion proteins thereof can also be adsorbed to the surface of lipid microspheres containing squalene or squalane emulsions prepared with a PLURONIC block-copolymer such as L-121 and stabilized with a detergent such as TWEEN 80 (see Allison and Byers, Vaccines: New Approaches to Immunological Problems (R. Ellis ed.) pp. 431-449, Butterworth-Hinemann, Stoneman N.Y. (1992)).

Vaccine formulations described herein comprise a stabilized coronavirus polypeptide as described herein or fusion proteins thereof in an "effective amount" or a "therapeutically effective amount." As used herein, the phrase "effective amount" or "therapeutically effective amount" refers to a dose sufficient to provide concentrations high enough to generate (or contribute to the generation of) an immune response in the recipient thereof. The specific effective dose level for any particular subject will depend upon a variety of factors including the disorder being treated, the severity of the disorder, the activity of the specific compound, the route of administration, the rate of clearance of the administered agent(s), the duration of treatment, the drugs used in combination or coincident with the administered agent(s), the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

The pH of the formulation can also vary. In general, it is between about pH 6.2 to about pH 8.0. In some embodiments, the pH is about 6.2, about 6.4, about 6.6, about 6.8, about 7.0, about 7.2, about 7.4, about 7.6, about 7.8, or about 8.0. Of course, the pH may also be within a range of values. Thus, in some embodiments the pH is between about 6.2 and about 8.0, between about 6.2 and 7.8, between about 6.2 and 7.6, between about 6.2 and 7.4, between about 6.2 and 7.2, between about 6.2 and 7.0, between about 6.2 and 6.8, between about 6.2 and about 6.6, or between about 6.2 and 6.4. In other embodiments, the pH is between 6.4 and about 8.0, between about 6.4 and 7.8, between about 6.4 and 7.6, between about 6.4 and 7.4, between about 6.4 and 7.2, between about 6.4 and 7.0, between about 6.4 and 6.8, or between about 6.4 and about 6.6. In still other embodiments, the pH is between about 6.6 and about 8.0, between about 6.6 and 7.8, between about 6.6 and 7.6, between about 6.6 and 7.4, between about 6.6 and 7.2, between about 6.6 and 7.0, or between about 6.6 and 6.8. In yet other embodiments, it is between about 6.8 and about 8.0, between about 6.8 and 7.8, between about 6.8 and 7.6, between about 6.8 and 7.4, between about 6.8 and 7.2, or between about 6.8 and 7.0. In still other embodiments, it is between about 7.0 and about 8.0, between about 7.0 and 7.8, between about 7.0 and 7.6, between about 7.0 and 7.4, between about 7.0 and 7.2, between about 7.2 and 8.0, between about 7.2 and 7.8, between about 7.2 and about 7.6, between about 7.2 and 7.4, between about 7.4 and about 8.0, about 7.4 and about 7.6, or between about 7.6 and about 8.0.

In some embodiments, the formulation can include one or more salts, such as sodium chloride, sodium phosphate, or a combination thereof. In general, each salt is present in the formulation at about 10 mM to about 200 mM. Thus, in some embodiments, any salt that is present is present at about 10 mM to about 200 mM, about 20 mM to about 200 mM, about 25 mM to about 200 mM, at about 30 mM to about 200 mM, at about 40 mM to about 200 mM, at about 50 mM to about 200 mM, at about 75 mM to about 200 mM, at about 100 mM to about 200 mM, at about 125 mM to about 200 mM, at about 150 mM to about 200 mM, or at about 175 mM to about 200 mM. In other embodiments, any salt that is present is present at about 10 mM to about 175 mM, about 20 mM to about 175 mM, about 25 mM to about 175 mM, at about 30 mM to about 175 mM, at about 40 mM to about 175 mM, at about 50 mM to about 175 mM, at about 75 mM to about 175 mM, at about 100 mM to about 175 mM, at about 125 mM to about 175 mM, or at about 150 mM to about 175 mM. In still other embodiments, any salt that is present is present at about 10 mM to about 150 mM, about 20 mM to about 150 mM, about 25 mM to about 150 mM, at about 30 mM to about 150 mM, at about 40 mM to about 150 mM, at about 50 mM to about 150 mM, at about 75 mM to about 150 mM, at about 100 mM to about 150 mM, or at about 125 mM to about 150 mM. In yet other embodiments, any salt that is present is present at about 10 mM to about 125 mM, about 20 mM to about 125 mM, about 25 mM to about 125 mM, at about 30 mM to about 125 mM, at about 40 mM to about 125 mM, at about 50 mM to about 125 mM, at about 75 mM to about 125 mM, or at about 100 mM to about 125 mM. In some embodiments, any salt that is present is present at about 10 mM to about 100 mM, about 20 mM to about 100 mM, about 25 mM to about 100 mM, at about 30 mM to about 100 mM, at about 40 mM to about 100 mM, at about 50 mM to about 100 mM, or about 75 mM to about 100 mM. In yet other embodiments, any salt that is present is present at about 10 mM to about 75 mM, about 20 mM to about 75 mM, about 25 mM to about 75 mM, at about 30 mM to about 75 mM, at about 40 mM to about 75 mM, or at about 50 mM to about 75 mM. In still other embodiments, any salt that is present is present at about 10 mM to about 50 mM, about 20 mM to about 50 mM, about 25 mM to about 50 mM, at about 30 mM to about 50 mM, or at about 40 mM to about 50 mM. In other embodiments, any salt that is present is present at about 10 mM to about 40 mM, about 20 mM to about 40 mM, about 25 mM to about 40 mM, at about 30 mM to about 40 mM, at about 10 mM to about 30 mM, at about 20 mM to about 30, at about 25 mM to about 30 mM, at about 10 mM to about 25 mM, at about 20 mM to about 25 mM, or at about 10 mM to about 20 mM. In one embodiment, the sodium chloride is present in the formulation at about 100 mM. In one embodiment, the sodium phosphate is present in the formulation at about 25 mM.

Formulations comprising the mutated coronavirus proteins described herein may further comprise a solubilizing agent such as a nonionic detergent. Such detergents include, but are not limited to polysorbate 80 (Tween® 80), TritonX100 and polysorbate 20.

Vaccine Administration and Efficacy

Vaccine formulations as described herein can further comprise a pharmaceutically acceptable carrier, including any suitable diluent or excipient, which includes any pharmaceutical agent that does not itself induce the production of an immune response harmful to the vertebrate receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans. These compositions can be useful as a vaccine and/or antigenic compositions for inducing a protective immune response in a vertebrate.

Pharmaceutically acceptable carriers or excipients include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the coronavirus vaccines described herein are administered in an effective amount or quantity sufficient to stimulate an immune response against one or more strains of coronavirus. Preferably, administration of a vaccine formulation elicits substantial immunity against at least one coronavirus. Typically, the dose can be adjusted based on, e.g., age, physical condition, body weight, sex, diet, time of administration, and other clinical factors.

While stimulation of substantial immunity with a single dose is preferred, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against a coronavirus infection. Similarly, adults who are particularly susceptible to serious disease or repeat infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

A prophylactic vaccine formulation can be systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery can result in an immune response, intranasal administration may confer the added benefit of eliciting mucosal immunity at one of the sites of entry of the coronavirus.

Non-limiting methods of administering a vaccine formulation as described herein include, but are not limited to, parenteral administration (e.g., intradermal, intramuscular, intravenous and subcutaneous), epidural, and mucosal (e.g., intranasal and oral or pulmonary routes or by suppositories). In a specific embodiment, vaccine compositions as described herein are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a vaccine composition as described herein may induce an antibody or other immune response that is substantially higher than other routes of administration. In another embodiment, intranasal or other mucosal routes of administration of a vaccine composition as described herein may induce an antibody or other immune response that will induce cross protection against other strains of coronaviruses. Administration can be systemic or local. In some embodiments, the vaccine formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccine formulations as described herein can also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the coronavirus include the guinea pig, Syrian hamster, chinchilla, hedgehog, chicken, rat, mouse, pig, bovine, bat and ferret. Bats in particular are thought to be a natural host to coronaviruses and can be particularly useful in researching or testing vaccines. However, any of the above animals can be dosed with a vaccine formulation as described herein, to partially characterize the immune response induced, and/or to determine if any neutralizing antibodies have been produced.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

Another method of inducing or enhancing an immune response can be accomplished by preparing a vaccine composition as described herein to include one or more immunes stimulators, such as one or more cytokines, lymphokines or chemokines with immunostimulatory, immunopotentiating, and/or pro-inflammatory activities (e.g., interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.) Such immunostimulatory molecules can be administered in the same formulation as the coronavirus vaccine formulation, or can be administered separately.

The RBD polypeptides or stabilized coronavirus spike proteins described herein can be used in vaccine formulations that can induce substantial immunity in a vertebrate (e.g. a human) when administered to the vertebrate. The substantial immunity results from an immune response against the RBD polypeptides or stabilized coronavirus spike proteins and protects against or ameliorates coronavirus infection or at least reduces a symptom of a coronavirus virus infection in said vertebrate. In some instances, a vaccinated subject that subsequently becomes infected will be asymptomatic. However, the response may be not a fully protective response and a partial immune response is also contemplated herein. For example, a partially protected subject that is subsequently infected with a coronavirus will experience reduced severity of symptoms or a shorter duration of symptoms compared to a non-immunized vertebrate. For example, a subject vaccinated with a formulation comprising a SARS-CoV-2 stabilized spike protein may not require a lengthy hospitalization stay or the use of a ventilator to treat COVID-19.

In one embodiment, provided herein are methods of inducing substantial immunity to infection by one or more coronaviruses or at least one symptom thereof in a subject, comprising administering at least one effective dose of a vaccine formulation comprising a RBD polypeptide or stabilized coronavirus S protein as described herein. In another embodiment, said induction of substantial immunity reduces the duration of coronavirus-associated disease symptoms (e.g., SARS, COVID-19).

In one embodiment, a vaccine formulation as described herein can elicit an immune response that will provide protection against more than one strain of coronavirus. This cross-protection of a vertebrate with a stabilized coronavirus S protein or an RBD polypeptide constructed from a particular strain, of a particular subgroup, can induce cross-protection against coronaviruses of different strains and/or subgroups.

Kits

Also provided herein are kits for vaccination of an individual or animal comprising one or more containers filled with one or more of the ingredients of the vaccine formulations as described herein. In one embodiment, the kit comprises two containers, one containing the stabilized coronavirus polypeptides or fusion proteins thereof and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The vaccine formulation be packaged in a hermetically sealed container such as an ampoule or sachette indicating the quantity of composition. In one embodiment, the vaccine composition is supplied as a liquid, in another embodiment, as a dry sterilized lyophilized powder or water free concentrate in a hermetically sealed container and can be reconstituted, e.g., with water or saline to the appropriate concentration for administration to a subject. In some embodiments, the vaccine composition is supplied as a dry sterile lyophilized powder in a hermetically sealed container at a unit dosage of preferably, about 1 µg, about 5 µg, about 10 µg, about 20 µg, about 25 µg, about 30 µg, about 50 µg, about 100 µg, about 125 µg, about 150 µg, or about 200 µg. Alternatively, the unit dosage of the vaccine composition is less than about 1 µg, (for example about 0.08 µg, about 0.04 µg; about 0.2 µg, about 0.4 µg, about 0.8 µg, about 0.5 µg or less, about 0.25 µg or less, or about 0.1 µg or less), or more than about 125 µg, (for example about 150 µg or more, about 250 µg or more, or about 500 µg or more). These doses can be measured as total coronavirus polypeptides or as µg of HA. The vaccine composition should be administered within about 12 hours, preferably within about 6 hours, within about 5 hours, within about 3 hours, or within about 1 hour after being reconstituted from the lyophilized powder.

In an alternative embodiment, a vaccine composition as described herein is supplied in liquid form in a hermetically sealed container indicating the quantity and concentration of the composition. Preferably, the liquid form of the vaccine composition is supplied in a hermetically sealed container at least about 50 µg/ml, more preferably at least about 100 µg/ml, at least about 200 µg/ml, at least 500 µg/ml, or at least 1 mg/ml.

EXAMPLES

Example 1

An ideal protein-based coronavirus vaccine must be both highly effective and scalably manufacturable, with the latter property largely being affected by vaccine yield and stability. Genetic vaccines using RNA or DNA immunization are also being more frequently explored against SARS-CoV-2, with their efficacy being influenced by expression levels of the target antigen. The receptor binding domain (RBD) of many coronaviruses, most particularly SARS-CoV-2 and related sarbecoviruses, is considered to be a highly valuable domain-based vaccine target due to the isolation of many RBD-directed antibodies that are potently neutralizing. While the RBD is amenable to production in many forms, limitations to its yield and stability could hinder the scalable manufacturing and distribution of RBD-based protein vaccines.

Provided herein are exemplary mutations in a coronavirus receptor binding domain (RBD) polypeptide designed to enhance yield and stability of immunogens containing such coronavirus RBDs. Immunogens containing the receptor binding domain were generated with sets of stabilizing mutations that demonstrate highly improved expression and/or yield, in addition to improved stability in solution compared to equivalent immunogens with native (i.e., wild-type) RBD sequences. As can be understood by those of skill in the art, increased expression of a given protein can be due, in part, to the improved stability of the protein. The designed immunogens are antigenically intact as validated by SARS-CoV-2-directed antibodies and the ACE2 receptor. Collectively, these sets of mutations allow for improved ability to scalably manufacture vaccines against diverse coronaviruses, which could also assist the performance of genetic vaccines directed to the RBD.

Base sequence and mutation numbers: The SARS-CoV-2 sequence (SEQ ID NO: 1) is used throughout the specification as the basis for mutation numbering in other coronaviruses. The receptor binding domain of the SARS-CoV-2 sequence is shown below with bold, underlined text (SEQ ID NO: 2): The following sequence (or receptor binding domain thereof; SEQ ID NO: 2) can be aligned with at least a second coronavirus sequence.

MFVFLVLLPLVSSQCVNLTTRTQLPPAYTNSFTR-GVYYPDKVFRSSVLHSTQDLFLPFFSNVTWFHAI HVSGTNGTKRFDNPVLPFNDGVYFASTEKSNIIR-GWIFGTTLDSKTQSLLIVNNATNVVIKVCEFQFC NDPFLGVYYHKNNKSWMESEFRVYSSANNCT-FEYVSQPFLMDLEGKQGNFKNLREFVFKNID-GYFKIY SKHTPINLVRDLPQGFSALEPLVDLPIG-INITRFQTLLALHRSYLTPGDSSSGWTAGAAAY-YVGYLQP RTFLLKYNENGTITDAVDCALDPL-SETKCTLKSFTVEKGIYQTSNFRVQPTESIV RFPNITNLCPFGE VFNATRFASVYANNRKRISNC-VADYSVLYNSASFSTFXCYGVSPTXLNDLCFTN-VYADSFVIRGDZVR QIAPGQTGKIADYNYKLP DDFGCVIANNSNNLDSKVGGNYLYRLFRKSNLP FZRDISTZIYQAG STPCNGVEGFNCYFPLQSYGF QPTNGVGYQPYRVVVLSFLLRHAATVCGPKK-STNLVKNKCVNFNFN GLTGTGVLTESNKKFLP FQQFGRDIADTTDAVRDPQTLEILDITPCSFGGVS VITPGTNTSNQVAVLY QDVNCTEVPVAIHADQL TPTWRVYSTGSNVFQTRAGCLIGAEHVNN-SYECDIPIGAGICASYQTQTNS PRRARSVASQSI-IAYTMSLGAENSVAYSNNSIAIPTNFTISVTTEIL-PVSMTKTSVDCTMYICGDSTE CSNLLLQYG SFCTQLNRALTGIAVEQDKNTQEVFAQVKQI YKTPPIKDFGGFNFSQILPDPSKPSKRS FIEDLL-FNKVTLADAGFIKQYGDCLGDIAARDLICAQ KFNGLTVLPPLLTDEMIAQYTSALLAGTITS GWTFGAGAALQIPFAMQMAYRFNGIGVTQNV LYENQKLIANQFNSAIGKIQDSLSSTASAL-GKLQDVV NQNAQALNTLVKQLSSNFGAIS-SVLNDILSRLDKVEAEVQIDRLITGRLQSLQTY VTQQLIRAAEIRA SANLAATKMSECVLGQSKR VDFCGKGYHLMSFPQSAPHGVVFLHVTYVPAQ EKNFTTAPAICHDGKAH FPREGVFVSNGTH-WFVTQRNFYEPQIITTDNTFVSGNCDVVI-GIVNNTVYDPLQPELDSFKEELDKYF KNHT-SPDVDLGDISGINASVVNIQKEIDRLNEVAKNLN ESLIDLQELGKYEQYIKWPWYIWLGFIAGL

IAIVMVTIMLCCMTSCCSCLKGCCSCGSCCKFD
EDDSEPVLKGVKLHYT (SEQ ID NO: 54)

An exemplary list of mutations that can enhance both yield and stability of a coronavirus protein is provided in the following list (all amino acid residue numbers are based on the "base sequence" above (SEQ ID NO: 1):

1. F338L/Y365W,
2. Y365W/L513M,
3. Y365W/F392W,
4. F338M/A363L/Y365F/F377V,
5. Y365F/F392W,
6. Y365F/V395I,
7. Y365F/F392W/V395I,
8. Y365W/L513I/F515L,
9. F338L/A363L/Y365M,
10. F338L/I358F/Y365W,
11. I358F/Y365W/L513M,
12. I358F/Y365W/F392W,
13. F338M/I358F/A363L/Y365F/F377V,
14. I358F/Y365F/F392W,
15. I358F/Y365F/V395I,
16. I358F/Y365F/F392W/V395I,
17. I358F/Y365W/L513I/F515L,
18. F338L/I358F/A363L/Y365M,
19. I358F/Y365W, and
20. I358F/F392W.

Materials and Methods

Expression and protein purification: Genes encoding mutant receptor binding domains (native receptor binding domain residues 328-531 of SEQ ID NO: 1, or equivalent sequence from variants, e.g., the B.1.351 variant) genetically fused to the I53-50 trimeric "A" component with a 16 residue linker were cloned in the pCMV/R vector using the XbaI and AvrII restriction sites.

The sequence of the I53-50 trimeric "A" component is:

(SEQ ID NO: 3)
MKMEELFKKHKIVAVLRANSVEEAIEKAVAVFAGGVHLIEITFTVP

DADTVIKALSVLKEKGAIIGAGTVTSVEQCRKAVESGAEFIVSPHLD

EEISQFCKEKGVFYMPGVMTPTELVKAMKLGHTILKLFPGEVVGPQ

FVKAMKGPFPNVKFVPTGGVNLDNVCEWFKAGVLAVGVGSALVK

GTPDEVREKAKAFVEKIRGCTE

All sequences were preceded by a "MGILPSPGM-PALLSLVSLLSVLLMGCVAETGT" (SEQ ID NO: 48) secretion signal and C-terminally tagged with a "GGSHHHHHHHH" (SEQ ID NO: 49) sequence to allow for purification. In some embodiments, the N-terminal methionine of the I53-50 trimeric component is replaced with the helical sequence "EKAAKAEEAAR" (SEQ ID NO: 50) to improve accessibility of the antigen. All cysteines in the I53-50 trimeric component were mutated to alanine. The human ACE2 ectodomain was genetically fused to a sequence encoding a thrombin cleavage site and a human Fc fragment at the C-terminal end. hACE2-Fc was synthesized and cloned by GenScript with a BM40 signal peptide. Genes encoding CR3022 heavy and light chains were ordered from GenScript and cloned into pCMV/R.

All proteins were produced in Expi293F cells grown in suspension using Expi293F expression medium (Life Technologies) at 33° C., 70% humidity, 8% CO2 rotating at 150 rpm. Cell cultures were transfected using PEI-MAX (Poly-science) with cells grown to a density of 3.0 million cells per mL and cultivated for 3 days. Supernatants were clarified by centrifugations at 4000 rcf, addition of PDADMAC to a final concentration of 0.0375% (Sigma Aldrich) and a second spin at 4000 rcf.

Proteins containing His tags were purified from clarified supernatants via a batch bind method where each clarified supernatant was supplemented with 1 M Tris-HCl pH 8.0 to a final concentration of 45 mM and 5 M NaCl to a final concentration of ~310 mM. Talon cobalt affinity resin (Takara) was added to the treated supernatants and allowed to incubate for 15 minutes with gentle shaking. Resin was collected using vacuum filtration with a 0.2 µm filter and transferred to a gravity column. The resin was washed with 20 mM Tris pH 8.0, 300 mM NaCl, and the protein was eluted with 3 column volumes of 20 mM Tris pH 8.0, 300 mM NaCl, 300 mM imidazole. Clarified supernatants of cells expressing monoclonal antibodies and human ACE2-Fc were purified using a MabSelect PrismA 2.6×5 cm column (Cytiva) on an AKTA Avant150 FPLC (Cytiva). Bound antibodies were washed with five column volumes of 20 mM NaPO4, 150 mM NaCl pH 7.2, then five column volumes of 20 mM NaPO4, 1 M NaCl pH 7.4 and eluted with three column volumes of 100 mM glycine at pH 3.0. The eluate was neutralized with 2 M Trizma base to 50 mM final concentration.

Bio-layer interferometry: For measuring secretion levels of proteins in supernatants, all supernatants from protein expressions were diluted 1:10 into KB1 (25 mM Tris pH 8.0, 150 mM NaCl, 0.5% bovine serum albumin and 0.01% TWEEN-20). Purified ACE2-Fc or CR3022 antibody were diluted into KB1 at 0.02 mg/mL and immobilized on AHC tips (Pall FortéBio/Sartorius) for 300 seconds using an 8-channel Octet system (Pall FortéBio/Sartorius). After a 60 second baseline was collected in KB1, the sensor was exposed to each of the diluted ACE2-Fc or CR3022 solutions for 300 seconds, followed by a 300 second dissociation step in KB1. For affinity measurements, all proteins and antibodies were diluted into phosphate buffered saline with 0.5% bovine serum albumin and 0.01% TWEEN-20 (KB2) in black 96-well Greiner Bio-one microplate at 200 µL per well, with the buffer alone used for baseline and dissociation steps. CV30 or CR3022 IgG at 10 ug/mL was loaded onto pre-hydrated Protein A biosensors (Pall FortéBio/Sartorius) for 150 s followed by a 60 s baseline. Biosensors were then transferred into an association step with one of five serial two-fold dilutions of wild-type or stabilized monomeric RBDs for 120 s, with RBD concentrations of 125 µM, 62.5 µM, 31.3 µM, 15.6 µM and 7.8 µM used for CV30 and 31.3 µM, 15.6 µM, 7.8 µM, 3.9 µM and 2.0 µM used for CR3022. After association, biosensors were transferred into buffer for 300 s of dissociation. Data from the association and dissociation steps were baseline subtracted and kinetics measurements were calculated globally across all five serial dilutions of RBD using a 1:1 binding model (FortéBio analysis software, version 12.0). For fractional antigenicity measurements of nanoparticle immunogens, binding of hACE2-Fc (dimerized receptor) and CR3022 IgG to monomeric RBD and RBD-I53-50 nanoparticles was analyzed at ambient temperature with shaking at 1000 rpm. Protein samples were diluted to 100 nM in Kinetics buffer (Pall FortéBio/Sartorius). Buffer, antibody, receptor, and immunogen were then applied to a black 96-well Greiner Bio-one microplate at 200 µL per well. Protein A biosensors were first hydrated for 10 min in Kinetics buffer, then dipped into either hACE2-Fc or CR3022 diluted to 10 µg/mL in Kinetics buffer in the immobilization step. After 500 s, the tips were transferred to Kinetics buffer for 90 s to reach a baseline. The association step was performed by dipping the loaded biosensors into the immunogens for 300 s, and the subsequent dissociation step was performed by dipping the biosensors back into Kinetics buffer for an additional 300 s. The data were baseline subtracted prior to plotting using the FortéBio analysis software (version 12.0).

Thermal melts: RBD-based samples were prepared in a buffer containing 50 mM Tris pH 8, 150 mM NaCl, 100 mM L-arginine, 5% glycerol, while HexaPro-foldon-based samples were prepared in a buffer containing 50 mM Tris pH 8.0, 150 mM NaCl, 0.25% w/v L-histidine, 5% glycerol. Non-equilibrium melting temperatures were determined using an UNcle™ (UNchained Labs) based on the barycentric mean of intrinsic tryptophan fluorescence emission spectra collected from 20-95° C. using a thermal ramp of 1° C. per minute. Melting temperatures were defined as the maximum point of the first derivative of the melting curve, with first derivatives calculated using GraphPad Prism software after smoothing with four neighboring points using 2nd order polynomial settings.

SYPRO Orange fluorescence: 5000×SYPRO Orange Protein Gel Stain (Thermo Fisher) was diluted into 25 mM Tris pH 8.0, 150 mM NaCl, 5% glycerol and further added to monomeric RBDs prepared in the same buffer, with final concentrations of 1.0 mg/mL for the RBDs and 20× for SYPRO Orange. Samples were loaded into an UNcle Nano-DSF (UNChained Laboratories) and fluorescence emission spectra were collected for all samples 5 min after the addition of SYPRO Orange to the samples.

In vitro nanoparticle assembly: Total protein concentration of purified individual nanoparticle components was determined by measuring absorbance at 280 nm using a UV/vis spectrophotometer (Agilent Cary 8454) and calculated extinction coefficients. The assembly steps were performed at room temperature with addition in the following order: wild-type or stabilized RBD-I53-50A trimeric fusion protein, followed by q.s. with buffer as needed to achieve desired final concentration, and finally I53-50B.4PT1 pentameric component (in 50 mM Tris pH 8, 500 mM NaCl, 0.75% w/v CHAPS, with a molar ratio of RBD-I53-50A: I53-50B.4PT1 of 1.1:1. q.s. buffer either contained 50 mM Tris pH 7.4, 185 mM NaCl, 100 mM L-arginine, 0.75% CHAPS, 4.5% glycerol or 50 mM Tris pH 8, 150 mM NaCl, 100 mM L-arginine, 5% glycerol. All RBD-I53-50 in vitro assemblies were incubated at 2-8° C. with gentle rocking for at least 30 min before subsequent purification by SEC in order to remove residual unassembled component. A Superose 6 Increase 10/300 GL column was used for nanoparticle production. Assembled particles elute at ~11 mL on the Superose 6 column. Assembled nanoparticles were sterile filtered (0.22 μm) immediately prior to column application and following pooling of SEC fractions.

Negative stain electron microscopy: Wild-type RBD-I53-50 nanoparticles and Rpk-I53-50 nanoparticles were first diluted to 75 μg/mL in 50 mM Tris pH 8, 150 mM NaCl, 100 mM L-arginine, 5% v/v glycerol prior to application of 3 μL of sample onto freshly glow-discharged 300-mesh copper grids. Sample was incubated on the grid for 1 minute before the grid was dipped in a 50 μL droplet of water and excess liquid blotted away with filter paper (Whatman). The grids were then dipped into 3 μL of 0.75% w/v uranyl formate stain. Stain was blotted off with filter paper, then the grids were dipped into another 6 μL of stain and incubated for ~90 seconds. Finally, the stain was blotted away and the grids were allowed to dry for 1 minute prior to storage or imaging. Prepared grids were imaged in a Talos model L120C transmission electron microscope using a Gatan camera at 57,000×.

Dynamic light scattering: Dynamic light scattering (DLS) was used to measure hydrodynamic diameter (Dh) and polydispersity (% Pd) of RBD-I53-50 nanoparticle samples on an UNcle (UNchained Laboratories). Sample was applied to an 8.8 μL quartz capillary cassette (UNi, UNchained Laboratories) and measured with 10 acquisitions of 5 s each, using auto-attenuation of the laser. Increased viscosity due to 5% v/v glycerol in the RBD nanoparticle buffer was accounted for by the UNcle Client software in Dh measurements.

Hydrogen/deuterium-exchange mass spectrometry: 3 mg of RBD-I53-50A, Rpk4-I53-50A, and Rpk9-I53-50A trimers were H/D exchanged (HDX) in deuteration buffer (pH*7.5, 85% DO, Cambridge Isotope Laboratories, Inc.) for 3, 15, 60, 1800, and 72000 seconds at 22° C. respectively. Exchanged samples were subsequently mixed 1:1 with ice-chilled quench buffer (200 mM tris(2-chlorethyl) phosphate (TCEP), 8 M Urea, 0.2% formic acid (FA)) for a final pH of 2.5 and immediately flash frozen in liquid nitrogen. Samples were analyzed by LC-MS on a Synapt G2-Si mass spectrometer using a loading system that maintained all columns, loops, valves, and lines at 0° C. Frozen samples were thawed on ice and loaded over an immobilized pepsin column (2.1×50 mm) with a 200 mL/min flow of 0.1% trifluoroacetic acid (TFA) with 2% acetonitrile. Peptides were trapped on a Waters CSH C18 trap cartridge (2.1×5 mm) prior to being resolved over a Waters CSH C18 1×100 mm 1.7 μm column with a linear gradient from 3% to 40% B over 18 min (A: 98% water, 2% acetonitrile, 0.1% FA, 0.025% TFA; B: 100% acetonitrile, 0.1% FA, flow rate of 40 mL/min). A series of washes were performed between sample runs to minimize carryover. All the water and organic solvents used, unless specifically stated, were MS grade (Optima™, Fisher). A fully deuterated control for each sample series was made by LC eluate collection from pepsin-digested undeuterated sample, speedvac drying, incubation in deuteration buffer for 1 hour at 85° C., and quenching the same as all other HDX samples. Internal exchange standards (Pro-Pro-Pro-Ile [PPPI] (SEQ ID NO: 51) and Pro-Pro-Pro-Phe [PPPF] (SEQ ID NO: 52)) were added in each sample to ensure consistent labeling conditions for all samples. Peptides were manually validated using DriftScope™ (Waters) and identified with orthogonal retention time and drift time coordinates. Deuterium uptake analysis was performed with HX-Express v2. Peaks were identified from the peptide spectra based on the peptide m/z values and binomial fitting was applied. The deuterium uptake level was normalized relative to fully deuterated controls.

Mouse immunizations: Female BALB/c (Stock: 000651) mice were purchased at the age of four weeks from The Jackson Laboratory, Bar Harbor, Maine, and maintained at the Comparative Medicine Facility at the University of Washington, Seattle, WA, accredited by the American Association for the Accreditation of Laboratory Animal Care International (AAALAC). At six weeks of age, 6 mice per dosing group were vaccinated with a prime immunization, and three weeks later mice were boosted with a second vaccination. Prior to inoculation, immunogen suspensions were gently mixed 1:1 vol/vol with AddaVax adjuvant (Invivogen, San Diego, CA) to reach a final concentration of 0.009 or 0.05 mg/mL antigen. Mice were injected intramuscularly into the gastrocnemius muscle of each hind leg using a 27-gauge needle (BD, San Diego, CA) with 50 μL per injection site (100 µL total) of immunogen under isoflurane anesthesia. To obtain sera all mice were bled two weeks after prime and boost immunizations. Blood was collected via submental venous puncture and rested in 1.5 mL plastic Eppendorf tubes at room temperature for 30 min to allow for coagulation. Serum was separated from hematocrit via centrifugation at 2,000 g for 10 min. Complement factors and pathogens in isolated serum were heat-inactivated via incubation at 56° C. for 60 min. Serum was stored at 4° C. or −80° C. until use. All experiments were conducted at the University of Washington, Seattle, WA according to approved Institutional Animal Care and Use Committee protocols.

ELISA: Enzyme-linked immunosorbent assays (ELISA) were used to determine the binding of mouse sera to the delivered antigens. In brief, Maxisorp (Nunc) ELISA plates were coated overnight at 4° C. with 0.08 µg/mL of protein of interest per well in 0.1 M sodium bicarbonate buffer, pH 9.4. Plates were then blocked with a 4% (w/v) solution of dried milk powder (BioRad) in TBS with 0.05% (v/v) Tween 20 (TBST) for 1 hour at room temperature. Serial dilutions of sera were added to the plates and, after washing, antibody binding was revealed using a hydrogen peroxidase coupled horse anti-mouse IgG antibody. Plates were then washed thoroughly in TBST, colorimetric substrate (TMB, Thermo Fisher) was added and absorbance was read at 450 nm. Area under curve (AUC) calculations were generated by addition of trapezoidal areas generated between adjacent pairs of absorbance measurements and baseline.

Pseudovirus neutralization assays: Spike-pseudotyped lentivirus neutralization assays used the spike HDM_Spikedelta21_D614G, which is available from Addgene (#158762) or BEI (NR-53765), with the full sequence available on the world wide web at addgene.org/158762). Briefly, 293T-ACE2 cells (BEI NR-52511) were seeded at 1.25×10' cells per well in 50 uL D10 growth media (DMEM with 10% heat-inactivated FBS, 2 mM L-glutamine, 100 U/mL penicillin, and 100 µg/mL streptomycin) in poly-L-lysine coated black-walled clear-bottom 96-well plates (Greiner 655930). The next day, mouse serum samples were heat inactivated for 30 min at 56° C. and then serially diluted in D10 growth media. Spike-pseudotyped lentivirus was diluted 1:50 to yield ~200,000 RLUs per well and incubated with the serum dilutions for 1 hr at 37° C. 100 µL of virus-serum mixture was then added to the cells and ~52 hours later luciferase activity was measured using the Bright-Glo Luciferase Assay System (Promega, E2610). Each batch of neutralization assays included a negative control sample of human serum collected in 2017-2018 and a known neutralizing antibody to ensure consistency between batches. Fraction infectivity for each well was calculated compared to two "no-serum" control wells in the same row of the plate. The "neutcurve" package (available on the world wide web at jbloomlab.github.io/neutcurve version 0.5.2) was used to calculate the inhibitory concentration 50% ($IC_{50}$) and the neutralization titer 50% (NT50), which is simply $1/IC_{50}$, for each serum sample by fitting a Hill curve with the bottom fixed at 0 and the top fixed at 1.

Quantification and statistical analysis: Multi-group comparisons were performed using nonparametric Kruskal-Wallis test with Dunn's post-hoc analysis in GraphPad Prism 8. Differences were considered significant when P values were less than 0.05.

Example 2: Materials and Methods

Cell Lines

Expi293F cells are derived from the HEK293F cell line, a female human embryonic kidney cell line transformed and adapted to grow in suspension (Life Technologies). Expi293F cells were grown in Expi293 Expression Medium (Life Technologies), cultured at 36.5° C. with 8% $CO_2$ and shaking at 150 rpm. VeroE6 is a female kidney epithelial cell from African green monkey. The HEK-ACE2 adherent cell line was obtained through BEI Resources, NIAID, NIH: Human Embryonic Kidney Cells (HEK293T) Expressing Human Angiotensin-Converting Enzyme 2, HEK293T-hACE2 Cell Line, NR-52511. All adherent cells were cultured at 37° C. with 8% $CO_2$ in flasks with DMEM+10% FBS (Hyclone)+1% penicillin-streptomycin. Cell lines other than Expi293F were not tested for *mycoplasma* contamination nor authenticated.

Mice

Female BALB/c mice (four weeks old) were obtained from Jackson Laboratory, Bar Harbor, Maine. Animal procedures were performed under the approvals of the Institutional Animal Care and Use Committee of University of Washington, Seattle, WA.

Design of Stabilizing Mutations

All calculations in Rosetta were made using version v2020.22-dev61287. All design trajectories assessed the RBD in the closed symmetric trimer conformation observed in a cryo-EM structure of the spike (PDB 6VXX), and in the context of a crystal structure of the RBD (PDB 6YZ5). The three-fold symmetry axis of PDB entry 6VXX was aligned with [0,0,1] and a single protomer was saved in .pdb format. An RBD monomer from PDB 6YZ5 was structurally superimposed with the protomer of PDB 6VXX and similarly saved. A design protocol was written using RosettaScripts (58, 59) that takes the aligned protomer and a custom resfile as inputs, with the resfile dictating the side chain identities and conformations sampled during design. The protocol applies two rounds of design to a symmetric model based on the input resfile, with side chain minimization applied after each design step. The protocol allows for backbone minimization to be simultaneously performed with side chain minimization, and trajectories were performed either with backbone minimization allowed or disallowed. Both design and minimization steps were allowed to repack or minimize residues within 10 Å of all mutable or packable residues listed in the resfile. Residue positions were manually picked to include positions 358, 365, 392 and surrounding residues based on spike and RBD structures, and possible residue identities were designated for each position in resfiles using the 'PIKAA' option. Resfile inputs were diversified to include various combinations of I358F, Y365F, Y365W, and/or F392W, while also either restricting or allowing mutations to surrounding residues. Further resfile inputs were similarly set up but did not restrict positions 358, 365, and 392 to specific identities. Design models and scores were manually inspected to identify interactions that appeared structurally favorable. Mutations were discarded if they buried polar groups that were natively solvent-exposed or involved in hydrogen bonds. To prevent undesired alterations to antigenicity, mutations to surface-exposed residues were not frequently considered. Favorable sets of mutations were iteratively retested from optimized resfiles and manually refined to finalize a diverse set of designs.

Plasmid Construction

Wild-type and stabilized sequences for the SARS-CoV-2 RBD were genetically fused to the N terminus of the trimeric I53-50A nanoparticle component using linkers of 16 glycine and serine residues. Each I53-50A fusion protein also bore a C-terminal octa-histidine tag (SEQ ID NO: 53), and monomeric sequences contained both Avi and octa-histidine tags (SEQ ID NO: 53). All sequences were cloned into pCMV/R using the XbaI and AvrII restriction sites and Gibson assembly. All RBD-bearing components contained an N-terminal mu-phosphatase signal peptide. hACE2-Fc was synthesized and cloned by GenScript with a BM40 signal peptide. The HexaPro-foldon construct used for immunization studies was produced as described (Hsieh et al. *Science* 369:1501-05 (2020)) and placed into pCMV/R with an octa-histidine tag (SEQ ID NO: 53). HexaPro-foldon constructs used for expression and stability comparisons with and without Rpk9 mutations contained a BM40 signal peptide and were placed into pCMV/R. Plasmids were transformed into the NEB Sa strain of *E. coli* (New England Biolabs) for subsequent DNA extraction from bacterial culture (NucleoBond Xtra Midi kit) to obtain plasmid for transient transfection into Expi293F cells. The amino acid sequences of all novel proteins used in this study are provided as SEQ ID NOs: 21-47.

```
>RBD-I53-50A trimer (16-GS linker, using wild type RBD from Wuhan-Hu-1)
                                                            SEQ ID NO: 21
MGILPSPGMPALLSLVSLLSVLLMGCVAETGTRFPNITNLCPFGEVFNATRFASVYAWNRKRISNCVADY

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEAIEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk1-I53-50A trimer;
                                                            SEQ ID NO: 22
MGILPSPGMPALLSLVSLLSVLLMGCVAETGTRFPNITNLCPFGEVFNATRFASVYAWNRKRISNCVADW

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEAIEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk2-I53-50A trimer;
                                                            SEQ ID NO: 23
MGILPSPGMPALLSLVSLLSVLLMGCVAETGTRFPNITNLCPLGEVFNATRFASVYAWNRKRISNCVADW

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEAIEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk3-I53-50A trimer;
                                                            SEQ ID NO: 24
MGILPSPGMPALLSLVSLLSVLLMGCVAETGTRFPNITNLCPFGEVFNATRFASVYAWNRKRISNCVADW

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVMSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH
```

```
>Rpk4-I53-50A;
                                                SEQ ID NO: 25
trimerMGILPSPGMPALLSLVSLLSVLLMGCVAETGTRFPNITNLCPFGEVFNATRFASVYAWNRKRISN

CVADYSVLYNSASFSTFKCYGVSPTKLNDLCWTNVYADSFVIRGDEVRQIAPGQTGKIADYNYKLPDDFTG

CVIAWNSNNLDSKVGGNYNYLRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk5-I53-50A trimer;
                                                SEQ ID NO: 26
MGILPSPGMPALLSLVSLLSVLLMGCVAETGTRFPNITNLCPFGEVFNATRFASVYAWNRKRISNCVADW

SVLYNSASFSTFKCYGVSPTKLNDLCWTNVYADSFVIRGDEVRQIAPGQTGKIADYNYKLPDDFTGCVIA

WNSNNLDSKVGGNYNYLRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk6-I53-50A trimer;
                                                SEQ ID NO: 27
MGILPSPGMPALLSLVSLLSVLLMGCVAETGTRFPNITNLCPMGEVFNATRFASVYAWNRKRISNCVLDF

SVLYNSASFSTVKCYGVSPTKLNDLCFTNVYADSFVIRGDEVRQIAPGQTGKIADYNYKLPDDFTGCVIA

WNSNNLDSKVGGNYNYLRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk7-I53-50A trimer;
                                                SEQ ID NO: 28
MGILPSPGMPALLSLVSLLSVLLMGCVAETGTRFPNITNLCPFGEVFNATRFASVYAWNRKRISNCVADF

SVLYNSASFSTFKCYGVSPTKLNDLCWTNVYADSFVIRGDEVRQIAPGQTGKIADYNYKLPDDFTGCVIA

WNSNNLDSKVGGNYNYLRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk8-I53-50A trimer;
                                                SEQ ID NO: 29
MGILPSPGMPALLSLVSLLSVLLMGCVAETGTRFPNITNLCPFGEVFNATRFASVYAWNRKRISNCVADF

SVLYNSASFSTFKCYGVSPTKLNDLCFTNIYADSFVIRGDEVRQIAPGQTGKIADYNYKLPDDFTGCVIAWNSNN

LDSKVGGNYNYLRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH
```

>Rpk9-I53-50A trimer;
SEQ ID NO: 30
MGILPSPGMPALLSLVSLLSVLLMGCVAETGTRFPNITNLCPFGEVFNATRFASVYAWNRKRISNCVADF
SVLYNSASFSTFKCYGVSPTKLNDLCWTNIYADSFVIRGDEVRQIAPGQTGKIADYNYKLPDDFTGCVIA
WNSNNLDSKVGGNYNYLYRLFRKSNLKPFERDISTEIYQAGSTPCNGVEGFNCYFPLQSYGFQPTNGVGY
QPYRVVVLSFELLHAPATVCGPKKSTGGSGGSGSGGSGGSGSEKAAKAEEAARKMEELFKKHKIVAVLRA
NSVEEATEKAVAVFAGGVHLIEITFTVPDADTVIKALSVLKEKGAIIGAGTVTSVEQARKAVESGAEFIV
SPHLDEEISQFAKEKGVFYMPGVMTPTELVKAMKLGHTILKLFPGEVVGPQFVKAMKGPFPNVKFVPTGG
VNLDNVAEWFKAGVLAVGVGSALVKGTPDEVREKAKAFVEKIRGATEGGSHHHHHHHH >Rpk10-I53-50A trimer;
SEQ ID NO: 31
MGILPSPGMPALLSLVSLLSVLLMGCVAETGTRFPNITNLCPFGEVFNATRFASVYAWNRKRISNCVADW
SVLYNSASFSTFKCYGVSPTKLNDLCFTNVYADSFVIRGDEVRQIAPGQTGKIADYNYKLPDDFTGCVIA
WNSNNLDSKVGGNYNYLYRLFRKSNLKPFERDISTEIYQAGSTPCNGVEGFNCYFPLQSYGFQPTNGVGY
QPYRVVVISLELLHAPATVCGPKKSTGGSGGSGSGGSGGSGSEKAAKAEEAARKMEELFKKHKIVAVLRA
NSVEEATEKAVAVFAGGVHLIEITFTVPDADTVIKALSVLKEKGAIIGAGTVTSVEQARKAVESGAEFIV
SPHLDEEISQFAKEKGVFYMPGVMTPTELVKAMKLGHTILKLFPGEVVGPQFVKAMKGPFPNVKFVPTGG
VNLDNVAEWFKAGVLAVGVGSALVKGTPDEVREKAKAFVEKIRGATEGGSHHHHHHHH >Rpk11-I53-50A trimer;
SEQ ID NO: 32
MGILPSPGMPALLSLVSLLSVLLMGCVAETGTRFPNITNLCPLGEVFNATRFASVYAWNRKRISNCVLDM
SVLYNSASFSTFKCYGVSPTKLNDLCFTNVYADSFVIRGDEVRQIAPGQTGKIADYNYKLPDDFTGCVIA
WNSNNLDSKVGGNYNYLYRLFRKSNLKPFERDISTEIYQAGSTPCNGVEGFNCYFPLQSYGFQPTNGVGY
QPYRVVVLSFELLHAPATVCGPKKSTGGSGGSGSGGSGGSGSEKAAKAEEAARKMEELFKKHKIVAVLRA
NSVEEATEKAVAVFAGGVHLIEITFTVPDADTVIKALSVLKEKGAIIGAGTVTSVEQARKAVESGAEFIV
SPHLDEEISQFAKEKGVFYMPGVMTPTELVKAMKLGHTILKLFPGEVVGPQFVKAMKGPFPNVKFVPTGG
VNLDNVAEWFKAGVLAVGVGSALVKGTPDEVREKAKAFVEKIRGATEGGSHHHHHHHH >Rpk12-I53-50A trimer;
SEQ ID NO: 33
MGILPSPGMPALLSLVSLLSVLLMGCVAETGTRFPNITNLCPFGEVFNATRFASVYAWNRKRFSNCVADW
SVLYNSASFSTFKCYGVSPTKLNDLCFTNVYADSFVIRGDEVRQIAPGQTGKIADYNYKLPDDFTGCVIA
WNSNNLDSKVGGNYNYLYRLFRKSNLKPFERDISTEIYQAGSTPCNGVEGFNCYFPLQSYGFQPTNGVGY
QPYRVVVLSFELLHAPATVCGPKKSTGGSGGSGSGGSGGSGSEKAAKAEEAARKMEELFKKHKIVAVLRANSVEE
AIEKAVAVFAGGVHLIEITFTVPDADTVIKALSVLKEKGAIIGAGTVTSVEQARKAVESGAEFIV
SPHLDEEISQFAKEKGVFYMPGVMTPTELVKAMKLGHTILKLFPGEVVGPQFVKAMKGPFPNVKFVPTGG
VNLDNVAEWFKAGVLAVGVGSALVKGTPDEVREKAKAFVEKIRGATEGGSHHHHHHHH >Rpk13-I53-50A trimer;
SEQ ID NO: 34
MGILPSPGMPALLSLVSLLSVLLMGCVAETGTRFPNITNLCPLGEVFNATRFASVYAWNRKRFSNCVADW
SVLYNSASFSTFKCYGVSPTKLNDLCFTNVYADSFVIRGDEVRQIAPGQTGKIADYNYKLPDDFTGCVIA
WNSNNLDSKVGGNYNYLYRLFRKSNLKPFERDISTEIYQAGSTPCNGVEGFNCYFPLQSYGFQPTNGVGY
QPYRVVVLSFELLHAPATVCGPKKSTGGSGGSGSGGSGGSGSEKAAKAEEAARKMEELFKKHKIVAVLRA
NSVEEATEKAVAVFAGGVHLIEITFTVPDADTVIKALSVLKEKGAIIGAGTVTSVEQARKAVESGAEFIV
SPHLDEEISQFAKEKGVFYMPGVMTPTELVKAMKLGHTILKLFPGEVVGPQFVKAMKGPFPNVKFVPTGG
VNLDNVAEWFKAGVLAVGVGSALVKGTPDEVREKAKAFVEKIRGATEGGSHHHHHHHH

```
>Rpk14-I53-50A trimer;
                                                            SEQ ID NO: 35
MGILPSPGMPALLSLVSLLSVLLMGCVAETGTRFPNITNLCPFGEVFNATRFASVYAWNRKRFSNCVADW

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVMSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk15-I53-50A trimer;
                                                            SEQ ID NO: 36
MGILPSPGMPALLSLVSLLSVLLMGCVAETGTRFPNITNLCPFGEVFNATRFASVYAWNRKRFSNCVADF

SVLYNSASFSTFKCYGVSPTKLNDLCFTNIYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVFYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk16-I53-50A trimer;
                                                            SEQ ID NO: 37
MGILPSPGMPALLSLVSLLSVLLMGCVAETGTRFPNITNLCPFGEVFNATRFASVYAWNRKRFSNCVADW

SVLYNSASFSTFKCYGVSPTKLNDLCWTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIVSPHLD

EEISQFAKEKGVEYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>Rpk17-I53-50A trimer;
                                                            SEQ ID NO: 38
MGILPSPGMPALLSLVSLLSVLLMGCVAETGTRFPNITNLCPFGEVFNATRFASVYAWNRKRFSNCVADF

SVLYNSASFSTFKCYGVSPTKLNDLCWTNIYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGGSGGSGSGGSGGSGSEKAAKAEEAARKMEELFKKHKIVAVLRA

NSVEEATEKAVAVFAGGVHLIEITFTVPDADTVIKALSVLKEKGAIIGAGTVTSVEQARKAVESGAEFIV

SPHLDEEISQFAKEKGVEYMPGVMTPTELVKAMKLGHTILKLFPGEVVGPQFVKAMKGPFPNVKFVPTGG

VNLDNVAEWFKAGVLAVGVGSALVKGTPDEVREKAKAFVEKIRGATEGGSHHHHHHHH

>RED monomer (with Avi and hexa-histidine tags);
                                                            SEQ ID NO: 39
MGILPSPGMPALLSLVSLLSVLLMGCVAETGTRFPNITNLCPFGEVFNATRFASVYAWNRKRISNCVADY

SVLYNSASFSTFKCYGVSPTKLNDLCFTNVYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGLNDIFEAQKIEWHEHHHHHHHH

>Rpk4 monomer (with Avi and hexa-histidine tags);
                                                            SEQ ID NO: 61
MGILPSPGMPALLSLVSLLSVLLMGCVAETGTRFPNITNLCPFGEVFNATRFASVYAWNRKRISNCVADY

SVLYNSASFSTFKCYGVSPTKLNDLCWTNVYADSFVIRGDEVRQIAPGQTGKIADYNYKLPDDFTGCVIA
```

```
WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGLNDIFEAQKIEWHEHHHHHHHH

>Rpk9 monomer (with Avi and hexa-histidine tags);
                                                             SEQ ID NO: 61
MGILPSPGMPALLSLVSLLSVLLMGCVAETGTRFPNITNLCPFGEVFNATRFASVYAWNRKRISNCVADF

SVLYNSASFSTFKCYGVSPTKLNDLCWTNIYADSFVIRGDEVRQIAPGQTGKIADYNYKLPDDFTGCVIA

WNSNNLDSKVGGNYNYLYRLFRKSNLKPFERDISTEIYQAGSTPCNGVEGFNCYFPLQSYGFQPTNGVGY

QPYRVVVLSFELLHAPATVCGPKKSTGLNDIFEAQKIEWHEHHHHHHH

>I53-50B.4PT1 pentamer;
                                                             SEQ ID NO: 61
MNQHSHKDHETVRIAVVRARWHAEIVDACVSAFEAAMRDIGGDRFAVDVFDVPGAYEIPLHARTLAETGR

YGAVLGTAFVVNGGIYRHEFVASAVINGMMNVQLNTGVPVLSAVLTPHNYDKSKAHTLLFLALFAVKGME

AARACVEILAAREKIAAGSLEHHHHHH

>20BXpentamer;
                                                             SEQ ID NO: 43
MNQHSHKDYETVRIAVVRARWHADIVDQCVSAFEAEMADIGGDRFAVDVEDVPGAYEIPLHARTLAETGR

YGAVLGTAFVVNGGIYRHEFVASAVIDGMMNVQLSTGVPVLSAVLTPHNYHDSAEHHRFFFEHFTVKGKE

AARACVEILAAREKIAAGSLEHHHHHH

>Hexapro-foldon, used for immunizations (Wuhan-Hu-1);
                                                             SEQ ID NO: 44
MFVFLVLLPLVSSQCVNLTTRTQLPPAYTNSFTRGVYYPDKVFRSSVLHSTQDLFLPFFSNVTWFHAIHV

SGTNGTKRFDNPVLPFNDGVYFASTEKSNIIRGWIFGTTLDSKTQSLLIVNNATNVVIKVCEFQFCNDPF

LGVYYHKNNKSWMESEFRVYSSANNCTFEYVSQPFLMDLEGKQGNFKNLREFVFKNIDGYFKIYSKHTPI

NLVRDLPQGFSALEPLVDLPIGINITRFQTLLALHRSYLTPGDSSSGWTAGAAAYYVGYLQPRTFLLKYN

ENGTITDAVDCALDPLSETKCTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCVNFNFNGLTGTGVLTESNKKFL

PFQQFGRDIADTTTDAVRDPQTLEILDITPCSFGGVSVITPGTNTSNQVAVLYQDVNCTEVPVAIHADQLT

PTWRVYSTGSNVFQTRAGCLIGAEHVNNSYECDIPIGAGICASYQTQTNSPGSASSVASQSITAYTMSLG

AENSVAYSNNSIAIPTNFTISVTTEILPVSMTKTSVDCTMYICGDSTECSNLLLQYGSFCTQLNRALTGI

AVEQDKNTQEVFAQVKQTYKTPPIKDFGGFNFSQILPDPSKPSKRSPIEDLLFNKVTLADAGFIKQYGDC

LGDIAARDLICAQKFNGLTVLPPLLTDEMIAQYTSALLAGTITSGWTFGAGPALQIPFPMQMAYRFNGIG

VTQNVLYENQKLIANQFNSAIGKIQDSLSSTPSALGKLQDVVNQNAQALNTLVKQLSSNFGAISSVLNDI

LSRLDPPEAEVQIDRLITGRLQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGTHWFVTQRNFYEPQIITTDNT

FVSGNCDVVIGIVNNTVYDPLQPELDSFKEELDKYFKNHTSPDVDLGDISGINASVVNIQKEIDRLNEVA

KNLNESLIDLQELGKYEQGSGYIPEAPRDGQAYVRKDGEWVLLSTFLGRSLEVLFQGPGHHHHHHHSAW

SHPQFEKGGGSGGGGSGGSAWSHPQFEK

>Hexapro-foldon, used for expression and stability comparisons
with Rpk9-Hexapro-foldon (Wuhan-Hu-1);
                                                             SEQ ID NO: 45
MARAWIFFLLCLAGRALAQCVNLTTRTQLPPAYTNSFTRGVYYPDKVFRSSVLHSTQDLFLPFFSNVTWF

HAIHVSGTNGTKRFDNPVLPFNDGVYFASTEKSNIIRGWIFGTTLDSKTQSLLIVNNATNVVIKVCEFQF

CNDPFLGVYYHKNNKSWMESEFRVYSSANNCTFEYVSQPFLMDLEGKQGNFKNLREFVFKNIDGYFKIYS

KHTPINLVRDLPQGFSALEPLVDLPIGINITRFQTLLALHRSYLTPGDSSSGWTAGAAAYYVGYLQPRTF
```

-continued

LLKYNENGTITDAVDCALDPLSETKCTLKSFTVEKGIYQTSNFRVQPTESIVRFPNITNLCPFGEVFNAT

RFASVYAWNRKRISNCVADYSVLYNSASFSTFKCYGVSPTKLNDLCFTNVYADSFVIRGDEVRQIAPGQT

GKIADYNYKLPDDFTGCVIAWNSNNLDSKVGGNYNYLYRLFRKSNLKPFERDISTEIYQAGSTPCNGVEG

FNCYFPLQSYGFQPTNGVGYQPYRVVVLSFELLHAPATVCGPKKSTNLVKNKCVNFNFNGLTGTGVLTES

NKKFLPFQQFGRDIADTTDAVRDPQTLEILDITPCSFGGVSVITPGTNTSNQVAVLYQDVNCTEVPVAIH

ADQLTPTWRVYSTGSNVFQTRAGCLIGAEHVNNSYECDIPIGAGICASYQTQTNSPGSASSVASQSITAY

TMSLGAENSVAYSNNSIAIPTNFTISVTTEILPVSMTKTSVDCTMYICGDSTECSNLLLQYGSFCTQLNR

ALTGIAVEQDKNTQEVFAQVKQTYKTPPIKDFGGFNFSQILPDPSKPSKRSPIEDLLFNKVTLADAGFIK

QYGDCLGDIAARDLICAQKFNGLTVLPPLLTDEMIAQYTSALLAGTITSGWTFGAGPALQIPFPMQMAYR

FNGIGVTQNVLYENQKLIANQFNSAIGKIQDSLSSTPSALGKLQDVVNQNAQALNTLVKQLSSNFGAISS

VLNDILSRLDPPEAEVQIDRLITGRLQSLQTYVTQQLIRAAEIRASANLAATKMSECVLGQSKRVDFCGK

GYHLMSFPQSAPHGVVFLHVTYVPAQEKNFTTAPAICHDGKAHFPREGVFVSNGTHWFVTQRNFYEPQII

TTDNTFVSGNCDVVIGIVNNTVYDPLQPELDSFKEELDKYFKNHTSPDVDLGDISGINASVVNIQKEIDR

LNEVAKNLNESLIDLQELGKYEQGSGYIPEAPRDGQAYVRKDGEWVLLSTFLGRSLEVLFQGPGHHHHHH

HH

>Rpk9-Hexapro-foldon(Wuhan-Hu-1);

SEQ ID NO: 46

MARAWIFFLLCLAGRALAQCVNLTTRTQLPPAYTNSFTRGVYYPDKVERSSVLHSTQDLFLPFFSNVTWF

HAIHVSGTNGTKREDNPVLPFNDGVYFASTEKSNIIRGWIEGTTLDSKTQSLLIVNNATNVVIKVCEFQF

CNDPFLGVYYHKNNKSWMESEFRVYSSANNCTFEYVSQPFLMDLEGKQGNFKNLREFVFKNIDGYFKIYS

KHTPINLVRDLPQGFSALEPLVDLPIGINITRFQTLLALHRSYLTPGDSSSGWTAGAAAYYVGYLQPRTF

LLKYNENGTITDAVDCALDPLSETKCTLKSFTVEKGIYQTSNERVQPTESIVRFPNITNLCPFGEVFNAT

RFASVYAWNRKRISNCVADFSVLYNSASFSTFKCYGVSPTKLNDLCWTNIYADSFVIRGDEVRQIAPGQT

GKIADYNYKLPDDFTGCVIAWNSNNLDSKVGGNYNYLYRLFRKSNLKPFERDISTEIYQAGSTPCNGVEG

FNCYFPLQSYGFQPTNGVGYQPYRVVVLSFELLHAPATVCGPKKSTNLVKNKCVNENENGLTGTGVLTES

NKKFLPFQQFGRDIADTTDAVRDPQTLEILDITPCSFGGVSVITPGTNTSNQVAVLYQDVNCTEVPVAIH

ADQLTPTWRVYSTGSNVFQTRAGCLIGAEHVNNSYECDIPIGAGICASYQTQTNSPGSASSVASQSITAY

TMSLGAENSVAYSNNSIAIPTNFTISVTTEILPVSMTKTSVDCTMYICGDSTECSNLLLQYGSFCTQLNR

ALTGIAVEQDKNTQEVFAQVKQTYKTPPIKDFGGFNFSQILPDPSKPSKRSPIEDLLFNKVTLADAGFIK

QYGDCLGDIAARDLICAQKFNGLTVLPPLLTDEMIAQYTSALLAGTITSGWTFGAGPALQIPFPMQMAYR

ENGIGVTQNVLYENQKLIANQFNSAIGKIQDSLSSTPSALGKLQDVVNQNAQALNTLVKQLSSNFGAISS

VLNDILSRLDPPEAEVQIDRLITGRLQSLQTYVTQQLIRAAEIRASANLAATKMSECVLGQSKRVDFCGK

GYHLMSFPQSAPHGVVELHVTYVPAQEKNETTAPAICHDGKAHFPREGVEVSNGTHWFVTQRNEYEPQII

TTDNTEVSGNCDVVIGIVNNTVYDPLQPELDSFKEELDKYFKNHTSPDVDLGDISGINASVVNIQKEIDR

LNEVAKNLNESLIDLQELGKYEQGSGYIPEAPRDGQAYVRKDGEWVLLSTFLGRSLEVLFQGPGHHHHHH

HH

>hACE2-FC;

SEQ ID NO: 47

MARAWIFFLLCLAGRALASTIEEQAKTFLDKFNHEAEDLFYQSSLASWNYNTNITEENVQNMNNAGDKWS

AFLKEQSTLAQMYPLQEIQNLTVKLQLQALQQNGSSVLSEDKSKRLNTILNTMSTIYSTGKVCNPDNPQE

CLLLEPGLNEIMANSLDYNERLWAWESWRSEVGKQLRPLYEEYVVLKNEMARANHYEDYGDYWRGDYEVN

GVDGYDYSRGQLIEDVEHTFEEIKPLYEHLHAYVRAKLMNAYPSYISPIGCLPAHLLGDMWGRFWTNLYS

LTVPFGQKPNIDVTDAMVDQAWDAQRIFKEAEKFFVSVGLPNMTQGFWENSMLTDPGNVQKAVCHPTAWD

-continued

```
LGKGDFRILMCTKVTMDDFLTAHHEMGHIQYDMAYAAQPFLLRNGANEGFHEAVGEIMSLSAATPKHLKS

IGLLSPDFQEDNETEINFLLKQALTIVGTLPFTYMLEKWRWMVFKGEIPKDQWMKKWWEMKREIVGVVEPVPHDE

TYCDPASLFHVSNDYSFIRYYTRTLYQFQFQEALCQAAKHEGPLHKCDISNSTEAGQKLFNMLRL

GKSEPWTLALENVVGAKNMNVRPLLNYFEPLFTWLKDQNKNSFVGWSTDWSPYADPLVPRGSGGGGDPEP

KSCDKTHTCPPCPAPELLGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRWQQG
```

Transient Transfection

SARS-CoV-2 S and ACE2-Fc proteins were produced in Expi293F cells grown in suspension using Expi293F expression medium (Life Technologies) at 33° C., 70% humidity, 8% $CO_2$, rotating at 150 rpm. The cultures were transfected using PEI-MAX (Polyscience) with cells grown to a density of 3.0 million cells per mL and cultivated for 3 days. Supernatants were clarified by centrifugation (5 min at 4000 rcf), addition of PDADMAC solution to a final concentration of 0.0375% (Sigma Aldrich, #409014), and a second centrifugation step (5 min at 4000 rcf).

Genes encoding CV30 and CR3022 heavy and light chains were ordered from GenScript and cloned into pCMV/R. Antibodies were expressed by transient co-transfection of both heavy and light chain plasmids in Expi293F cells using PEI MAX (Polyscience) transfection reagent. Cell supernatants were harvested and clarified after 3 or 6 days as described above.

Purification of Glycoproteins

Proteins containing His tags were purified from clarified supernatants via a batch bind method where each clarified supernatant was supplemented with 1 M Tris-HCl pH 8.0 to a final concentration of 45 mM and 5 M NaCl to a final concentration of 313 mM. Talon cobalt affinity resin (Takara) was added to the treated supernatants and allowed to incubate for 15 min with gentle shaking. Resin was collected using vacuum filtration with a 0.45 µm filter and transferred to a gravity column. The resin was washed with 10 column volumes of 20 mM Tris pH 8.0, 300 mM NaCl, and bound protein was eluted with 3 column volumes of 20 mM Tris pH 8.0, 300 mM NaCl, 300 mM imidazole. The batch bind process was then repeated on the same supernatant sample and the first and second elutions were combined. SDS-PAGE was used to assess purity. For quantification of yields of RBD-based constructs, IMAC elutions from comparable cell culture conditions and volumes were supplemented with 100 mM L-arginine and 5% glycerol and concentrated to 1.5 mL. The concentrated samples were subsequently loaded into a 1 mL loop and applied to a Superdex 75 Increase 10/300 GL column (for monomeric RBDs) or a Superdex 200 Increase 10/300 GL column (for RBD fusions to the I53-50A trimer) pre-equilibrated with 50 mM Tris pH 8, 150 mM NaCl, 100 mM L-arginine, 5% glycerol. For quantification of yields of HexaPro-foldon constructs with and without Rpk9 mutations, IMAC elutions from comparable cell culture conditions and volumes were supplemented with 5% glycerol and concentrated to 1.5 mL, which was subsequently loaded into a 1 mL loop and applied to a Superose 6 Increase 10/300 GL column pre-equilibrated with 50 mM Tris pH 8.0, 150 mM NaCl, 0.25% w/v L-histidine, 5% glycerol. HexaPro-foldon for immunization studies was purified by IMAC and dialyzed three times against 50 mM Tris pH 8.0, 150 mM NaCl, 0.25% w/v L-histidine, 5% glycerol for four hours at room temperature.

Thermal Denaturation (nanoDSF)

RBD-based samples were prepared in a buffer containing 50 mM Tris pH 8, 150 mM NaCl, 100 mM L-arginine, 5% glycerol, while HexaPro-foldon-based samples were prepared in a buffer containing 50 mM Tris pH 8.0, 150 mM NaCl, 0.25% w/v L-histidine, 5% glycerol. Non-equilibrium melting temperatures were determined using an UNcle™ (UNchained Labs) based on the barycentric mean of intrinsic tryptophan fluorescence emission spectra collected from 20-95° C. using a thermal ramp of 1° C. per minute. Melting temperatures were defined as the maximum point of the first derivative of the melting curve, with first derivatives calculated using GraphPad Prism software after smoothing with four neighboring points using 2nd order polynomial settings.

SYPRO Orange Fluorescence

5000×SYPRO™ Orange Protein Gel Stain (Thermo Fisher) was mixed diluted into 25 mM Tris pH 8.0, 150 mM NaCl, 5% glycerol and further added to monomeric RBDs prepared in the same buffer, with final concentrations of 1.0 mg/mL for the RBDs and 20× for SYPRO™ Orange. Samples were loaded into an UNcle™ Nano-DSF (UN-Chained Laboratories) and fluorescence emission spectra were collected for all samples 5 min after the addition of SYPRO™ Orange to the samples.

Microbial Protein Expression and Purification of I53-50B.4PT1

The complementary pentameric nanoparticle component to RBD-I53-50A, I53-50B.4PT1 (SEQ ID NO: 17), was produced as described in U.S. Patent. Pub. No 2016/0122392, the content of which is incorporated by reference herein in its entirety, and the same protocol was used for purification of the 2OBX non-assembling control pentamer.

In Vitro Nanoparticle Assembly

Total protein concentration of purified individual nanoparticle components was determined by measuring absorbance at 280 nm using a UV/vis spectrophotometer (Agilent Cary 8454) and calculated extinction coefficients. The assembly steps were performed at room temperature with addition in the following order: wild-type or stabilized RBD-I53-50A trimeric fusion protein, followed by q.s. with buffer as needed to achieve desired final concentration, and finally I53-50B.4PT1 pentameric component (SEQ ID NO: 17) (in 50 mM Tris pH 8, 500 mM NaCl, 0.75% w/v CHAPS, with a molar ratio of RBD-I53-50A:I53-50B.4PT1 of 1.1:1. q.s. buffer either contained 50 mM Tris pH 7.4, 185 mM NaCl, 100 mM L-arginine, 0.75% CHAPS, 4.5% glycerol (for solution stability studies) or 50 mM Tris pH 8, 150 mM NaCl, 100 mM L-arginine, 5% glycerol. All RBD-I53-50 in vitro assemblies were incubated at 2-8° C. with gentle rocking for at least 30 min before subsequent purification by SEC in order to remove residual unassembled component. A Superose™ 6 Increase 10/300 GL column was used for nanoparticle production. Assembled particles elute at ~11 mL on the Superose™ 6 column. Assembled nanoparticles were sterile filtered (0.22 μm) immediately prior to column application and following pooling of SEC fractions.

Bio-Layer Interferometry for Kinetic Analysis of Monomeric RBDs

Kinetic measurements were performed using an Octet™ Red 96 System (Pall FortéBio/Sartorius®) at 25° C. with shaking at 1000 rpm. All proteins and antibodies were diluted into phosphate buffered saline (PBS) with 0.5% bovine serum albumin and 0.01% TWEEN-20 in black 96-well Greiner Bio-one microplate at 200 μL per well, with the buffer alone used for baseline and dissociation steps. CV30 or CR3022 IgG at 10 ug/mL was loaded onto pre-hydrated Protein A biosensors (Pall FortéBio/Sartorius®) for 150 s followed by a 60 s baseline. Biosensors were then transferred into an association step with one of five serial two-fold dilutions of wild-type or stabilized monomeric RBDs for 120 s, with RBD concentrations of 125 μM, 62.5 μM, 31.3 μM, 15.6 μM and 7.8 μM used for CV30 and 31.3 μM, 15.6 μM, 7.8 μM, 3.9 μM and 2.0 μM used for CR3022. After association, biosensors were transferred into buffer for 300 s of dissociation. Data from the association and dissociation steps were baseline subtracted and kinetics measurements were calculated globally across all five serial dilutions of RBD using a 1:1 binding model (FortéBio4® analysis software, version 12.0).

Bio-Layer Interferometry for Fractional Antigenicity of RBD Nanoparticles

Binding of hACE2-Fc (dimerized receptor) and CR3022 IgG to monomeric RBD and RBD-I53-50 nanoparticles was analyzed for real-time stability studies using an Octet™ Red 96 System at ambient temperature with shaking at 1000 rpm. Protein samples were diluted to 100 nM in Kinetics buffer (Pall FortéBio/Sartorius®). Buffer, antibody, receptor, and immunogen were then applied to a black 96-well Greiner Bio-one microplate at 200 μL per well. Protein A biosensors were first hydrated for 10 min in Kinetics buffer, then dipped into either hACE2-Fc or CR3022 diluted to 10 μg/mL in Kinetics buffer in the immobilization step. After 500 s, the tips were transferred to Kinetics buffer for 90 s to reach a baseline. The association step was performed by dipping the loaded biosensors into the immunogens for 300 s, and the subsequent dissociation steps was performed by dipping the biosensors back into Kinetics buffer for an additional 300 s. The data were baseline subtracted prior to plotting using the FortéBio® analysis software (version 12.0).

Negative Stain Electron Microscopy

Wild-type RBD-I53-50 nanoparticles and Rpk-I53-50 nanoparticles were first diluted to 75 μg/mL in 50 mM Tris pH 8, 150 mM NaCl, 100 mM L-arginine, 5% v/v glycerol prior to application of 3 μL of sample onto freshly glow-discharged 300-mesh copper grids. Sample was incubated on the grid for 1 minute before the grid was dipped in a 50 μL droplet of water and excess liquid blotted away with filter paper. The grids were then dipped into 3 μL of 0.75% w/v uranyl formate stain. Stain was blotted off with filter paper, then the grids were dipped into another 6 μL of stain and incubated for ~90 seconds. Finally, the stain was blotted away and the grids were allowed to dry for 1 minute prior to storage or imaging. Prepared grids were imaged in a Talos™ model L120C transmission electron microscope using a Gatan™ camera at 57,000×.

Dynamic Light Scattering

Dynamic light scattering (DLS) was used to measure hydrodynamic diameter (Dh) and polydispersity (% Pd) of RBD-I53-50 nanoparticle samples on an UNcle™ (UNchained Laboratories). Sample was applied to an 8.8 μL quartz capillary cassette (UNi™, UNchained Laboratories) and measured with 10 acquisitions of 5 s each, using auto-attenuation of the laser. Increased viscosity due to 5% v/v glycerol in the RBD nanoparticle buffer was accounted for by the UNcle™ Client software in Dh measurements.

Endotoxin Measurements

Endotoxin levels in protein samples were measured using the EndoSafe™ Nexgen-MCS System (Charles River). Samples were diluted 1:50 or 1:100 in Endotoxin-free LAL reagent water, and applied into wells of an EndoSafe™ LAL reagent cartridge. Charles River EndoScan™-V software was used to analyze endotoxin content, which automatically back-calculates for the dilution factor. Endotoxin values were reported as EU/mL which were then converted to EU/mg based on UV-Vis measurements. Our threshold for samples suitable for immunization was <100 EU/mg.

UV-Vis

Ultraviolet-visible spectrophotometry (UV-Vis) measurements were taken using an Agilent Technologies Cary 8454. Samples were applied to a 10 mm, 50 μL quartz cell (Starna Cells, Inc.) and absorbance was measured from 180 to 1000 nm. Net absorbance at 280 nm, obtained from measurement and single reference wavelength baseline subtraction, was used with calculated extinction coefficients and molecular weights to obtain protein concentration. The ratio of absorbance at 320/280 nm was used to determine relative aggregation levels in real-time stability study samples. Samples were diluted with respective blanking buffers to obtain an absorbance between 0.1 and 1.0. All data produced from the UV/vis instrument was processed in the 845×UV/visible System software.

Hydrogen/Deuterium-Exchange Mass Spectrometry 3 mg of RBD-I53-50A, Rpk4-I53-50A, and Rpk9-I53-50A trimers were H/D exchanged (HDX) in the deuteration buffer (pH*7.5, 85% D20, Cambridge Isotope Laboratories, Inc.) for 3, 15, 60, 1800, and 72000 seconds at 22° C. respectively. Exchanged samples were subsequently mixed 1:1 with ice-chilled quench buffer (200 mM tris(2-chlorethyl) phosphate (TCEP), 8 M Urea, 0.2% formic acid (FA)) for a final pH of 2.5 and immediately flash frozen in liquid nitrogen. Samples were analyzed by LC-MS on a Synapt™ G2-Si mass spectrometer using a custom-built loading system that maintained all columns, loops, valves, and lines at 0° C. Frozen samples were thawed on ice and loaded over a custom packed immobilized pepsin column (2.1×50 mm) with a 200 mL/min flow of 0.1% trifluoroacetic acid (TFA) with 2% acetonitrile. Peptides were trapped on a Waters CSH C18 trap cartridge (2.1×5 mm) prior to being resolved over a Waters CSH C18 1×100 mm 1.7 μm column with a linear gradient from 3% to 40% B over 18 min (A: 98% water, 2% acetonitrile, 0.1% FA, 0.025% TFA; B: 100% acetonitrile, 0.1% FA, flow rate of 40 mL/min). A series of washes were performed between sample runs to minimize carryover. All the water and organic solvent used, unless specifically stated, were MS grade (Optima™, Fisher). A fully deuterated control for each sample series was made by LC eluate collection from pepsin-digested undeuterated sample, speedvac drying, incubation in deuteration buffer for 1 hour at 85° C., and quenching the same as all other HDX samples. Internal exchange standards (Pro-Pro-Pro-lie [PPPI] (SEQ ID NO: 51) and Pro-Pro-Pro-Phe [PPPF] (SEQ ID NO: 52)) were added in each sample to ensure consistent labeling conditions for all samples).

The peptide reference list was updated from wild-type RBD peptide list with addition of new peptides covering mutations. These peptides were manually validated using DriftScope™ and identified with orthogonal retention time and drift time coordinates. Deuterium uptake analysis was performed with HX-Express v2. Peaks were identified from the peptide spectra based on the peptide m/z values and binomial fitting was applied. The deuterium uptake level was normalized relative to fully deuterated controls.

Mouse Immunizations

Female BALB/c (Stock: 000651) mice were purchased at the age of four weeks. At six weeks of age, 6 mice per dosing group were vaccinated with a prime immunization, and three weeks later mice were boosted with a second vaccination. Prior to inoculation, immunogen suspensions were gently mixed 1:1 vol/vol with AddaVax™ adjuvant to reach a final concentration of 0.009 or 0.05 mg/mL antigen. Mice were injected intramuscularly into the gastrocnemius muscle of each hind leg using a 27-gauge needle with 50 μL per injection site (100 μL total) of immunogen under isoflurane anesthesia. To obtain sera all mice were bled two weeks after prime and boost immunizations. Blood was collected via submental venous puncture and rested in 1.5 mL plastic Eppendorf tubes at room temperature for 30 min to allow for coagulation. Serum was separated from hematocrit via centrifugation at 2,000 g for 10 min. Complement factors and pathogens in isolated serum were heat-inactivated via incubation at 56° C. for 60 min. Serum was stored at 4° C. or −80° C. until use.

ELISA

Enzyme-linked immunosorbent assays (ELISA) were used to determine the binding of mouse sera to the delivered antigens. In brief, Maxisorp™ (Nunc®) ELISA plates were coated overnight at 4° C. with 0.08 μg/mL of protein of interest per well in 0.1 M sodium bicarbonate buffer, pH 9.4. Plates were then blocked with a 4% (w/v) solution of dried milk powder in TBS with 0.05% (v/v) Tween 20 (TBST) for 1 hour at room temperature. Serial dilutions of sera were added to the plates and, after washing, antibody binding was revealed using a hydrogen peroxidase coupled horse anti-mouse IgG antibody. Plates were then washed thoroughly in TBST, colorimetric substrate (TMB, Thermo Fisher) was added and absorbance was read at 450 nm. Area under curve (AUC) calculations were generated by addition of trapezoidal areas generated between adjacent pairs of absorbance measurements and baseline. Midpoint titers calculations ($EC_{50}$) were generated based on fitted four point logistic equations using the SciPy library in Python, in which the $EC_{50}$ was the serum dilution at which the curve reached 50% of its maximum.

Lentivirus-Based Pseudovirus Neutralization Assays

Spike-pseudotyped lentivirus neutralization assays were carried out essentially as described in (67). The protocol was modified for this study to use a SARS-CoV-2 spike with a 21 amino-acid cytoplasmic tail truncation, which increases spike-pseudotyped lentivirus titers, and the D614G mutation, which is now predominant in human SARS-CoV-2. The plasmid encoding this spike, HDM_Spikedelta21_D614G, is available from Addgene (#158762) or BET (NR-53765), and the full sequence is at available on the world wide web at addgene.org/158762).

Briefly, 293T-ACE2 cells (BEI NR-52511) were seeded at $1.25 \times 10^4$ cells per well in 50 uL D10 growth media (DMEM with 10% heat-inactivated FBS, 2 mM L-glutamine, 100 U/mL penicillin, and 100 μg/mL streptomycin) in poly-L-lysine coated black-walled clear-bottom 96-well plates (Greiner 655930). The next day, mouse serum samples were heat inactivated for 30 min at 56° C. and then serially diluted in D10 growth media. Spike-pseudotyped lentivirus was diluted 1:50 to yield ~200,000 RLUs per well and incubated with the serum dilutions for 1 hr at 37° C. 100 μL of virus-serum mixture was then added to the cells and ~52 hours later luciferase activity was measured using the Bright-Glo™ Luciferase Assay System (Promega®, E2610). Each batch of neutralization assays included a negative control sample of human serum collected in 2017-2018 and a known neutralizing antibody to ensure consistency between batches. Fraction infectivity for each well was calculated compared to two "no-serum" control wells in the same row of the plate. The "neutcurve" package (available on the world wide web at jbloomlab.github.io/neutcurve version 0.5.2) was used to calculate the inhibitory concentration 50% ($IC_{50}$) and the neutralization titer 50% (NT50), which is simply $1/IC_{50}$, for each serum sample by fitting a Hill curve with the bottom fixed at 0 and the top fixed at 1. All neutralization assay data is available on the world wide web at github.com/jbloomlab/RBD_nanoparticle_vaccine.

MLV-Based Pseudovirus Neutralization Assays

MLV-based SARS-CoV-2 S pseudotypes were prepared as described (A C Walls et al. *Cell* 181, 281-292.e6 (2020); A C Walls et al. *Cell* 183, 1367-1382.e17 (2020); A C Walls et al. Elicitation of broadly protective sarbecovirus immunity by receptor-binding domain nanoparticle vaccines, dx.doi.org/10.1101/2021.03.15.435528; J K Millet & G R Whittaker. *Bio Protoc* 6 (2016)). Briefly, HEK293T cells were co-transfected using Lipofectamine™ 2000 (Life Technologies) with an SARS-CoV-2 S-encoding plasmid, an MLV Gag-Pol packaging construct, and the MLV transfer vector encoding a luciferase reporter according to the manufacturer's instructions. Cells were washed 3× with Opti-MEM and incubated for 5 h at 37° C. with transfection medium. DMEM containing 10% FBS was added for 60 h. The supernatants were harvested by spinning at 2,500 g, filtered through a 0.45 μm filter, concentrated with a 100 kDa membrane for 10 min at 2,500 g and then aliquoted and stored at −80° C.

For neutralization assays, HEK-hACE2 cells were cultured in DMEM with 10% FBS (Hyclone) and 1% PenStrep with 8% $CO_2$ in a 37° C. incubator (ThermoFisher). One day or more prior to infection, 40 μL of poly-lysine (Sigma) was placed into 96-well plates and incubated with rotation for 5 min. Poly-lysine was removed, plates were dried for 5 min then washed 1× with water prior to plating cells HEK-hACE2 cells. The following day, cells were checked to be at 80% confluence. In a half-area 96-well plate, a 1:3 serial dilution of sera was made in DMEM in 22 μL final volume. 22 μL of pseudovirus was then added to the serial dilution and incubated at room temperature for 30-60 min. The mixture was added to cells and 2 hours later 44 μL of DMEM supplemented with 20% FBS and 2% PenStrep was added and cells were incubated for 48 hours. After 48 h 40 μL/well of One-Glo-EX™ substrate (Promega) was added to the cells and incubated in the dark for 5-10 min prior to reading on a BioTek™ plate reader. Nonlinear regression of log(inhibitor) versus normalized response was used to determine $IC_{50}$ values from curve fits.

Quantification and Statistical Analysis

Multi-group comparisons were performed using nonparametric Kruskal-Wallis test with Dunn's post-hoc analysis in GraphPad Prism 8. Differences were considered significant when P values were less than 0.05. Statistical methods and P value ranges can be found in the Figures and Figure legends.

Results

Five mutations of the SARS-CoV-2 S RBD were considered as starting points for the design of stabilized RBD antigens: I358F, Y365F, Y365W, V367F and F392W. A cryo-EM structure of the prefusion S ectodomain trimer (PDB ID 6VXX) was used to analyze the five mutations in PyMol™ and Rosetta™. Only the V367F mutation was found to be exposed to solvent and was therefore not considered for inclusion in stabilized RBD designs to avoid the risk of unfavorably altering antigenicity. The other four mutations were observed to be near or within a recently identified linoleic acid (LA) binding pocket, with Y365 identified as a key gating residue for this interaction (FIGS. 2A-2B). The improved expression and stability observed by DMS for several mutations in the LA binding pocket indicated that this region of the RBD is structurally suboptimal.

It was next explored whether combinations of these mutations could further improve these and other properties of the RBD. Computational protocols were developed in Rosetta™ that modelled one or more of I358F, Y365F, Y365W and/or F392W while also allowing nearby residues to mutate (FIG. 2C). Design trajectories that did not force inclusion of any of these four validated mutations within the LA binding pocket were also performed, instead allowing Rosetta™ to design novel sets of stabilizing mutations in the same region. All design trajectories were performed both in the context of the complete S ectodomain (PDB ID 6VXX) and a crystal structure of an RBD monomer (PDB ID 6YZ5) that showed a subtly distinct backbone conformation in the region surrounding the LA binding pocket. Seventeen repacked designs (abbreviated as "Rpk") possessing mutations that filled cavities and/or removed buried polar groups were selected for experimental analysis, with some of the DMS-identified individual mutations also included for comparison (Table 1).

TABLE 1

Mutations included in each stabilized RBD design. Mutations are separated into reported DMS-identified mutations or mutations identified by Rosetta.

| Mutation set | Mutations identified by DMS | Mutations identified by Rosetta |
| --- | --- | --- |
| Rpk1 | Y365W | n/a |
| Rpk2 | Y365W | F338L |
| Rpk3 | Y365W | L513M |
| Rpk4 | F392W | n/a |
| Rpk5 | Y365W, F392W | n/a |
| Rpk6 | Y365F | F338M, A363L, F377V |
| Rpk7 | Y365F, F392W | n/a |
| Rpk8 | Y365F | V395I |
| Rpk9 | Y365F, F392W | V395I |
| Rpk10 | Y365W | L513I, F515L |
| Rpk11 | n/a | F338L, A363L, Y365M |
| Rpk12 | I358F, Y365W | n/a |
| Rpk13 | I358F, Y365W | F338L |
| Rpk14 | I358F, Y365W | L513M |
| Rpk15 | I358F, Y365F | V395I |
| Rpk16 | I358F, Y365W, F392W | n/a |
| Rpk17 | I358F, Y365F, F392W | V395I |

* n/a, not applicable

The designs were screened in the context of genetic fusions of the Wuhan-Hu-1 RBD to the I53-50A nanoparticle trimer, which can be incorporated into the icosahedral I53-50 nanoparticle, to enable their evaluation as vaccine candidates displaying 60 copies of the RBD. Stabilized RBD amino acid sequences were therefore cloned into a vector for mammalian expression with the I53-50A sequence C-terminally fused to the antigen and the two domains joined by a 16-residue flexible Gly-Ser linker.

Stabilized designs were secreted from HEK293F cells alongside the wild-type RBD ("RBD") fused to the I53-50A trimer and a negative control plasmid. Reducing SDS-PAGE of cell culture supernatants showed increased expression for all designs compared to wild-type (FIG. 1A). Furthermore, non-reducing SDS-PAGE showed striking differences in the amounts of disulfide-linked dimers formed by each design (FIG. 1A). Designs including the F392W mutation yielded noticeably lower levels of disulfide-linked dimers. In addition to F392W partially filling the LA binding pocket cavity, the proximity of this mutation to the disulfide between C391 and C525 indicates that it disfavors off-target intermolecular disulfide formation involving these cysteines.

Figure 4A:
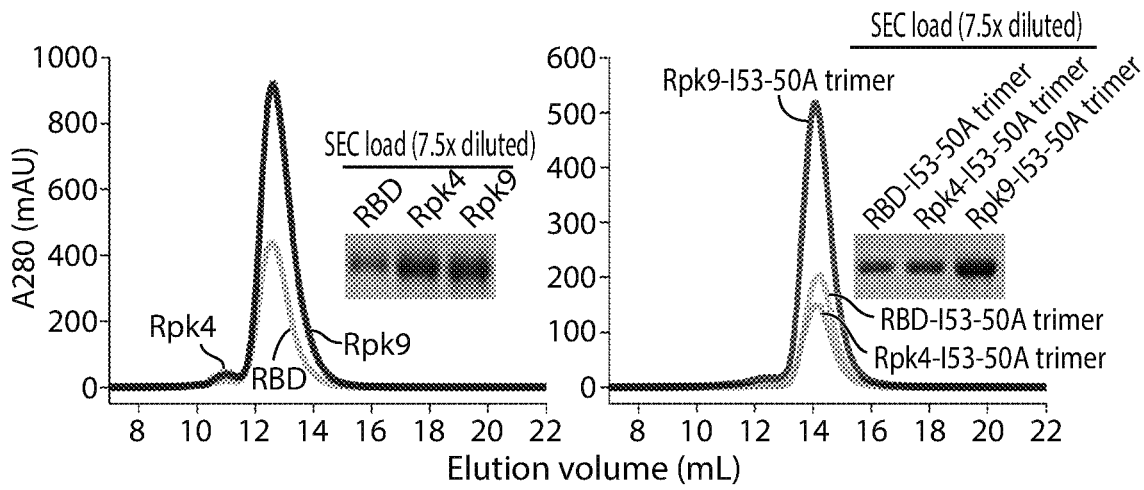
FIGS. 4A-4E. Biochemical, biophysical and antigenic characterization of stabilized RBDs containing Rpk4 or Rpk9 mutations in monomeric form and when fused to the I53-50A trimer (designated by addition of "-I53-50A"). Expression, thermal stability and local structural order were all improved while maintaining similar antigenicity to wild-type SARS-CoV-2 RBD.
Figure 4B:
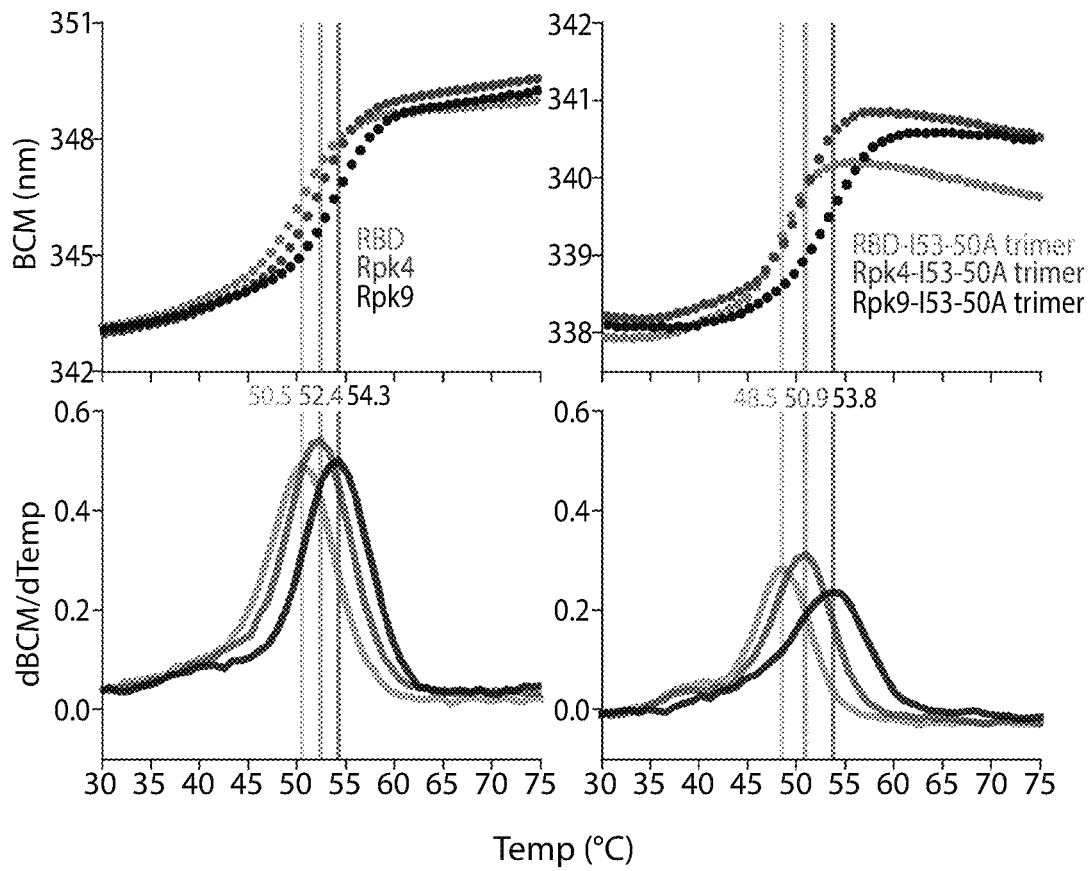
Figure 4C:
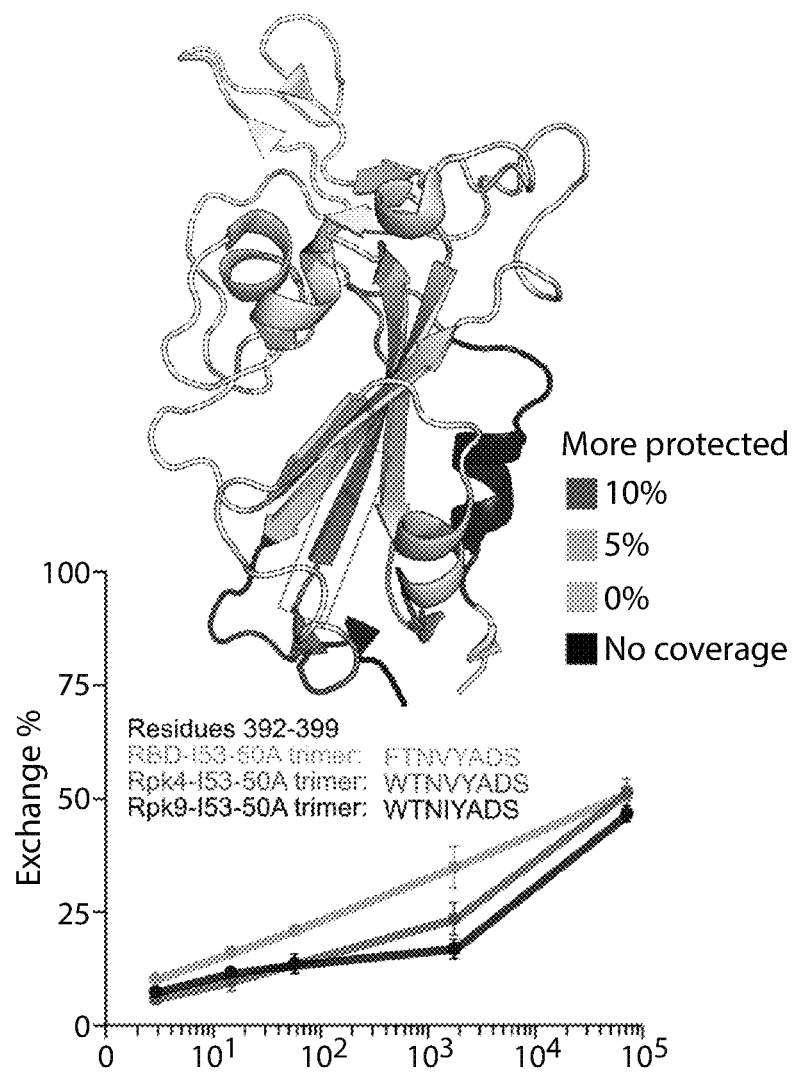
Figure 4D:
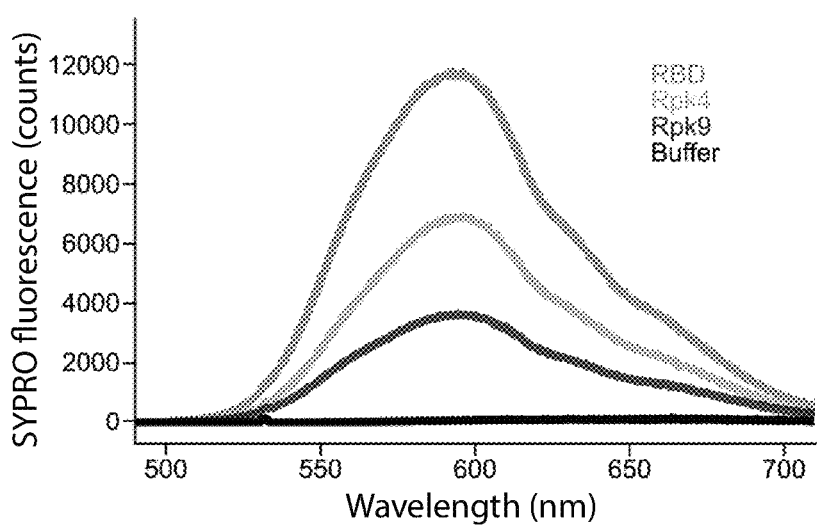
Figure 4E:
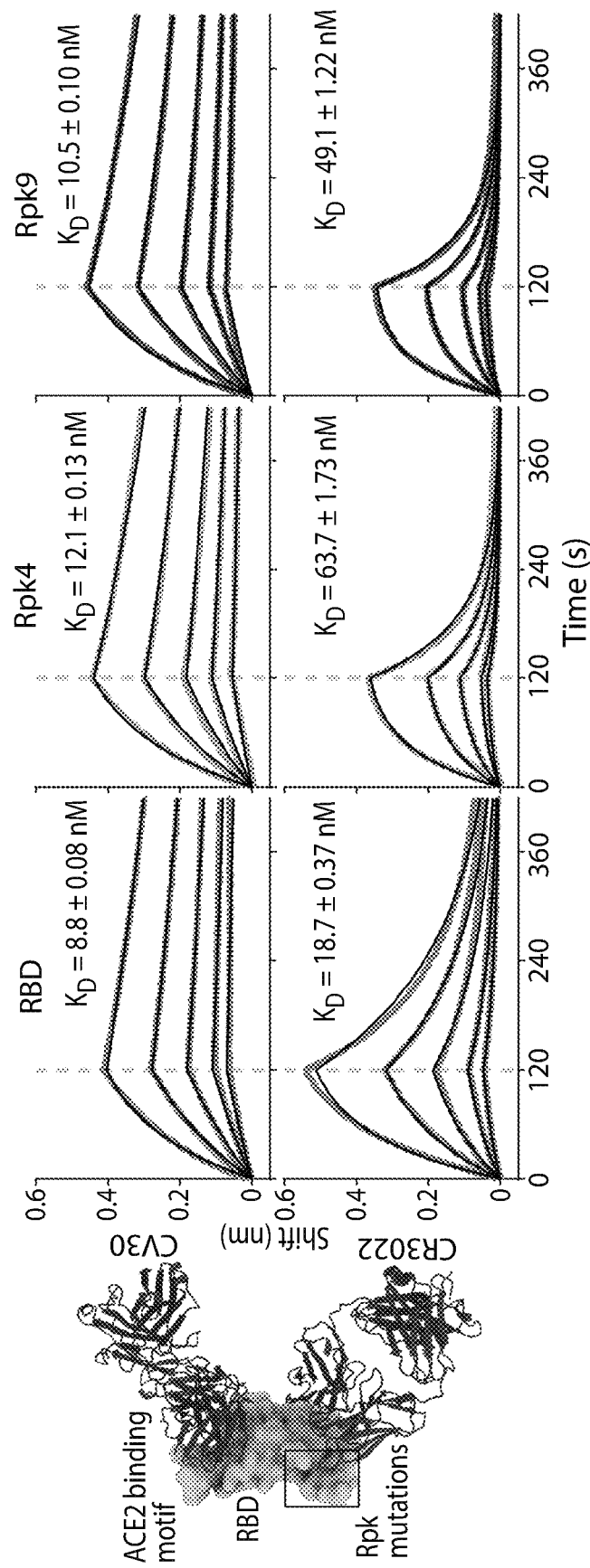
Figure 10:
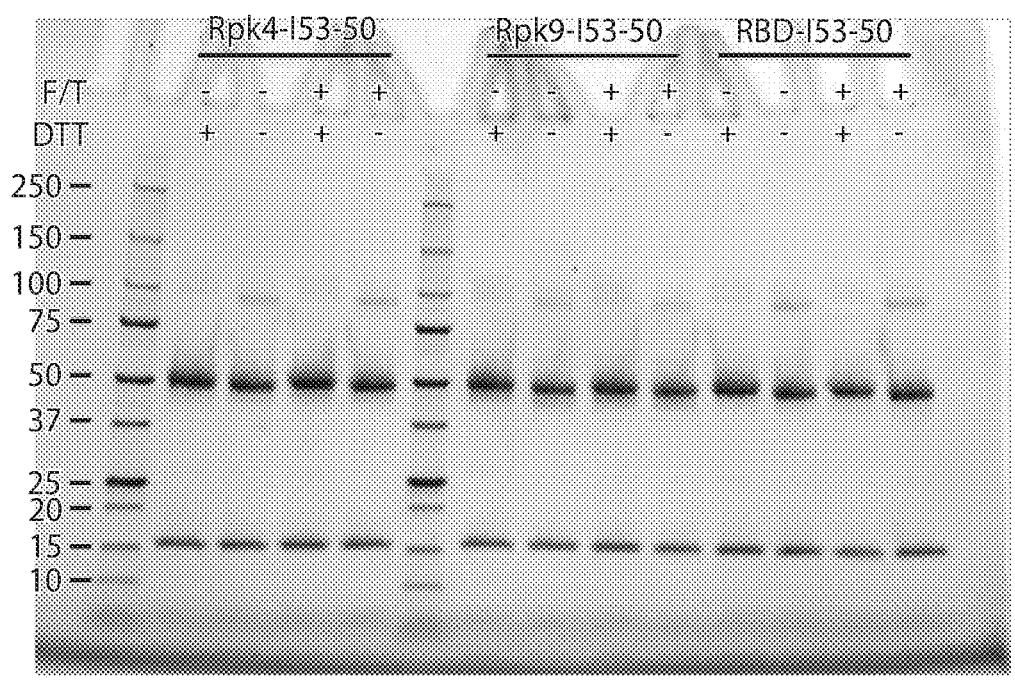
FIG. 10 SDS-PAGE for nanoparticles in TBS, 5% glycerol, 0.75% CHAPS, 100 mM L-arginine. The integrity of samples in 50 mM Tris pH 7.4, 185 mM NaCl, 4.5% glycerol, 0.75% CHAPS, 100 mM L-arginine was analyzed by SDS-PAGE. Molecular weights of the standard are noted in kDa. Each sample was analyzed +/− reducing agent (DTT), pre- and post-freeze thaw (F/T).
Figure 11:
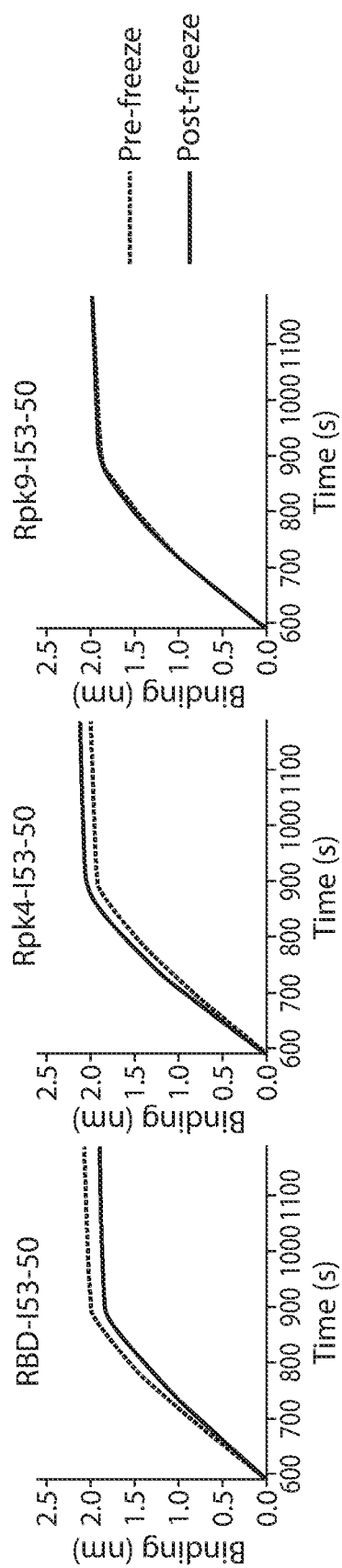
FIG. 11 hACE2-Fc binding for nanoparticles in TBS, 5% glycerol, 0.75% CHAPS, 100 mM L-arginine. hACE2-Fc binding of antigen in 50 mM Tris pH 7.4, 185 mM NaCl, 4.5% glycerol, 0.75% CHAPS, 100 mM L-arginine was analyzed by bio-layer interferometry (BLI). Protein A biosensors loaded with hACE2-Fc were incubated with immunogen (association, x=590-889 s) and then buffer (dissociation, x=890-1190 s).

Two designs were selected for more detailed analysis both as monomers and trimers: Rpk4, which features F392W alone, and Rpk9, which combines F392W with the DMS-identified Y365F to remove the buried side chain hydroxyl group and the Rosetta-identified V395I to refill the resulting cavity with hydrophobic packing (data not shown). Scaled-up expression from HEK293F cells and purification by immobilized metal affinity chromatography (IMAC) and size exclusion chromatography (SEC) confirmed increased yields for Rpk4 and Rpk9 both as monomers and as fusions to the I53-50A trimer, with Rpk9 showing a clear advantage for I53-50A trimers (FIGS. 4A & 10A). All constructs featured low levels of off-target disulfide-linked dimer formation, highlighting the importance of including F392W in stabilized RBD designs. Melting temperatures ($T_m$) were measured for both monomers and trimers by nano differential scanning fluorimetry (nanoDSF), monitoring intrinsic tryptophan fluorescence, which showed increases of 1.9-2.4° C. for the Rpk4 proteins and 3.8-5.3° C. for the Rpk9 proteins compared to their wild-type counterparts (FIG. 4B). All of the monomeric RBDs were indistinguishable by circular dichroism and appeared to refold after denaturation at 95° C. (FIG. 10B). Moreover, hydrogen/deuterium-exchange mass spectrometry (HDX-MS) of the stabilized RBDs fused to the I53-50A trimer showed decreased deuterium uptake in two distinct peptide segments in the LA binding pocket compared to the wild-type RBD (FIG. 4C, FIG. 11), indicating improved local ordering in the stabilized designs. Peptide segments distant from the LA binding pocket, including those in the ACE2 binding motif, showed preserved structural order compared to wild-type. To further assess structural order, all three monomeric RBDs were separately mixed with SYPRO Orange dye to measure the exposure of hydrophobic groups (FIG. 4D). Both Rpk4 with Rpk9 showed decreased signal compared to the wild-type RBD, with Rpk9 yielding the least fluorescence, indicating that the improved local order of the LA binding pocket in the stabilized RBDs results in less hydrophobic exposure. Consistent with the HDX-MS data, neither set of stabilizing mutations impacted the antigenicity of the ACE2 binding motif, as assessed by binding of the antibody CV30 (Hurlbut et al. *Nature Communications* 11:5413 (2020)), which recognizes antigenic site Ia (FIG. 4E). Affinity to the non-neutralizing antibody CR3022 (Yuan et al. *Science* 386:630-644 (2020)), against site IIc and closer to the LA binding pocket, was slightly decreased (<3.5-fold). In summary, both sets of stabilizing mutations enhanced expression, thermal stability, and structural order of the antigen while minimally impacting antigenicity, with Rpk9 showing superior improvement in all categories for both monomeric RBDs and their genetic fusions to the I53-50A trimer.

Figure 5A:
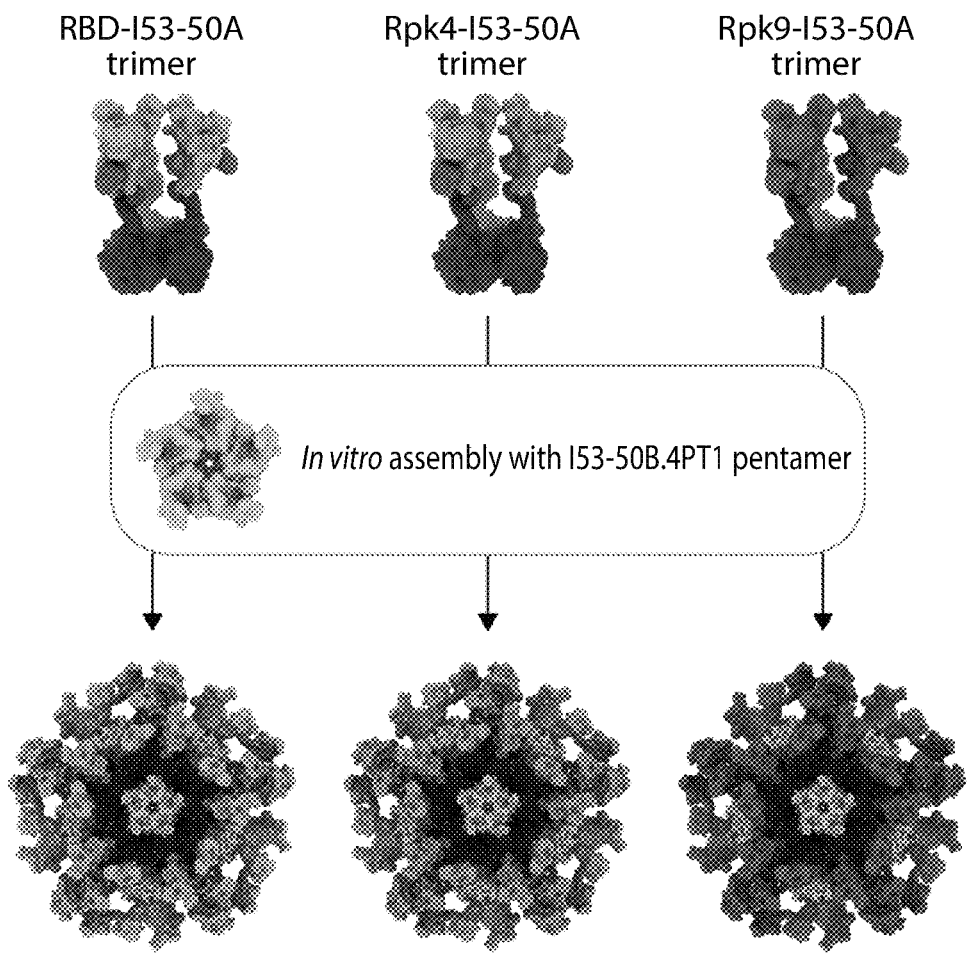
FIGS. 5A-5E. Stabilized RBDs presented on assembled I53-50 nanoparticles enhance solution stability compared to the wild-type RBD.
Figure 5B:
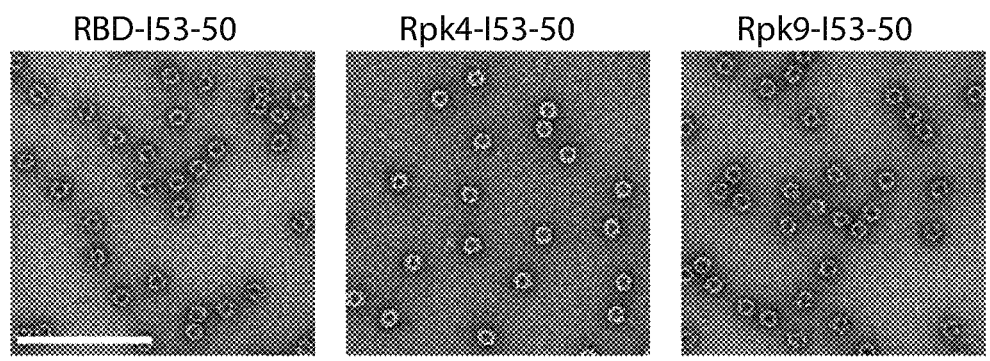
Figure 5C:
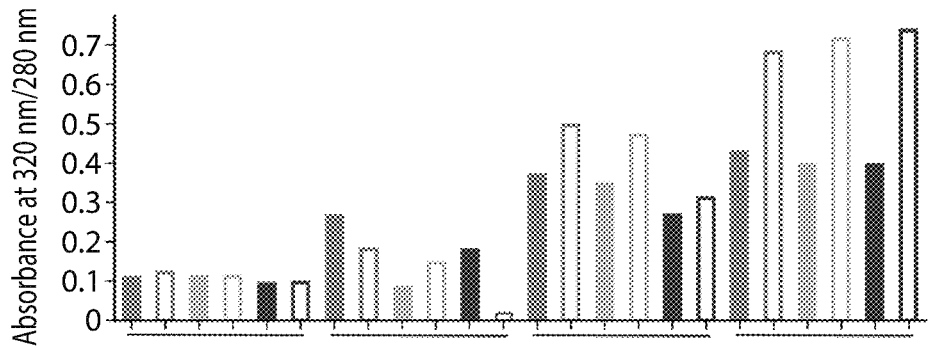
Figure 8A:
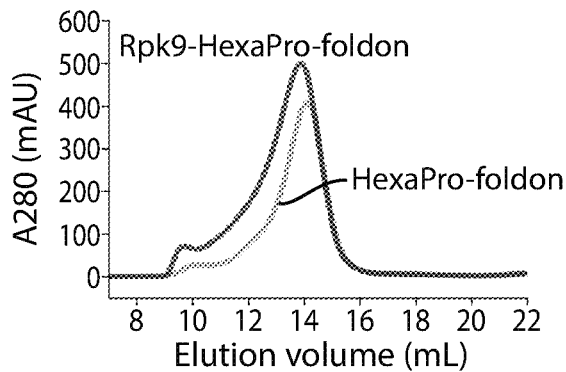
FIGS. 8A-8D. Rpk9 mutations can be incorporated into full length SARS-CoV-2 S ectodomains containing HexaPro mutations.
Figure 8C:
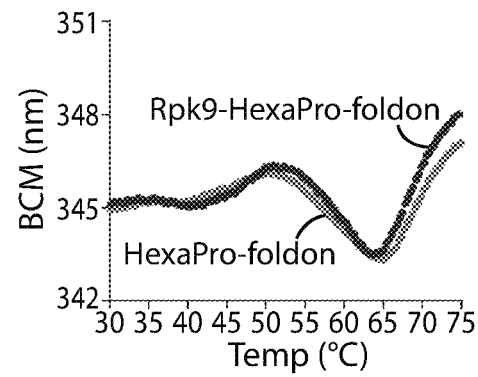
Figure 8B:
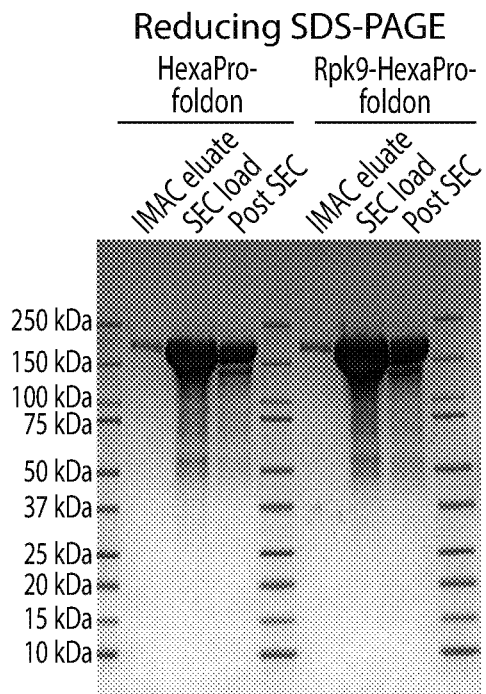
Figure 8B:
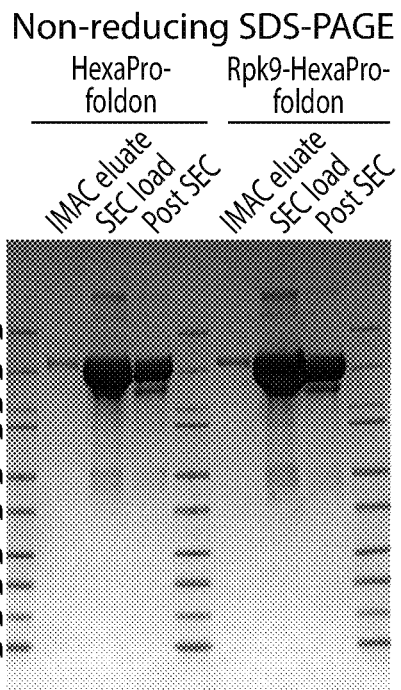
Figure 8D:
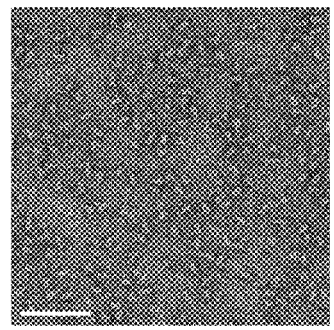
Figure 9:
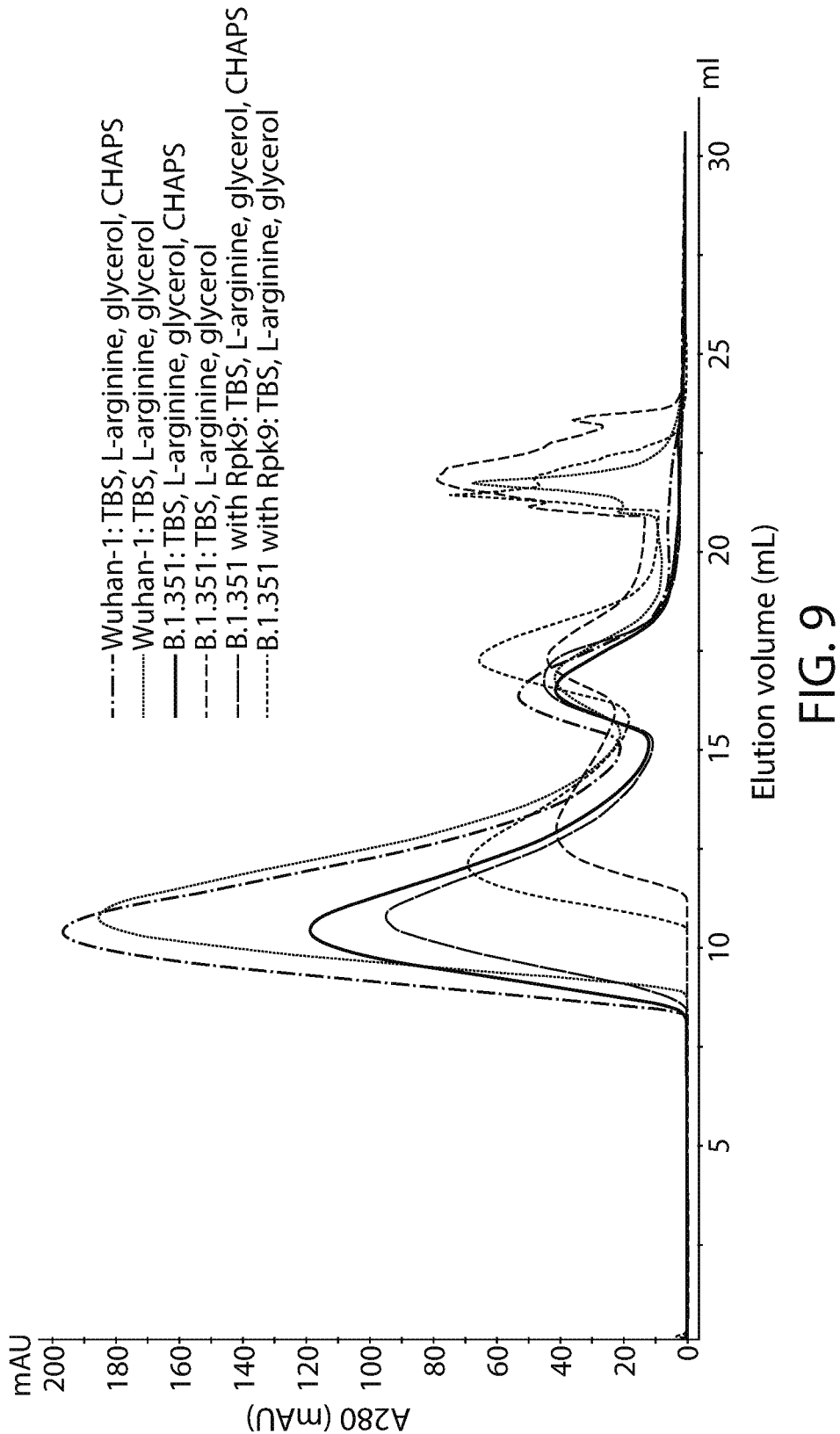
FIG. 9. When added to the RBD of the B.1.351 variant, the Rpk9 mutations improved relative recovery of I53-50 nanoparticles displaying the RBD at the proper SEC elution volume in simpler buffer formulations, which shows that Rpk mutations improve the integrity of immunogens containing RBDs from different variants. Assembly and SEC was either performed in 50 mM Tris pH 7.4, 185 mM NaCl, 100 mM L-arginine, 0.75% CHAPS, 4.5% glycerol or 50 mM Tris pH 8, 150 mM NaCl, 100 mM L-arginine, 5% glycerol for I53-50 nanoparticles displaying either the Wuhan-1 RBD (no Rpk mutations), the B.1.351 RBD without Rpk9 mutations and the B.1.351 RBD with Rpk9 mutations. While the Rpk9 mutations increased yield and other measures of RBD stability in either buffer condition, compared to the equivalent sample without Rpk9 mutations, the nanoparticles displaying B.1.351 RBD with Rpk9 mutations better maintained relative yield and SEC migration without CHAPS detergent.

Although the stabilizing mutations were designed with isolated RBDs in mind, such mutations were also evaluated in the context of the full S ectodomain. Total yield of the prefusion-stabilized HexaPro antigen fused to T4 fibritin foldon was measured with the Rpk9 mutations (Rpk9-HexaPro-foldon) and compared with the wild-type version (HexaPro-foldon). The term "HexaPro" refers to a spike protein with four beneficial proline substitutions (F817P, A892P, A899P, A942P) as well as the two proline substitutions in S-2P (prolines at 986 and 987). See Hsieh et al. Science 369:1501-05 (2020); A modest improvement in yield was seen with the Rpk9 mutations, however a slightly earlier SEC elution volume was observed, which could indicate a decrease in stability in the context of S ectodomains. Rpk9-HexaPro-foldon showed a similar nanoDSF profile to HexaPro-foldon, although changes in intrinsic fluorescence occurring above 60° C. were slightly accelerated with Rpk9-HexaPro-foldon (FIG. 5C). Negative stain electron microscopy (nsEM) revealed that the typical prefusion spike morphology was predominantly maintained with the mutations (FIG. 8D). These data indicate that although it is possible to incorporate mutations to the LA binding pocket into prefusion spike trimers, the stabilizing effects of the Rpk9 mutations appear unique to isolated RBDs.

Figure 5D:
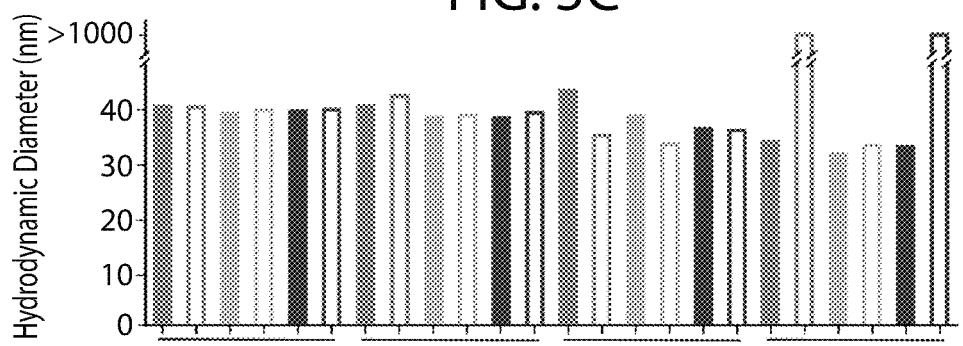
Figure 5E:
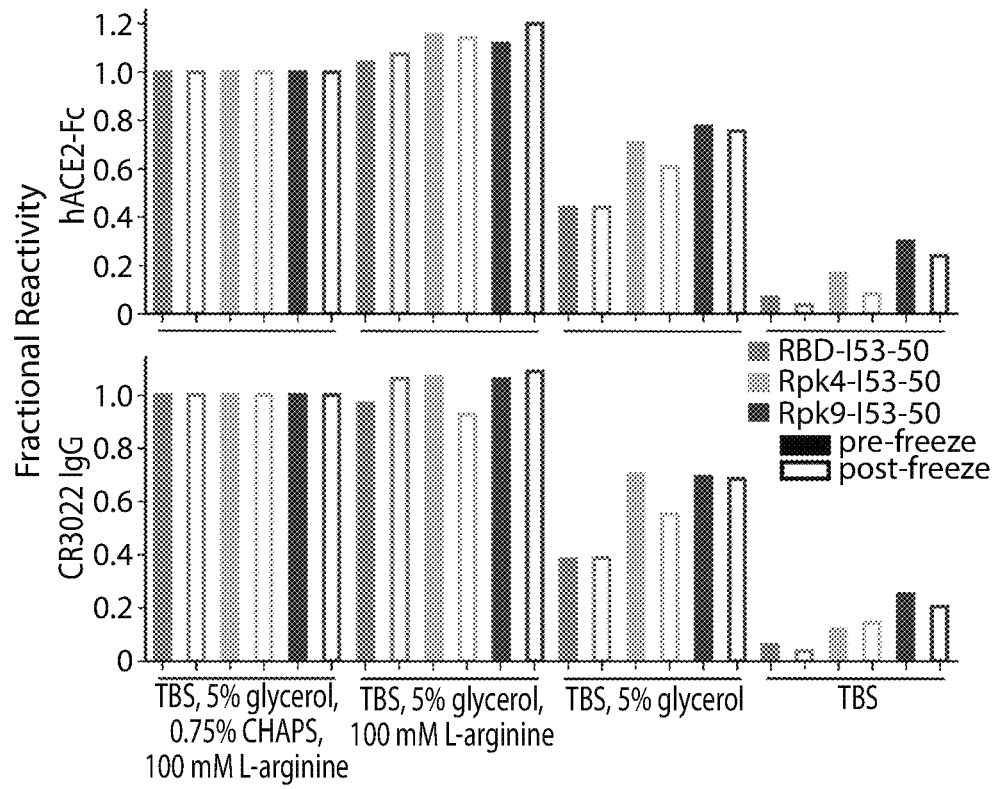

It was next investigated whether the RBD-stabilizing mutations would improve the stability of the nanoparticles in simpler buffers, lacking excipients such as glycerol, L-arginine, and the detergent 3-[(3-cholamidopropyl)dimethylammonio]-1-propanesulfonate (CHAPS), which otherwise could be used to stabilize preparations of the nanoparticle immunogens. The wild-type and stabilized RBD-I53-50A trimers were assembled into nanoparticles (RBD-I53-50, Rpk4-I53-50, and Rpk9-I53-50) by addition of the complementary I53-50B.4PT1 pentameric component (SEQ ID NO: 17) (FIG. 5A). Excess residual components were removed by SEC using a mobile phase comprising Tris-buffered saline (TBS) with glycerol, L-arginine, and CHAPS, and the formation of highly monodisperse nanoparticles was confirmed by negative stain electron microscopy (nsEM) (FIG. 5B). The purified nanoparticles were then dialyzed into buffered solutions with fewer excipients to evaluate solution stability before and after a single freeze/thaw cycle (FIGS. 5C-5E). In TBS supplemented with glycerol and L-arginine, the wild-type RBD-I53-50 showed minor indications of aggregation by UV-Vis spectroscopy (FIG. 5C) and dynamic light scattering (DLS) (FIG. 5D) that were not observed for Rpk4-I53-50 and Rpk9-I53-50. Differences in solution stability were further contrasted after dialysis into TBS with only glycerol: Rpk4-I53-50 and Rpk9-I53-50 were both more resistant to aggregation than RBD-I53-50 and better maintained binding to immobilized human ACE2 (hACE2-Fc) and CR3022 (FIG. 5E). Dialysis into TBS alone showed clear evidence of aggregation of all samples and loss of antigenicity, with Rpk9-I53-50 retaining slightly better antigenicity than RBD-I53-50 and Rpk4-I53-50. The improved solution stability observed for the stabilized RBDs appears consistent with their enhanced thermal stability and structural order, and offers a subtle but important improvement in formulation stability that is highly relevant to vaccine manufacturing.

The immunogenicity of the stabilized RBDs was then evaluated in immunization studies in mice. Immunogens comprising the wild-type and stabilized RBDs were prepared in two formats: I53-50 nanoparticles displaying each antigen, and non-assembling controls of nearly equivalent proteins in which the trimeric fusions to I53-50A were mixed with a slightly modified pentameric scaffold lacking the hydrophobic interface that drives nanoparticle assembly ("2OBX"; SEQ ID NO: 43; FIG. 6A). In addition to allowing evaluation of the immunogenicity of the different RBDs in trimer and nanoparticle formats, this comparison also directly controls for the effects of nanoparticle assembly. All nanoparticle immunogens were prepared in Tris-buffered saline (TBS) supplemented with glycerol and L-arginine, while the wild-type RBD-I53-50 nanoparticle was also prepared in a buffer that further comprises CHAPS to enable direct comparison to other immunogenicity studies. HexaPro-foldon (featuring the wild-type RBD) was included as a comparator. Female BALB/c mice were immunized twice with each immunogen three weeks apart, with serum collection two weeks after each immunization (FIG. 6A). All doses were administered with equimolar amounts of RBD and included AddaVax adjuvant.

Figure 12:
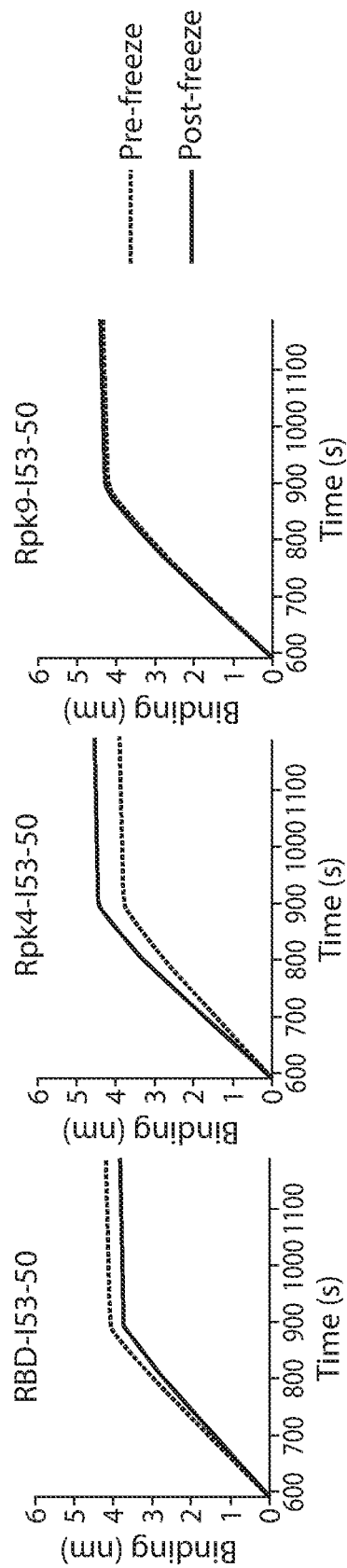
FIG. 12 CR3022 binding for nanoparticles in TBS, 5% glycerol, 0.75% CHAPS, 100 mM L-arginine. CR3022 IgG binding of antigen in 50 mM Tris pH 7.4, 185 mM NaCl, 4.5% glycerol, 0.75% CHAPS, 100 mM L-arginine was analyzed by bio-layer interferometry (BLI). Protein A biosensors loaded with CR3022 IgG were incubated with immunogen (association, x=590-889 s) and then buffer (dissociation, x=890-1190 s).
Figure 13:
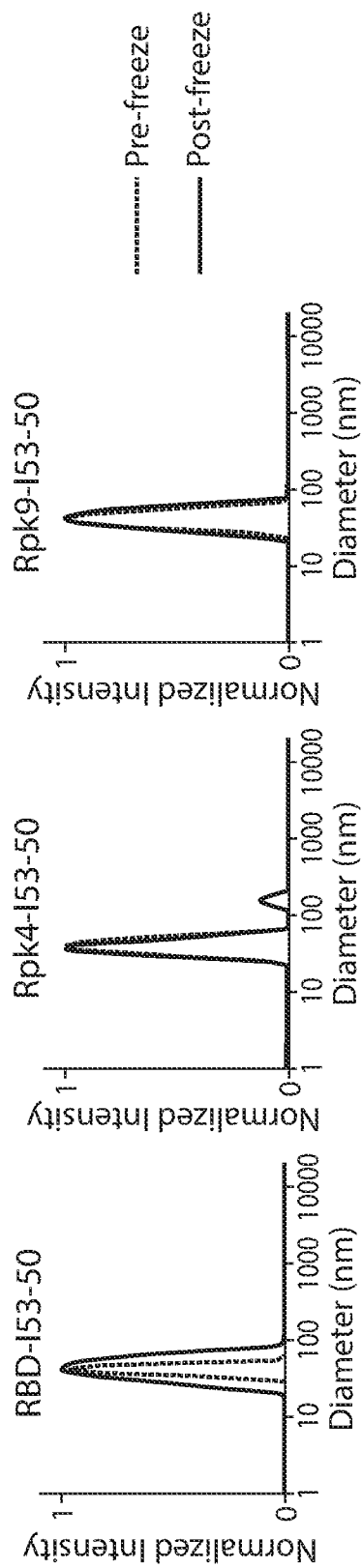
FIG. 13 Dynamic light scattering for nanoparticles in TBS, 5% glycerol, 0.75% CHAPS, 100 mM L-arginine. Hydrodynamic diameter (nm) for each sample in 50 mM Tris pH 7.4, 185 mM NaCl, 4.5% glycerol, 0.75% CHAPS, 100 mM L-arginine, plotted as normalized intensity.
Figure 14:
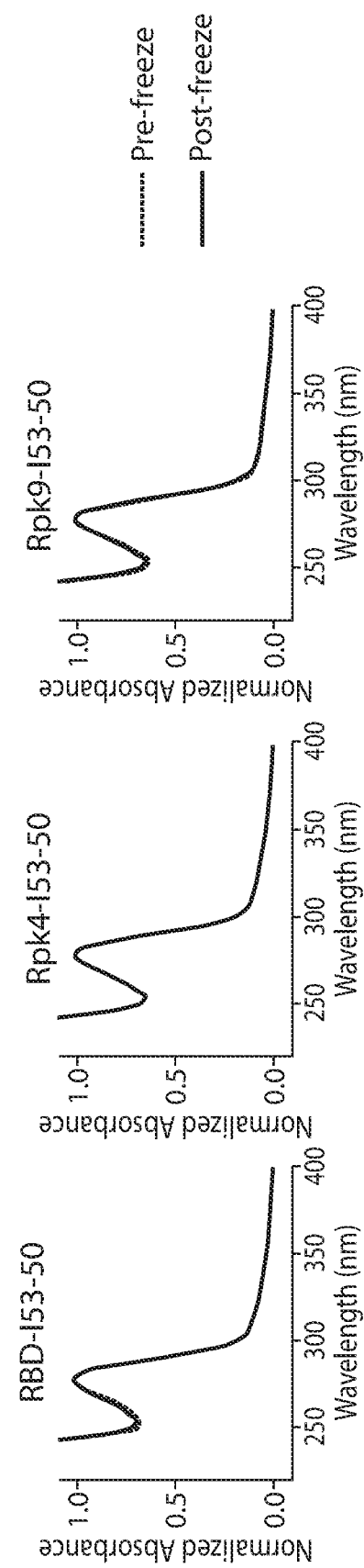
FIG. 14 UV-Vis for nanoparticles in TBS, 5% glycerol, 0.75% CHAPS, 100 mM L-arginine. UV-Vis spectra (nm) for each sample in 50 mM Tris pH 7.4, 185 mM NaCl, 4.5% glycerol, 0.75% CHAPS, 100 mM L-arginine, plotted as normalized absorbance.
Figure 15:
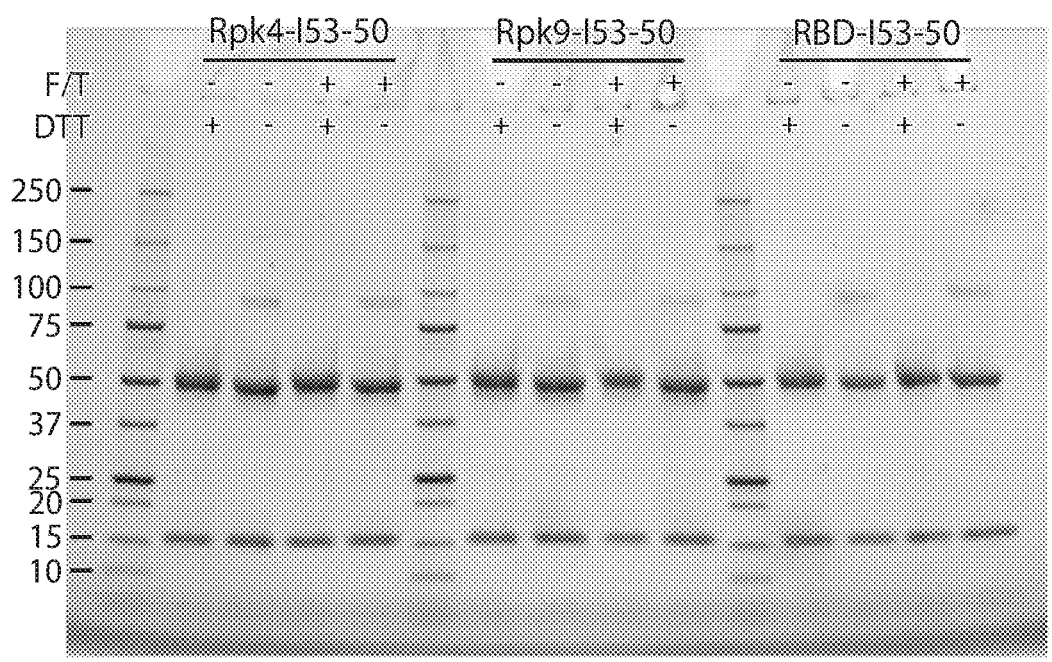
FIG. 15 SDS-PAGE for nanoparticles in TBS, 5% glycerol, 100 mM L-arginine. The integrity of samples in 50 mM Tris pH 8, 150 mM NaCl, 5% glycerol, 100 mM L-arginine was analyzed by SDS-PAGE. Molecular weights of the standard are noted in kDa. Each sample was analyzed +/− reducing agent (DTT, pre- and post-freeze thaw (F/T).
Figure 16:
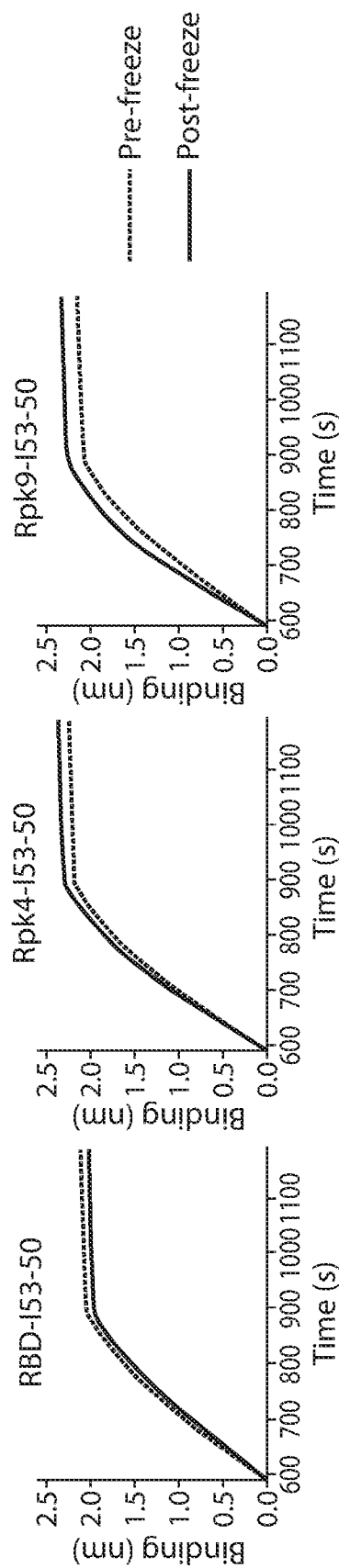
FIG. 16 hACE2-Fc binding for nanoparticles in TBS, 5% glycerol, 100 mM L-arginine. hACE2-Fc binding of antigen in 50 mM Tris pH 8, 150 mM NaCl, 5% glycerol, 100 mM L-arginine was analyzed by bio-layer interferometry (BLI). Protein A biosensors loaded with hACE2-Fc were incubated with immunogen (association, x=590-889 s) and then buffer (dissociation, x=890-1190 s).
Figure 17:
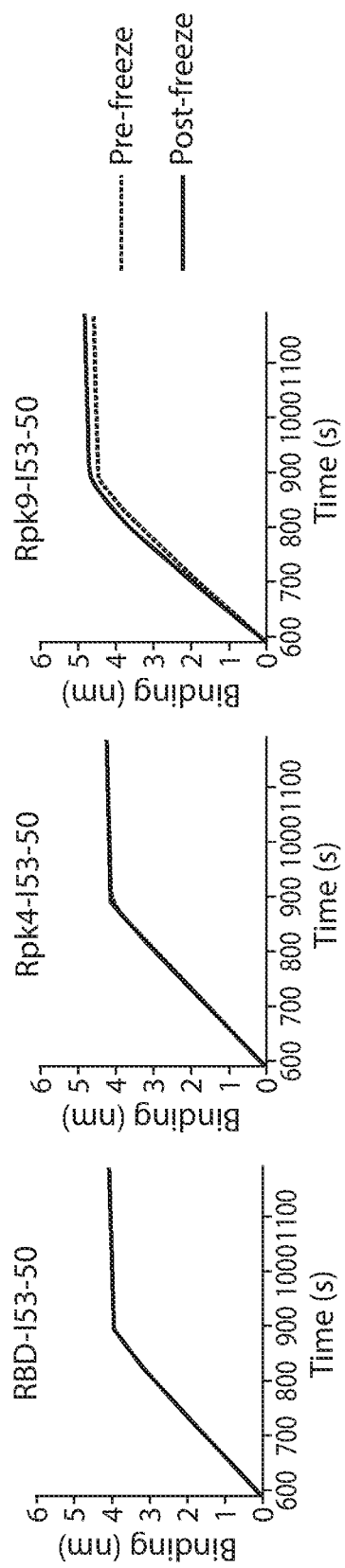
FIG. 17 CR3022 binding for nanoparticles in TBS, 5% glycerol, 100 mM L-arginine. CR3022 IgG binding of antigen in 50 mM Tris pH 8, 150 mM NaCl, 5% glycerol, 100 mM L-arginine was analyzed by bio-layer interferometry (BLI). Protein A biosensors loaded with CR3022 IgG were incubated with immunogen (association, x=590-889 s) and then buffer (dissociation, x=890-1190 s).
Figure 18:
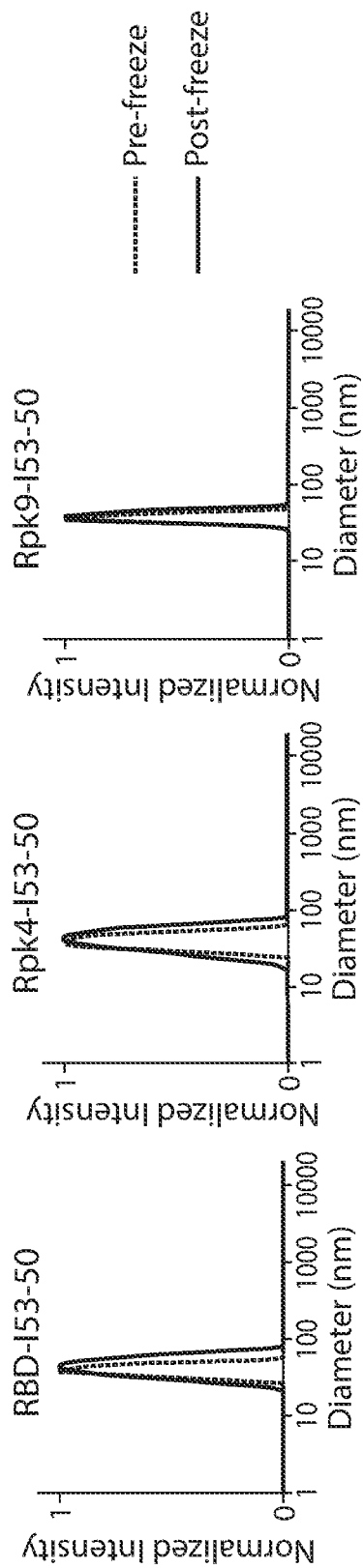
FIG. 18 Dynamic light scattering for nanoparticles in TBS, 5% glycerol, 100 mM L-arginine. Hydrodynamic diameter (nm) for each sample in 50 mM Tris pH 8, 150 mM NaCl, 5% glycerol, 100 mM L-arginine, plotted as normalized intensity.
Figure 19:
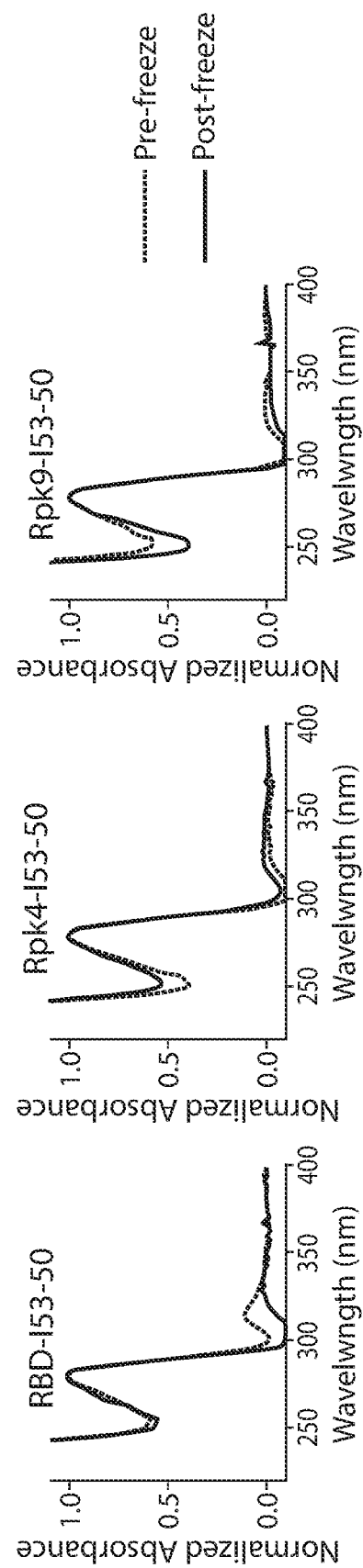
FIG. 19 UV-Vis for nanoparticles in TBS, 5% glycerol, 100 mM L-arginine. UV-Vis spectra (nm) for each sample in 50 mM Tris pH 8, 150 mM NaCl, 5% glycerol, 100 mM L-arginine, plotted as normalized absorbance.
Figure 20:
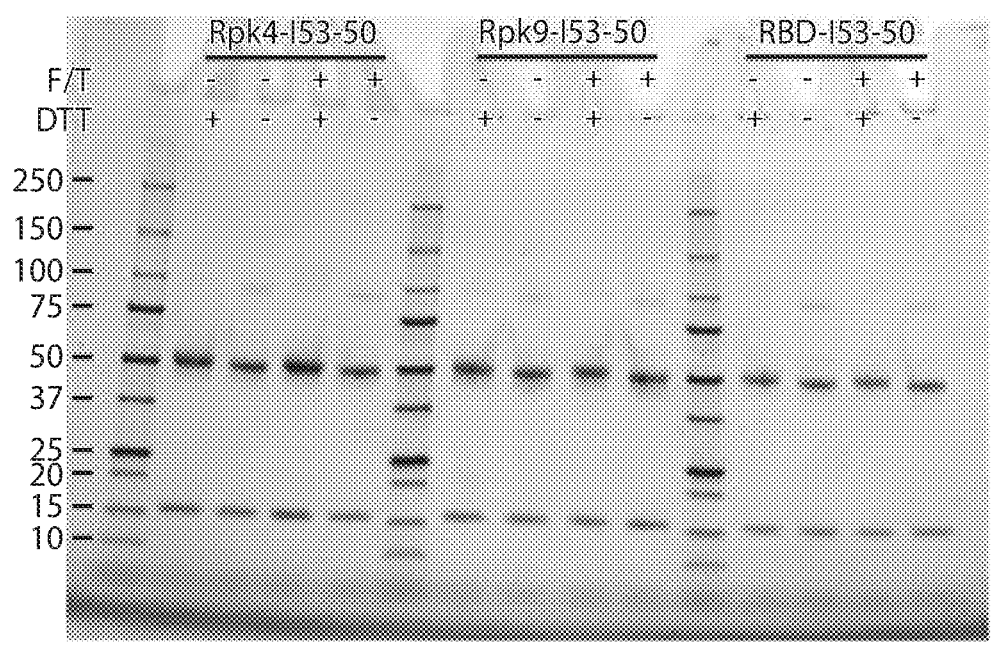
FIG. 20 SDS-PAGE for nanoparticles in TBS, 5% glycerol. The integrity of samples in 50 mM Tris pH 8, 150 mM NaCl, 5% glycerol was analyzed by SDS-PAGE. Molecular weights of the standard are noted in kDa. Each sample was analyzed +/- reducing agent (DTT), pre- and post-freeze thaw (FIT).
Figure 21:
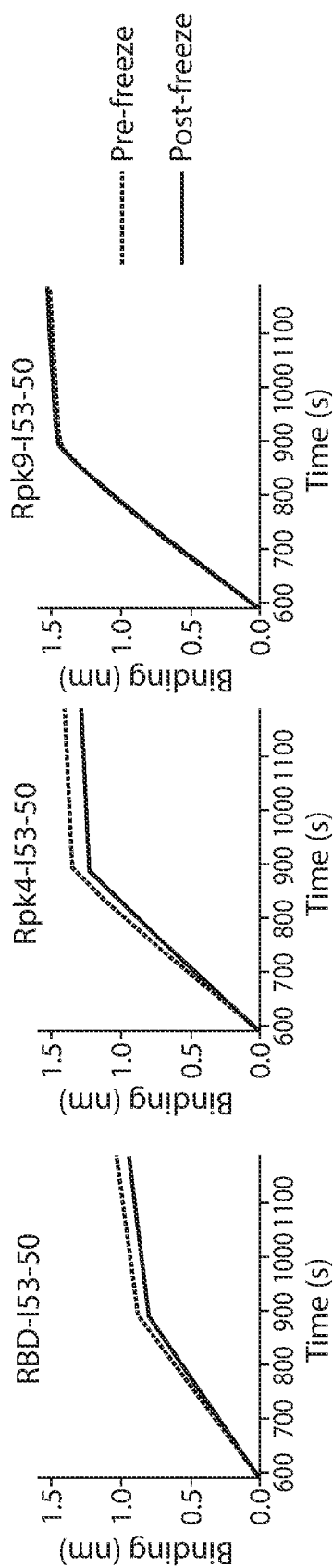
FIG. 21 hACE2-Fc binding for nanoparticles in TBS, 5% glycerol. ACE2-Fc binding of antigen in 50 mM Tris pH 8, 150 mM NaCl, 5% glycerol was analyzed by bio-layer interferometry (BLI). Protein A biosensors loaded with hACE2-Fc were incubated with immunogen (association, x=590M889 s) and then buffer (dissociation, x=890-1190 s).
Figure 22:
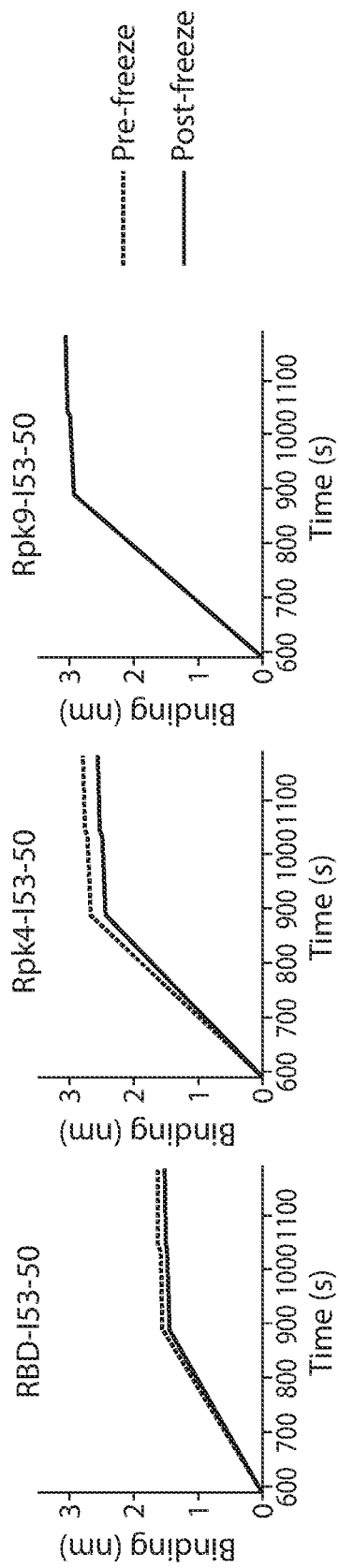
FIG. 22 CR3022 binding for nanoparticles in TBS, 5% glycerol. CR3022 IgG binding of antigen in 50 mM Tris pH 8, 150 mM NaCl, 5% glycerol was analyzed by bio-layer interferometry (BLI). Protein A biosensors loaded with CR3022 IgG were incubated with immunogen (association, x=590-889 s) and then buffer (dissociation, x=890-1190 s).
Figure 23:
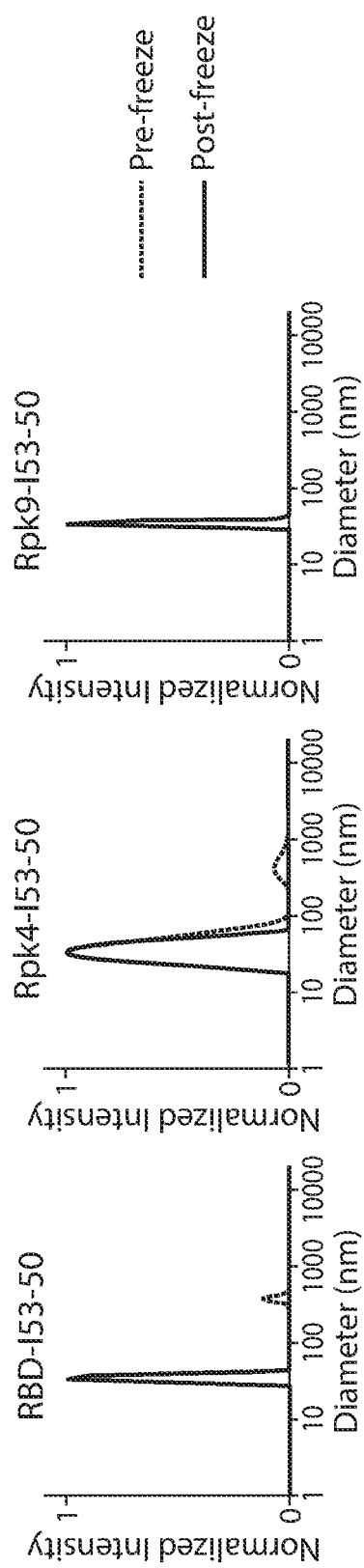
FIG. 23 Dynamic light scattering for nanoparticles in TBS, 5% glycerol. Hydrodynamic diameter (nm) for each sample in 50 mM Tris pH 8, 150 mM NaCl, 5% glycerol, plotted as normalized intensity.
Figure 24:
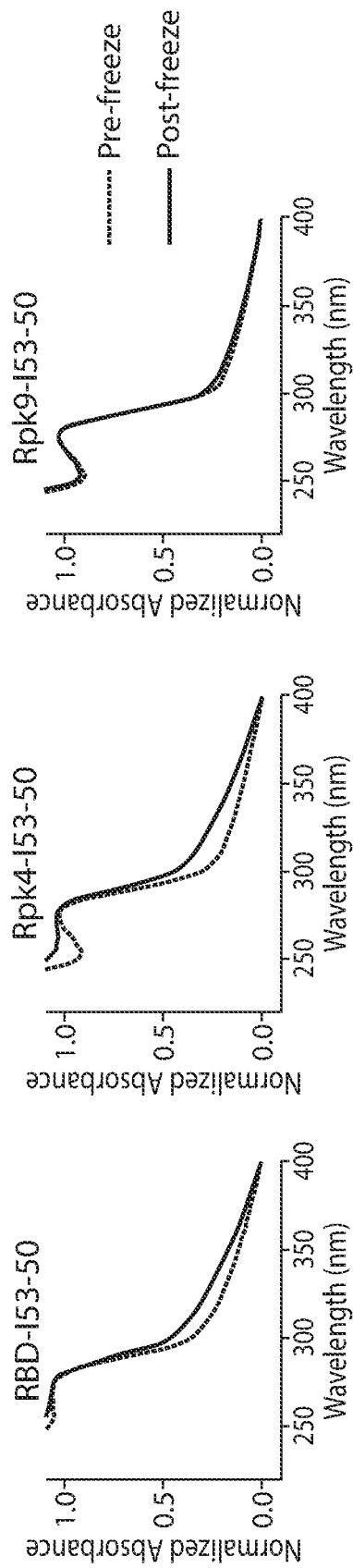
FIG. 24 UV-Vis for nanoparticles in TBS, 5% glycerol. UV-Vis spectra (nm) for each sample in 50 mM Tris pH 8, 150 mM NaCl, 5% glycerol, plotted as normalized absorbance.
Figure 25:
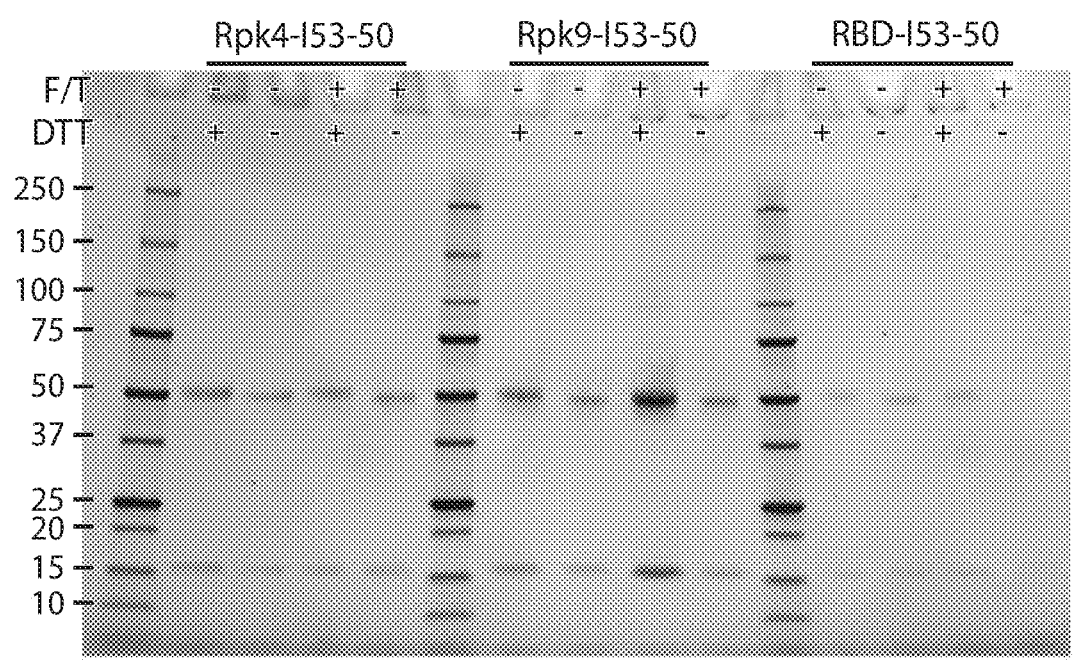
FIG. 25 SDS-PAGE for nanoparticles in TBS. The integrity of samples in 50 mM Tris pH 8, 150 mM NaCl was analyzed by SDS-PAGE. Molecular weights of the standard are noted in kDa. Each sample was analyzed +/- reducing agent (DTT), pre- and post-freeze thaw (F/T).
Figure 26:
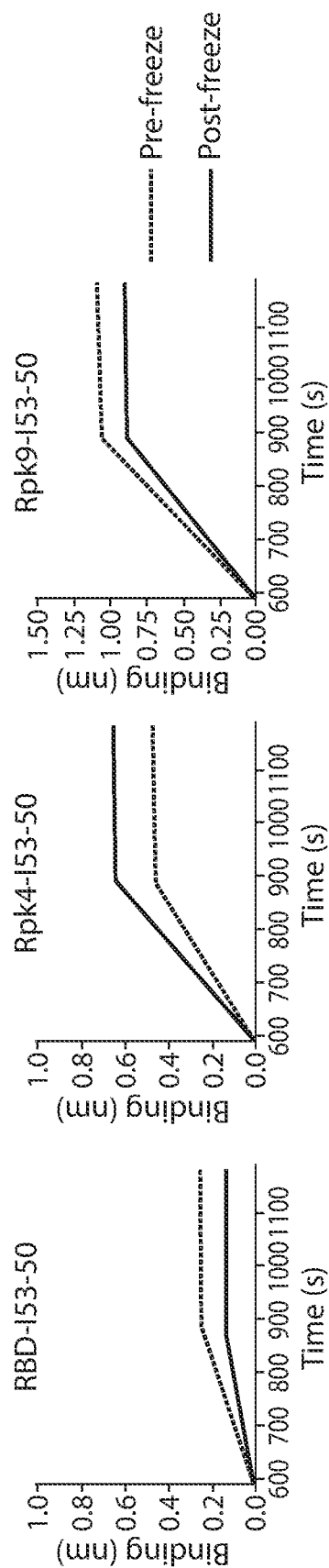
FIG. 26 hACE2-Fc binding for nanoparticles in TBS. H ACE2-Fc binding of antigen in 50 mM Tris pH 8, 150 mM NaCl was analyzed by bio-layer interferometry (BLI). Protein A biosensors loaded with hACE2-Fc were incubated with immunogen (association, x=590-889 s) and then buffer (dissociation, x=890-1190 s).
Figure 27:
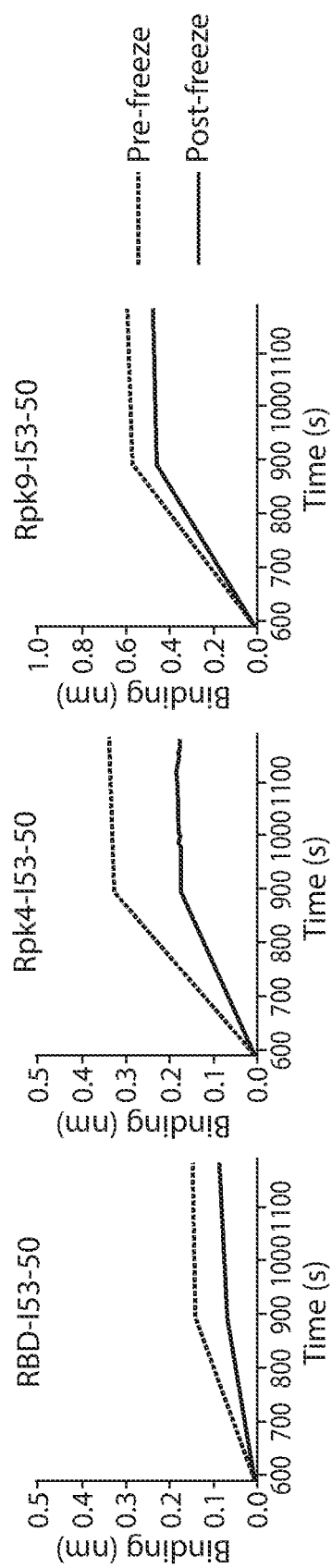
FIG. 27 CR3022 binding for nanoparticles in TBS. CR3022 IgG binding of antigen in 50 mM Tris pH 8, 150 mM NaCl was analyzed by bio-layer interferometry (BLI). Protein A biosensors loaded with CR3022 IgG were incubated with immunogen (association, x=590-889 s) and then buffer (dissociation, x=890-1190 s).
Figure 28:
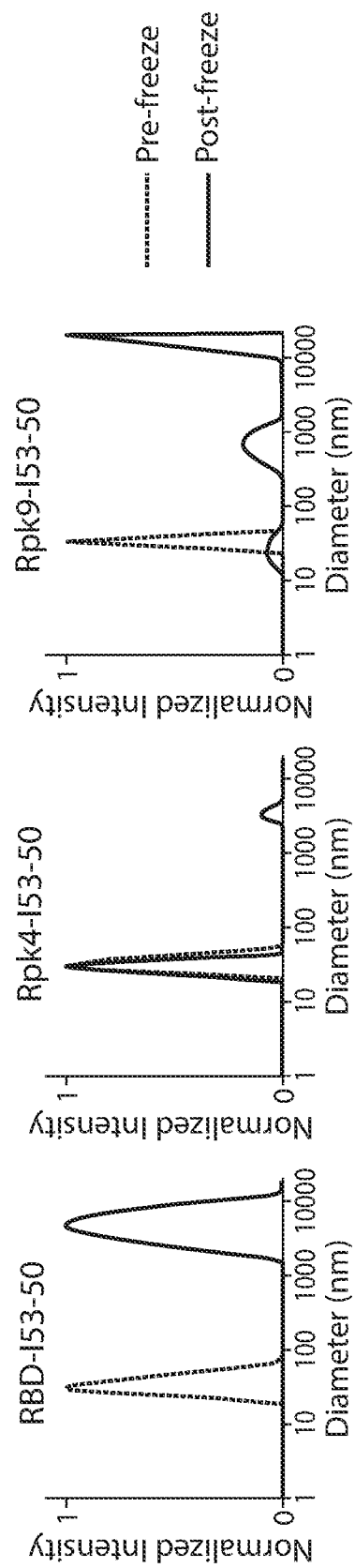
FIG. 28 Dynamic light scattering for nanoparticles in TBS. Hydrodynamic diameter (nm) for each sample in 50 mM Tris pH 8, 150 mM NaCl, plotted as normalized intensity.
Figure 29:
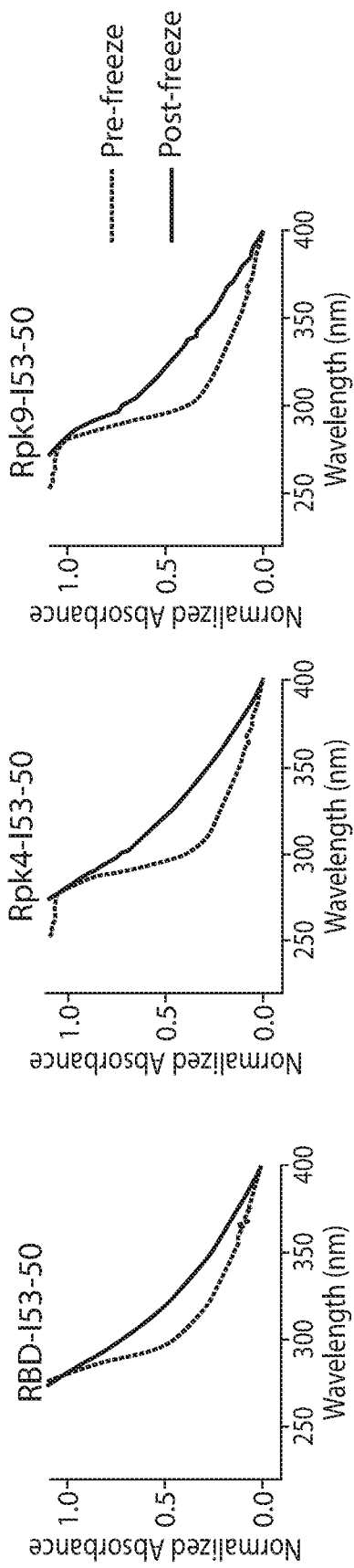
FIG. 29 UV-Vis for nanoparticles in TBS. UV-vis spectra (nm) for each sample in 50 mM Tris pH 8, 150 mM NaCl, plotted as normalized absorbance.
Figure 30:
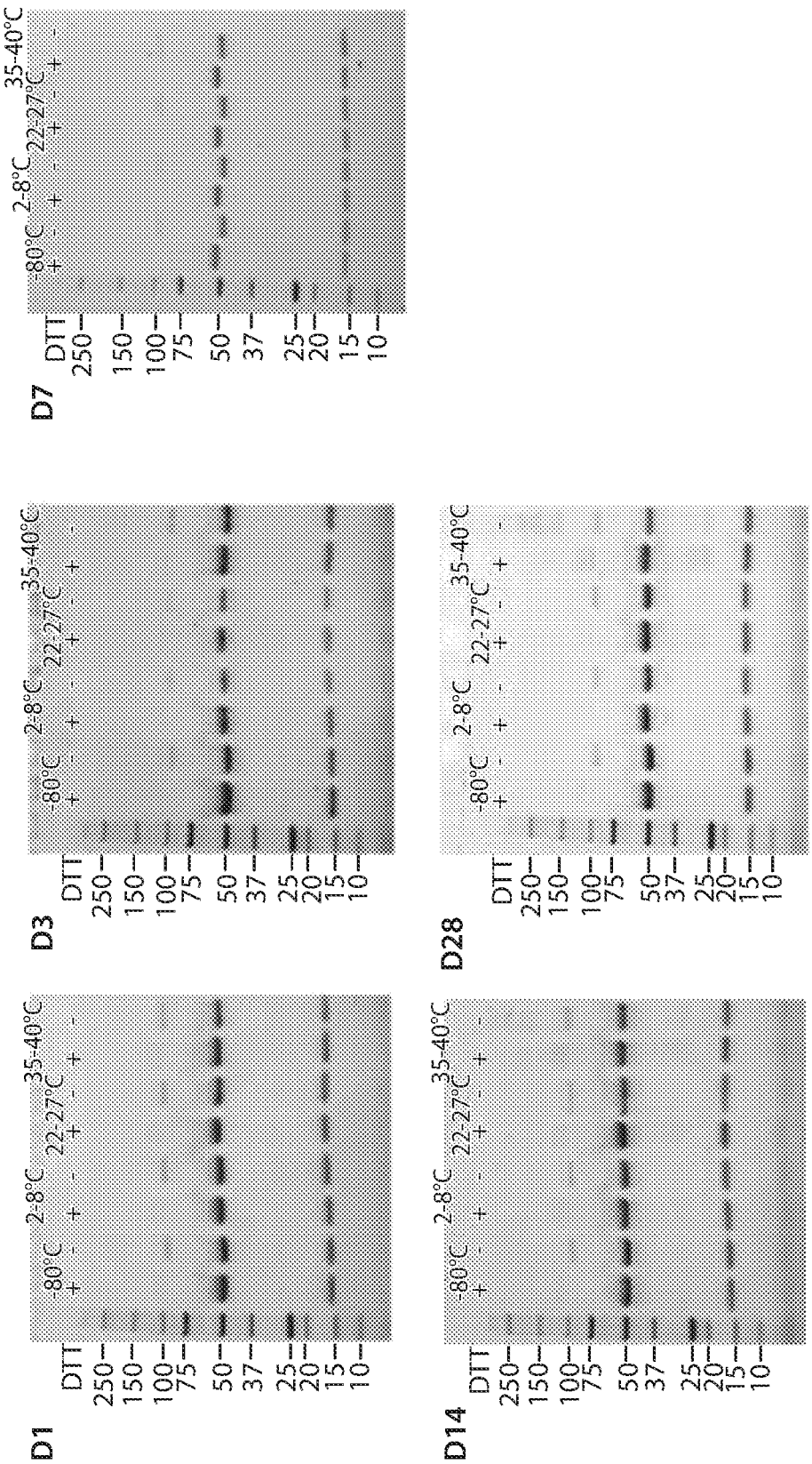
FIG. 30 SDS-PAGE for RBD-I53-50 nanoparticle. The integrity of samples after incubation at four temperatures over a 28 day (D) study was analyzed by SDS-PAGE. Molecular weights of the standard are noted in kDa. Each sample was analyzed +/- reducing agent (DTT).
Figure 31:
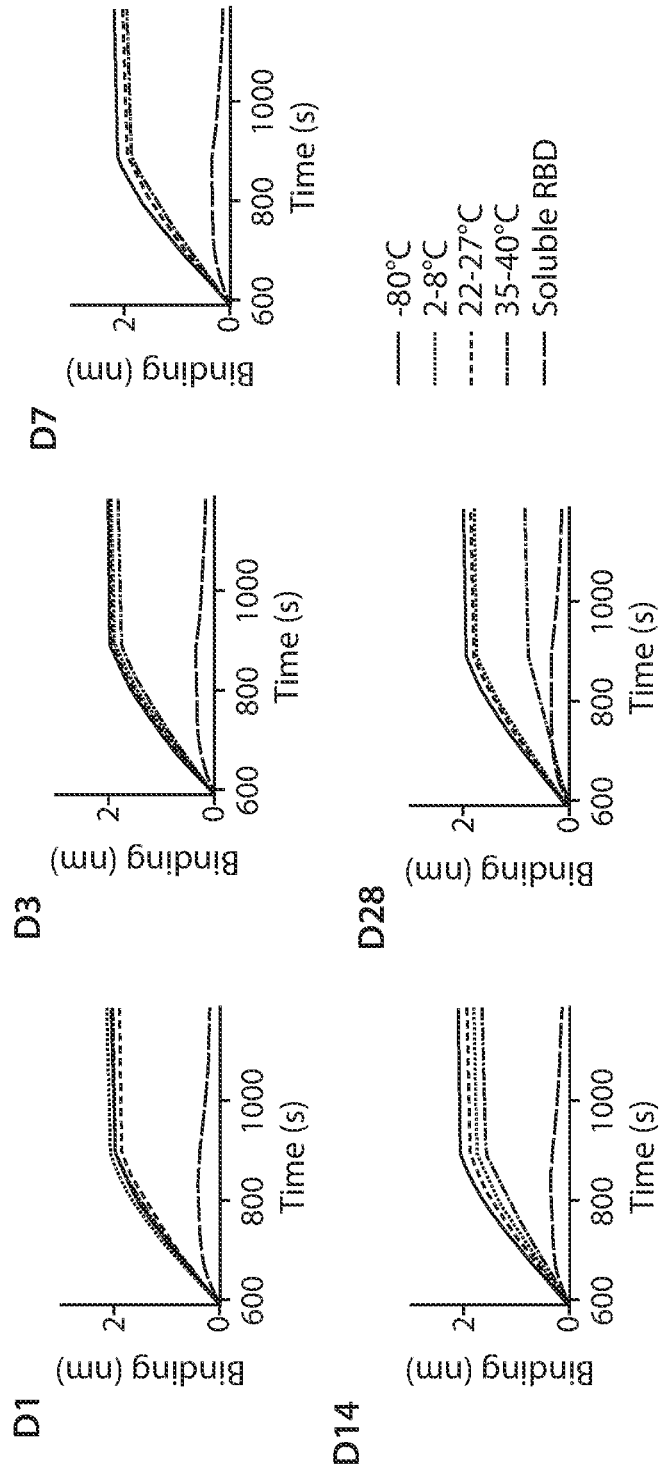
FIG. 31 hACE2-Fc binding for RBD-I53-50 nanoparticle. hACE2-Fc binding of antigen incubated at four different temperatures for 28 days (D) was analyzed by bio-layer Interferometry (BLI). Protein A biosensors loaded with hACE2-Fc were incubated with immunogen (association, x=590-889 s) and then buffer (dissociation, x=890-1190 s).
Figure 32:
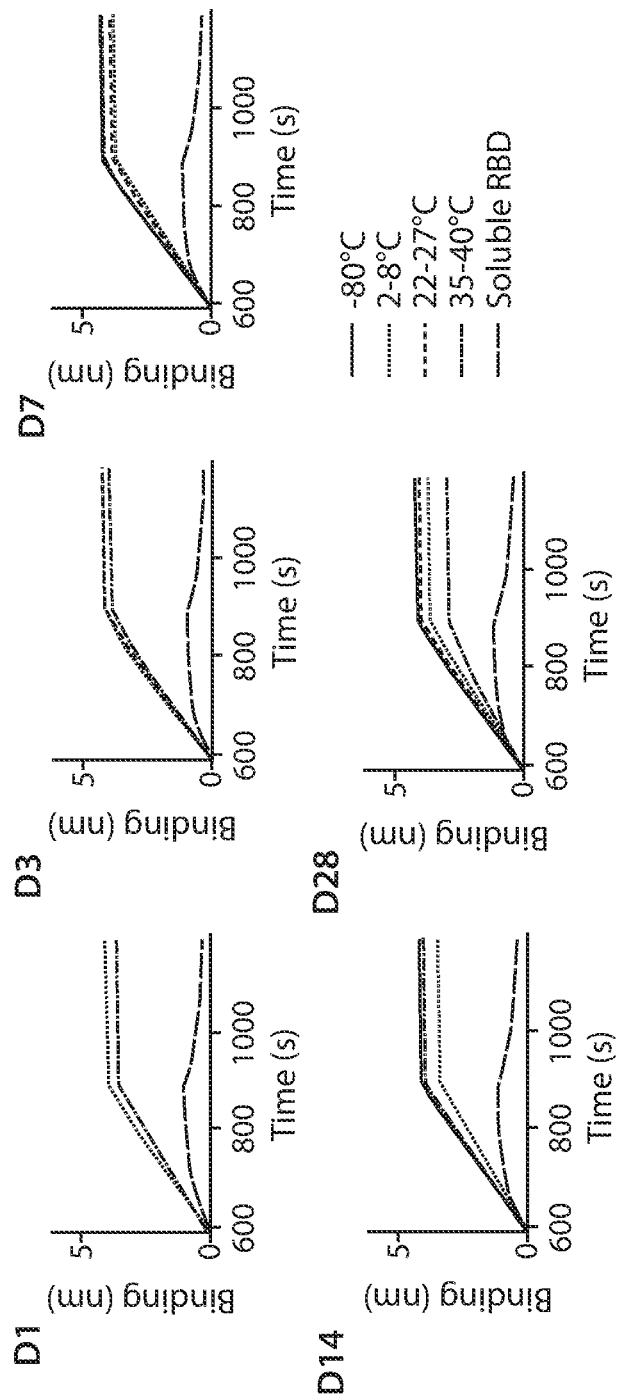
FIG. 32 CR3022 binding for RBD-I53-50 nanoparticle. CR3022 IgG binding of antigen incubated at four different temperatures for 28 days (D) was analyzed by bio-layer Interferometry (BLI). Protein A biosensors loaded with CR3022 were incubated with immunogen (association, x=590-889 s) and then buffer (dissociation, x=890-1190 s).
Figure 33:
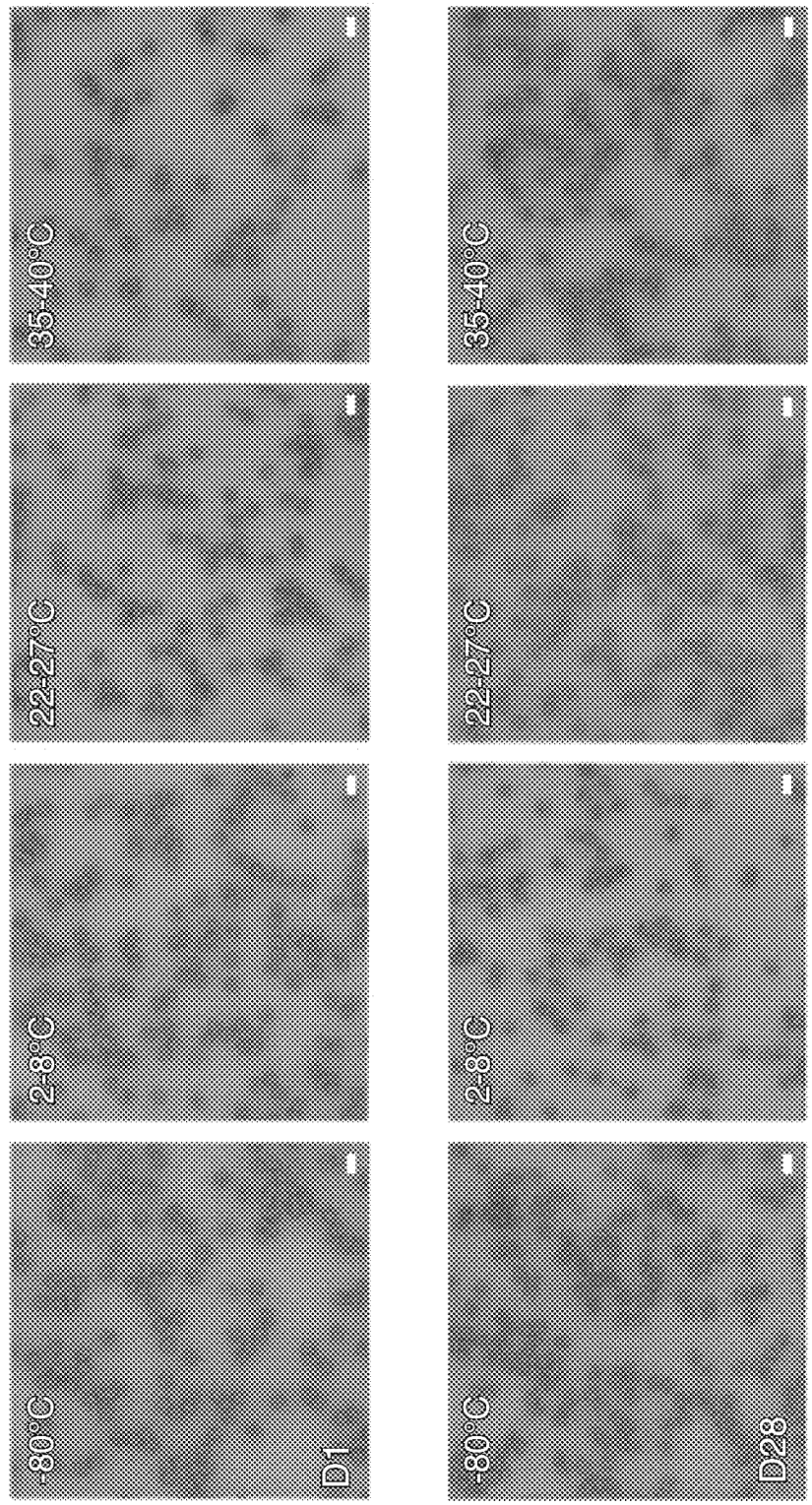
FIG. 33 nsEM for RBD-I53-50 nanoparticle. Representative negative stain electron micrographs for each sample at days (D) 1 and 28 following incubation at four temperatures. Scale bar, 50 nm.
Figure 34:
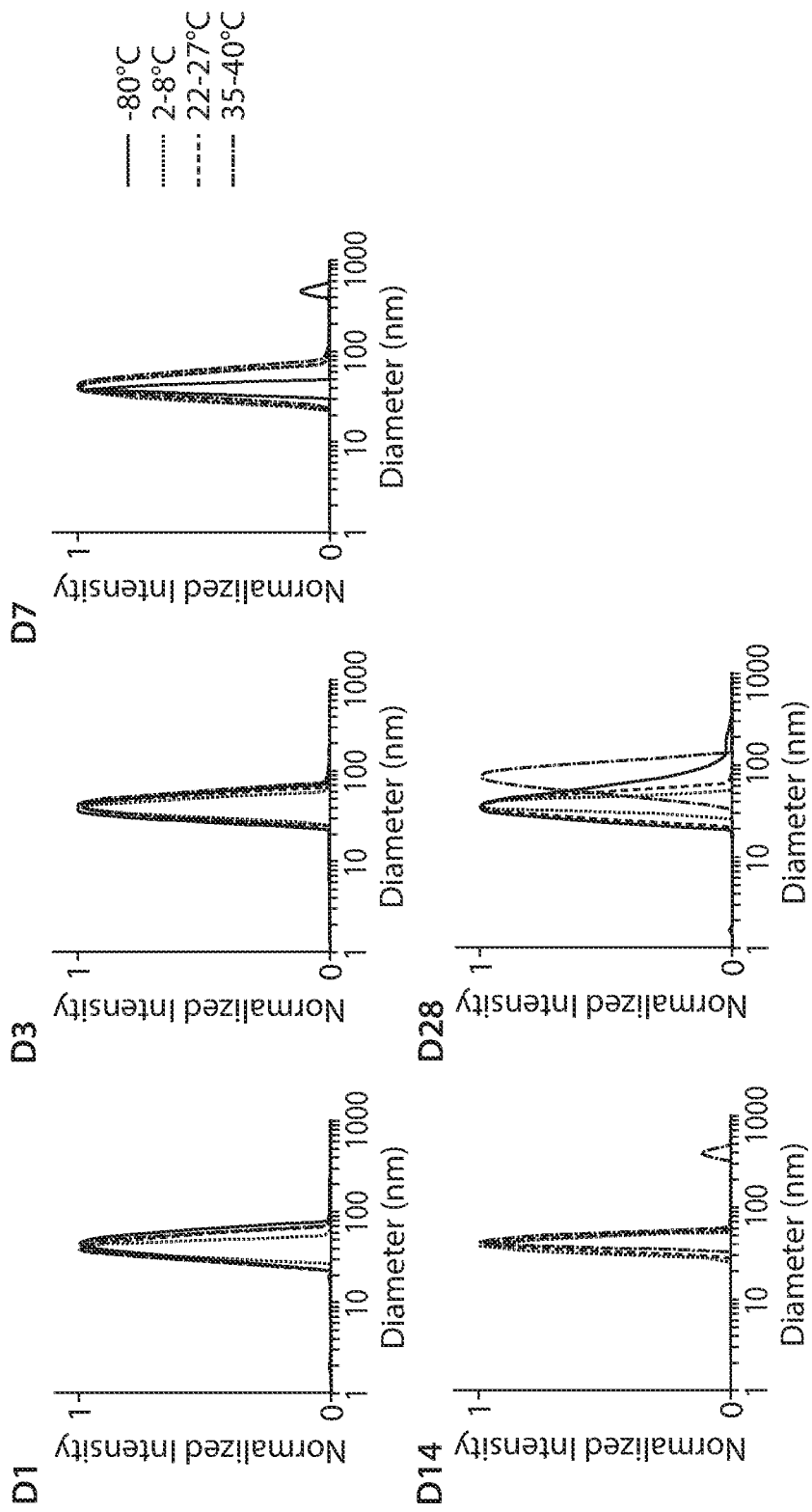
FIG. 34 Dynamic light scattering for RBD-I53-50 nanoparticle. Hydrodynamic diameter (nm) for each sample over a 28 day (D) period, plotted as normalized intensity.
Figure 35:
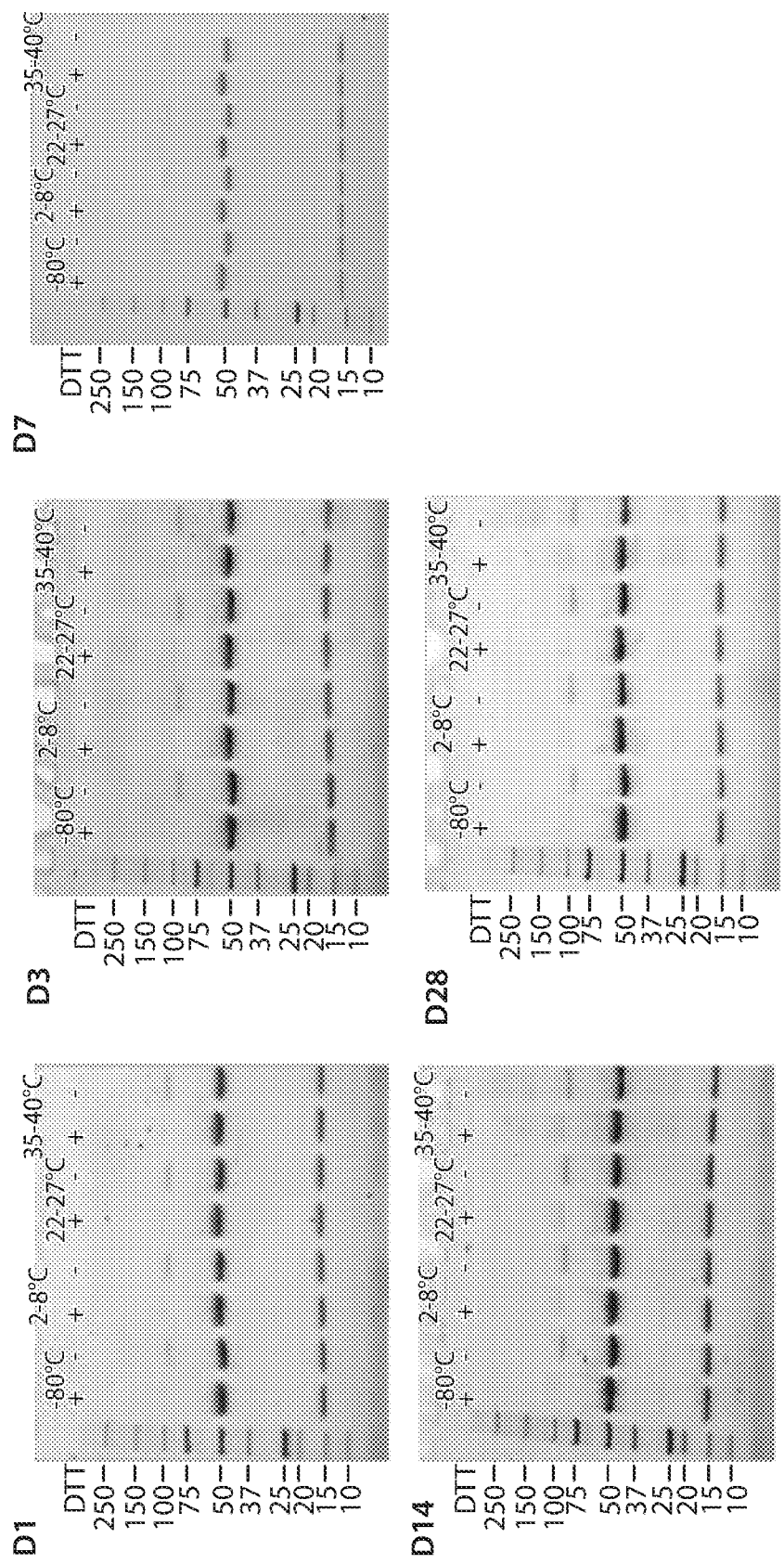
FIG. 35 SDS-PAGE for Rpk4-I53-50 nanoparticle. The integrity of samples after incubation at four temperatures over a 28 day (D) study was analyzed by SDS-PAGE. Molecular weights of the standard are noted in kDa. Each sample was analyzed +/- reducing agent (DTT).
Figure 36:
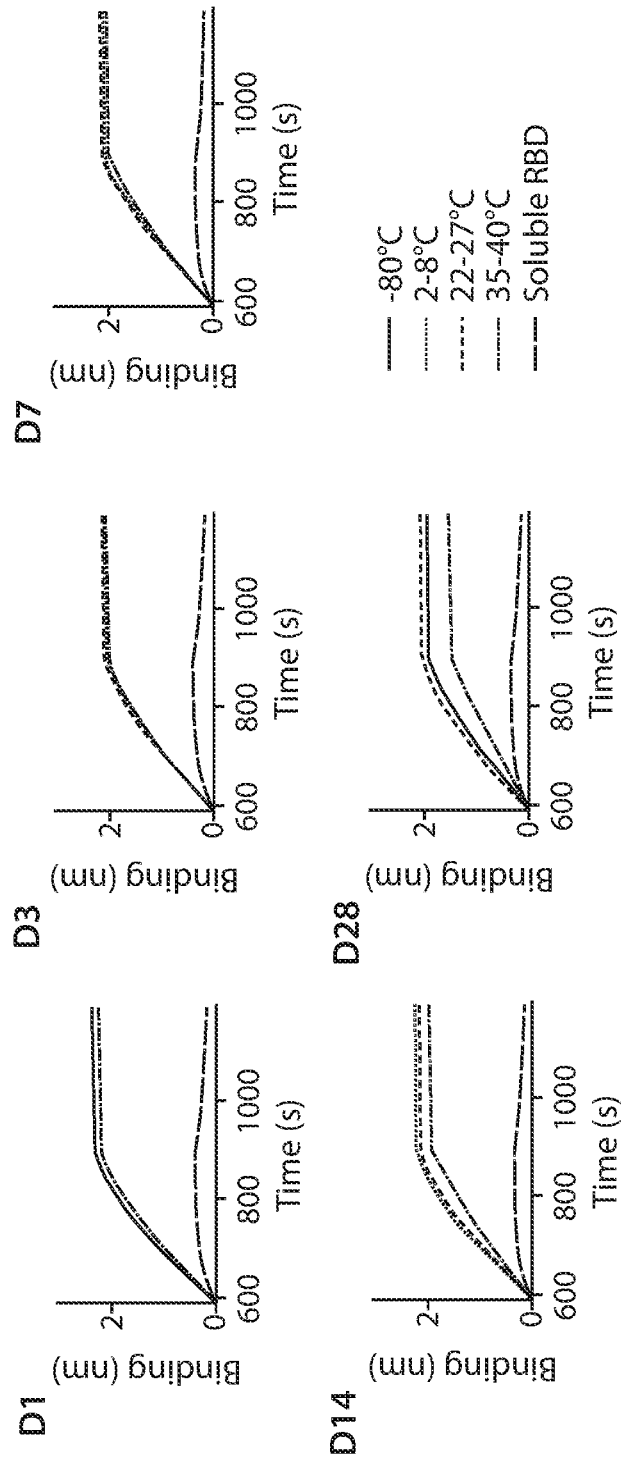
FIG. 36 hACE2-Fc binding for Rpk4-I53-50 nanoparticle. hACE2-Fc binding of antigen incubated at four different temperatures for 28 days (D) was analyzed by bio-layer Interferometry (BLI). Protein A biosensors loaded with hACE2-Fc were incubated with immunogen (association, x=590-889 s) and then buffer (dissociation, x=890-1190 s).
Figure 37:
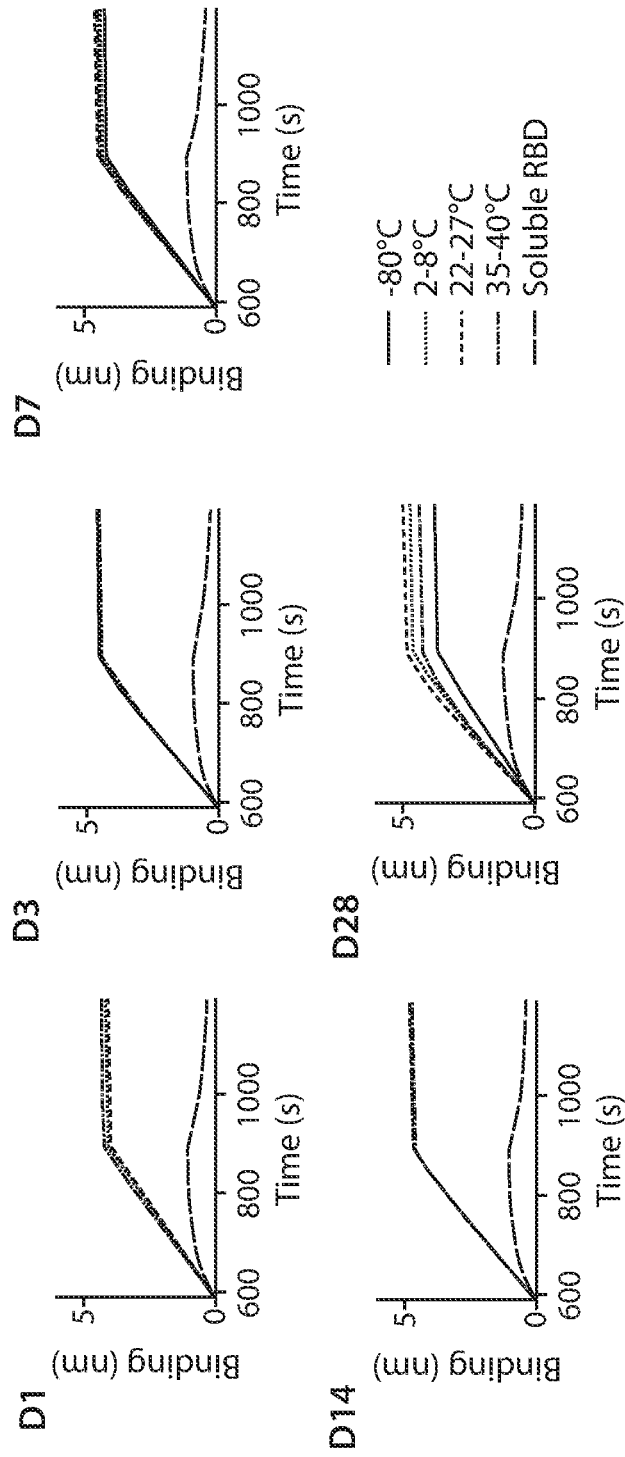
FIG. 37 CR3022 binding for Rpk4-I53-50 nanoparticle. CR3022 IgG binding of antigen incubated at four different temperatures for 28 days (D) was analyzed by bio-layer Interferometry (BLI). Protein A biosensors loaded with CR3022 were incubated with immunogen (association, x=590-889 s) and then buffer (dissociation, x=890-1190 s).
Figure 38:
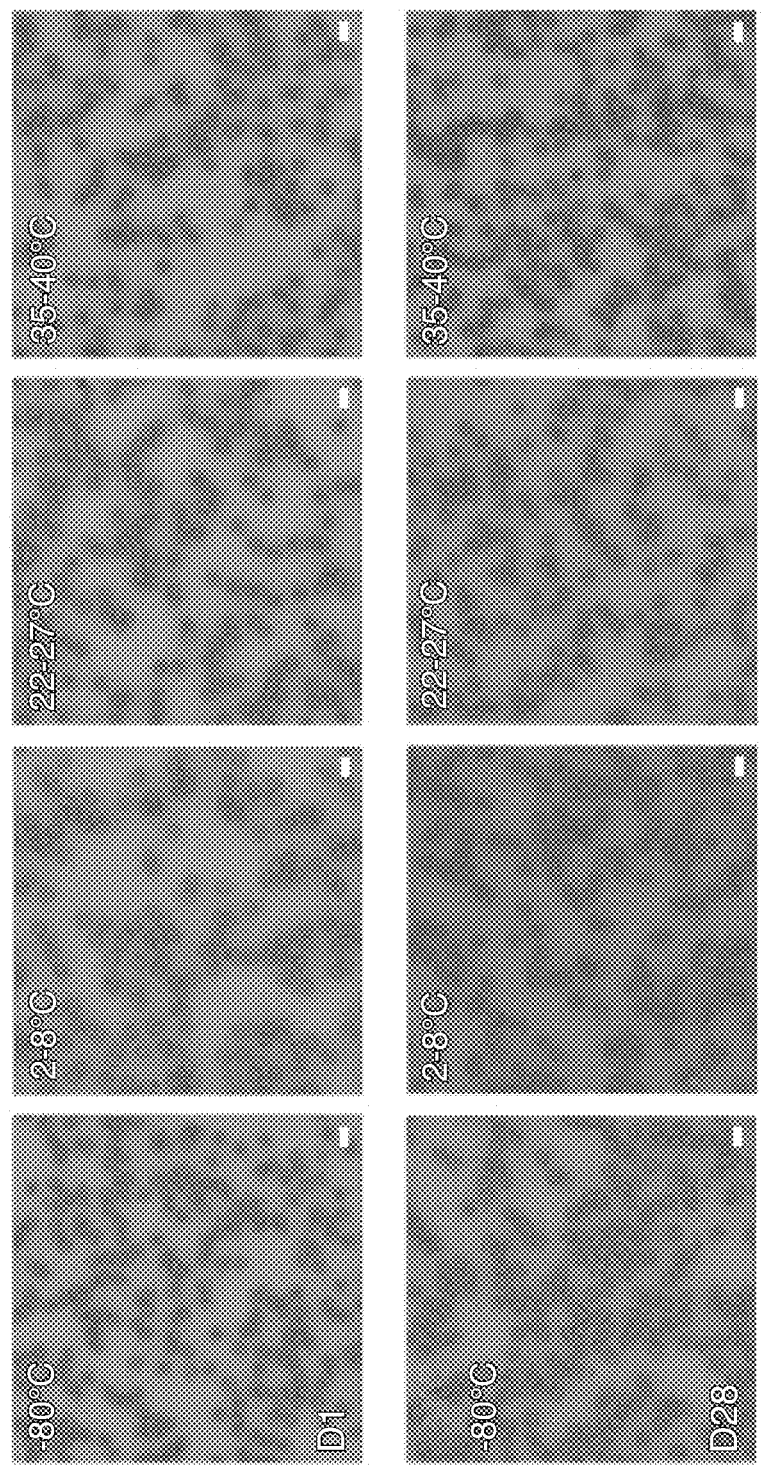
FIG. 38 nsEM for Rpk4-I53-50 nanoparticle. Representative negative stain electron micrographs for each sample at days (D) 1 and 28 following incubation at four temperatures. Scale bar, 50 nm.
Figure 39:
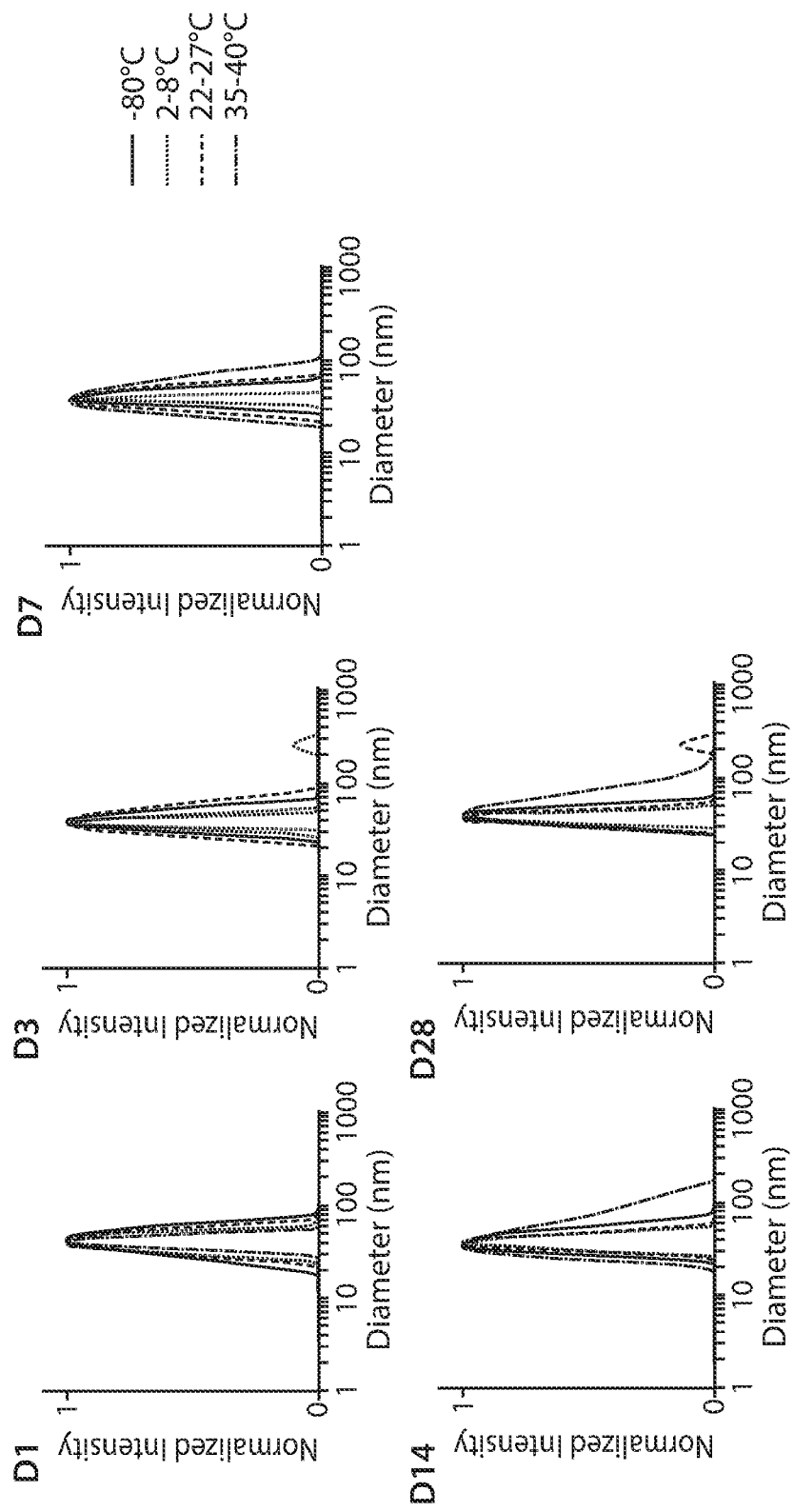
FIG. 39 Dynamic light scattering for Rpk4-I53-50 nanoparticle. Hydrodynamic diameter (nm) for each sample over a 28 day (D) period, plotted as normalized intensity.
Figure 40:
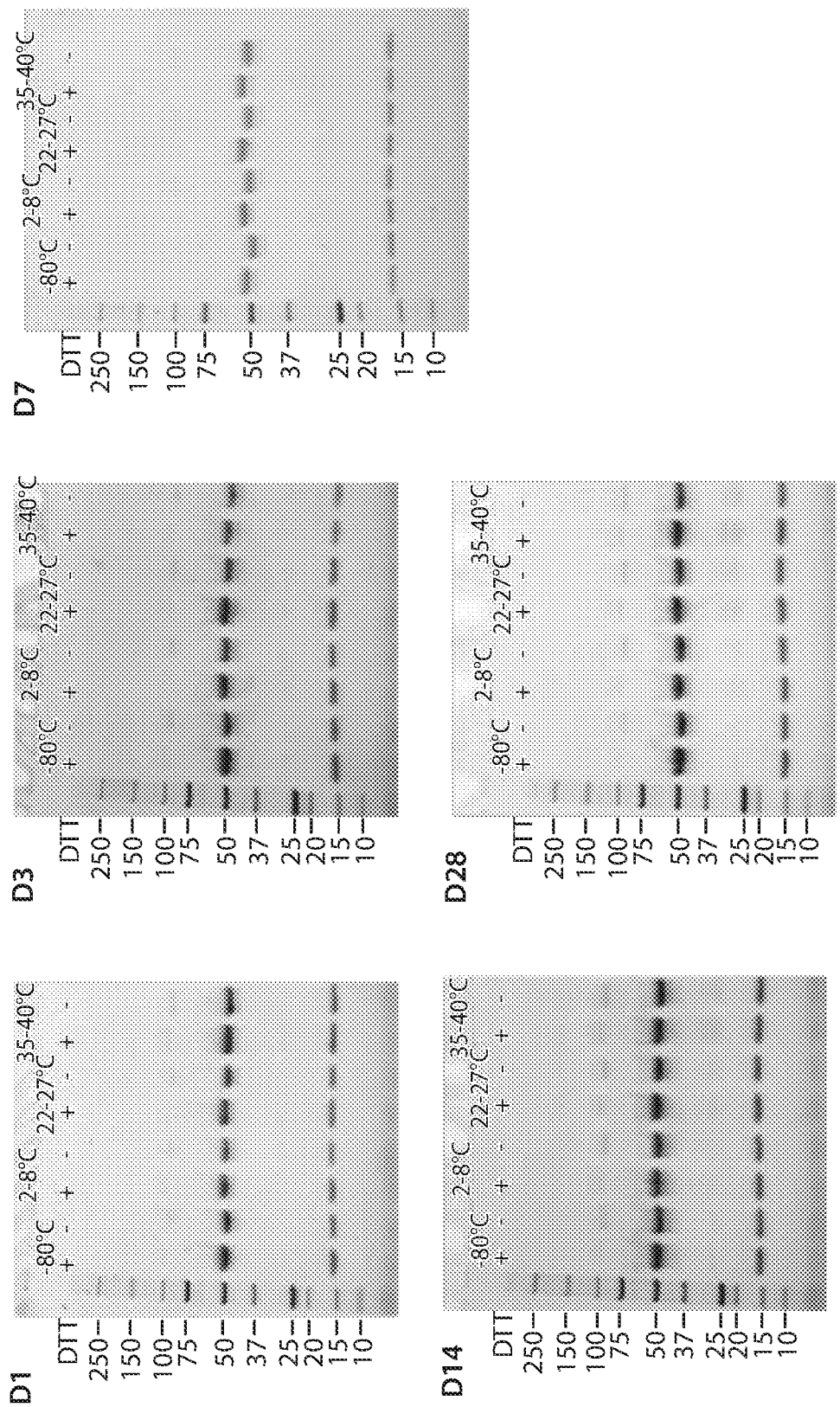
FIG. 40 SDS-PAGE for Rpk9-I53-50 nanoparticle. The integrity of samples after incubation at four temperatures over a 28 day (D) study was analyzed by SDS-PAGE. Molecular weights of the standard are noted in kDa. Each sample was analyzed +/- reducing agent (DTT).
Figure 41:
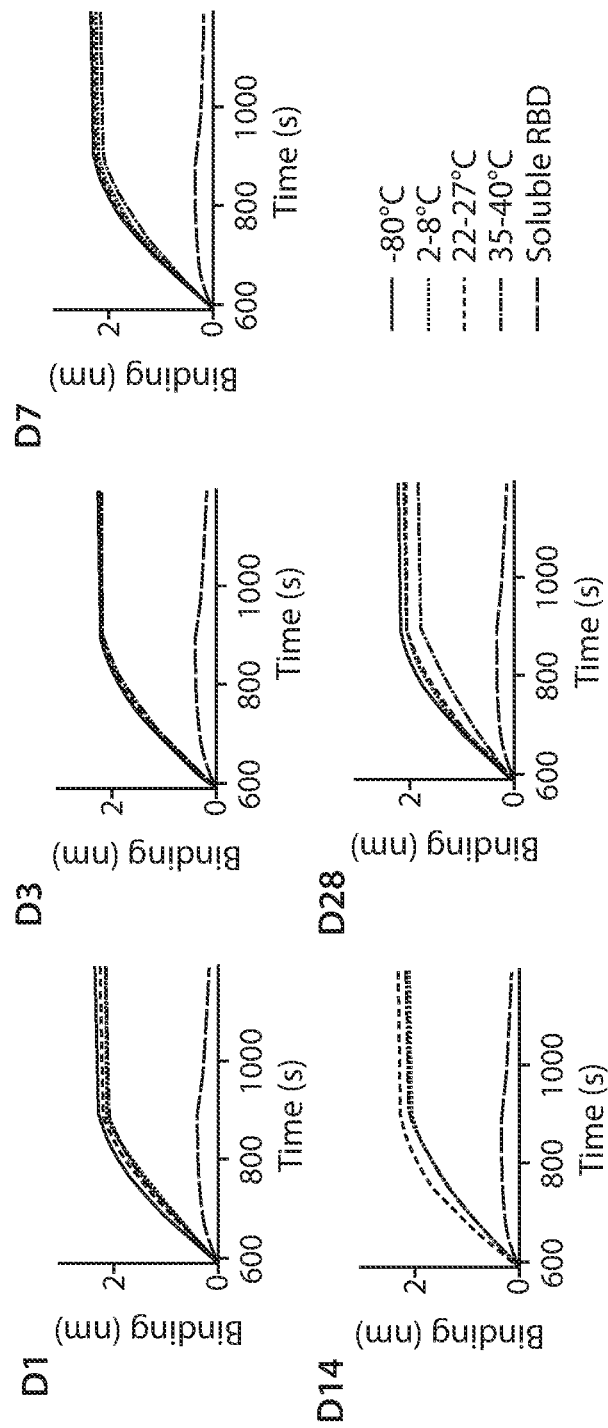
FIG. 41 hACE2-Fc binding for Rpk9-I53-50 nanoparticle. hACE2-Fc binding of antigen incubated at four different temperatures for 28 days (D) was analyzed by bio-layer Interferometry (BLI). Protein A biosensors loaded with hACE2-Fc were incubated with immunogen (association, x=590-889 s) and then buffer (dissociation, x=890-1190 s).
Figure 42:
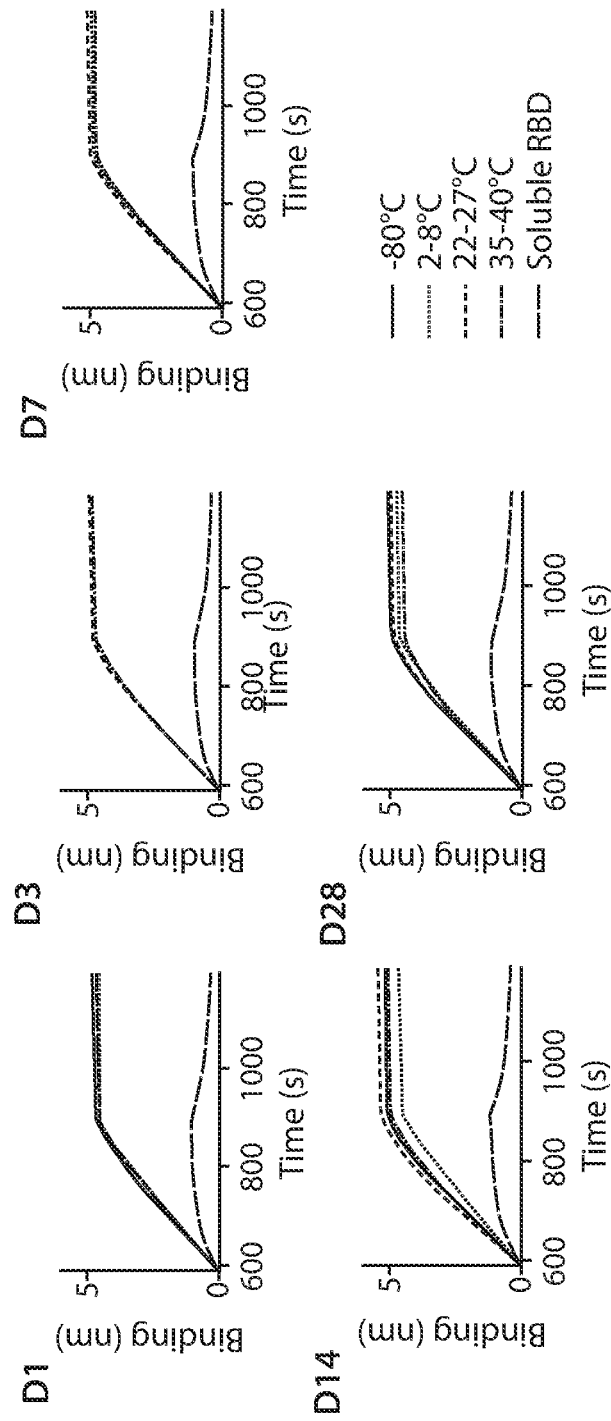
FIG. 42 CR3022 binding for Rpk9-I53-50 nanoparticle. CR3022 IgG binding of antigen incubated at four different temperatures for 28 days (D) was analyzed by bio-layer Interferometry (BLI). Protein A biosensors loaded with CR3022 were incubated with immunogen (association, x=590-889 s) and then buffer (dissociation, x=890-1190 s).
Figure 43:
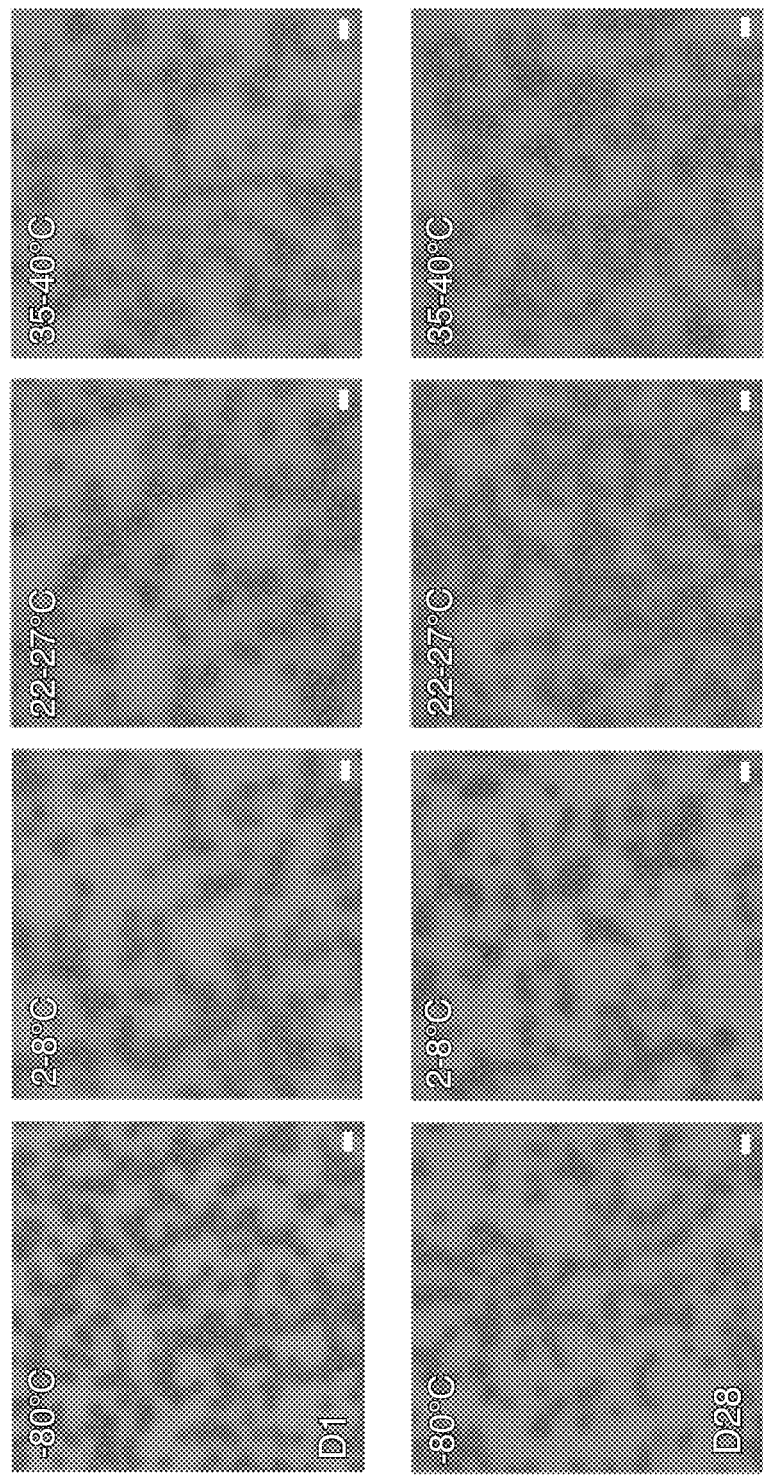
FIG. 43 nsEM for Rpk9-I53-50 nanoparticle. Representative negative stain electron micrographs for each sample at days (D) 1 and 28 following incubation at four temperatures. Scale bar, 50 nm.
Figure 44:
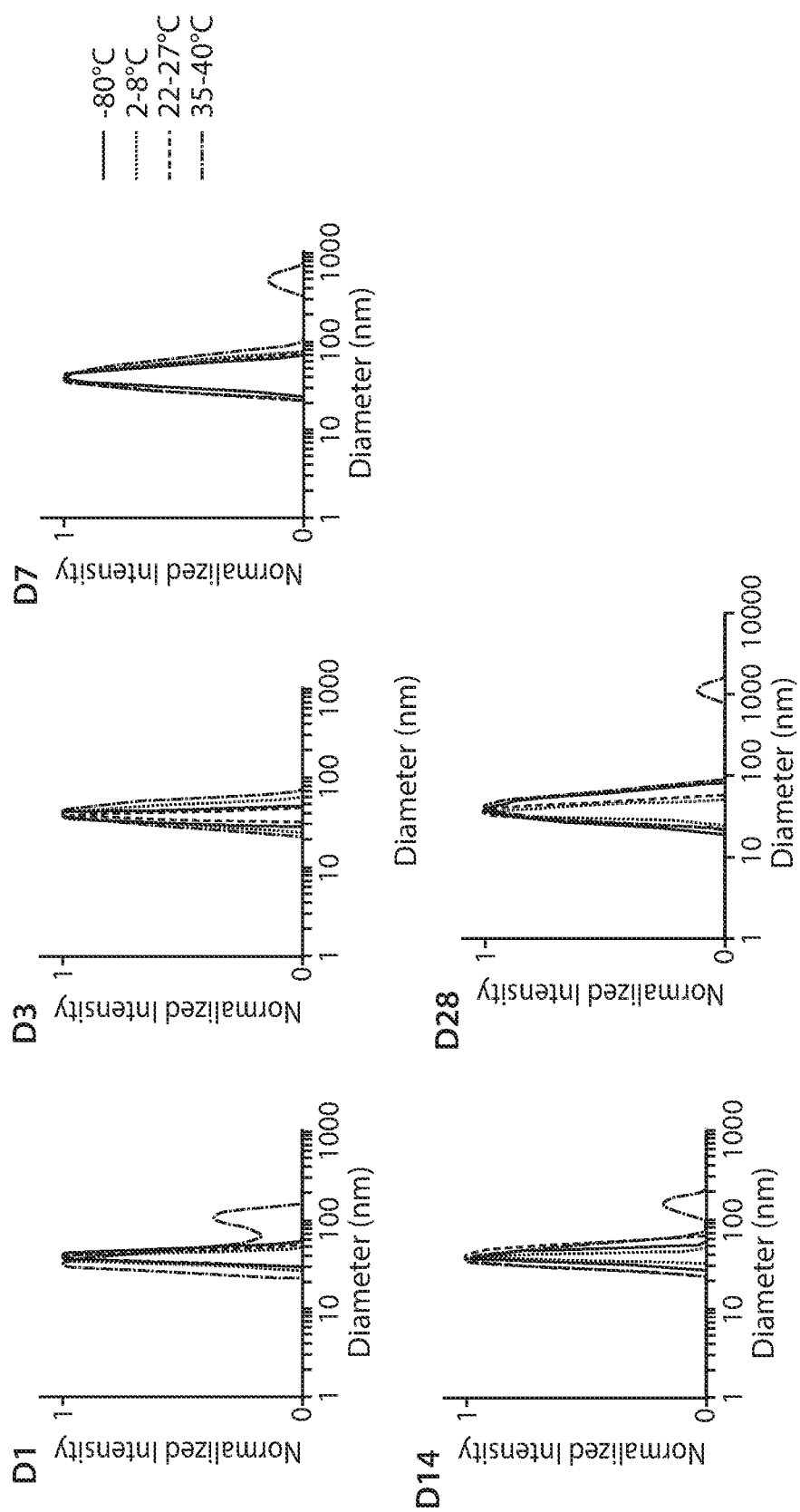
FIG. 44 Dynamic light scattering for Rpk9-I53-50 nanoparticle. Hydrodynamic diameter (nm) for each sample over a 28 day (D) period, plotted as normalized intensity.

Binding titers were measured against HexaPro-foldon using enzyme-linked immunosorbent assays (ELISA) and analyzed by measuring area under the curve (AUC) (FIG. 6B) and midpoint titers (FIG. 12A). Sera from all nanoparticle groups showed levels of antigen-specific antibody after the prime that were slightly higher than HexaPro-foldon and markedly higher than the non-assembling controls. Binding signal increased for all groups after the second immunization, with less separation between them. Pseudovirus neutralization using a lentiviral backbone showed similar trends after the prime, with all nanoparticle groups exhibiting significantly higher neutralizing activity than the non-assembling controls and nearly two orders of magnitude more potent neutralization than HexaPro-foldon (FIG. 6C). Neutralization strongly increased for all groups after the second immunization, with the nanoparticles and HexaPro-foldon showing the highest levels of neutralizing activity. There were no significant differences in neutralizing activity between the various nanoparticle groups or between the various non-assembling control groups at each timepoint. Comparable results were obtained with a different pseudovirus assay using a murine leukemia virus (MLV) backbone (FIG. 12B). These data establish that the stabilized RBDs are similarly immunogenic to the wild-type RBD when presented in either trimeric or particulate formats, with nanoparticle presentation significantly enhancing RBD immunogenicity, most notably after a single immunization.

Figure 7A:
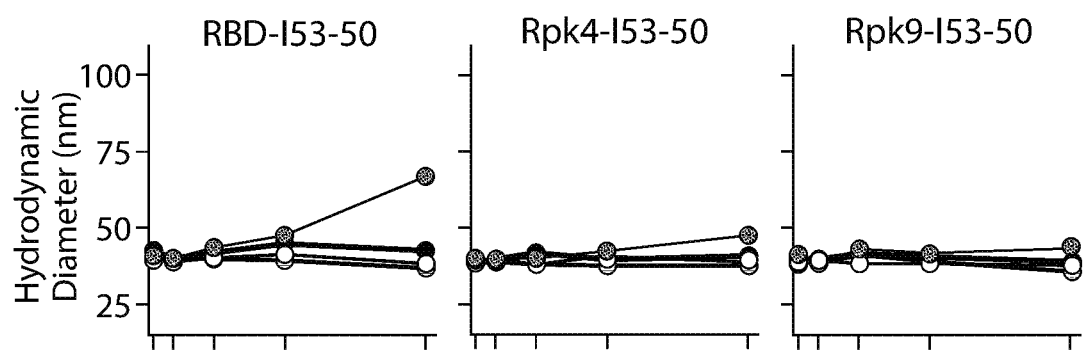
FIGS. 7A-7C. Shelf-life stability of RBD-based nanoparticle immunogens is improved by Rpk mutations.
Figure 7B:
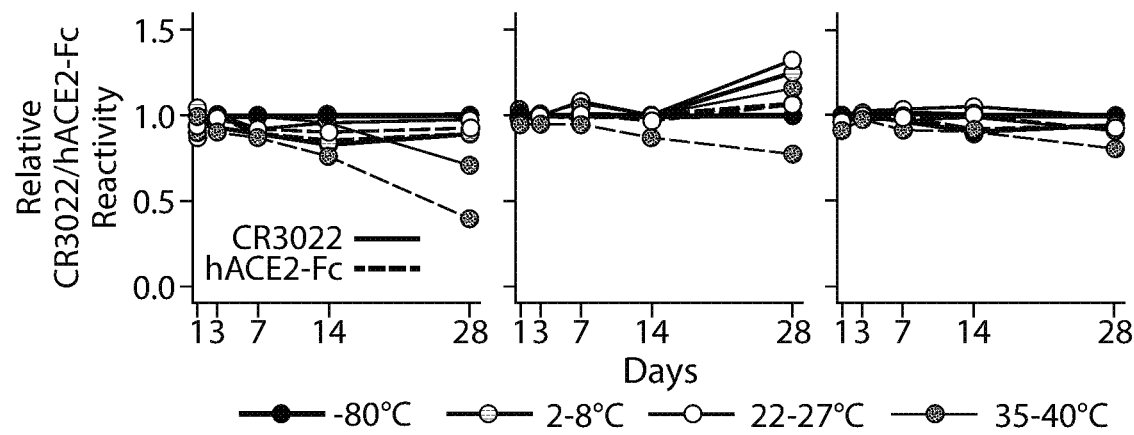
Figure 7C:
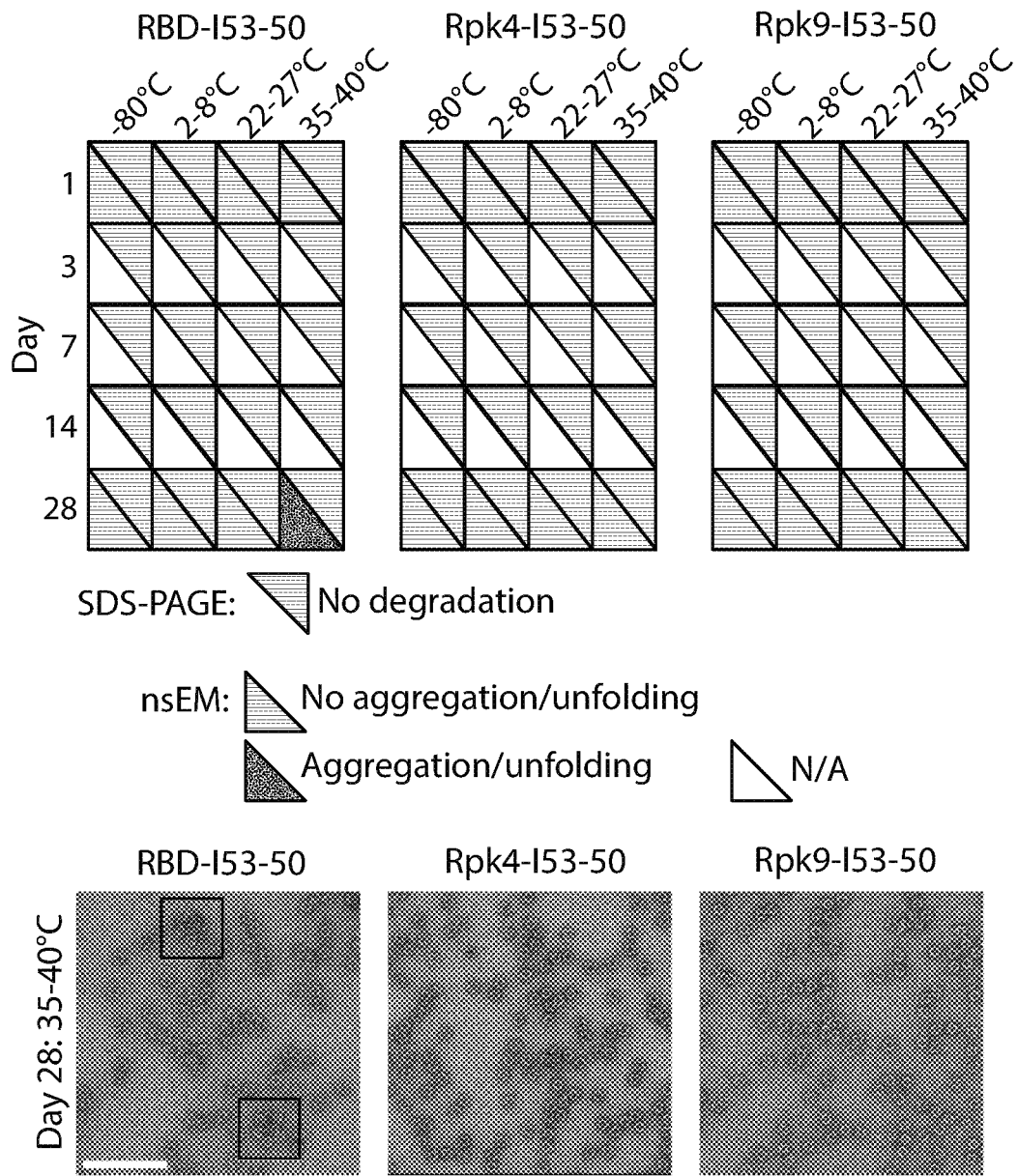

Improvements to the shelf-life stability of SARS-CoV-2 vaccines have the potential to directly enhance global vaccination efforts by simplifying manufacturing and distribution. The stability of the two stabilized RBD nanoparticle immunogens was compared to the wild-type RBD-I53-50 over 28 days of storage at −80° C., 2-8° C., 22-27° C. and 35-40° C. by DLS (FIG. 7A), BLI (FIG. 7B), SDS-PAGE, and nsEM (FIG. 7C). No significant deviations from baseline were observed for any immunogen at −80° C., 2-8° C., or 22-27° C. over the course of the study. However, storage of the wild-type RBD-I53-50 at 35-40° C. for 28 days led to aggregation that was detectable by DLS and nsEM and significant reductions in antigenicity. In contrast, both particle stability and antigenicity were maintained for Rpk4-I53-50 and Rpk9-I53-50 after 28 days of storage at 35-40° C. These results establish that the stabilizing mutations identified in the RBD can improve the manufacturability and stability of RBD-based nanoparticle immunogens without compromising their potent immunogenicity.

Structure-based protein design can be greatly facilitated by experimental information that narrows the potential design space to particularly valuable regions and mutations.

Here, the utility of DMS data in guiding viral glycoprotein stabilization was demonstrated by characterizing the LA binding pocket of the SARS-CoV-2 S RBD as a structurally suboptimal region and providing identities of potential stabilizing mutations. Guided by these data, structural modeling in Rosetta™ identified additional stabilizing mutations as well as promising combinations of mutations. All of the designs screened experimentally were successful at improving upon the expression of the wild-type RBD, which is an unusually high efficiency compared to many purely structure-based design experiments.

This thorough biochemical and biophysical characterization of RBD variants enabled the inventors to select designs that enhanced expression; minimized off-target disulfides; improved local structural order; and increased thermal, solution, and shelf-life stability; all while maintaining the potent immunogenicity of the wild-type RBD displayed on the I53-50 nanoparticle. Of the two mutants studied in detail, Rpk4 (F392W) was more conservative, featuring only a single amino acid change, but less stabilizing compared to Rpk9 (Y365F, F392W, V395I), which included additional mutations that particularly improved expression and thermal stability. Without wishing to be bound by theory, the inventors speculate that the improved solution properties of Rpk4- and Rpk9-I53-50 most likely derive from improvements in local structural order and reduced hydrophobic surface area exposure, as indicated by HDX-MS and SYPRO Orange fluorescence. More generally, these results raise the possibility that other RBD antigens may adopt dynamic conformations not observed in existing structures of S ectodomains or isolated RBDs, such as transitions between the open and closed states of the LA binding pocket.

The similarly potent immunogenicity of Rpk4- and Rpk9-I53-50 compared to the wild-type RBD-I53-50 nanoparticle is consistent with the native-like antigenicity of the ACE2 binding motif, the major focus of neutralizing responses against the RBD, and the fact that the stabilizing mutations are not exposed on the surface of the antigen. These immunogenicity data also clearly demonstrate that high-valency RBD nanoparticle immunogens are far more immunogenic than trimeric forms of RBDs, especially after a single immunization. The trimeric spike (HexaPro-foldon) elicited higher levels of neutralizing activity than the trimeric RBDs. This result demonstrates that removing the RBD from the context of the spike while maintaining its oligomeric state is not inherently advantageous for improving antibody responses against the RBD, and emphasizes the importance of nanoparticle presentation in RBD-based vaccines.

The improvements in manufacturability, stability, and solution properties that were observed could have a significant impact on the manufacturing and distribution of protein-based vaccines for SARS-CoV-2. As SARS-CoV-2 vaccines are already being updated in response to antigenic drift, such improvements could be important for maximizing the scale and speed of vaccine production and buffering against unanticipated changes in the stability or solution properties of antigens derived from novel SARS-CoV-2 strains. Moreover, improved resistance to denaturation and shelf-life stability at various temperatures could be particularly impactful for reliable distribution in less developed regions of the world that lack cold chain infrastructure. Finally, as knowledge of the prefusion-stabilizing "2P" mutations prior to the emergence of SARS-CoV-2 proved critical to pandemic response efforts, the ability to reliably improve vaccine manufacturability using stabilizing mutations to the RBD may be an important tool for optimizing vaccine designs against other coronaviruses circulating in zoonotic reservoirs that threaten to cross over to humans.

The invention claimed is:

1. A non-naturally occurring polypeptide comprising:
a coronavirus receptor binding domain (RBD) comprising an amino acid sequence having at least 90% sequence identity to the amino acid sequence of residues 328-531 of SEQ ID NO:1 and further comprising at least two mutations relative to SEQ ID NO: 1,
wherein the polypeptide exhibits a melting temperature measured by nano differential scanning fluorimetry at least 2° C. higher than a polypeptide comprising residues 328-531 of SEQ ID NO: 1 and lacking the at least two mutations, and wherein the at least two mutations are selected from the group consisting of:
F338L and Y365W;
Y365W and L513M;
Y365W and F392W;
F338M and A363L and Y365F and F377V;
Y365F and F392W;
Y365F and V395I;
Y365F and F392W and V395I;
Y365W and L513I and F515L;
F338L and A363L and Y365M;

F338L and I358F and Y365W;
I358F and Y365W and L513M;
I358F and Y365W and F392W;
I358F and Y365F and V395I; and
I358F and Y365F and F392W and V395I.

2. The polypeptide of claim 1, wherein the at least two mutations comprise F338L and Y365W.

3. The polypeptide of claim 1, wherein the at least two mutations comprise Y365W and L513M.

4. The polypeptide of claim 1, wherein the at least two mutations comprise Y365W and F392W.

5. The polypeptide of claim 1, wherein the at least two mutations comprise F338M and A363L and Y365F and F377V.

6. The polypeptide of claim 1, wherein the at least two mutations comprise Y365F and F392W.

7. The polypeptide of claim 1, wherein the at least two mutations comprise Y365F and V395I.

8. The polypeptide of claim 1, wherein the at least two mutations comprise Y365F and F392W and V395I.

9. The polypeptide of claim 1, wherein the at least two mutations comprise Y365W and L513I and F515L.

10. The polypeptide of claim 1, wherein the at least two mutations comprise F338L and A363L and Y365M.

11. The polypeptide of claim 1, wherein the at least two mutations comprise F338L and I358F and Y365W.

12. The polypeptide of claim 1, wherein the at least two mutations comprise I358F and Y365W and L513M.

13. The polypeptide of claim 1, wherein the at least two mutations comprise I358F and Y365W and F392W.

14. The polypeptide of claim 1, wherein the at least two mutations comprise I358F and Y365F and V395I.

15. The polypeptide of claim 1, wherein the at least two mutations comprise I358F and Y365F and F392W and V395I.

16. The polypeptide of claim 1, wherein the RBD comprises an amino acid sequence having at least 95% sequence identity to residues 328-531 of SEQ ID NO:1 and the at least two mutations comprise Y365F and F392W and V395I.

17. The polypeptide of claim 1, wherein the RBD comprises an amino acid sequence having at least 98% sequence identity to residues 328-531 of SEQ ID NO:1 and the at least two mutations comprise Y365F and F392W and V395I.

18. The polypeptide of claim 1, wherein the polypeptide comprises an amino acid sequence having at least 90% sequence identity to SEQ ID NO: 21.

19. The polypeptide of claim 1, wherein the polypeptide comprises an amino acid sequence having at least 95% sequence identity to SEQ ID NO: 30 and the at least two mutations comprise Y365F and F392W and V395I.

20. The polypeptide of claim 1, wherein the polypeptide comprises an amino acid sequence having at least 98% sequence identity to SEQ ID NO: 30 and the at least two mutations comprise Y365F and F392W and V395I.

21. A non-naturally occurring polypeptide comprising:
a coronavirus spike (S) protein comprising an amino acid sequence having at least 90% sequence identity to the amino acid sequence of SEQ ID NO: 1, and further comprising at least two mutations relative to SEQ ID NO: 1,
wherein the polypeptide exhibits a melting temperature measured by nano differential scanning fluorimetry at least 2° C. higher than a polypeptide comprising SEQ ID NO: 1 and lacking the at least two mutations, and
wherein the at least two mutations are selected from the group consisting of:
F338L and Y365W;
Y365W and L513M;
Y365W and F392W;
F338M and A363L and Y365F and F377V;
Y365F and F392W;
Y365F and V395I;
Y365F and F392W and V395I;
Y365W and L513I and F515L;
F338L and A363L and Y365M;
F338L and I358F and Y365W;
I358F and Y365W and L513M;
I358F and Y365W and F392W;
I358F and Y365F and V395I; and
I358F and Y365F and F392W and V395I.

22. The polypeptide of claim 21, wherein the at least two mutations comprise Y365F and F392W and V395I.

23. The polypeptide of claim 21, wherein the S protein comprises an amino acid sequence having at least 95% sequence identity to SEQ ID NO: 1 and the at least two mutations comprise Y365F and F392W and V395I.

24. The polypeptide of claim 21, wherein the S protein comprises an amino acid sequence having at least 98% sequence identity to SEQ ID NO: 1 and the at least two mutations comprise Y365F and F392W and V395I.

25. A pharmaceutical composition comprising the polypeptide of claim 1, a pharmaceutically acceptable carrier, and an adjuvant.

26. The pharmaceutical composition of claim 25, wherein the RBD comprises an amino acid sequence having at least 98% sequence identity to residues 328-531 of SEQ ID NO: 1 and the at least two mutations comprise Y365F and F392W and V395I.

27. The pharmaceutical composition of claim 25, wherein the polypeptide comprises an amino acid sequence having at least 90% sequence identity to SEQ ID NO: 21.

28. The pharmaceutical composition of claim 25, wherein the polypeptide comprises an amino acid sequence having at least 95% sequence identity to SEQ ID NO: 30 and the at least two mutations comprise Y365F and F392W and V395I.

29. The pharmaceutical composition of claim 25, wherein the polypeptide comprises an amino acid sequence having at least 98% sequence identity to SEQ ID NO: 30 and the at least two mutations comprise Y365F and F392W and V395I.

30. The pharmaceutical composition of claim 25, wherein the pharmaceutical composition exhibits no protein aggregation detectable by dynamic light scattering after 28 days storage at 35-40° C.

31. The pharmaceutical composition of claim 25, wherein the polypeptide comprises an amino acid sequence having at least 95% sequence identity to SEQ ID NO: 30 and the at least two mutations comprise Y365F and F392W and V395I, and wherein the pharmaceutical composition exhibits no protein aggregation detectable by dynamic light scattering after 28 days storage at 35-40° C.

* * * * *